(12) United States Patent
Gunde et al.

(10) Patent No.: US 11,578,133 B2
(45) Date of Patent: *Feb. 14, 2023

(54) ANTIBODIES TARGETING CD137 AND METHODS OF USE THEREOF

(71) Applicant: Numab Therapeutics AG, Wädenswil (CH)

(72) Inventors: Tea Gunde, Zurich (CH); Matthias Brock, Aesch (CH); Christian Hess, Zurich (CH); Alexandre Simonin, Rosenau (FR)

(73) Assignee: Namab Therapeutics AG, Wädenswil (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/754,097

(22) PCT Filed: Oct. 9, 2018

(86) PCT No.: PCT/EP2018/077514
§ 371 (c)(1),
(2) Date: Apr. 6, 2020

(87) PCT Pub. No.: WO2019/072870
PCT Pub. Date: Apr. 18, 2019

(65) Prior Publication Data
US 2020/0332015 A1    Oct. 22, 2020

(30) Foreign Application Priority Data

Oct. 10, 2017  (EP) ..................................... 17195780
Apr. 12, 2018  (EP) ..................................... 18167092
Jun. 29, 2018  (EP) ..................................... 18180815

(51) Int. Cl.
*C07K 16/28*         (2006.01)

(52) U.S. Cl.
CPC ...... *C07K 16/2878* (2013.01); *C07K 2317/31* (2013.01); *C07K 2317/33* (2013.01); *C07K 2317/565* (2013.01); *C07K 2317/567* (2013.01); *C07K 2317/622* (2013.01); *C07K 2317/75* (2013.01); *C07K 2317/92* (2013.01)

(58) Field of Classification Search
CPC ............ C07K 16/2878; C07K 2317/31; C07K 2317/33; C07K 2317/565; C07K 2317/622; C07K 2317/75; C07K 2317/92
See application file for complete search history.

(56) References Cited

FOREIGN PATENT DOCUMENTS

WO    2012/032433 A1      3/2012
WO    WO-2019072868 A1 *  4/2019  .............. A61P 35/00

OTHER PUBLICATIONS

International Search Report and Written Opinion, International Application No. PCT/EP2018/077514.
Fisher et al., Cancer Immunology, Immunotherapy 61 (10) (Mar. 11, 2012).

* cited by examiner

*Primary Examiner* — Julie Wu
*Assistant Examiner* — Cheom-Gil Cheong
(74) *Attorney, Agent, or Firm* — Prismatic Law Group, PLLC; Ron Kamis

(57) ABSTRACT

The present invention relates generally to an isolated antibody which specifically binds human CD137, and pharmaceutical compositions and methods of use thereof, a nucleic acid comprising a nucleotide sequence encoding said antibody, a vector comprising said nucleic acid, a host cell comprising said nucleic acid or said vector, and a method of producing said antibody.

15 Claims, 19 Drawing Sheets

Specification includes a Sequence Listing.

Figure 2:

| Heatmap | Urelumab | Utomilumab | PRO885 | PRO951 |
|---------|----------|------------|--------|--------|
| PRO885  | 29%      | 35%        | 0%     | 48%    |
| PRO951  | 34%      | 0%         | 22%    | 0%     |

Bindinglevel normalized to theoretical Rmax [%]

Table 26

| PRO ID | Clone ID PD-L1 | Clone ID CD137 | Clone ID SA | Format | Activation of NF-kB reporter gene CHO-PD-L1 | | | Activation of NF-kB reporter gene HCC827 -IFNg | | | Activation of NF-kB reporter gene HCC827 +IFNg | | |
|---|---|---|---|---|---|---|---|---|---|---|---|---|---|
| | | | | | IC$_{50}$ (ng/ml) rel. IC$_{50}$$^a$ & max. activation (%) | | HSA | IC$_{50}$ (ng/ml) rel. IC$_{50}$$^a$ & max. activation (%) | | | IC$_{50}$ (ng/ml) rel. IC$_{50}$$^a$ & max. activation (%) | | HSA |
| PRO885 | 33-03-G02 CDR | 38-02-A04 CDR | NA | scDb | 11.72 | 6.75 | 499.42 | no | 13.96 | 8.42 | 111.10 | 8.88 | 16.30 | 134.20 | no |
| PRO951 | 33-03-G02 CDR | 38-27-C05 CDR | NA | scDb | 33.68 | 2.35 | 431.70 | no | ND | ND | ND | ND | ND | ND | ND |
| PRO1123 | 33-03-G02 CDR | 38-02-A04 IF | NA | scDb | 5.75 | 18.11 | 219.20 | no | 16.12 | 6.82 | 123.20 | 11.87 | 12.20 | 154.40 | no |
| PRO1324 | 33-03-G02 CDR | 38-02-A04 STR | NA | scDb | 3.68 | 23.50 | 228.60 | no | 5.62 | 19.89 | 113.20 | 4.83 | 22.59 | 188.50 | no |
| PRO1125 | 33-03-G02 STR | 38-02-A04 CDR | NA | scDb | 6.00 | 14.43 | 242.10 | no | 6.97 | 16.04 | 135.10 | 5.48 | 19.74 | 207.70 | no |
| PRO963 | 33-03-G02 CDR | 38-02-A04 CDR | 19-01-H04 STR | scDb-scFv | ND | ND | 368.67 | yes, 24h | ND | ND | ND | ND | ND | ND | ND |
| PRO1057 | 33-03-G02 CDR | 38-02-A04 CDR | 23-13-A01 STR | scDb-scFv | 792.40 | 0.10 | 662.79 | yes, 24h | 76.61 | 0.62 | 68.99 | 115.00 | 0.46 | 135.34 | yes, 24h |
| PRO1058 | 33-03-G02 CDR | 38-27-C05 CDR | 23-13-A03 STR | scDb-scFv | 121.40 | 0.64 | 36.23 | yes, 24h | ND | ND | ND | ND | ND | ND | ND |
| PRO1059 | 33-03-G02 CDR | 38-02-A04 CDR | NA | Morrison-L | 289.10 | 0.09 | 189.09 | no, 24h | ND | ND | ND | ND | ND | ND | ND |
| PRO1060 | 33-03-G02 CDR | 38-02-A04 CDR | NA | Morrison-H | 80.85 | 0.38 | 144.13 | no, 24h | 13.57 | 3.59 | 54.94 | 17.51 | 3.01 | 97.04 | no, 24h |
| PRO1061 | 33-03-G02 CDR | 38-27-C05 CDR | NA | Morrison-L | ND | ND | ND | ND | ND | ND | ND | ND | ND | ND | ND |
| PRO1062 | 33-03-G02 CDR | 38-27-C05 CDR | NA | Morrison-H | 96.87 | 0.54 | 133.52 | no, 24h | ND | ND | ND | ND | ND | ND | ND |
| PRO1286 | 37-20-B03 sc01 | 38-02-A04 sc01 | 23-13-A01 sc03 | scDb-scFv | 50.96 | 0.97 | 152.06 | yes, 24h | ND | ND | ND | 16.68 | 1.88 | 128.83 | yes, 24h |

NA: not applicable
ND: not determined $^a$: IC$_{50}$ reference (ng/ml)/IC$_{50}$ test molecule (ng/ml)

SEQUENCE LISTING

```
<160> NUMBER OF SEQ ID NOS: 158

<210> SEQ ID NO 1
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 1

Gly Phe Ser Phe Ser Asn Ser Tyr Trp Ile Cys
1               5                   10

<210> SEQ ID NO 2
<211> LENGTH: 18
<212> TYPE: PRT
<213> ORGANISM: Artificial Sequence
<220> FEATURE:
<223> OTHER INFORMATION: sequence of recombinant antibody or functional
      part thereof

<400> SEQUENCE: 2

Cys Thr Phe Val Gly Ser Ser Asp Ser Thr Tyr Tyr Ala Asn Trp Ala
1               5                   10                  15

Lys Gly

<210> SEQ ID NO 3
<211> LENGTH: 14
<212> TYPE: PRT
<213> ORGANISM: Artificial Sequence
<220> FEATURE:
<223> OTHER INFORMATION: sequence of recombinant antibody or functional
``` part thereof

<400> SEQUENCE: 3

Arg His Pro Ser Asp Ala Val Tyr Gly Tyr Ala Asn Asn Leu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 4

Val Ser Gly Phe Ser Phe Ser Asn Ser Tyr Trp
1               5                   10

<210> SEQ ID NO 5
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 5

Ala Ser Gly Phe Ser Phe Ser Asn Ser Tyr Trp
1               5                   10

<210> SEQ ID NO 6
<211> LENGTH: 18
<212> TYPE: PRT
<213> ORGANISM: Artificial Sequence
<220> FEATURE:
<223> OTHER INFORMATION: sequence of recombinant antibody or functional
      part thereof

<400> SEQUENCE: 6

Thr Phe Val Gly Ser Ser Asp Ser Thr Tyr Tyr Ala Asn Trp Ala Lys
1               5                   10                  15

Gly Arg

<210> SEQ ID NO 7
<211> LENGTH: 12
<212> TYPE: PRT
<213> ORGANISM: Artificial Sequence
<220> FEATURE:
<223> OTHER INFORMATION: sequence of recombinant antibody or functional
      part thereof

<400> SEQUENCE: 7

His Pro Ser Asp Ala Val Tyr Gly Tyr Ala Asn Asn
1               5                   10

<210> SEQ ID NO 8
<211> LENGTH: 6
<212> TYPE: PRT
<213> ORGANISM: Artificial Sequence
<220> FEATURE:
<223> OTHER INFORMATION: sequence of recombinant antibody or functional
      part thereof

<400> SEQUENCE: 8

Asn Ser Tyr Trp Ile Cys
1               5

<210> SEQ ID NO 9
<211> LENGTH: 18
<212> TYPE: PRT
<213> ORGANISM: Artificial Sequence
<220> FEATURE:
<223> OTHER INFORMATION: sequence of recombinant antibody or functional
      part thereof

<400> SEQUENCE: 9

Cys Thr Phe Val Gly Ser Ser Asp Ser Thr Tyr Tyr Ala Asn Trp Ala
1               5                   10                  15

Lys Gly

<210> SEQ ID NO 10
<211> LENGTH: 13
<212> TYPE: PRT
<213> ORGANISM: Artificial Sequence
<220> FEATURE:
<223> OTHER INFORMATION: sequence of recombinant antibody or functional
      part thereof

<400> SEQUENCE: 10

His Pro Ser Asp Ala Val Tyr Gly Tyr Ala Asn Asn Leu
1               5                   10

<210> SEQ ID NO 11
<211> LENGTH: 8
<212> TYPE: PRT
<213> ORGANISM: Artificial Sequence
<220> FEATURE:
<223> OTHER INFORMATION: sequence of recombinant antibody or functional
      part thereof

<400> SEQUENCE: 11

Gly Phe Ser Phe Ser Asn Ser Tyr
1               5

<210> SEQ ID NO 12
<211> LENGTH: 5
<212> TYPE: PRT
<213> ORGANISM: Artificial Sequence
<220> FEATURE:
<223> OTHER INFORMATION: sequence of recombinant antibody or functional
      part thereof

<400> SEQUENCE: 12

Val Gly Ser Ser Asp
1               5

<210> SEQ ID NO 13
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 13

Pro Ser Asp Ala Val Tyr Gly Tyr Ala Asn Asn
1               5                   10

<210> SEQ ID NO 14
<211> LENGTH: 124
<212> TYPE: PRT
<213> ORGANISM: Artificial Sequence
<220> FEATURE:
<223> OTHER INFORMATION: sequence of recombinant antibody or functional part thereof

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Asn Ser
            20                  25                  30

Tyr Trp Ile Cys Trp Ile Arg Gln Pro Pro Gly Lys Gly Leu Glu Trp
        35                  40                  45

Ile Gly Cys Thr Phe Val Gly Ser Ser Asp Ser Thr Tyr Tyr Ala Asn
    50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg His Pro Ser Asp Ala Val Tyr Gly Tyr Ala Asn Asn
            100                 105                 110

Leu Trp Gly Gln Gly Thr Leu Val Thr Val Ser Ser
        115                 120

<210> SEQ ID NO 15
<211> LENGTH: 124
<212> TYPE: PRT
<213> ORGANISM: Artificial Sequence
<220> FEATURE:
<223> OTHER INFORMATION: sequence of recombinant antibody or functional
      part thereof

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Asn Ser
            20                  25                  30

Tyr Trp Ile Cys Trp Val Arg Gln Pro Pro Gly Lys Gly Leu Glu Trp
        35                  40                  45

Ile Gly Cys Thr Phe Val Gly Ser Ser Asp Ser Thr Tyr Tyr Ala Asn
    50                  55                  60

Trp Ala Lys Gly Arg Val Thr Ile Ser Val Asp Ser Ser Lys Asn Gln
65                  70                  75                  80

Val Ser Leu Lys Leu Ser Ser Val Thr Ala Ala Asp Thr Ala Val Tyr
                85                  90                  95

Phe Cys Ala Arg His Pro Ser Asp Ala Val Tyr Gly Tyr Ala Asn Asn
            100                 105                 110

Leu Trp Gly Gln Gly Thr Leu Val Thr Val Ser Ser
        115                 120

<210> SEQ ID NO 16
<211> LENGTH: 124
<212> TYPE: PRT
<213> ORGANISM: Artificial Sequence
<220> FEATURE:
<223> OTHER INFORMATION: sequence of recombinant antibody or functional
      part thereof

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Lys Ala Ser Gly Phe Ser Phe Ser Asn Ser
            20                  25                  30

Tyr Trp Ile Cys Trp Val Arg Gln Pro Pro Gly Lys Gly Leu Glu Trp
            35                  40                  45

Ile Gly Cys Thr Phe Val Gly Ser Ser Asp Ser Thr Tyr Tyr Ala Asn
 50                  55                  60

Trp Ala Lys Gly Arg Val Thr Ile Ser Lys Asp Ser Lys Asn Gln
 65                  70                  75                  80

Val Ser Leu Lys Leu Ser Ser Val Thr Ala Ala Asp Thr Ala Val Tyr
                85                  90                  95

Phe Cys Ala Arg His Pro Ser Asp Ala Val Tyr Gly Tyr Ala Asn Asn
                    100                 105                 110

Leu Trp Gly Gln Gly Thr Leu Val Thr Val Ser Ser
        115                 120

<210> SEQ ID NO 17
<211> LENGTH: 124
<212> TYPE: PRT
<213> ORGANISM: Artificial Sequence
<220> FEATURE:
<223> OTHER INFORMATION: sequence of recombinant antibody or functional
      part thereof

<400> SEQUENCE: 17

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Ser Phe Ser Asn Ser
                20                  25                  30

Tyr Trp Ile Cys Trp Val Arg Gln Ala Pro Gly Lys Cys Leu Glu Trp
            35                  40                  45

Ile Gly Cys Thr Phe Val Gly Ser Ser Asp Ser Thr Tyr Tyr Ala Asn
 50                  55                  60

Trp Ala Lys Gly Arg Phe Thr Ile Ser Arg Asp Asn Ser Lys Asn Thr
 65                  70                  75                  80

Val Tyr Leu Gln Met Asn Ser Leu Arg Ala Glu Asp Thr Ala Val Tyr
                85                  90                  95

Tyr Cys Ala Arg His Pro Ser Asp Ala Val Tyr Gly Tyr Ala Asn Asn
                    100                 105                 110

Leu Trp Gly Gln Gly Thr Leu Val Thr Val Ser Ser
        115                 120

<210> SEQ ID NO 18
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 18

Gln Ala Ser Gln Ser Ile Asn Asn Val Leu Ala
 1               5                   10

<210> SEQ ID NO 19
<211> LENGTH: 7
<212> TYPE: PRT
<213> ORGANISM: Artificial Sequence
<220> FEATURE:
<223> OTHER INFORMATION: sequence of recombinant antibody or functional
      part thereof

<400> SEQUENCE: 19

Arg Ala Ser Thr Leu Ala Ser
1               5

<210> SEQ ID NO 20
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 20

Gln Ser Ser Tyr Gly Asn Tyr Gly Asp
1               5

<210> SEQ ID NO 21
<211> LENGTH: 8
<212> TYPE: PRT
<213> ORGANISM: Artificial Sequence
<220> FEATURE:
<223> OTHER INFORMATION: sequence of recombinant antibody or functional
      part thereof

<400> SEQUENCE: 21

Ala Ser Gln Ser Ile Asn Asn Val
1               5

<210> SEQ ID NO 22
<211> LENGTH: 12
<212> TYPE: PRT
<213> ORGANISM: Artificial Sequence
<220> FEATURE:
<223> OTHER INFORMATION: sequence of recombinant antibody or functional
      part thereof

<400> SEQUENCE: 22

Arg Ala Ser Thr Leu Ala Ser Gly Val Pro Ser Arg
1               5                   10

<210> SEQ ID NO 23
<211> LENGTH: 6
<212> TYPE: PRT
<213> ORGANISM: Artificial Sequence
<220> FEATURE:
<223> OTHER INFORMATION: sequence of recombinant antibody or functional
      part thereof

<400> SEQUENCE: 23

Ser Tyr Gly Asn Tyr Gly
1               5

<210> SEQ ID NO 24
<211> LENGTH: 7
<212> TYPE: PRT
<213> ORGANISM: Artificial Sequence
<220> FEATURE:
<223> OTHER INFORMATION: sequence of recombinant antibody or functional
      part thereof

<400> SEQUENCE: 24

Ser Gln Ser Ile Asn Asn Val
1               5

<210> SEQ ID NO 25
<211> LENGTH: 3
<212> TYPE: PRT
<213> ORGANISM: Artificial Sequence
<220> FEATURE:

-continued

<223> OTHER INFORMATION: sequence of recombinant antibody or functional
      part thereof

<400> SEQUENCE: 25

Arg Ala Ser
1

<210> SEQ ID NO 26
<211> LENGTH: 6
<212> TYPE: PRT
<213> ORGANISM: Artificial Sequence
<220> FEATURE:
<223> OTHER INFORMATION: sequence of recombinant antibody or functional
      part thereof

<400> SEQUENCE: 26

Ser Tyr Gly Asn Tyr Gly
1               5

<210> SEQ ID NO 27
<211> LENGTH: 108
<212> TYPE: PRT
<213> ORGANISM: Artificial Sequence
<220> FEATURE:
<223> OTHER INFORMATION: sequence of recombinant antibody or functional
      part thereof

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
                20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Thr Gly Thr Lys Val Thr Val Leu Gly
            100                 105

<210> SEQ ID NO 28
<211> LENGTH: 108
<212> TYPE: PRT
<213> ORGANISM: Artificial Sequence
<220> FEATURE:
<223> OTHER INFORMATION: sequence of recombinant antibody or functional
      part thereof

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
                20                  25                  30

Leu Ala Trp Tyr Gln Gln Lys Pro Gly Lys Pro Pro Lys Leu Leu Ile
            35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Ser Ser Tyr Gly Asn Tyr Gly
                85                  90                  95

Asp Phe Gly Thr Gly Thr Lys Val Thr Val Leu Gly
            100                 105

<210> SEQ ID NO 29
<211> LENGTH: 108
<212> TYPE: PRT
<213> ORGANISM: Artificial Sequence
<220> FEATURE:
<223> OTHER INFORMATION: sequence of recombinant antibody or functional
      part thereof

<400> SEQUENCE: 29

Asp Leu Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
                20                  25                  30

Leu Ala Trp Tyr Gln Gln Lys Pro Gly Lys Pro Pro Lys Leu Leu Ile
            35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Thr Gly Thr Lys Val Thr Val Leu Gly
            100                 105

<210> SEQ ID NO 30
<211> LENGTH: 108
<212> TYPE: PRT
<213> ORGANISM: Artificial Sequence
<220> FEATURE:
<223> OTHER INFORMATION: sequence of recombinant antibody or functional
      part thereof

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
                20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Cys Gly Thr Lys Val Thr Val Leu Gly
            100                 105

<210> SEQ ID NO 31
<211> LENGTH: 20
<212> TYPE: PRT
<213> ORGANISM: Artificial Sequence
<220> FEATURE:
<223> OTHER INFORMATION: sequence of recombinant antibody or functional
      part thereof
```

<400> SEQUENCE: 31

Gly Gly Gly Gly Ser Gly Gly Gly Ser Gly Gly Gly Gly Ser Gly
1               5                   10                  15

Gly Gly Gly Ser
            20

<210> SEQ ID NO 32
<211> LENGTH: 252
<212> TYPE: PRT
<213> ORGANISM: Artificial Sequence
<220> FEATURE:
<223> OTHER INFORMATION: sequence of recombinant antibody or functional
      part thereof

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Gly Asn Tyr Gly
                85                  90                  95

Asp Phe Gly Thr Gly Thr Lys Val Thr Val Leu Gly Gly Gly Gly
            100                 105                 110

Ser Gly Gly Gly Ser Gly Gly Gly Ser Gly Gly Gly Ser
            115                 120                 125

Gln Val Gln Leu Gln Glu Ser Gly Pro Gly Leu Val Lys Pro Ser Glu
    130                 135                 140

Thr Leu Ser Leu Thr Cys Lys Val Ser Gly Phe Ser Phe Ser Asn Ser
145                 150                 155                 160

Tyr Trp Ile Cys Trp Ile Arg Gln Pro Pro Gly Lys Gly Leu Glu Trp
                165                 170                 175

Ile Gly Cys Thr Phe Val Gly Ser Ser Asp Ser Thr Tyr Tyr Ala Asn
            180                 185                 190

Trp Ala Lys Gly Arg Val Thr Ile Ser Val Asp Ser Lys Asn Gln
        195                 200                 205

Phe Ser Leu Lys Leu Ser Ser Val Thr Ala Ala Asp Thr Ala Val Tyr
    210                 215                 220

Tyr Cys Ala Arg His Pro Ser Asp Ala Val Tyr Gly Tyr Ala Asn Asn
225                 230                 235                 240

Leu Trp Gly Gln Gly Thr Leu Val Thr Val Ser Ser
                245                 250

<210> SEQ ID NO 33
<211> LENGTH: 252
<212> TYPE: PRT
<213> ORGANISM: Artificial Sequence
<220> FEATURE:
<223> OTHER INFORMATION: sequence of recombinant antibody or functional
      part thereof

<400> SEQUENCE: 33

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Pro Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Thr Gly Thr Lys Val Thr Val Leu Gly Gly Gly Gly Gly
                100                 105                 110

Ser Gly Gly Gly Gly Ser Gly Gly Gly Ser Gly Gly Gly Gly Gly Ser
            115                 120                 125

Gln Val Gln Leu Gln Glu Ser Gly Pro Gly Leu Val Lys Pro Ser Glu
        130                 135                 140

Thr Leu Ser Leu Thr Cys Lys Val Ser Gly Phe Ser Phe Ser Asn Ser
145                 150                 155                 160

Tyr Trp Ile Cys Trp Val Arg Gln Pro Pro Gly Lys Gly Leu Glu Trp
                165                 170                 175

Ile Gly Cys Thr Phe Val Gly Ser Ser Asp Ser Thr Tyr Tyr Ala Asn
                180                 185                 190

Trp Ala Lys Gly Arg Val Thr Ile Ser Val Asp Ser Ser Lys Asn Gln
        195                 200                 205

Val Ser Leu Lys Leu Ser Ser Val Thr Ala Ala Asp Thr Ala Val Tyr
    210                 215                 220

Phe Cys Ala Arg His Pro Ser Asp Ala Val Tyr Gly Tyr Ala Asn Asn
225                 230                 235                 240

Leu Trp Gly Gln Gly Thr Leu Val Thr Val Ser Ser
                245                 250

<210> SEQ ID NO 34
<211> LENGTH: 252
<212> TYPE: PRT
<213> ORGANISM: Artificial Sequence
<220> FEATURE:
<223> OTHER INFORMATION: sequence of recombinant antibody or functional
      part thereof

<400> SEQUENCE: 34

Asp Leu Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Pro Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Thr Gly Thr Lys Val Thr Val Leu Gly Gly Gly Gly Gly
                100                 105                 110
```

```
Ser Gly Gly Gly Gly Ser Gly Gly Gly Ser Gly Gly Gly Ser
            115                 120                 125

Gln Val Gln Leu Gln Glu Ser Gly Pro Gly Leu Val Lys Pro Ser Glu
    130                 135                 140

Thr Leu Ser Leu Thr Cys Lys Ala Ser Gly Phe Ser Phe Ser Asn Ser
145                 150                 155                 160

Tyr Trp Ile Cys Trp Val Arg Gln Pro Pro Gly Lys Gly Leu Glu Trp
                165                 170                 175

Ile Gly Cys Thr Phe Val Gly Ser Ser Asp Ser Thr Tyr Tyr Ala Asn
            180                 185                 190

Trp Ala Lys Gly Arg Val Thr Ile Ser Lys Asp Ser Lys Asn Gln
        195                 200                 205

Val Ser Leu Lys Leu Ser Ser Val Thr Ala Ala Asp Thr Ala Val Tyr
    210                 215                 220

Phe Cys Ala Arg His Pro Ser Asp Ala Val Tyr Gly Tyr Ala Asn Asn
225                 230                 235                 240

Leu Trp Gly Gln Gly Thr Leu Val Thr Val Ser Ser
                245                 250

<210> SEQ ID NO 35
<211> LENGTH: 252
<212> TYPE: PRT
<213> ORGANISM: Artificial Sequence
<220> FEATURE:
<223> OTHER INFORMATION: sequence of recombinant antibody or functional
      part thereof

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Cys Gly Thr Lys Val Thr Val Leu Gly Gly Gly Gly
            100                 105                 110

Ser Gly Gly Gly Gly Ser Gly Gly Gly Ser Gly Gly Gly Gly Ser
            115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Ser Phe Ser Asn Ser
145                 150                 155                 160

Tyr Trp Ile Cys Trp Val Arg Gln Ala Pro Gly Lys Cys Leu Glu Trp
                165                 170                 175

Ile Gly Cys Thr Phe Val Gly Ser Ser Asp Ser Thr Tyr Tyr Ala Asn
            180                 185                 190

Trp Ala Lys Gly Arg Phe Thr Ile Ser Arg Asp Asn Ser Lys Asn Thr
        195                 200                 205

Val Tyr Leu Gln Met Asn Ser Leu Arg Ala Glu Asp Thr Ala Val Tyr
```

Tyr Cys Ala Arg His Pro Ser Asp Ala Val Tyr Gly Tyr Ala Asn Asn
225                 230                 235                 240

Leu Trp Gly Gln Gly Thr Leu Val Thr Val Ser Ser
            245                 250

<210> SEQ ID NO 36
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 36

Gly Phe Ser Phe Asn Asn Asp Tyr Asp Met Cys
1               5                   10

<210> SEQ ID NO 37
<211> LENGTH: 17
<212> TYPE: PRT
<213> ORGANISM: Artificial Sequence
<220> FEATURE:
<223> OTHER INFORMATION: sequence of recombinant antibody or functional
      part thereof

<400> SEQUENCE: 37

Cys Ile Asp Thr Gly Asp Gly Ser Thr Tyr Tyr Ala Ser Trp Ala Lys
1               5                   10                  15

Gly

<210> SEQ ID NO 38
<211> LENGTH: 16
<212> TYPE: PRT
<213> ORGANISM: Artificial Sequence
<220> FEATURE:
<223> OTHER INFORMATION: sequence of recombinant antibody or functional
      part thereof

<400> SEQUENCE: 38

Arg Glu Ala Ala Ser Ser Ser Gly Tyr Gly Met Gly Tyr Phe Asp Leu
1               5                   10                  15

<210> SEQ ID NO 39
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 39

Val Ser Gly Phe Ser Phe Asn Asn Asp Tyr Asp
1               5                   10

<210> SEQ ID NO 40
<211> LENGTH: 17
<212> TYPE: PRT
<213> ORGANISM: Artificial Sequence
<220> FEATURE:
<223> OTHER INFORMATION: sequence of recombinant antibody or functional
      part thereof

<400> SEQUENCE: 40

Ile Asp Thr Gly Asp Gly Ser Thr Tyr Tyr Ala Ser Trp Ala Lys Gly
1               5                   10                  15

Arg

<210> SEQ ID NO 41
<211> LENGTH: 14
<212> TYPE: PRT
<213> ORGANISM: Artificial Sequence
<220> FEATURE:
<223> OTHER INFORMATION: sequence of recombinant antibody or functional
      part thereof

<400> SEQUENCE: 41

Glu Ala Ala Ser Ser Ser Gly Tyr Gly Met Gly Tyr Phe Asp
1               5                   10

<210> SEQ ID NO 42
<211> LENGTH: 6
<212> TYPE: PRT
<213> ORGANISM: Artificial Sequence
<220> FEATURE:
<223> OTHER INFORMATION: sequence of recombinant antibody or functional
      part thereof

<400> SEQUENCE: 42

Asn Asp Tyr Asp Met Cys
1               5

<210> SEQ ID NO 43
<211> LENGTH: 17
<212> TYPE: PRT
<213> ORGANISM: Artificial Sequence
<220> FEATURE:
<223> OTHER INFORMATION: sequence of recombinant antibody or functional
      part thereof

<400> SEQUENCE: 43

Cys Ile Asp Thr Gly Asp Gly Ser Thr Tyr Tyr Ala Ser Trp Ala Lys
1               5                   10                  15
Gly

<210> SEQ ID NO 44
<211> LENGTH: 15
<212> TYPE: PRT
<213> ORGANISM: Artificial Sequence
<220> FEATURE:
<223> OTHER INFORMATION: sequence of recombinant antibody or functional
      part thereof

<400> SEQUENCE: 44

Glu Ala Ala Ser Ser Ser Gly Tyr Gly Met Gly Tyr Phe Asp Leu
1               5                   10                  15

<210> SEQ ID NO 45
<211> LENGTH: 8
<212> TYPE: PRT
<213> ORGANISM: Artificial Sequence
<220> FEATURE:
<223> OTHER INFORMATION: sequence of recombinant antibody or functional
      part thereof

<400> SEQUENCE: 45

Gly Phe Ser Phe Asn Asn Asp Tyr
1               5

<210> SEQ ID NO 46
<211> LENGTH: 4
<212> TYPE: PRT

```
<213> ORGANISM: Artificial Sequence
<220> FEATURE:
<223> OTHER INFORMATION: sequence of recombinant antibody or functional
      part thereof

<400> SEQUENCE: 46

Thr Gly Asp Gly
1

<210> SEQ ID NO 47
<211> LENGTH: 13
<212> TYPE: PRT
<213> ORGANISM: Artificial Sequence
<220> FEATURE:
<223> OTHER INFORMATION: sequence of recombinant antibody or functional
      part thereof

<400> SEQUENCE: 47

Ala Ala Ser Ser Ser Gly Tyr Gly Met Gly Tyr Phe Asp
1               5                   10

<210> SEQ ID NO 48
<211> LENGTH: 125
<212> TYPE: PRT
<213> ORGANISM: Artificial Sequence
<220> FEATURE:
<223> OTHER INFORMATION: sequence of recombinant antibody or functional
      part thereof

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Asn Asn Asp
            20                  25                  30

Tyr Asp Met Cys Trp Ile Arg Gln Pro Pro Gly Lys Gly Leu Glu Trp
        35                  40                  45

Ile Gly Cys Ile Asp Thr Gly Asp Gly Ser Thr Tyr Tyr Ala Ser Trp
    50                  55                  60

Ala Lys Gly Arg Val Thr Ile Ser Val Asp Ser Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ala Ala Ser Ser Ser Gly Tyr Gly Met Gly Tyr Phe
            100                 105                 110

Asp Leu Trp Gly Gln Gly Thr Leu Val Thr Val Ser Ser
        115                 120                 125

<210> SEQ ID NO 49
<211> LENGTH: 13
<212> TYPE: PRT
<213> ORGANISM: Artificial Sequence
<220> FEATURE:
<223> OTHER INFORMATION: sequence of recombinant antibody or functional
      part thereof

<400> SEQUENCE: 49

Gln Ser Ser Gln Ser Val Tyr Asp Asn Asn Trp Leu Ala
1               5                   10

<210> SEQ ID NO 50
<211> LENGTH: 7
<212> TYPE: PRT
<213> ORGANISM: Artificial Sequence
<220> FEATURE:
```

```
<223> OTHER INFORMATION: sequence of recombinant antibody or functional
      part thereof

<400> SEQUENCE: 50

Arg Ala Ser Asn Leu Ala Ser
1               5

<210> SEQ ID NO 51
<211> LENGTH: 12
<212> TYPE: PRT
<213> ORGANISM: Artificial Sequence
<220> FEATURE:
<223> OTHER INFORMATION: sequence of recombinant antibody or functional
      part thereof

<400> SEQUENCE: 51

Gln Gly Thr Tyr Leu Ser Ser Asn Trp Tyr Trp Ala
1               5                   10

<210> SEQ ID NO 52
<211> LENGTH: 10
<212> TYPE: PRT
<213> ORGANISM: Artificial Sequence
<220> FEATURE:
<223> OTHER INFORMATION: sequence of recombinant antibody or functional
      part thereof

<400> SEQUENCE: 52

Ser Ser Gln Ser Val Tyr Asp Asn Asn Trp
1               5                   10

<210> SEQ ID NO 53
<211> LENGTH: 12
<212> TYPE: PRT
<213> ORGANISM: Artificial Sequence
<220> FEATURE:
<223> OTHER INFORMATION: sequence of recombinant antibody or functional
      part thereof

<400> SEQUENCE: 53

Arg Ala Ser Asn Leu Ala Ser Gly Val Pro Ser Arg
1               5                   10

<210> SEQ ID NO 54
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 54

Thr Tyr Leu Ser Ser Asn Trp Tyr Trp
1               5

<210> SEQ ID NO 55
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 55

Ser Gln Ser Val Tyr Asp Asn Asn Trp
1               5
```

```
<210> SEQ ID NO 56
<211> LENGTH: 3
<212> TYPE: PRT
<213> ORGANISM: Artificial Sequence
<220> FEATURE:
<223> OTHER INFORMATION: sequence of recombinant antibody or functional
      part thereof

<400> SEQUENCE: 56

Arg Ala Ser
1

<210> SEQ ID NO 57
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 57

Thr Tyr Leu Ser Ser Asn Trp Tyr Trp
1               5

<210> SEQ ID NO 58
<211> LENGTH: 113
<212> TYPE: PRT
<213> ORGANISM: Artificial Sequence
<220> FEATURE:
<223> OTHER INFORMATION: sequence of recombinant antibody or functional
      part thereof

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Tyr Asp Asn
            20                  25                  30

Asn Trp Leu Ala Trp Tyr Gln Gln Lys Pro Gly Lys Ala Pro Lys Leu
        35                  40                  45

Leu Ile Tyr Arg Ala Ser Asn Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gly Thr Tyr Leu Ser
                85                  90                  95

Ser Asn Trp Tyr Trp Ala Phe Gly Thr Gly Thr Lys Val Thr Val Leu
            100                 105                 110

Gly

<210> SEQ ID NO 59
<211> LENGTH: 20
<212> TYPE: PRT
<213> ORGANISM: Artificial Sequence
<220> FEATURE:
<223> OTHER INFORMATION: sequence of recombinant antibody or functional
      part thereof

<400> SEQUENCE: 59

Gly Gly Gly Gly Ser Gly Gly Gly Ser Gly Gly Gly Gly Ser Gly
1               5                   10                  15

Gly Gly Gly Ser
            20
```

```
<210> SEQ ID NO 60
<211> LENGTH: 258
<212> TYPE: PRT
<213> ORGANISM: Artificial Sequence
<220> FEATURE:
<223> OTHER INFORMATION: sequence of recombinant antibody or functional
      part thereof

<400> SEQUENCE: 60

Asp Ile Gln Met Thr Gln Ser Pro Ser Leu Ser Ala Ser Val Gly
1               5                   10                  15

Asp Arg Val Thr Ile Thr Cys Gln Ser Ser Gln Ser Val Tyr Asp Asn
                20                  25                  30

Asn Trp Leu Ala Trp Tyr Gln Gln Lys Pro Gly Lys Ala Pro Lys Leu
            35                  40                  45

Leu Ile Tyr Arg Ala Ser Asn Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gly Thr Tyr Leu Ser
                85                  90                  95

Ser Asn Trp Tyr Trp Ala Phe Gly Thr Gly Thr Lys Val Thr Val Leu
            100                 105                 110

Gly Gly Gly Gly Ser Gly Gly Gly Ser Gly Gly Gly Gly Ser
        115                 120                 125

Gly Gly Gly Gly Ser Gln Val Gln Leu Gln Glu Ser Gly Pro Gly Leu
130                 135                 140

Val Lys Pro Ser Glu Thr Leu Ser Leu Thr Cys Lys Val Ser Gly Phe
145                 150                 155                 160

Ser Phe Asn Asn Asp Tyr Asp Met Cys Trp Ile Arg Gln Pro Pro Gly
                165                 170                 175

Lys Gly Leu Glu Trp Ile Gly Cys Ile Asp Thr Gly Asp Gly Ser Thr
            180                 185                 190

Tyr Tyr Ala Ser Trp Ala Lys Gly Arg Val Thr Ile Ser Val Asp Ser
    195                 200                 205

Ser Lys Asn Gln Phe Ser Leu Lys Leu Ser Ser Val Thr Ala Ala Asp
        210                 215                 220

Thr Ala Val Tyr Tyr Cys Ala Arg Glu Ala Ala Ser Ser Ser Gly Tyr
225                 230                 235                 240

Gly Met Gly Tyr Phe Asp Leu Trp Gly Gln Gly Thr Leu Val Thr Val
                245                 250                 255

Ser Ser

<210> SEQ ID NO 61
<211> LENGTH: 255
<212> TYPE: PRT
<213> ORGANISM: Homo sapiens

<400> SEQUENCE: 61

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60
```

```
Cys Arg Gln Cys Lys Gly Val Phe Arg Thr Arg Lys Glu Cys Ser Ser
 65                  70                  75                  80

Thr Ser Asn Ala Glu Cys Asp Cys Thr Pro Gly Phe His Cys Leu Gly
                 85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 62
<211> LENGTH: 11
<212> TYPE: PRT
<213> ORGANISM: Homo sapiens

<400> SEQUENCE: 62

Phe Gly Thr Gly Thr Lys Val Thr Val Leu Gly
1               5                   10

<210> SEQ ID NO 63
<211> LENGTH: 11
<212> TYPE: PRT
<213> ORGANISM: Homo sapiens

<400> SEQUENCE: 63

Phe Gly Gly Gly Thr Lys Leu Thr Val Leu Gly
1               5                   10

<210> SEQ ID NO 64
<211> LENGTH: 11
<212> TYPE: PRT
<213> ORGANISM: Homo sapiens

<400> SEQUENCE: 64

Phe Gly Gly Gly Thr Gln Leu Ile Ile Leu Gly
1               5                   10

<210> SEQ ID NO 65
<211> LENGTH: 11
<212> TYPE: PRT
<213> ORGANISM: Homo sapiens

<400> SEQUENCE: 65

Phe Gly Glu Gly Thr Glu Leu Thr Val Leu Gly
```

-continued

```
1               5                   10

<210> SEQ ID NO 66
<211> LENGTH: 11
<212> TYPE: PRT
<213> ORGANISM: Homo sapiens

<400> SEQUENCE: 66

Phe Gly Ser Gly Thr Lys Val Thr Val Leu Gly
1               5                   10

<210> SEQ ID NO 67
<211> LENGTH: 11
<212> TYPE: PRT
<213> ORGANISM: Homo sapiens

<400> SEQUENCE: 67

Phe Gly Gly Gly Thr Gln Leu Thr Val Leu Gly
1               5                   10

<210> SEQ ID NO 68
<211> LENGTH: 11
<212> TYPE: PRT
<213> ORGANISM: Homo sapiens

<400> SEQUENCE: 68

Phe Gly Gly Gly Thr Gln Leu Thr Ala Leu Gly
1               5                   10

<210> SEQ ID NO 69
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
    130                 135                 140

Phe Ser Asn Ser Tyr Trp Ile Cys Trp Ile Arg Gln Pro Pro Gly Lys
145                 150                 155                 160

Gly Leu Glu Trp Ile Gly Cys Thr Phe Val Gly Ser Ser Asp Ser Thr
                165                 170                 175
```

```
Tyr Tyr Ala Asn Trp Ala Lys Gly Arg Val Thr Ile Ser Val Asp Ser
            180                 185                 190

Ser Lys Asn Gln Phe Ser Leu Lys Leu Ser Ser Val Thr Ala Ala Asp
        195                 200                 205

Thr Ala Val Tyr Tyr Cys Ala Arg His Pro Ser Asp Ala Val Tyr Gly
    210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Ser Gly Gly Gly Gly Ser
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Ala Pro Lys
    290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Thr Gly Thr Lys Val Thr Val Leu Gly Gly
        355                 360                 365

Gly Gly Gly Ser Gln Val Gln Leu Gln Glu Ser Gly Pro Gly Leu Val
    370                 375                 380

Lys Pro Ser Glu Thr Leu Ser Leu Thr Cys Lys Val Ser Gly Phe Ser
385                 390                 395                 400

Phe Ser Ser Gly Tyr Asp Met Cys Trp Ile Arg Gln Pro Pro Gly Lys
                405                 410                 415

Gly Leu Glu Trp Ile Gly Cys Val Val Ala Gly Ser Val Asp Ile Thr
            420                 425                 430

Tyr Tyr Ala Ser Trp Ala Lys Gly Arg Val Thr Ile Ser Val Asp Ser
        435                 440                 445

Ser Lys Asn Gln Phe Ser Leu Lys Leu Ser Ser Val Thr Ala Ala Asp
450                 455                 460

Thr Ala Val Tyr Tyr Cys Ala Arg Lys Asp Ala Tyr Ser Asp Ala Phe
465                 470                 475                 480

Asn Leu Trp Gly Gln Gly Thr Leu Val Thr Val Ser Ser
                485                 490

<210> SEQ ID NO 70
<211> LENGTH: 499
<212> TYPE: PRT
<213> ORGANISM: Artificial Sequence
<220> FEATURE:
<223> OTHER INFORMATION: sequence of recombinant antibody or functional
      part thereof

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45
```

```
Tyr Lys Ala Ser Thr Leu Ala Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Gly Tyr Ile Ile Thr Asp
                 85                  90                  95
Ile Asp Asn Val Phe Gly Thr Gly Thr Lys Val Thr Val Leu Gly Gly
                100                 105                 110
Gly Gly Gly Ser Glu Val Gln Leu Val Glu Ser Gly Gly Gly Leu Val
             115                 120                 125
Gln Pro Gly Gly Ser Leu Arg Leu Ser Cys Ala Ala Ser Gly Phe Ser
130                 135                 140
Phe Asn Asn Asp Tyr Asp Met Cys Trp Val Arg Gln Ala Pro Gly Lys
145                 150                 155                 160
Gly Leu Glu Trp Ile Gly Cys Ile Asp Thr Gly Asp Gly Ser Thr Tyr
                165                 170                 175
Tyr Ala Ser Trp Ala Lys Gly Arg Phe Thr Ile Ser Arg Asp Asn Ser
                180                 185                 190
Lys Asn Thr Val Tyr Leu Gln Met Asn Ser Leu Arg Ala Glu Asp Thr
            195                 200                 205
Ala Val Tyr Tyr Cys Ala Arg Glu Ala Ala Ser Ser Gly Tyr Gly
210                 215                 220
Met Gly Tyr Phe Asp Leu Trp Gly Gln Gly Thr Leu Val Thr Val Ser
225                 230                 235                 240
Ser Gly Gly Gly Gly Ser Gly Gly Gly Ser Gly Gly Gly Gly Ser
                245                 250                 255
Gly Gly Gly Gly Ser Ile Gln Met Thr Gln Ser Pro Ser Ser Leu Ser
            260                 265                 270
Ala Ser Val Gly Asp Arg Val Thr Ile Thr Cys Gln Ser Ser Gln Ser
            275                 280                 285
Val Tyr Asp Asn Asn Trp Leu Ala Trp Tyr Gln Gln Lys Pro Gly Lys
290                 295                 300
Ala Pro Lys Leu Leu Ile Tyr Arg Ala Ser Asn Leu Ala Ser Gly Val
305                 310                 315                 320
Pro Ser Arg Phe Ser Gly Ser Gly Ser Gly Thr Asp Phe Thr Leu Thr
                325                 330                 335
Ile Ser Ser Leu Gln Pro Glu Asp Phe Ala Thr Tyr Tyr Cys Gln Gly
            340                 345                 350
Thr Tyr Leu Ser Ser Asn Trp Tyr Trp Ala Phe Gly Thr Gly Thr Lys
            355                 360                 365
Val Thr Val Leu Gly Gly Gly Gly Ser Gln Val Gln Leu Gln Glu
        370                 375                 380
Ser Gly Pro Gly Leu Val Lys Pro Ser Glu Thr Leu Ser Leu Thr Cys
385                 390                 395                 400
Lys Val Ser Gly Phe Ser Phe Ser Ser Gly Tyr Asp Met Cys Trp Ile
                405                 410                 415
Arg Gln Pro Pro Gly Lys Gly Leu Glu Trp Ile Gly Cys Val Val Ala
            420                 425                 430
Gly Ser Val Asp Ile Thr Tyr Tyr Ala Ser Trp Ala Lys Gly Arg Val
        435                 440                 445
Thr Ile Ser Val Asp Ser Ser Lys Asn Gln Phe Ser Leu Lys Leu Ser
450                 455                 460
```

```
Ser Val Thr Ala Ala Asp Thr Ala Val Tyr Tyr Cys Ala Arg Lys Asp
465                 470                 475                 480

Ala Tyr Ser Asp Ala Phe Asn Leu Trp Gly Gln Gly Thr Leu Val Thr
                485                 490                 495

Val Ser Ser

<210> SEQ ID NO 71
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
130                 135                 140

Phe Ser Asn Ser Tyr Trp Ile Cys Trp Val Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
            180                 185                 190

Ser Lys Asn Gln Val Ser Leu Lys Leu Ser Ser Val Thr Ala Ala Asp
        195                 200                 205

Thr Ala Val Tyr Phe Cys Ala Arg His Pro Ser Asp Ala Val Tyr Gly
210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Ser Gly Gly Gly Gly Ser Gly
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Pro Pro Lys
290                 295                 300

Leu Leu Ile Tyr Arg Ala Ser Thr Leu Ala Ser Gly Val Pro Ser Arg
305                 310                 315                 320
```

```
Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Thr Gly Thr Lys Val Thr Val Leu Gly Gly
            355                 360                 365

Gly Gly Gly Ser Gln Val Gln Leu Gln Glu Ser Gly Pro Gly Leu Val
            370                 375                 380

Lys Pro Ser Glu Thr Leu Ser Leu Thr Cys Lys Val Ser Gly Phe Ser
385                 390                 395                 400

Phe Ser Ser Gly Tyr Asp Met Cys Trp Ile Arg Gln Pro Pro Gly Lys
            405                 410                 415

Gly Leu Glu Trp Ile Gly Cys Val Val Ala Gly Ser Val Asp Ile Thr
            420                 425                 430

Tyr Tyr Ala Ser Trp Ala Lys Gly Arg Val Thr Ile Ser Val Asp Ser
            435                 440                 445

Ser Lys Asn Gln Phe Ser Leu Lys Leu Ser Ser Val Thr Ala Ala Asp
            450                 455                 460

Thr Ala Val Tyr Tyr Cys Ala Arg Lys Asp Ala Tyr Ser Asp Ala Phe
465                 470                 475                 480

Asn Leu Trp Gly Gln Gly Thr Leu Val Thr Val Ser Ser
            485                 490

<210> SEQ ID NO 72
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
            35                  40                  45

Tyr Lys Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
            85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
            115                 120                 125

Lys Pro Ser Glu Thr Leu Ser Leu Thr Cys Lys Ala Ser Gly Phe Ser
            130                 135                 140

Phe Ser Asn Ser Tyr Trp Ile Cys Trp Val Arg Gln Pro Pro Gly Lys
145                 150                 155                 160

Gly Leu Glu Trp Ile Gly Cys Thr Phe Val Gly Ser Ser Asp Ser Thr
            165                 170                 175

Tyr Tyr Ala Asn Trp Ala Lys Gly Arg Val Thr Ile Ser Lys Asp Ser
            180                 185                 190
```

-continued

```
Ser Lys Asn Gln Val Ser Leu Lys Leu Ser Ser Val Thr Ala Ala Asp
        195                 200                 205

Thr Ala Val Tyr Phe Cys Ala Arg His Pro Ser Asp Ala Val Tyr Gly
    210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Ser Gly Gly Gly Ser Gly
                245                 250                 255

Gly Gly Gly Ser Leu Gln Met Thr Gln Ser Pro Ser Ser Leu Ser Ala
                260                 265                 270

Ser Val Gly Asp Arg Val Thr Ile Thr Cys Gln Ala Ser Gln Ser Ile
            275                 280                 285

Asn Asn Val Leu Ala Trp Tyr Gln Gln Lys Pro Gly Lys Pro Pro Lys
        290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Thr Gly Thr Lys Val Thr Val Leu Gly Gly
        355                 360                 365

Gly Gly Gly Ser Gln Val Gln Leu Gln Glu Ser Gly Pro Gly Leu Val
    370                 375                 380

Lys Pro Ser Glu Thr Leu Ser Leu Thr Cys Lys Val Ser Gly Phe Ser
385                 390                 395                 400

Phe Ser Ser Gly Tyr Asp Met Cys Trp Ile Arg Gln Pro Pro Gly Lys
                405                 410                 415

Gly Leu Glu Trp Ile Gly Cys Val Val Ala Gly Ser Val Asp Ile Thr
            420                 425                 430

Tyr Tyr Ala Ser Trp Ala Lys Gly Arg Val Thr Ile Ser Val Asp Ser
        435                 440                 445

Ser Lys Asn Gln Phe Ser Leu Lys Leu Ser Ser Val Thr Ala Ala Asp
    450                 455                 460

Thr Ala Val Tyr Tyr Cys Ala Arg Lys Asp Ala Tyr Ser Asp Ala Phe
465                 470                 475                 480

Asn Leu Trp Gly Gln Gly Thr Leu Val Thr Val Ser Ser
                485                 490

<210> SEQ ID NO 73
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ser Pro Lys Leu Leu Ile
        35                  40                  45

Tyr Lys Ala Ser Thr Leu Ala Ser Gly Val Pro Ser Arg Phe Ser Gly
```

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Ile Ile Thr Asp
                 85                  90                  95

Ile Asp Asn Val Phe Gly Thr Gly Thr Lys Val Thr Val Leu Gly Gly
                100                 105                 110

Gly Gly Gly Ser Gln Val Gln Leu Gln Glu Ser Gly Pro Gly Leu Val
                115                 120                 125

Lys Pro Ser Glu Thr Leu Ser Leu Thr Cys Lys Val Ser Gly Phe Ser
        130                 135                 140

Phe Ser Asn Ser Tyr Trp Ile Cys Trp Ile Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
                180                 185                 190

Ser Lys Asn Gln Phe Ser Leu Lys Leu Ser Ser Val Thr Ala Ala Asp
        195                 200                 205

Thr Ala Val Tyr Tyr Cys Ala Arg His Pro Ser Asp Ala Val Tyr Gly
210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Ser Gly Gly Gly Gly Ser Gly
                245                 250                 255

Gly Gly Gly Ser Ile Gln Met Thr Gln Ser Pro Ser Ser Leu Ser Ala
                260                 265                 270

Ser Val Gly Asp Arg Val Thr Ile Thr Cys Gln Ala Ser Gln Ser Ile
                275                 280                 285

Asn Asn Val Leu Ala Trp Tyr Gln Gln Lys Pro Gly Lys Ala Pro Lys
        290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
                340                 345                 350

Asn Tyr Gly Asp Phe Gly Thr Gly Thr Lys Val Thr Val Leu Gly Gly
                355                 360                 365

Gly Gly Gly Ser Gln Val Gln Leu Gln Glu Ser Gly Pro Gly Leu Val
        370                 375                 380

Lys Pro Ser Glu Thr Leu Ser Leu Thr Cys Lys Val Ser Gly Phe Ser
385                 390                 395                 400

Phe Ser Ser Gly Tyr Asp Met Cys Trp Val Arg Gln Pro Pro Gly Lys
                405                 410                 415

Gly Leu Glu Trp Ile Ala Cys Val Val Ala Gly Ser Val Asp Ile Thr
                420                 425                 430

Tyr Tyr Ala Ser Trp Ala Lys Gly Arg Val Thr Ile Ser Val Asp Ser
                435                 440                 445

Ser Lys Asn Gln Phe Ser Leu Lys Leu Ser Ser Val Thr Ala Ala Asp
        450                 455                 460

Thr Ala Val Tyr Phe Cys Ala Arg Lys Asp Ala Tyr Ser Asp Ala Phe
465                 470                 475                 480
```

Asn Leu Trp Gly Gln Gly Thr Leu Val Thr Val Ser Ser
                485                 490

<210> SEQ ID NO 74
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 74

Asp Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ser Pro Lys Leu Leu Ile
        35                  40                  45

Tyr Lys Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
        115                 120                 125

Lys Pro Ser Glu Thr Leu Ser Leu Thr Cys Lys Val Ser Gly Phe Ser
130                 135                 140

Phe Ser Asn Ser Tyr Trp Ile Cys Trp Ile Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
            180                 185                 190

Ser Lys Asn Gln Phe Ser Leu Lys Leu Ser Ser Val Thr Ala Ala Asp
        195                 200                 205

Thr Ala Val Tyr Tyr Cys Ala Arg His Pro Ser Asp Ala Val Tyr Gly
210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Ser Gly Gly Gly Ser Gly
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
        275                 280                 285

Asn Asn Val Leu Ala Trp Tyr Gln Gln Lys Pro Gly Lys Ala Pro Lys
290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly

```
              340                 345                 350
Asn Tyr Gly Asp Phe Gly Thr Gly Thr Lys Val Thr Val Leu Gly Gly
            355                 360                 365

Gly Gly Gly Ser Gln Ser Gln Leu Gln Glu Ser Gly Pro Gly Leu Val
            370                 375                 380

Lys Pro Ser Glu Thr Leu Ser Leu Thr Cys Lys Ala Ser Gly Phe Ser
385                 390                 395                 400

Phe Ser Ser Gly Tyr Asp Met Cys Trp Val Arg Gln Pro Pro Gly Lys
                405                 410                 415

Gly Leu Glu Trp Ile Ala Cys Val Ala Gly Ser Val Asp Ile Thr
            420                 425                 430

Tyr Tyr Ala Ser Trp Ala Lys Gly Arg Val Thr Ile Ser Lys Asp Ser
            435                 440                 445

Ser Lys Asn Gln Val Ser Leu Lys Leu Ser Ser Val Thr Ala Ala Asp
            450                 455                 460

Thr Ala Val Tyr Phe Cys Ala Arg Lys Asp Ala Tyr Ser Asp Ala Phe
465                 470                 475                 480

Asn Leu Trp Gly Gln Gly Thr Leu Val Thr Val Ser Ser
                485                 490

<210> SEQ ID NO 75
<211> LENGTH: 493
<212> TYPE: PRT
<213> ORGANISM: Artificial Sequence
<220> FEATURE:
<223> OTHER INFORMATION: sequence of recombinant antibody or functional
      part thereof

<400> SEQUENCE: 75

Asp Ile Gln Met Thr Gln Ser Pro Ser Ser Leu Ser Ala Ser Val Gly
1               5                   10                  15

Asp Ala Val Thr Ile Thr Cys Gln Ala Ser Gln Ser Ile Asn Asp Tyr
            20                  25                  30

Leu Ala Trp Tyr Gln Gln Lys Pro Gly Lys Ser Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
            115                 120                 125

Lys Pro Ser Glu Thr Leu Ser Leu Thr Cys Lys Val Ser Gly Phe Ser
            130                 135                 140

Phe Ser Asn Ser Tyr Trp Ile Cys Trp Ile Arg Gln Pro Pro Gly Lys
145                 150                 155                 160

Gly Leu Glu Trp Ile Gly Cys Thr Phe Val Gly Ser Ser Asp Ser Thr
                165                 170                 175

Tyr Tyr Ala Asn Trp Ala Lys Gly Arg Val Thr Ile Ser Val Asp Ser
            180                 185                 190

Ser Lys Asn Gln Phe Ser Leu Lys Leu Ser Ser Val Thr Ala Ala Asp
        195                 200                 205
```

```
Thr Ala Val Tyr Tyr Cys Ala Arg His Pro Ser Asp Ala Val Tyr Gly
            210                 215                 220

Tyr Ala Asn Asn Leu Trp Gly Gln Gly Thr Leu Val Thr Val Ser Ser
225                 230                 235                 240

Gly Gly Gly Gly Ser Gly Gly Gly Ser Gly Gly Gly Gly Ser Gly
                245                 250                 255

Gly Gly Gly Ser Ile Gln Met Thr Gln Ser Pro Ser Ser Leu Ser Ala
            260                 265                 270

Ser Val Gly Asp Arg Val Thr Ile Thr Cys Gln Ala Ser Gln Ser Ile
                275                 280                 285

Asn Asn Val Leu Ala Trp Tyr Gln Gln Lys Pro Gly Lys Ala Pro Lys
            290                 295                 300

Leu Leu Ile Tyr Arg Ala Ser Thr Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Ser Ser Tyr Gly
            340                 345                 350

Asn Tyr Gly Asp Phe Gly Thr Gly Thr Lys Val Thr Val Leu Gly Gly
            355                 360                 365

Gly Gly Gly Ser Glu Val Gln Leu Val Glu Ser Gly Gly Gly Leu Val
370                 375                 380

Gln Pro Gly Gly Ser Leu Arg Leu Ser Cys Ala Ala Ser Gly Phe Ser
385                 390                 395                 400

Phe Ser Ser Gly Tyr Asp Met Cys Trp Val Arg Gln Ala Pro Gly Lys
                405                 410                 415

Gly Leu Glu Trp Val Gly Cys Val Val Ala Gly Ser Val Asp Ile Thr
            420                 425                 430

Tyr Tyr Ala Ser Trp Ala Lys Gly Arg Phe Thr Ile Ser Arg Asp Asn
            435                 440                 445

Ser Lys Asn Thr Val Tyr Leu Gln Met Asn Ser Leu Arg Ala Glu Asp
450                 455                 460

Thr Ala Thr Tyr Tyr Cys Ala Arg Lys Asp Ala Tyr Ser Asp Ala Phe
465                 470                 475                 480

Asn Leu Trp Gly Pro Gly Thr Leu Val Thr Val Ser Ser
                485                 490

<210> SEQ ID NO 76
<211> LENGTH: 755
<212> TYPE: PRT
<213> ORGANISM: Artificial Sequence
<220> FEATURE:
<223> OTHER INFORMATION: sequence of recombinant antibody or functional
      part thereof

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
                20                  25                  30

Leu Ala Trp Tyr Gln Gln Lys Pro Gly Lys Ala Pro Lys Leu Leu Ile
            35                  40                  45

Tyr Lys Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Gly Tyr Ile Ile Thr Asp
                85                  90                  95
Ile Asp Asn Val Phe Gly Thr Gly Thr Lys Val Thr Val Leu Gly Gly
            100                 105                 110
Gly Gly Gly Ser Gln Val Gln Leu Gln Glu Ser Gly Pro Gly Leu Val
        115                 120                 125
Lys Pro Ser Glu Thr Leu Ser Leu Thr Cys Lys Val Ser Gly Phe Ser
130                 135                 140
Phe Ser Asn Ser Tyr Trp Ile Cys Trp Ile Arg Gln Pro Pro Gly Lys
145                 150                 155                 160
Gly Leu Glu Trp Ile Gly Cys Thr Phe Val Gly Ser Ser Asp Ser Thr
            165                 170                 175
Tyr Tyr Ala Asn Trp Ala Lys Gly Arg Val Thr Ile Ser Val Asp Ser
            180                 185                 190
Ser Lys Asn Gln Phe Ser Leu Lys Leu Ser Ser Val Thr Ala Ala Asp
        195                 200                 205
Thr Ala Val Tyr Tyr Cys Ala Arg His Pro Ser Asp Ala Val Tyr Gly
210                 215                 220
Tyr Ala Asn Asn Leu Trp Gly Gln Gly Thr Leu Val Thr Val Ser Ser
225                 230                 235                 240
Gly Gly Gly Gly Ser Gly Gly Gly Ser Gly Gly Gly Gly Ser Gly
            245                 250                 255
Gly Gly Gly Ser Ile Gln Met Thr Gln Ser Pro Ser Ser Leu Ser Ala
        260                 265                 270
Ser Val Gly Asp Arg Val Thr Ile Thr Cys Gln Ala Ser Gln Ser Ile
            275                 280                 285
Asn Asn Val Leu Ala Trp Tyr Gln Gln Lys Pro Gly Lys Ala Pro Lys
290                 295                 300
Leu Leu Ile Tyr Arg Ala Ser Thr Leu Ala Ser Gly Val Pro Ser Arg
305                 310                 315                 320
Phe Ser Gly Ser Gly Ser Gly Thr Asp Phe Thr Leu Thr Ile Ser Ser
            325                 330                 335
Leu Gln Pro Glu Asp Phe Ala Thr Tyr Tyr Cys Gln Ser Ser Tyr Gly
        340                 345                 350
Asn Tyr Gly Asp Phe Gly Thr Gly Thr Lys Val Thr Val Leu Gly Gly
            355                 360                 365
Gly Gly Gly Ser Gln Val Gln Leu Gln Glu Ser Gly Pro Gly Leu Val
        370                 375                 380
Lys Pro Ser Glu Thr Leu Ser Leu Thr Cys Lys Val Ser Gly Phe Ser
385                 390                 395                 400
Phe Ser Ser Gly Tyr Asp Met Cys Trp Ile Arg Gln Pro Pro Gly Lys
            405                 410                 415
Gly Leu Glu Trp Ile Gly Cys Val Val Ala Gly Ser Val Asp Ile Thr
            420                 425                 430
Tyr Tyr Ala Ser Trp Ala Lys Gly Arg Val Thr Ile Ser Val Asp Ser
            435                 440                 445
Ser Lys Asn Gln Phe Ser Leu Lys Leu Ser Ser Val Thr Ala Ala Asp
        450                 455                 460
Thr Ala Val Tyr Tyr Cys Ala Arg Lys Asp Ala Tyr Ser Asp Ala Phe
465                 470                 475                 480
Asn Leu Trp Gly Gln Gly Thr Leu Val Thr Val Ser Ser Gly Gly Gly
            485                 490                 495
```

Gly Ser Gly Gly Gly Ser Ile Gln Met Thr Gln Ser Pro Ser Ser
            500                 505                 510

Leu Ser Ala Ser Val Gly Asp Arg Val Thr Ile Thr Cys Gln Ser Ser
        515                 520                 525

Glu Ser Val Tyr Ser Asn Asn Gln Leu Ser Trp Tyr Gln Gln Lys Pro
    530                 535                 540

Gly Gln Pro Pro Lys Leu Leu Ile Tyr Asp Ala Ser Asp Leu Ala Ser
545                 550                 555                 560

Gly Val Pro Ser Arg Phe Ser Gly Ser Gly Ser Gly Thr Asp Phe Thr
                565                 570                 575

Leu Thr Ile Ser Ser Leu Gln Pro Glu Asp Phe Ala Thr Tyr Tyr Cys
            580                 585                 590

Ala Gly Gly Phe Ser Ser Ser Asp Thr Ala Phe Gly Gly Gly Thr
        595                 600                 605

Lys Leu Thr Val Leu Gly Gly Gly Gly Ser Gly Gly Gly Gly Ser
            610                 615                 620

Gly Gly Gly Gly Ser Gly Gly Gly Gly Ser Glu Val Gln Leu Val Glu
625                 630                 635                 640

Ser Gly Gly Gly Leu Val Gln Pro Gly Gly Ser Leu Arg Leu Ser Cys
                645                 650                 655

Ala Ala Ser Gly Phe Ser Leu Ser Ser Asn Ala Met Gly Trp Val Arg
            660                 665                 670

Gln Ala Pro Gly Lys Gly Leu Glu Tyr Ile Gly Ile Ile Ser Val Gly
        675                 680                 685

Gly Phe Thr Tyr Tyr Ala Ser Trp Ala Lys Gly Arg Phe Thr Ile Ser
    690                 695                 700

Arg Asp Asn Ser Lys Asn Thr Val Tyr Leu Gln Met Asn Ser Leu Arg
705                 710                 715                 720

Ala Glu Asp Thr Ala Thr Tyr Phe Cys Ala Arg Asp Arg His Gly Gly
                725                 730                 735

Asp Ser Ser Gly Ala Phe Tyr Leu Trp Gly Gln Gly Thr Leu Val Thr
            740                 745                 750

Val Ser Ser
        755

<210> SEQ ID NO 77
<211> LENGTH: 761
<212> TYPE: PRT
<213> ORGANISM: Artificial Sequence
<220> FEATURE:
<223> OTHER INFORMATION: sequence of recombinant antibody or functional
      part thereof

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

```
Ile Asp Asn Val Phe Gly Thr Gly Thr Lys Val Thr Val Leu Gly Gly
            100                 105                 110

Gly Gly Gly Ser Gln Val Gln Leu Gln Glu Ser Gly Pro Gly Leu Val
            115                 120                 125

Lys Pro Ser Glu Thr Leu Ser Leu Thr Cys Lys Val Ser Gly Phe Ser
            130                 135                 140

Phe Asn Asn Asp Tyr Asp Met Cys Trp Ile Arg Gln Pro Pro Gly Lys
145                 150                 155                 160

Gly Leu Glu Trp Ile Gly Cys Ile Asp Thr Gly Asp Gly Ser Thr Tyr
                165                 170                 175

Tyr Ala Ser Trp Ala Lys Gly Arg Val Thr Ile Ser Val Asp Ser Ser
                180                 185                 190

Lys Asn Gln Phe Ser Leu Lys Leu Ser Ser Val Thr Ala Ala Asp Thr
                195                 200                 205

Ala Val Tyr Tyr Cys Ala Arg Glu Ala Ala Ser Ser Gly Tyr Gly
            210                 215                 220

Met Gly Tyr Phe Asp Leu Trp Gly Gln Gly Thr Leu Val Thr Val Ser
225                 230                 235                 240

Ser Gly Gly Gly Ser Gly Gly Gly Ser Gly Gly Gly Ser
                245                 250                 255

Gly Gly Gly Ser Ile Gln Met Thr Gln Ser Pro Ser Ser Leu Ser
            260                 265                 270

Ala Ser Val Gly Asp Arg Val Thr Ile Thr Cys Gln Ser Ser Gln Ser
            275                 280                 285

Val Tyr Asp Asn Asn Trp Leu Ala Trp Tyr Gln Gln Lys Pro Gly Lys
            290                 295                 300

Ala Pro Lys Leu Leu Ile Tyr Arg Ala Ser Asn Leu Ala Ser Gly Val
305                 310                 315                 320

Pro Ser Arg Phe Ser Gly Ser Gly Ser Gly Thr Asp Phe Thr Leu Thr
                325                 330                 335

Ile Ser Ser Leu Gln Pro Glu Asp Phe Ala Thr Tyr Tyr Cys Gln Gly
                340                 345                 350

Thr Tyr Leu Ser Ser Asn Trp Tyr Trp Ala Phe Gly Thr Gly Thr Lys
                355                 360                 365

Val Thr Val Leu Gly Gly Gly Gly Ser Gln Val Gln Leu Gln Glu
            370                 375                 380

Ser Gly Pro Gly Leu Val Lys Pro Ser Glu Thr Leu Ser Leu Thr Cys
385                 390                 395                 400

Lys Val Ser Gly Phe Ser Phe Ser Ser Gly Tyr Asp Met Cys Trp Ile
                405                 410                 415

Arg Gln Pro Pro Gly Lys Gly Leu Glu Trp Ile Gly Cys Val Val Ala
                420                 425                 430

Gly Ser Val Asp Ile Thr Tyr Tyr Ala Ser Trp Ala Lys Gly Arg Val
            435                 440                 445

Thr Ile Ser Val Asp Ser Ser Lys Asn Gln Phe Ser Leu Lys Leu Ser
450                 455                 460

Ser Val Thr Ala Ala Asp Thr Ala Val Tyr Tyr Cys Ala Arg Lys Asp
465                 470                 475                 480

Ala Tyr Ser Asp Ala Phe Asn Leu Trp Gly Gln Gly Thr Leu Val Thr
                485                 490                 495

Val Ser Ser Gly Gly Gly Gly Ser Gly Gly Gly Gly Ser Ile Gln Met
            500                 505                 510
```

```
Thr Gln Ser Pro Ser Ser Leu Ser Ala Ser Val Gly Asp Arg Val Thr
            515                 520                 525
Ile Thr Cys Gln Ser Ser Glu Ser Val Tyr Ser Asn Asn Gln Leu Ser
530                 535                 540
Trp Tyr Gln Gln Lys Pro Gly Gln Pro Pro Lys Leu Leu Ile Tyr Asp
545                 550                 555                 560
Ala Ser Asp Leu Ala Ser Gly Val Pro Ser Arg Phe Ser Gly Ser Gly
                565                 570                 575
Ser Gly Thr Asp Phe Thr Leu Thr Ile Ser Ser Leu Gln Pro Glu Asp
                580                 585                 590
Phe Ala Thr Tyr Tyr Cys Ala Gly Gly Phe Ser Ser Ser Ser Asp Thr
            595                 600                 605
Ala Phe Gly Gly Gly Thr Lys Leu Thr Val Leu Gly Gly Gly Gly Gly
        610                 615                 620
Ser Gly Gly Gly Gly Ser Gly Gly Gly Gly Ser Gly Gly Gly Gly Ser
625                 630                 635                 640
Glu Val Gln Leu Val Glu Ser Gly Gly Gly Leu Val Gln Pro Gly Gly
                645                 650                 655
Ser Leu Arg Leu Ser Cys Ala Ala Ser Gly Phe Ser Leu Ser Ser Asn
                660                 665                 670
Ala Met Gly Trp Val Arg Gln Ala Pro Gly Lys Gly Leu Glu Tyr Ile
            675                 680                 685
Gly Ile Ile Ser Val Gly Gly Phe Thr Tyr Tyr Ala Ser Trp Ala Lys
        690                 695                 700
Gly Arg Phe Thr Ile Ser Arg Asp Asn Ser Lys Asn Thr Val Tyr Leu
705                 710                 715                 720
Gln Met Asn Ser Leu Arg Ala Glu Asp Thr Ala Thr Tyr Phe Cys Ala
                725                 730                 735
Arg Asp Arg His Gly Gly Asp Ser Ser Gly Ala Phe Tyr Leu Trp Gly
                740                 745                 750
Gln Gly Thr Leu Val Thr Val Ser Ser
            755                 760

<210> SEQ ID NO 78
<211> LENGTH: 753
<212> TYPE: PRT
<213> ORGANISM: Artificial Sequence
<220> FEATURE:
<223> OTHER INFORMATION: sequence of recombinant antibody or functional
      part thereof

<400> SEQUENCE: 78

Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Ser Ile Asn Asp Tyr
            20                  25                  30
Leu Ala Trp Tyr Gln Gln Lys Pro Gly Lys Ala Pro Lys Leu Leu Ile
        35                  40                  45
Tyr Lys Ala Ser Thr Leu Ala Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Tyr Ile Ile Thr Asp
                85                  90                  95
Ile Asp Asn Val Phe Gly Thr Gly Thr Lys Val Thr Val Leu Gly Gly
            100                 105                 110
```

```
Gly Gly Gly Ser Gln Val Gln Leu Gln Glu Ser Gly Pro Gly Leu Val
        115                 120                 125
Lys Pro Ser Glu Thr Leu Ser Leu Thr Cys Lys Val Ser Gly Phe Ser
        130                 135                 140
Phe Ser Asn Ser Tyr Trp Ile Cys Trp Ile Arg Gln Pro Pro Gly Lys
145                 150                 155                 160
Gly Leu Glu Trp Ile Gly Cys Thr Phe Val Gly Ser Ser Asp Ser Thr
                165                 170                 175
Tyr Tyr Ala Asn Trp Ala Lys Gly Arg Val Thr Ile Ser Val Asp Ser
                180                 185                 190
Ser Lys Asn Gln Phe Ser Leu Lys Leu Ser Ser Val Thr Ala Ala Asp
        195                 200                 205
Thr Ala Val Tyr Tyr Cys Ala Arg His Pro Ser Asp Ala Val Tyr Gly
        210                 215                 220
Tyr Ala Asn Asn Leu Trp Gly Gln Gly Thr Leu Val Thr Val Ser Ser
225                 230                 235                 240
Gly Gly Gly Gly Ser Gly Gly Gly Ser Gly Gly Gly Gly Ser Gly
                245                 250                 255
Gly Gly Gly Ser Ile Gln Met Thr Gln Ser Pro Ser Ser Leu Ser Ala
        260                 265                 270
Ser Val Gly Asp Arg Val Thr Ile Thr Cys Gln Ala Ser Gln Ser Ile
        275                 280                 285
Asn Asn Val Leu Ala Trp Tyr Gln Gln Lys Pro Gly Lys Ala Pro Lys
        290                 295                 300
Leu Leu Ile Tyr Arg Ala Ser Thr Leu Ala Ser Gly Val Pro Ser Arg
305                 310                 315                 320
Phe Ser Gly Ser Gly Ser Gly Thr Asp Phe Thr Leu Thr Ile Ser Ser
                325                 330                 335
Leu Gln Pro Glu Asp Phe Ala Thr Tyr Tyr Cys Gln Ser Ser Tyr Gly
                340                 345                 350
Asn Tyr Gly Asp Phe Gly Thr Gly Thr Lys Val Thr Val Leu Gly Gly
        355                 360                 365
Gly Gly Gly Ser Gln Val Gln Leu Gln Glu Ser Gly Pro Gly Leu Val
        370                 375                 380
Lys Pro Ser Glu Thr Leu Ser Leu Thr Cys Lys Val Ser Gly Phe Ser
385                 390                 395                 400
Phe Ser Ser Gly Tyr Asp Met Cys Trp Ile Arg Gln Pro Pro Gly Lys
                405                 410                 415
Gly Leu Glu Trp Ile Gly Cys Val Val Ala Gly Ser Val Asp Ile Thr
                420                 425                 430
Tyr Tyr Ala Ser Trp Ala Lys Gly Arg Val Thr Ile Ser Val Asp Ser
                435                 440                 445
Ser Lys Asn Gln Phe Ser Leu Lys Leu Ser Ser Val Thr Ala Ala Asp
        450                 455                 460
Thr Ala Val Tyr Tyr Cys Ala Arg Lys Asp Ala Tyr Ser Asp Ala Phe
465                 470                 475                 480
Asn Leu Trp Gly Gln Gly Thr Leu Val Thr Val Ser Ser Gly Gly Gly
                485                 490                 495
Gly Ser Gly Gly Gly Gly Ser Val Val Met Thr Gln Ser Pro Ser Ser
        500                 505                 510
Leu Ser Ala Ser Val Gly Asp Arg Val Thr Ile Thr Cys Gln Ala Ser
        515                 520                 525
```

```
Gln Ile Ile Ser Ser Arg Ser Ala Trp Tyr Gln Gln Lys Pro Gly Gln
        530                 535                 540

Pro Pro Lys Leu Leu Ile Tyr Gln Ala Ser Lys Leu Ala Ser Gly Val
545                 550                 555                 560

Pro Ser Arg Phe Ser Gly Ser Gly Ser Gly Thr Asp Phe Thr Leu Thr
                565                 570                 575

Ile Ser Ser Leu Gln Pro Glu Asp Phe Ala Thr Tyr Tyr Cys Gln Cys
            580                 585                 590

Thr Tyr Ile Asp Ser Asn Phe Gly Ala Phe Gly Gly Thr Lys Leu
        595                 600                 605

Thr Val Leu Gly Gly Gly Gly Ser Gly Gly Gly Ser Gly Gly
    610                 615                 620

Gly Gly Ser Gly Gly Gly Ser Glu Val Gln Leu Val Glu Ser Gly
625                 630                 635                 640

Gly Gly Leu Val Gln Pro Gly Gly Ser Leu Arg Leu Ser Cys Ala Ala
                645                 650                 655

Ser Gly Phe Ser Phe Ser Ser Tyr Trp Ile Cys Trp Val Arg Gln
            660                 665                 670

Ala Pro Gly Lys Gly Leu Glu Trp Val Gly Cys Val Phe Thr Gly Asp
                675                 680                 685

Gly Thr Thr Tyr Tyr Ala Ser Trp Ala Lys Gly Arg Phe Thr Ile Ser
        690                 695                 700

Arg Asp Asn Ser Lys Asn Thr Val Tyr Leu Gln Met Asn Ser Leu Arg
705                 710                 715                 720

Ala Glu Asp Thr Ala Thr Tyr Phe Cys Ala Arg Pro Val Ser Val Tyr
                725                 730                 735

Tyr Tyr Gly Met Asp Leu Trp Gly Gln Gly Thr Leu Val Thr Val Ser
                740                 745                 750

Ser
```

<210> SEQ ID NO 79
<211> LENGTH: 759
<212> TYPE: PRT
<213> ORGANISM: Artificial Sequence
<220> FEATURE:
<223> OTHER INFORMATION: sequence of recombinant antibody or functional
      part thereof

<400> SEQUENCE: 79

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
                20                  25                  30

Leu Ala Trp Tyr Gln Gln Lys Pro Gly Lys Ala Pro Lys Leu Leu Ile
            35                  40                  45

Tyr Lys Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
                100                 105                 110

Gly Gly Gly Ser Gln Val Gln Leu Gln Glu Ser Gly Pro Gly Leu Val
            115                 120                 125
```

```
Lys Pro Ser Glu Thr Leu Ser Leu Thr Cys Lys Val Ser Gly Phe Ser
    130                 135                 140

Phe Asn Asn Asp Tyr Asp Met Cys Trp Ile Arg Gln Pro Pro Gly Lys
145                 150                 155                 160

Gly Leu Glu Trp Ile Gly Cys Ile Asp Thr Gly Asp Gly Ser Thr Tyr
            165                 170                 175

Tyr Ala Ser Trp Ala Lys Gly Arg Val Thr Ile Ser Val Asp Ser Ser
                180                 185                 190

Lys Asn Gln Phe Ser Leu Lys Leu Ser Ser Val Thr Ala Ala Asp Thr
            195                 200                 205

Ala Val Tyr Tyr Cys Ala Arg Glu Ala Ala Ser Ser Gly Tyr Gly
    210                 215                 220

Met Gly Tyr Phe Asp Leu Trp Gly Gln Gly Thr Leu Val Thr Val Ser
225                 230                 235                 240

Ser Gly Gly Gly Gly Ser Gly Gly Gly Ser Gly Gly Gly Gly Ser
            245                 250                 255

Gly Gly Gly Gly Ser Ile Gln Met Thr Gln Ser Pro Ser Ser Leu Ser
            260                 265                 270

Ala Ser Val Gly Asp Arg Val Thr Ile Thr Cys Gln Ser Ser Gln Ser
    275                 280                 285

Val Tyr Asp Asn Asn Trp Leu Ala Trp Tyr Gln Gln Lys Pro Gly Lys
    290                 295                 300

Ala Pro Lys Leu Leu Ile Tyr Arg Ala Ser Asn Leu Ala Ser Gly Val
305                 310                 315                 320

Pro Ser Arg Phe Ser Gly Ser Gly Ser Gly Thr Asp Phe Thr Leu Thr
                325                 330                 335

Ile Ser Ser Leu Gln Pro Glu Asp Phe Ala Thr Tyr Tyr Cys Gln Gly
            340                 345                 350

Thr Tyr Leu Ser Ser Asn Trp Tyr Trp Ala Phe Gly Thr Gly Thr Lys
        355                 360                 365

Val Thr Val Leu Gly Gly Gly Gly Ser Gln Val Gln Leu Gln Glu
    370                 375                 380

Ser Gly Pro Gly Leu Val Lys Pro Ser Glu Thr Leu Ser Leu Thr Cys
385                 390                 395                 400

Lys Val Ser Gly Phe Ser Phe Ser Ser Gly Tyr Asp Met Cys Trp Ile
                405                 410                 415

Arg Gln Pro Pro Gly Lys Gly Leu Glu Trp Ile Gly Cys Val Val Ala
            420                 425                 430

Gly Ser Val Asp Ile Thr Tyr Tyr Ala Ser Trp Ala Lys Gly Arg Val
            435                 440                 445

Thr Ile Ser Val Asp Ser Ser Lys Asn Gln Phe Ser Leu Lys Leu Ser
    450                 455                 460

Ser Val Thr Ala Ala Asp Thr Ala Val Tyr Tyr Cys Ala Arg Lys Asp
465                 470                 475                 480

Ala Tyr Ser Asp Ala Phe Asn Leu Trp Gly Gln Gly Thr Leu Val Thr
                485                 490                 495

Val Ser Ser Gly Gly Gly Gly Ser Gly Gly Gly Gly Ser Val Val Met
            500                 505                 510

Thr Gln Ser Pro Ser Ser Leu Ser Ala Ser Val Gly Asp Arg Val Thr
    515                 520                 525

Ile Thr Cys Gln Ala Ser Gln Ile Ile Ser Ser Arg Ser Ala Trp Tyr
    530                 535                 540

Gln Gln Lys Pro Gly Gln Pro Pro Lys Leu Leu Ile Tyr Gln Ala Ser
```

```
                    545                 550                 555                 560
    Lys Leu Ala Ser Gly Val Pro Ser Arg Phe Ser Gly Ser Gly Ser Gly
                        565                 570                 575

Thr Asp Phe Thr Leu Thr Ile Ser Ser Leu Gln Pro Glu Asp Phe Ala
                580                 585                 590

Thr Tyr Tyr Cys Gln Cys Thr Tyr Ile Asp Ser Asn Phe Gly Ala Phe
                    595                 600                 605

Gly Gly Gly Thr Lys Leu Thr Val Leu Gly Gly Gly Gly Ser Gly
                610                 615                 620

Gly Gly Gly Ser Gly Gly Gly Ser Gly Gly Gly Ser Glu Val
    625                 630                 635                 640

Gln Leu Val Glu Ser Gly Gly Leu Val Gln Pro Gly Gly Ser Leu
                    645                 650                 655

Arg Leu Ser Cys Ala Ala Ser Gly Phe Ser Phe Ser Ser Tyr Trp
                    660                 665                 670

Ile Cys Trp Val Arg Gln Ala Pro Gly Lys Gly Leu Glu Trp Val Gly
                    675                 680                 685

Cys Val Phe Thr Gly Asp Gly Thr Thr Tyr Tyr Ala Ser Trp Ala Lys
                690                 695                 700

Gly Arg Phe Thr Ile Ser Arg Asp Asn Ser Lys Asn Thr Val Tyr Leu
    705                 710                 715                 720

Gln Met Asn Ser Leu Arg Ala Glu Asp Thr Ala Thr Tyr Phe Cys Ala
                        725                 730                 735

Arg Pro Val Ser Val Tyr Tyr Tyr Gly Met Asp Leu Trp Gly Gln Gly
                    740                 745                 750

Thr Leu Val Thr Val Ser Ser
            755

<210> SEQ ID NO 80
<211> LENGTH: 478
<212> TYPE: PRT
<213> ORGANISM: Artificial Sequence
<220> FEATURE:
<223> OTHER INFORMATION: sequence of recombinant antibody or functional
      part thereof

<400> SEQUENCE: 80

Asp Ile Gln Met Thr Gln Ser Pro Ser Ser Leu Ser Ala Ser Val Gly
    1               5                   10                  15

Asp Arg Val Thr Ile Thr Cys Gln Ala Ser Gln Ser Ile Asn Asp Tyr
                20                  25                  30

Leu Ala Trp Tyr Gln Gln Lys Pro Gly Lys Ala Pro Lys Leu Leu Ile
                35                  40                  45

Tyr Lys Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
    65                  70                  75                  80

Glu Asp Phe Ala Thr Tyr Tyr Cys Gln Gln Gly Tyr Ile Ile Thr Asp
                    85                  90                  95

Ile Asp Asn Val Phe Gly Thr Gly Thr Lys Val Thr Val Leu Gly Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140
```

-continued

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
            165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys Gly Gly Gly Ser Gly Gly
210                 215                 220

Gly Gly Ser Ile Gln Met Thr Gln Ser Pro Ser Ser Leu Ser Ala Ser
225                 230                 235                 240

Val Gly Asp Arg Val Thr Ile Thr Cys Gln Ala Ser Gln Ser Ile Asn
            245                 250                 255

Asn Val Leu Ala Trp Tyr Gln Gln Lys Pro Gly Lys Ala Pro Lys Leu
            260                 265                 270

Leu Ile Tyr Arg Ala Ser Thr Leu Ala Ser Gly Val Pro Ser Arg Phe
            275                 280                 285

Ser Gly Ser Gly Ser Gly Thr Asp Phe Thr Leu Thr Ile Ser Ser Leu
290                 295                 300

Gln Pro Glu Asp Phe Ala Thr Tyr Tyr Cys Gln Ser Ser Tyr Gly Asn
305                 310                 315                 320

Tyr Gly Asp Phe Gly Thr Gly Thr Lys Val Thr Val Leu Gly Gly Gly
            325                 330                 335

Gly Gly Ser Gly Gly Gly Ser Gly Gly Gly Ser Gly Gly Gly
            340                 345                 350

Gly Ser Gln Val Gln Leu Gln Glu Ser Gly Pro Gly Leu Val Lys Pro
            355                 360                 365

Ser Glu Thr Leu Ser Leu Thr Cys Lys Val Ser Gly Phe Ser Phe Ser
370                 375                 380

Asn Ser Tyr Trp Ile Cys Trp Ile Arg Gln Pro Pro Gly Lys Gly Leu
385                 390                 395                 400

Glu Trp Ile Gly Cys Thr Phe Val Gly Ser Ser Asp Ser Thr Tyr Tyr
            405                 410                 415

Ala Asn Trp Ala Lys Gly Arg Val Thr Ile Ser Val Asp Ser Ser Lys
            420                 425                 430

Asn Gln Phe Ser Leu Lys Leu Ser Ser Val Thr Ala Ala Asp Thr Ala
            435                 440                 445

Val Tyr Tyr Cys Ala Arg His Pro Ser Asp Ala Val Tyr Gly Tyr Ala
            450                 455                 460

Asn Asn Leu Trp Gly Gln Gly Thr Leu Val Thr Val Ser Ser
465                 470                 475

<210> SEQ ID NO 81
<211> LENGTH: 451
<212> TYPE: PRT
<213> ORGANISM: Artificial Sequence
<220> FEATURE:
<223> OTHER INFORMATION: sequence of recombinant antibody or functional
      part thereof

<400> SEQUENCE: 81

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30

```
Tyr Asp Met Cys Trp Ile Arg Gln Pro Pro Gly Lys Gly Leu Glu Trp
         35                  40                  45

Ile Gly Cys Val Val Ala Gly Ser Val Asp Ile Thr Tyr Tyr Ala Ser
 50                  55                  60

Trp Ala Lys Gly Arg Val Thr Ile Ser Val Asp Ser Ser Lys Asn Gln
 65                  70                  75                  80

Phe Ser Leu Lys Leu Ser Ser Val Thr Ala Ala Asp Thr Ala Val Tyr
                 85                  90                  95

Tyr Cys Ala Arg Lys Asp Ala Tyr Ser Asp Ala Phe Asn Leu Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445
```

```
Pro Gly Lys
    450

<210> SEQ ID NO 82
<211> LENGTH: 217
<212> TYPE: PRT
<213> ORGANISM: Artificial Sequence
<220> FEATURE:
<223> OTHER INFORMATION: sequence of recombinant antibody or functional
      part thereof

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 83
<211> LENGTH: 712
<212> TYPE: PRT
<213> ORGANISM: Artificial Sequence
<220> FEATURE:
<223> OTHER INFORMATION: sequence of recombinant antibody or functional
      part thereof

<400> SEQUENCE: 83

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30

Tyr Asp Met Cys Trp Ile Arg Gln Pro Pro Gly Lys Gly Leu Glu Trp
        35                  40                  45

Ile Gly Cys Val Val Ala Gly Ser Val Asp Ile Thr Tyr Tyr Ala Ser
    50                  55                  60
```

```
Trp Ala Lys Gly Arg Val Thr Ile Ser Val Asp Ser Ser Lys Asn Gln
 65                  70                  75                  80

Phe Ser Leu Lys Leu Ser Ser Val Thr Ala Ala Asp Thr Ala Val Tyr
                 85                  90                  95

Tyr Cys Ala Arg Lys Asp Ala Tyr Ser Asp Ala Phe Asn Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Ile Gln Met
    450                 455                 460

Thr Gln Ser Pro Ser Ser Leu Ser Ala Ser Val Gly Asp Arg Val Thr
465                 470                 475                 480

Ile Thr Cys Gln Ala Ser Gln Ser Ile Asn Asn Val Leu Ala Trp Tyr
```

```
                485                 490                 495
Gln Gln Lys Pro Gly Lys Ala Pro Lys Leu Leu Ile Tyr Arg Ala Ser
            500                 505                 510

Thr Leu Ala Ser Gly Val Pro Ser Arg Phe Ser Gly Ser Gly Ser Gly
            515                 520                 525

Thr Asp Phe Thr Leu Thr Ile Ser Ser Leu Gln Pro Glu Asp Phe Ala
            530                 535                 540

Thr Tyr Tyr Cys Gln Ser Ser Tyr Gly Asn Tyr Gly Asp Phe Gly Thr
545                 550                 555                 560

Gly Thr Lys Val Thr Val Leu Gly Gly Gly Gly Ser Gly Gly Gly
                565                 570                 575

Gly Ser Gly Gly Gly Ser Gly Gly Gly Ser Gln Val Gln Leu
            580                 585                 590

Gln Glu Ser Gly Pro Gly Leu Val Lys Pro Ser Glu Thr Leu Ser Leu
            595                 600                 605

Thr Cys Lys Val Ser Gly Phe Ser Phe Ser Asn Ser Tyr Trp Ile Cys
            610                 615                 620

Trp Ile Arg Gln Pro Pro Gly Lys Gly Leu Glu Trp Ile Gly Cys Thr
625                 630                 635                 640

Phe Val Gly Ser Ser Asp Ser Thr Tyr Tyr Ala Asn Trp Ala Lys Gly
                645                 650                 655

Arg Val Thr Ile Ser Val Asp Ser Ser Lys Asn Gln Phe Ser Leu Lys
                660                 665                 670

Leu Ser Ser Val Thr Ala Ala Asp Thr Ala Val Tyr Tyr Cys Ala Arg
                675                 680                 685

His Pro Ser Asp Ala Val Tyr Gly Tyr Ala Asn Asn Leu Trp Gly Gln
            690                 695                 700

Gly Thr Leu Val Thr Val Ser Ser
705                 710

<210> SEQ ID NO 84
<211> LENGTH: 478
<212> TYPE: PRT
<213> ORGANISM: Artificial Sequence
<220> FEATURE:
<223> OTHER INFORMATION: sequence of recombinant antibody or functional
      part thereof

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Thr
            100                 105                 110

Val Ala Ala Pro Ser Val Phe Ile Phe Pro Pro Ser Asp Glu Gln Leu
        115                 120                 125
```

```
Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Gly Gly Gly Ser Gly Gly
    210                 215                 220

Gly Gly Ser Ile Gln Met Thr Gln Ser Pro Ser Ser Leu Ser Ala Ser
225                 230                 235                 240

Val Gly Asp Arg Val Thr Ile Thr Cys Gln Ala Ser Gln Ser Ile Asn
                245                 250                 255

Asn Val Leu Ala Trp Tyr Gln Gln Lys Pro Gly Lys Ala Pro Lys Leu
            260                 265                 270

Leu Ile Tyr Arg Ala Ser Thr Leu Ala Ser Gly Val Pro Ser Arg Phe
        275                 280                 285

Ser Gly Ser Gly Ser Gly Thr Asp Phe Thr Leu Thr Ile Ser Ser Leu
    290                 295                 300

Gln Pro Glu Asp Phe Ala Thr Tyr Tyr Cys Gln Ser Ser Tyr Gly Asn
305                 310                 315                 320

Tyr Gly Asp Phe Gly Thr Gly Thr Lys Val Thr Val Leu Gly Gly Gly
                325                 330                 335

Gly Gly Ser Gly Gly Gly Gly Ser Gly Gly Gly Ser Gly Gly Gly
            340                 345                 350

Gly Ser Gln Val Gln Leu Gln Glu Ser Gly Pro Gly Leu Val Lys Pro
        355                 360                 365

Ser Glu Thr Leu Ser Leu Thr Cys Lys Val Ser Gly Phe Ser Phe Ser
    370                 375                 380

Asn Ser Tyr Trp Ile Cys Trp Ile Arg Gln Pro Pro Gly Lys Gly Leu
385                 390                 395                 400

Glu Trp Ile Gly Cys Thr Phe Val Gly Ser Ser Asp Ser Thr Tyr Tyr
                405                 410                 415

Ala Asn Trp Ala Lys Gly Arg Val Thr Ile Ser Val Asp Ser Ser Lys
            420                 425                 430

Asn Gln Phe Ser Leu Lys Leu Ser Ser Val Thr Ala Ala Asp Thr Ala
        435                 440                 445

Val Tyr Tyr Cys Ala Arg His Pro Ser Asp Ala Val Tyr Gly Tyr Ala
    450                 455                 460

Asn Asn Leu Trp Gly Gln Gly Thr Leu Val Thr Val Ser Ser
465                 470                 475

<210> SEQ ID NO 85
<211> LENGTH: 451
<212> TYPE: PRT
<213> ORGANISM: Artificial Sequence
<220> FEATURE:
<223> OTHER INFORMATION: sequence of recombinant antibody or functional
      part thereof

<400> SEQUENCE: 85

Gln Val Gln Leu Gln Glu Ser Gly Pro Gly Leu Val Lys Pro Ser Glu
1               5                   10                  15
```

```
Thr Leu Ser Leu Thr Cys Lys Val Ser Gly Phe Ser Phe Ser Ser Gly
            20                  25                  30

Tyr Asp Met Cys Trp Ile Arg Gln Pro Pro Gly Lys Gly Leu Glu Trp
            35                  40                  45

Ile Gly Cys Val Val Ala Gly Ser Val Asp Ile Thr Tyr Tyr Ala Ser
 50                  55                  60

Trp Ala Lys Gly Arg Val Thr Ile Ser Val Asp Ser Ser Lys Asn Gln
 65                  70                  75                  80

Phe Ser Leu Lys Leu Ser Ser Val Thr Ala Ala Asp Thr Ala Val Tyr
                85                  90                  95

Tyr Cys Ala Arg Lys Asp Ala Tyr Ser Asp Ala Phe Asn Leu Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
            210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

His Glu Ala Leu His Asn His Tyr Thr Gln Lys Ser Leu Ser Leu Ser
            435                 440                 445

Pro Gly Lys
    450

<210> SEQ ID NO 86
<211> LENGTH: 217
<212> TYPE: PRT
<213> ORGANISM: Artificial Sequence
<220> FEATURE:
<223> OTHER INFORMATION: sequence of recombinant antibody or functional
      part thereof

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 87
<211> LENGTH: 712
<212> TYPE: PRT
<213> ORGANISM: Artificial Sequence
<220> FEATURE:
<223> OTHER INFORMATION: sequence of recombinant antibody or functional
      part thereof

<400> SEQUENCE: 87

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30

Tyr Asp Met Cys Trp Ile Arg Gln Pro Pro Gly Lys Gly Leu Glu Trp
        35                  40                  45

```
Ile Gly Cys Val Val Ala Gly Ser Val Asp Ile Thr Tyr Ala Ser
     50              55                  60
Trp Ala Lys Gly Arg Val Thr Ile Ser Val Asp Ser Ser Lys Asn Gln
 65              70                  75                  80
Phe Ser Leu Lys Leu Ser Ser Val Thr Ala Ala Asp Thr Ala Val Tyr
                 85                  90                  95
Tyr Cys Ala Arg Lys Asp Ala Tyr Ser Asp Ala Phe Asn Leu Trp Gly
                100                 105                 110
Gln Gly Thr Leu Val Thr Val Ser Ala Ser Thr Lys Gly Pro Ser
                115                 120                 125
Val Phe Pro Leu Ala Pro Ser Ser Lys Ser Thr Ser Gly Gly Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Gln Thr Tyr Ile Cys Asn Val Asn His
                195                 200                 205
Lys Pro Ser Asn Thr Lys Val Asp Lys Arg Val Glu Pro Lys Ser Cys
210                 215                 220
Asp Lys Thr His Thr Cys Pro Pro Cys Pro Ala Pro Glu Ala Ala Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
                260                 265                 270
Glu Asp Pro Glu Val Lys Phe Asn Trp Tyr Val Asp Gly Val Glu Val
                275                 280                 285
His Asn Ala Lys Thr Lys Pro Arg Glu Glu Gln Tyr Asn Ser Thr Tyr
                290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Gly Ala Pro Ile
                325                 330                 335
Glu Lys Thr Ile Ser Lys Ala Lys Gly Gln Pro Arg Glu Pro Gln Val
                340                 345                 350
Tyr Thr Leu Pro Pro Ser Arg Glu Glu Met Thr Lys Asn Gln Val Ser
                355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
Pro Gly Lys Gly Gly Gly Gly Ser Gly Gly Gly Gly Ser Ile Gln Met
450                 455                 460
Thr Gln Ser Pro Ser Ser Leu Ser Ala Ser Val Gly Asp Arg Val Thr
```

```
                465                 470                 475                 480
        Ile Thr Cys Gln Ala Ser Gln Ser Ile Asn Asn Val Leu Ala Trp Tyr
                        485                 490                 495

Gln Gln Lys Pro Gly Lys Ala Pro Lys Leu Leu Ile Tyr Arg Ala Ser
                        500                 505                 510

Thr Leu Ala Ser Gly Val Pro Ser Arg Phe Ser Gly Ser Gly Ser Gly
                        515                 520                 525

Thr Asp Phe Thr Leu Thr Ile Ser Ser Leu Gln Pro Glu Asp Phe Ala
                        530                 535                 540

Thr Tyr Tyr Cys Gln Ser Ser Tyr Gly Asn Tyr Gly Asp Phe Gly Thr
        545                 550                 555                 560

Gly Thr Lys Val Thr Val Leu Gly Gly Gly Gly Ser Gly Gly Gly
                                565                 570                 575

Gly Ser Gly Gly Gly Ser Gly Gly Gly Ser Gln Val Gln Leu
                        580                 585                 590

Gln Glu Ser Gly Pro Gly Leu Val Lys Pro Ser Glu Thr Leu Ser Leu
                        595                 600                 605

Thr Cys Lys Val Ser Gly Phe Ser Phe Ser Asn Ser Tyr Trp Ile Cys
                        610                 615                 620

Trp Ile Arg Gln Pro Pro Gly Lys Gly Leu Glu Trp Ile Gly Cys Thr
        625                 630                 635                 640

Phe Val Gly Ser Ser Asp Ser Thr Tyr Tyr Ala Asn Trp Ala Lys Gly
                        645                 650                 655

Arg Val Thr Ile Ser Val Asp Ser Ser Lys Asn Gln Phe Ser Leu Lys
                        660                 665                 670

Leu Ser Ser Val Thr Ala Ala Asp Thr Ala Val Tyr Tyr Cys Ala Arg
                        675                 680                 685

His Pro Ser Asp Ala Val Tyr Gly Tyr Ala Asn Asn Leu Trp Gly Gln
                        690                 695                 700

Gly Thr Leu Val Thr Val Ser Ser
        705                 710

<210> SEQ ID NO 88
<211> LENGTH: 214
<212> TYPE: PRT
<213> ORGANISM: Artificial Sequence
<220> FEATURE:
<223> OTHER INFORMATION: sequence of recombinant antibody or functional
      part thereof

<400> SEQUENCE: 88

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Thr Gly Thr Lys Val Thr Val Leu Gly Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
    195                 200                 205

Phe Asn Arg Gly Glu Cys
    210
```

<210> SEQ ID NO 89
<211> LENGTH: 451
<212> TYPE: PRT
<213> ORGANISM: Artificial Sequence
<220> FEATURE:
<223> OTHER INFORMATION: sequence of recombinant antibody or functional
      part thereof

<400> SEQUENCE: 89

```
Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Asn Ser
            20                  25                  30

Tyr Trp Ile Cys Trp Ile Arg Gln Pro Pro Gly Lys Gly Leu Glu Trp
        35                  40                  45

Ile Gly Cys Thr Phe Val Gly Ser Ser Asp Ser Thr Tyr Tyr Ala Asn
    50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg His Pro Ser Asp Ala Val Tyr Gly Tyr Ala Asn Asn
            100                 105                 110

Leu Trp Gly Gln Gly Thr Leu Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser Gln
            260                 265                 270

Glu Asp Pro Glu Val Gln Phe Asn Trp Tyr Val Asp Val Glu Val
        275                 280                 285

His Asn Ala Lys Thr Lys Pro Arg Glu Glu Gln Phe Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450

<210> SEQ ID NO 90
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 90

Gly Phe Ser Phe Asn Ser Asp Tyr Trp Ile Tyr
1               5                   10

<210> SEQ ID NO 91
<211> LENGTH: 18
<212> TYPE: PRT
<213> ORGANISM: Artificial Sequence
<220> FEATURE:
<223> OTHER INFORMATION: sequence of recombinant antibody or functional
      part thereof

<400> SEQUENCE: 91

Ser Ile Tyr Gly Gly Ser Ser Gly Asn Thr Gln Tyr Ala Ser Trp Ala
1               5                   10                  15

Gln Gly

<210> SEQ ID NO 92
<211> LENGTH: 12
<212> TYPE: PRT
<213> ORGANISM: Artificial Sequence
<220> FEATURE:
<223> OTHER INFORMATION: sequence of recombinant antibody or functional
      part thereof
```

```
<400> SEQUENCE: 92

Arg Gly Tyr Val Asp Tyr Gly Gly Ala Thr Asp Leu
1               5                   10

<210> SEQ ID NO 93
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 93

Val Ser Gly Phe Ser Phe Asn Ser Asp Tyr Trp
1               5                   10

<210> SEQ ID NO 94
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 94

Ala Ser Gly Phe Ser Phe Asn Ser Asp Tyr Trp
1               5                   10

<210> SEQ ID NO 95
<211> LENGTH: 18
<212> TYPE: PRT
<213> ORGANISM: Artificial Sequence
<220> FEATURE:
<223> OTHER INFORMATION: sequence of recombinant antibody or functional
      part thereof

<400> SEQUENCE: 95

Ile Tyr Gly Gly Ser Ser Gly Asn Thr Gln Tyr Ala Ser Trp Ala Gln
1               5                   10                  15

Gly Arg

<210> SEQ ID NO 96
<211> LENGTH: 10
<212> TYPE: PRT
<213> ORGANISM: Artificial Sequence
<220> FEATURE:
<223> OTHER INFORMATION: sequence of recombinant antibody or functional
      part thereof

<400> SEQUENCE: 96

Gly Tyr Val Asp Tyr Gly Gly Ala Thr Asp
1               5                   10

<210> SEQ ID NO 97
<211> LENGTH: 6
<212> TYPE: PRT
<213> ORGANISM: Artificial Sequence
<220> FEATURE:
<223> OTHER INFORMATION: sequence of recombinant antibody or functional
      part thereof

<400> SEQUENCE: 97

Ser Asp Tyr Trp Ile Tyr
1               5

<210> SEQ ID NO 98
```

```
<211> LENGTH: 18
<212> TYPE: PRT
<213> ORGANISM: Artificial Sequence
<220> FEATURE:
<223> OTHER INFORMATION: sequence of recombinant antibody or functional
      part thereof

<400> SEQUENCE: 98

Ser Ile Tyr Gly Gly Ser Ser Gly Asn Thr Gln Tyr Ala Ser Trp Ala
1               5                   10                  15
Gln Gly

<210> SEQ ID NO 99
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 99

Gly Tyr Val Asp Tyr Gly Gly Ala Thr Asp Leu
1               5                   10

<210> SEQ ID NO 100
<211> LENGTH: 8
<212> TYPE: PRT
<213> ORGANISM: Artificial Sequence
<220> FEATURE:
<223> OTHER INFORMATION: sequence of recombinant antibody or functional
      part thereof

<400> SEQUENCE: 100

Gly Phe Ser Phe Asn Ser Asp Tyr
1               5

<210> SEQ ID NO 101
<211> LENGTH: 5
<212> TYPE: PRT
<213> ORGANISM: Artificial Sequence
<220> FEATURE:
<223> OTHER INFORMATION: sequence of recombinant antibody or functional
      part thereof

<400> SEQUENCE: 101

Gly Gly Ser Ser Gly
1               5

<210> SEQ ID NO 102
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 102

Tyr Val Asp Tyr Gly Gly Ala Thr Asp
1               5

<210> SEQ ID NO 103
<211> LENGTH: 122
<212> TYPE: PRT
<213> ORGANISM: Artificial Sequence
<220> FEATURE:
<223> OTHER INFORMATION: sequence of recombinant antibody or functional
      part thereof
```

<400> SEQUENCE: 103

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Asn Ser Asp
            20                  25                  30

Tyr Trp Ile Tyr Trp Ile Arg Gln Pro Pro Gly Lys Gly Leu Glu Trp
        35                  40                  45

Ile Gly Ser Ile Tyr Gly Gly Ser Ser Gly Asn Thr Gln Tyr Ala Ser
    50                  55                  60

Trp Ala Gln Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Gly Tyr Val Asp Tyr Gly Gly Ala Thr Asp Leu Trp
            100                 105                 110

Gly Gln Gly Thr Leu Val Thr Val Ser Ser
        115                 120

<210> SEQ ID NO 104
<211> LENGTH: 122
<212> TYPE: PRT
<213> ORGANISM: Artificial Sequence
<220> FEATURE:
<223> OTHER INFORMATION: sequence of recombinant antibody or functional
      part thereof

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Phe Ser Phe Asn Ser Asp
            20                  25                  30

Tyr Trp Ile Tyr Trp Val Arg Gln Ala Pro Gly Gln Gly Leu Glu Trp
        35                  40                  45

Met Gly Ser Ile Tyr Gly Gly Ser Ser Gly Asn Thr Gln Tyr Ala Ser
    50                  55                  60

Trp Ala Gln Gly Arg Val Thr Met Thr Arg Asp Thr Ser Ile Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Gly Tyr Val Asp Tyr Gly Gly Ala Thr Asp Leu Trp
            100                 105                 110

Gly Gln Gly Thr Leu Val Thr Val Ser Ser
        115                 120

<210> SEQ ID NO 105
<211> LENGTH: 122
<212> TYPE: PRT
<213> ORGANISM: Artificial Sequence
<220> FEATURE:
<223> OTHER INFORMATION: sequence of recombinant antibody or functional
      part thereof

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Asn Ser Asp
            20                  25                  30

Tyr Trp Ile Tyr Trp Val Arg Gln Ala Pro Gly Lys Gly Leu Glu Trp

```
                35                  40                  45
Ile Ala Ser Ile Tyr Gly Gly Ser Gly Asn Thr Gln Tyr Ala Ser
         50                  55                  60

Trp Ala Gln Gly Arg Phe Thr Ile Ser Arg Asp Asn Ser Lys Asn Thr
 65                  70                  75                  80

Val Tyr Leu Gln Met Asn Ser Leu Arg Ala Glu Asp Thr Ala Val Tyr
                 85                  90                  95

Phe Cys Ala Arg Gly Tyr Val Asp Tyr Gly Ala Thr Asp Leu Trp
            100                 105                 110

Gly Gln Gly Thr Leu Val Thr Val Ser Ser
        115                 120

<210> SEQ ID NO 106
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 106

Gln Ala Ser Gln Ser Ile Gly Thr Tyr Leu Ala
 1               5                  10

<210> SEQ ID NO 107
<211> LENGTH: 7
<212> TYPE: PRT
<213> ORGANISM: Artificial Sequence
<220> FEATURE:
<223> OTHER INFORMATION: sequence of recombinant antibody or functional
      part thereof

<400> SEQUENCE: 107

Arg Ala Phe Ile Leu Ala Ser
 1               5

<210> SEQ ID NO 108
<211> LENGTH: 15
<212> TYPE: PRT
<213> ORGANISM: Artificial Sequence
<220> FEATURE:
<223> OTHER INFORMATION: sequence of recombinant antibody or functional
      part thereof

<400> SEQUENCE: 108

Gln Ser Asn Phe Tyr Ser Asp Ser Thr Thr Ile Gly Pro Asn Ala
 1               5                  10                  15

<210> SEQ ID NO 109
<211> LENGTH: 8
<212> TYPE: PRT
<213> ORGANISM: Artificial Sequence
<220> FEATURE:
<223> OTHER INFORMATION: sequence of recombinant antibody or functional
      part thereof

<400> SEQUENCE: 109

Ala Ser Gln Ser Ile Gly Thr Tyr
 1               5

<210> SEQ ID NO 110
<211> LENGTH: 12
<212> TYPE: PRT
<213> ORGANISM: Artificial Sequence
<220> FEATURE:
```

<223> OTHER INFORMATION: sequence of recombinant antibody or functional
     part thereof

<400> SEQUENCE: 110

Arg Ala Phe Ile Leu Ala Ser Gly Val Pro Ser Arg
1               5                   10

<210> SEQ ID NO 111
<211> LENGTH: 12
<212> TYPE: PRT
<213> ORGANISM: Artificial Sequence
<220> FEATURE:
<223> OTHER INFORMATION: sequence of recombinant antibody or functional
     part thereof

<400> SEQUENCE: 111

Asn Phe Tyr Ser Asp Ser Thr Thr Ile Gly Pro Asn
1               5                   10

<210> SEQ ID NO 112
<211> LENGTH: 7
<212> TYPE: PRT
<213> ORGANISM: Artificial Sequence
<220> FEATURE:
<223> OTHER INFORMATION: sequence of recombinant antibody or functional
     part thereof

<400> SEQUENCE: 112

Ser Gln Ser Ile Gly Thr Tyr
1               5

<210> SEQ ID NO 113
<211> LENGTH: 3
<212> TYPE: PRT
<213> ORGANISM: Artificial Sequence
<220> FEATURE:
<223> OTHER INFORMATION: sequence of recombinant antibody or functional
     part thereof

<400> SEQUENCE: 113

Arg Ala Phe
1

<210> SEQ ID NO 114
<211> LENGTH: 12
<212> TYPE: PRT
<213> ORGANISM: Artificial Sequence
<220> FEATURE:
<223> OTHER INFORMATION: sequence of recombinant antibody or functional
     part thereof

<400> SEQUENCE: 114

Asn Phe Tyr Ser Asp Ser Thr Thr Ile Gly Pro Asn
1               5                   10

<210> SEQ ID NO 115
<211> LENGTH: 114
<212> TYPE: PRT
<213> ORGANISM: Artificial Sequence
<220> FEATURE:
<223> OTHER INFORMATION: sequence of recombinant antibody or functional
     part thereof

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Thr Tyr

```
                20                  25                  30
Leu Ala Trp Tyr Gln Gln Lys Pro Gly Lys Ala Pro Lys Leu Leu Ile
            35                  40                  45

Tyr Arg Ala Phe Ile Leu Ala Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly

<210> SEQ ID NO 116
<211> LENGTH: 114
<212> TYPE: PRT
<213> ORGANISM: Artificial Sequence
<220> FEATURE:
<223> OTHER INFORMATION: sequence of recombinant antibody or functional
      part thereof

<400> SEQUENCE: 116

Asp Ile Gln Met Thr Gln Ser Pro Ala Ser Leu Ser Ala Ser Val Gly
 1               5                  10                  15

Asp Arg Val Thr Ile Thr Cys Gln Ala Ser Gln Ser Ile Gly Thr Tyr
                20                  25                  30

Leu Ala Trp Tyr Gln Gln Lys Pro Gly Lys Pro Pro Lys Leu Leu Ile
            35                  40                  45

Tyr Arg Ala Phe Ile Leu Ala Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly

<210> SEQ ID NO 117
<211> LENGTH: 20
<212> TYPE: PRT
<213> ORGANISM: Artificial Sequence
<220> FEATURE:
<223> OTHER INFORMATION: sequence of recombinant antibody or functional
      part thereof

<400> SEQUENCE: 117

Gly Gly Gly Gly Ser Gly Gly Gly Ser Gly Gly Gly Gly Ser Gly
 1               5                  10                  15

Gly Gly Gly Ser
            20

<210> SEQ ID NO 118
<211> LENGTH: 256
<212> TYPE: PRT
<213> ORGANISM: Artificial Sequence
<220> FEATURE:
<223> OTHER INFORMATION: sequence of recombinant antibody or functional
      part thereof
```

-continued

```
<400> SEQUENCE: 118

Asp Ile Gln Met Thr Gln Ser Pro Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Ala Pro Lys Leu Leu Ile
        35                  40                  45

Tyr Arg Ala Phe Ile Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

Leu Gly Gly Gly Gly Ser Gly Gly Gly Ser Gly Gly Gly Gly
        115                 120                 125

Ser Gly Gly Gly Ser Gln Val Gln Leu Gln Glu Ser Gly Pro Gly
    130                 135                 140

Leu Val Lys Pro Ser Glu Thr Leu Ser Leu Thr Cys Lys Val Ser Gly
145                 150                 155                 160

Phe Ser Phe Asn Ser Asp Tyr Trp Ile Tyr Trp Ile Arg Gln Pro Pro
                165                 170                 175

Gly Lys Gly Leu Glu Trp Ile Gly Ser Ile Tyr Gly Ser Ser Gly
            180                 185                 190

Asn Thr Gln Tyr Ala Ser Trp Ala Gln Gly Arg Val Thr Ile Ser Val
        195                 200                 205

Asp Ser Ser Lys Asn Gln Phe Ser Leu Lys Leu Ser Ser Val Thr Ala
    210                 215                 220

Ala Asp Thr Ala Val Tyr Tyr Cys Ala Arg Gly Tyr Val Asp Tyr Gly
225                 230                 235                 240

Gly Ala Thr Asp Leu Trp Gly Gln Gly Thr Leu Val Thr Val Ser Ser
                245                 250                 255

<210> SEQ ID NO 119
<211> LENGTH: 256
<212> TYPE: PRT
<213> ORGANISM: Artificial Sequence
<220> FEATURE:
<223> OTHER INFORMATION: sequence of recombinant antibody or functional
      part thereof

<400> SEQUENCE: 119

Asp Ile Gln Met Thr Gln Ser Pro Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Ala Pro Lys Leu Leu Ile
        35                  40                  45

Tyr Arg Ala Phe Ile Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95
```

Thr Thr Ile Gly Pro Asn Ala Phe Gly Thr Gly Lys Val Thr Val
            100                 105                 110

Leu Gly Gly Gly Gly Ser Gly Gly Gly Ser Gly Gly Gly Gly
        115                 120                 125

Ser Gly Gly Gly Ser Gln Val Gln Leu Val Gln Ser Gly Ala Glu
    130                 135                 140

Val Lys Lys Pro Gly Ala Ser Val Lys Val Ser Cys Lys Ala Ser Gly
145                 150                 155                 160

Phe Ser Phe Asn Ser Asp Tyr Trp Ile Tyr Trp Val Arg Gln Ala Pro
                165                 170                 175

Gly Gln Gly Leu Glu Trp Met Gly Ser Ile Tyr Gly Gly Ser Ser Gly
        180                 185                 190

Asn Thr Gln Tyr Ala Ser Trp Ala Gln Gly Arg Val Thr Met Thr Arg
    195                 200                 205

Asp Thr Ser Ile Ser Thr Ala Tyr Met Glu Leu Ser Ser Leu Arg Ser
210                 215                 220

Glu Asp Thr Ala Val Tyr Tyr Cys Ala Arg Gly Tyr Val Asp Tyr Gly
225                 230                 235                 240

Gly Ala Thr Asp Leu Trp Gly Gln Gly Thr Leu Val Thr Val Ser Ser
            245                 250                 255

<210> SEQ ID NO 120
<211> LENGTH: 256
<212> TYPE: PRT
<213> ORGANISM: Artificial Sequence
<220> FEATURE:
<223> OTHER INFORMATION: sequence of recombinant antibody or functional
      part thereof

<400> SEQUENCE: 120

Asp Ile Gln Met Thr Gln Ser Pro Ala Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Pro Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Lys Val Thr Val
            100                 105                 110

Leu Gly Gly Gly Gly Ser Gly Gly Gly Ser Gly Gly Gly Gly
        115                 120                 125

Ser Gly Gly Gly Ser Glu Val Gln Leu Val Glu Ser Gly Gly
    130                 135                 140

Leu Val Gln Pro Gly Gly Ser Leu Arg Leu Ser Cys Ala Ala Ser Gly
145                 150                 155                 160

Phe Ser Phe Asn Ser Asp Tyr Trp Ile Tyr Trp Val Arg Gln Ala Pro
                165                 170                 175

Gly Lys Gly Leu Glu Trp Ile Ala Ser Ile Tyr Gly Gly Ser Ser Gly
        180                 185                 190

Asn Thr Gln Tyr Ala Ser Trp Ala Gln Gly Arg Phe Thr Ile Ser Arg
    195                 200                 205

```
Asp Asn Ser Lys Asn Thr Val Tyr Leu Gln Met Asn Ser Leu Arg Ala
        210                 215                 220

Glu Asp Thr Ala Val Tyr Phe Cys Ala Arg Gly Tyr Val Asp Tyr Gly
225                 230                 235                 240

Gly Ala Thr Asp Leu Trp Gly Gln Gly Thr Leu Val Thr Val Ser Ser
                245                 250                 255

<210> SEQ ID NO 121
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 121

Gly Phe Ser Phe Ser Ser Gly Tyr Asp Met Cys
1               5                   10

<210> SEQ ID NO 122
<211> LENGTH: 18
<212> TYPE: PRT
<213> ORGANISM: Artificial Sequence
<220> FEATURE:
<223> OTHER INFORMATION: sequence of recombinant antibody or functional
      part thereof

<400> SEQUENCE: 122

Cys Val Val Ala Gly Ser Val Asp Ile Thr Tyr Tyr Ala Ser Trp Ala
1               5                   10                  15

Lys Gly

<210> SEQ ID NO 123
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 123

Arg Lys Asp Ala Tyr Ser Asp Ala Phe Asn Leu
1               5                   10

<210> SEQ ID NO 124
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 124

Val Ser Gly Phe Ser Phe Ser Ser Gly Tyr Asp
1               5                   10

<210> SEQ ID NO 125
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 125
```

```
Ala Ser Gly Phe Ser Phe Ser Ser Gly Tyr Asp
1               5                   10
```

<210> SEQ ID NO 126
<211> LENGTH: 18
<212> TYPE: PRT
<213> ORGANISM: Artificial Sequence
<220> FEATURE:
<223> OTHER INFORMATION: sequence of recombinant antibody or functional
      part thereof

<400> SEQUENCE: 126

```
Val Val Ala Gly Ser Val Asp Ile Thr Tyr Tyr Ala Ser Trp Ala Lys
1               5                   10                  15

Gly Arg
```

<210> SEQ ID NO 127
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 127

```
Lys Asp Ala Tyr Ser Asp Ala Phe Asn
1               5
```

<210> SEQ ID NO 128
<211> LENGTH: 6
<212> TYPE: PRT
<213> ORGANISM: Artificial Sequence
<220> FEATURE:
<223> OTHER INFORMATION: sequence of recombinant antibody or functional
      part thereof

<400> SEQUENCE: 128

```
Ser Gly Tyr Asp Met Cys
1               5
```

<210> SEQ ID NO 129
<211> LENGTH: 18
<212> TYPE: PRT
<213> ORGANISM: Artificial Sequence
<220> FEATURE:
<223> OTHER INFORMATION: sequence of recombinant antibody or functional
      part thereof

<400> SEQUENCE: 129

```
Cys Val Val Ala Gly Ser Val Asp Ile Thr Tyr Tyr Ala Ser Trp Ala
1               5                   10                  15

Lys Gly
```

<210> SEQ ID NO 130
<211> LENGTH: 10
<212> TYPE: PRT
<213> ORGANISM: Artificial Sequence
<220> FEATURE:
<223> OTHER INFORMATION: sequence of recombinant antibody or functional
      part thereof

<400> SEQUENCE: 130

```
Lys Asp Ala Tyr Ser Asp Ala Phe Asn Leu
1               5                   10
```

<210> SEQ ID NO 131

```
<211> LENGTH: 8
<212> TYPE: PRT
<213> ORGANISM: Artificial Sequence
<220> FEATURE:
<223> OTHER INFORMATION: sequence of recombinant antibody or functional
      part thereof

<400> SEQUENCE: 131

Gly Phe Ser Phe Ser Ser Gly Tyr
1               5

<210> SEQ ID NO 132
<211> LENGTH: 5
<212> TYPE: PRT
<213> ORGANISM: Artificial Sequence
<220> FEATURE:
<223> OTHER INFORMATION: sequence of recombinant antibody or functional
      part thereof

<400> SEQUENCE: 132

Ala Gly Ser Val Asp
1               5

<210> SEQ ID NO 133
<211> LENGTH: 8
<212> TYPE: PRT
<213> ORGANISM: Artificial Sequence
<220> FEATURE:
<223> OTHER INFORMATION: sequence of recombinant antibody or functional
      part thereof

<400> SEQUENCE: 133

Asp Ala Tyr Ser Asp Ala Phe Asn
1               5

<210> SEQ ID NO 134
<211> LENGTH: 121
<212> TYPE: PRT
<213> ORGANISM: Artificial Sequence
<220> FEATURE:
<223> OTHER INFORMATION: sequence of recombinant antibody or functional
      part thereof

<400> SEQUENCE: 134

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30

Tyr Asp Met Cys Trp Ile Arg Gln Pro Pro Gly Lys Gly Leu Glu Trp
        35                  40                  45

Ile Gly Cys Val Val Ala Gly Ser Val Asp Ile Thr Tyr Tyr Ala Ser
    50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Lys Asp Ala Tyr Ser Asp Ala Phe Asn Leu Trp Gly
            100                 105                 110

Gln Gly Thr Leu Val Thr Val Ser Ser
        115                 120

<210> SEQ ID NO 135
<211> LENGTH: 121
<212> TYPE: PRT
```

```
<213> ORGANISM: Artificial Sequence
<220> FEATURE:
<223> OTHER INFORMATION: sequence of recombinant antibody or functional
      part thereof

<400> SEQUENCE: 135

Gln Ser Gln Leu Gln Glu Ser Gly Pro Gly Leu Val Lys Pro Ser Glu
1               5                   10                  15

Thr Leu Ser Leu Thr Cys Lys Ala Ser Gly Phe Ser Phe Ser Ser Gly
            20                  25                  30

Tyr Asp Met Cys Trp Val Arg Gln Pro Pro Gly Lys Gly Leu Glu Trp
        35                  40                  45

Ile Ala Cys Val Val Ala Gly Ser Val Asp Ile Thr Tyr Tyr Ala Ser
    50                  55                  60

Trp Ala Lys Gly Arg Val Thr Ile Ser Lys Asp Ser Lys Asn Gln
65                  70                  75                  80

Val Ser Leu Lys Leu Ser Ser Val Thr Ala Ala Asp Thr Ala Val Tyr
                85                  90                  95

Phe Cys Ala Arg Lys Asp Ala Tyr Ser Asp Ala Phe Asn Leu Trp Gly
            100                 105                 110

Gln Gly Thr Leu Val Thr Val Ser Ser
        115                 120

<210> SEQ ID NO 136
<211> LENGTH: 121
<212> TYPE: PRT
<213> ORGANISM: Artificial Sequence
<220> FEATURE:
<223> OTHER INFORMATION: sequence of recombinant antibody or functional
      part thereof

<400> SEQUENCE: 136

Gln Val Gln Leu Gln Glu Ser Gly Pro Gly Leu Val Lys Pro Ser Glu
1               5                   10                  15

Thr Leu Ser Leu Thr Cys Lys Ala Ser Gly Phe Ser Phe Ser Ser Gly
            20                  25                  30

Tyr Asp Met Cys Trp Val Arg Gln Pro Pro Gly Lys Gly Leu Glu Trp
        35                  40                  45

Ile Ala Cys Val Val Ala Gly Ser Val Asp Ile Thr Tyr Tyr Ala Ser
    50                  55                  60

Trp Ala Lys Gly Arg Val Thr Ile Ser Lys Asp Ser Lys Asn Gln
65                  70                  75                  80

Val Ser Leu Lys Leu Ser Ser Val Thr Ala Ala Asp Thr Ala Val Tyr
                85                  90                  95

Tyr Cys Ala Arg Lys Asp Ala Tyr Ser Asp Ala Phe Asn Leu Trp Gly
            100                 105                 110

Gln Gly Thr Leu Val Thr Val Ser Ser
        115                 120

<210> SEQ ID NO 137
<211> LENGTH: 11
<212> TYPE: PRT
<213> ORGANISM: Artificial Sequence
<220> FEATURE:
<223> OTHER INFORMATION: sequence of recombinant antibody or functional
      part thereof

<400> SEQUENCE: 137

Gln Ala Ser Gln Ser Ile Asn Asp Tyr Leu Ala
1               5                   10
```

<210> SEQ ID NO 138
<211> LENGTH: 7
<212> TYPE: PRT
<213> ORGANISM: Artificial Sequence
<220> FEATURE:
<223> OTHER INFORMATION: sequence of recombinant antibody or functional
      part thereof

<400> SEQUENCE: 138

Lys Ala Ser Thr Leu Ala Ser
1               5

<210> SEQ ID NO 139
<211> LENGTH: 12
<212> TYPE: PRT
<213> ORGANISM: Artificial Sequence
<220> FEATURE:
<223> OTHER INFORMATION: sequence of recombinant antibody or functional
      part thereof

<400> SEQUENCE: 139

Gln Gln Gly Tyr Ile Ile Thr Asp Ile Asp Asn Val
1               5                   10

<210> SEQ ID NO 140
<211> LENGTH: 8
<212> TYPE: PRT
<213> ORGANISM: Artificial Sequence
<220> FEATURE:
<223> OTHER INFORMATION: sequence of recombinant antibody or functional
      part thereof

<400> SEQUENCE: 140

Ala Ser Gln Ser Ile Asn Asp Tyr
1               5

<210> SEQ ID NO 141
<211> LENGTH: 12
<212> TYPE: PRT
<213> ORGANISM: Artificial Sequence
<220> FEATURE:
<223> OTHER INFORMATION: sequence of recombinant antibody or functional
      part thereof

<400> SEQUENCE: 141

Lys Ala Ser Thr Leu Ala Ser Gly Val Pro Ser Arg
1               5                   10

<210> SEQ ID NO 142
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 142

Gly Tyr Ile Ile Thr Asp Ile Asp Asn
1               5

<210> SEQ ID NO 143
<211> LENGTH: 7
<212> TYPE: PRT
<213> ORGANISM: Artificial Sequence
<220> FEATURE:
<223> OTHER INFORMATION: sequence of recombinant antibody or functional
      part thereof

```
<400> SEQUENCE: 143

Ser Gln Ser Ile Asn Asp Tyr
1               5

<210> SEQ ID NO 144
<211> LENGTH: 3
<212> TYPE: PRT
<213> ORGANISM: Artificial Sequence
<220> FEATURE:
<223> OTHER INFORMATION: sequence of recombinant antibody or functional
      part thereof

<400> SEQUENCE: 144

Lys Ala Ser
1

<210> SEQ ID NO 145
<211> LENGTH: 9
<212> TYPE: PRT
<213> ORGANISM: Artificial Sequence
<220> FEATURE:
<223> OTHER INFORMATION: sequence of recombinant antibody or functional
      part thereof

<400> SEQUENCE: 145

Gly Tyr Ile Ile Thr Asp Ile Asp Asn
1               5

<210> SEQ ID NO 146
<211> LENGTH: 111
<212> TYPE: PRT
<213> ORGANISM: Artificial Sequence
<220> FEATURE:
<223> OTHER INFORMATION: sequence of recombinant antibody or functional
      part thereof

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly
            100                 105                 110

<210> SEQ ID NO 147
<211> LENGTH: 111
<212> TYPE: PRT
<213> ORGANISM: Artificial Sequence
<220> FEATURE:
<223> OTHER INFORMATION: sequence of recombinant antibody or functional
      part thereof

<400> SEQUENCE: 147

Asp Phe Gln Leu Thr Gln Ser Pro Ser Ser Leu Ser Ala Ser Val Gly
1               5                   10                  15
```

```
Asp Arg Val Thr Ile Thr Cys Gln Ala Ser Gln Ser Ile Asn Asp Tyr
                20                  25                  30

Leu Ala Trp Tyr Gln Gln Lys Pro Gly Lys Ser Pro Lys Leu Leu Ile
            35                  40                  45

Tyr Lys Ala Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Ile Ile Thr Asp
                 85                  90                  95

Ile Asp Asn Val Phe Gly Thr Gly Thr Lys Val Thr Val Leu Gly
                100                 105                 110

<210> SEQ ID NO 148
<211> LENGTH: 20
<212> TYPE: PRT
<213> ORGANISM: Artificial Sequence
<220> FEATURE:
<223> OTHER INFORMATION: sequence of recombinant antibody or functional
      part thereof

<400> SEQUENCE: 148

Gly Gly Gly Gly Ser Gly Gly Gly Ser Gly Gly Gly Gly Ser Gly
1               5                   10                  15

Gly Gly Gly Ser
            20

<210> SEQ ID NO 149
<211> LENGTH: 252
<212> TYPE: PRT
<213> ORGANISM: Artificial Sequence
<220> FEATURE:
<223> OTHER INFORMATION: sequence of recombinant antibody or functional
      part thereof

<400> SEQUENCE: 149

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
                20                  25                  30

Leu Ala Trp Tyr Gln Gln Lys Pro Gly Lys Ala Pro Lys Leu Leu Ile
            35                  40                  45

Tyr Lys Ala Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Ile Ile Thr Asp
                 85                  90                  95

Ile Asp Asn Val Phe Gly Thr Gly Thr Lys Val Thr Val Leu Gly Gly
                100                 105                 110

Gly Gly Gly Ser Gly Gly Gly Gly Ser Gly Gly Gly Gly Ser Gly Gly
            115                 120                 125

Gly Gly Ser Gln Val Gln Leu Gln Glu Ser Gly Pro Gly Leu Val Lys
        130                 135                 140

Pro Ser Glu Thr Leu Ser Leu Thr Cys Lys Val Ser Gly Phe Ser Phe
145                 150                 155                 160

Ser Ser Gly Tyr Asp Met Cys Trp Ile Arg Gln Pro Pro Gly Lys Gly
                165                 170                 175
```

-continued

Leu Glu Trp Ile Gly Cys Val Ala Gly Ser Val Asp Ile Thr Tyr
            180                 185                 190

Tyr Ala Ser Trp Ala Lys Gly Arg Val Thr Ile Ser Val Asp Ser Ser
        195                 200                 205

Lys Asn Gln Phe Ser Leu Lys Leu Ser Ser Val Thr Ala Ala Asp Thr
    210                 215                 220

Ala Val Tyr Tyr Cys Ala Arg Lys Asp Ala Tyr Ser Asp Ala Phe Asn
225                 230                 235                 240

Leu Trp Gly Gln Gly Thr Leu Val Thr Val Ser Ser
                245                 250

<210> SEQ ID NO 150
<211> LENGTH: 252
<212> TYPE: PRT
<213> ORGANISM: Artificial Sequence
<220> FEATURE:
<223> OTHER INFORMATION: sequence of recombinant antibody or functional
      part thereof

<400> SEQUENCE: 150

Asp Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ser Pro Lys Leu Leu Ile
        35                  40                  45

Tyr Lys Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Gln Ser Gln Leu Gln Glu Ser Gly Pro Gly Leu Val Lys
130                 135                 140

Pro Ser Glu Thr Leu Ser Leu Thr Cys Lys Ala Ser Gly Phe Ser Phe
145                 150                 155                 160

Ser Ser Gly Tyr Asp Met Cys Trp Val Arg Gln Pro Pro Gly Lys Gly
                165                 170                 175

Leu Glu Trp Ile Ala Cys Val Val Ala Gly Ser Val Asp Ile Thr Tyr
            180                 185                 190

Tyr Ala Ser Trp Ala Lys Gly Arg Val Thr Ile Ser Lys Asp Ser Ser
        195                 200                 205

Lys Asn Gln Val Ser Leu Lys Leu Ser Ser Val Thr Ala Ala Asp Thr
    210                 215                 220

Ala Val Tyr Phe Cys Ala Arg Lys Asp Ala Tyr Ser Asp Ala Phe Asn
225                 230                 235                 240

Leu Trp Gly Gln Gly Thr Leu Val Thr Val Ser Ser
                245                 250

<210> SEQ ID NO 151
<211> LENGTH: 252
<212> TYPE: PRT

<213> ORGANISM: Artificial Sequence
<220> FEATURE:
<223> OTHER INFORMATION: sequence of recombinant antibody or functional part thereof

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gly Gly Gly Ser Gly Gly Gly Ser Gly Gly
                115                 120                 125

Gly Gly Ser Gln Val Gln Leu Gln Glu Ser Gly Pro Gly Leu Val Lys
130                 135                 140

Pro Ser Glu Thr Leu Ser Leu Thr Cys Lys Ala Ser Gly Phe Ser Phe
145                 150                 155                 160

Ser Ser Gly Tyr Asp Met Cys Trp Val Arg Gln Pro Pro Gly Lys Gly
                165                 170                 175

Leu Glu Trp Ile Ala Cys Val Val Ala Gly Ser Val Asp Ile Thr Tyr
            180                 185                 190

Tyr Ala Ser Trp Ala Lys Gly Arg Val Thr Ile Ser Lys Asp Ser Ser
        195                 200                 205

Lys Asn Gln Val Ser Leu Lys Leu Ser Ser Val Thr Ala Ala Asp Thr
210                 215                 220

Ala Val Tyr Tyr Cys Ala Arg Lys Asp Ala Tyr Ser Asp Ala Phe Asn
225                 230                 235                 240

Leu Trp Gly Gln Gly Thr Leu Val Thr Val Ser Ser
            245                 250

<210> SEQ ID NO 152
<211> LENGTH: 217
<212> TYPE: PRT
<213> ORGANISM: Artificial Sequence
<220> FEATURE:
<223> OTHER INFORMATION: sequence of recombinant antibody or functional part thereof

<400> SEQUENCE: 152

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Gly Tyr Ile Ile Thr Asp
                    85                  90                  95

Ile Asp Asn Val Phe Gly Thr Gly Thr Lys Val Thr Val Leu Gly Thr
                100                 105                 110

Val Ala Ala Pro Ser Val Phe Ile Phe Pro Pro Ser Asp Glu Gln Leu
                115                 120                 125

Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
                195                 200                 205

Thr Lys Ser Phe Asn Arg Gly Glu Cys
    210                 215

<210> SEQ ID NO 153
<211> LENGTH: 451
<212> TYPE: PRT
<213> ORGANISM: Artificial Sequence
<220> FEATURE:
<223> OTHER INFORMATION: sequence of recombinant antibody or functional
      part thereof

<400> SEQUENCE: 153

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
                20                  25                  30

Tyr Asp Met Cys Trp Ile Arg Gln Pro Pro Gly Lys Gly Leu Glu Trp
            35                  40                  45

Ile Gly Cys Val Val Ala Gly Ser Val Asp Ile Thr Tyr Tyr Ala Ser
        50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Lys Asp Ala Tyr Ser Asp Ala Phe Asn Leu Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205
```

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 154
<211> LENGTH: 220
<212> TYPE: PRT
<213> ORGANISM: Artificial Sequence
<220> FEATURE:
<223> OTHER INFORMATION: sequence of recombinant antibody or functional
      part thereof

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Gly Thr Tyr
            20                  25                  30

Leu Ala Trp Tyr Gln Gln Lys Pro Gly Lys Ala Pro Lys Leu Leu Ile
        35                  40                  45

Tyr Arg Ala Phe Ile Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Asn Phe Tyr Ser Asp Ser
                85                  90                  95

Thr Thr Ile Gly Pro Asn Ala Phe Gly Thr Gly Thr Lys Val Thr Val
            100                 105                 110

```
Leu Gly Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
        210                 215                 220

<210> SEQ ID NO 155
<211> LENGTH: 452
<212> TYPE: PRT
<213> ORGANISM: Artificial Sequence
<220> FEATURE:
<223> OTHER INFORMATION: sequence of recombinant antibody or functional
      part thereof

<400> SEQUENCE: 155

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Asn Ser Asp
            20                  25                  30

Tyr Trp Ile Tyr Trp Ile Arg Gln Pro Pro Gly Lys Gly Leu Glu Trp
        35                  40                  45

Ile Gly Ser Ile Tyr Gly Gly Ser Ser Gly Asn Thr Gln Tyr Ala Ser
    50                  55                  60

Trp Ala Gln Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Gly Tyr Val Asp Tyr Gly Gly Ala Thr Asp Leu Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
```

```
                245                 250                 255
Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 156
<211> LENGTH: 5
<212> TYPE: PRT
<213> ORGANISM: Artificial sequence
<220> FEATURE:
<223> OTHER INFORMATION: artificial linker sequence
<220> FEATURE:
<221> NAME/KEY: Repeat
<222> LOCATION: (1)..(5)
<223> OTHER INFORMATION: (GGGGS)n with n being 1 or 2, preferably 1

<400> SEQUENCE: 156

Gly Gly Gly Gly Ser
1               5

<210> SEQ ID NO 157
<211> LENGTH: 5
<212> TYPE: PRT
<213> ORGANISM: Artificial sequence
<220> FEATURE:
<223> OTHER INFORMATION: artificial linker sequence
<220> FEATURE:
<221> NAME/KEY: repeat
<222> LOCATION: (1)..(5)
<223> OTHER INFORMATION: (GGGGS)n with n being 1, 2, 3, 4, 5, 6, 7, or
      8, preferably 4

<400> SEQUENCE: 157

Gly Gly Gly Gly Ser
1               5

<210> SEQ ID NO 158
<211> LENGTH: 5
```

```
<212> TYPE: PRT
<213> ORGANISM: Artificial sequence
<220> FEATURE:
<223> OTHER INFORMATION: artificial linker sequence
<220> FEATURE:
<221> NAME/KEY: repeat
<222> LOCATION: (1)..(5)
<223> OTHER INFORMATION: (GGGGS)n with n being 1, 2, 3, 4, 5, 6, 7, or
      8, preferably 2

<400> SEQUENCE: 158

Gly Gly Gly Gly Ser
1               5
```

ANTIBODIES TARGETING CD137 AND METHODS OF USE THEREOF

CROSS-REFERENCE TO RELATED APPLICATIONS

This application is a 371 National Phase of International Patent Application No. PCT/EP2018/077514 filed on Oct. 9, 2018, which claims priority to EP 17195780.6 filed on Oct. 10, 2017, EP 18167092.8 filed on Apr. 12, 2018 and EP 18180815.5 filed on Jun. 29, 2018

INCORPORATION OF SEQUENCE LISTING

This application contains a sequence listing submitted electronically via EFS-web, which serves as both the paper copy and the computer readable form (CRF) and consists of a file entitled "WRN16NP_seqlist v2.txt", which was created on Dec. 21, 2021, which is 183,795 bytes in size, and which is herein incorporated by reference in its entirety.

FIELD OF THE INVENTION

The present invention relates to an isolated antibody which specifically binds human CD137, and pharmaceutical compositions and methods of use thereof. The present invention further relates to a nucleic acid encoding said antibody, a vector comprising said nucleic acid, a host cell comprising said nucleic acid or said vector, and a method of producing said antibody.

BACKGROUND OF THE INVENTION

The tumor necrosis factor receptor superfamily (TNFRSF) is a protein superfamily of receptors characterized by their ability to bind tumor necrosis factors (TNFs) via cysteine-rich pseudorepeats in the extracellular domain (Locksley et al., 2001, Cell. 104: 487-501). At present, 27 TNF family members have been identified. TNFRSF members and their ligands are expressed mostly on immune cells, where they are playing a role of immunomodulators in T-cell-mediated immune responses. TNFRSF members play a role in enhancement of dendritic cell survival and priming capacity of T cells, optimal generation of effector T cells, optimal antibody responses, and amplification of inflammatory reactions.

CD137 (4-1BB, TNF-receptor superfamily 9, TNFRSF9) is a surface glycoprotein of the TNFR superfamily. It is an inducible costimulatory T cell receptor. CD137 expression is activation-dependent, and encompasses a broad subset of immune cells including activated NK and NKT cells, regulatory T cells, dendritic cells (DC) including follicular DC, stimulated mast cells, differentiating myeloid cells, monocytes, neutrophils, eosinophils (Wang et al, Immunol Rev. 229(1): 192-215 (2009)), and activated B cells (Zhang et al, J Immunol. 184(2):787-795 (2010)). In addition, CD137 expression has also been demonstrated on tumor vasculature (Broil K et al., Am J Clin Pathol. 115(4):543-549 (2001); Seaman et al, Cancer Cell 11(6):539-554 (2007)) and atherosclerotic endothelium (Olofsson et al, Circulation 117 (10): 1292 1301 (2008)).

CD137-Ligand (CD137L, 4-1BBL or tnfsf9), a molecule of the TNF family, is an intercellular natural ligand known for CD137 (Alderson, M. R., et al., Eur. J. Immunol. 24:2219-2227 (1994); Pollok K., et al., Eur. J. Immunol. 24:367-374 (1994); Goodwin, R. G., et al., Eur. J. Immunol. 23: 2631-2641 (1993)). The ligand for CD137 forms a homotrimer, and the signaling via CD137 proceeds from ligated molecules at the cell surface, which become cross-linked by trimerized ligand (Won, E. Y., et al., J. Biol. Chem. 285: 9202-9210 (2010)). The higher order clustering of CD137 was suggested to be necessary for mediating the signaling. CD137 associates with the adaptors TRAF-2 and TRAF-1 in its cytoplasmic tail, resulting in coimmunoprecipitation, which is enhanced upon CD137 activation in T cells (Saoulli, K., et al., J. Exp. Med. 187: 1849-1862 (1998); Sabbagh, L., et al., J. Immunol. 180: 8093-8101 (2008)). Recruitment of TRAF-1 and TRAF-2 by CD137 results in downstream activation of NFkB and the Mitogen Activated Protein (MAP) Kinase cascade including ERK, JNK, and p38 MAP kinases. NFkB activation leads to upregulation of Bfl-1 and Bcl-XL, pro-survival members of the Bcl-2 family. The pro-apoptotic protein Bim is downregulated in a TRAF-1 and ERK dependent manner (Sabbagh et al., J Immunol. 180(12):8093-8101 (2008)). It has been suggested that the main action of CD137 is to place two or more TRAF-2 molecules in close molecular proximity to each other (Sanchez-Paulete, A. R., et al., Eur. J. Immunology 46(3): 513-522 (2016)). Based on this it was postulated that the major factor driving CD137 signaling is the relative density of TRAF-2-assembled CD137 moieties in micropatches of plasma membrane (Sanchez-Paulete, A. R., et al., Eur. J. Immunology 46(3): 513-522 (2016)). Overall, CD137 signaling is fostered by multimerization, and it was proposed that cross-linking CD137 molecules is the key factor in CD137 co-stimulatory activity.

CD137 co-stimulates T cells to carry out effector functions such as eradication of established tumors, broadening primary $CD8^+$ T cell responses, and enhancing the memory pool of antigen-specific $CD8^+$ T cells, induction of interferon-gamma (IFN-γ) synthesis. The critical role of CD137 stimulation in $CD8^+$ T-cell function and survival could be potentially utilized for the treatment of tumors through manipulation of the CD137/CD137L function. In fact, in vivo efficacy studies in mice have demonstrated that treatment with anti-CD137 antibodies led to tumor regressions in multiple tumor models. For example, agonistic anti-mouse CD137 antibodies were demonstrated to induce an immune response against P815 mastocytoma tumors, and low immunogenic tumor model Ag104 (I. Melero et al., Nat. Med., 3(6):682-5 (1997)). The efficacy of CD137 agonist mAbs in prophylactic and therapeutic settings for both monotherapy and combination therapy and anti-tumor protective T cell memory responses has been reported in several studies (Lynch et al., Immunol Rev. 222:277-286 (2008)). CD137 agonists also inhibit autoimmune reactions in a variety of autoimmunity models (Vinay et al, J Mol Med 84(9):726-736 (2006)).

Various antibodies against CD137 are already known (see, for example, WO 00/29445 and WO 2004/010947), and at least two anti-CD137 antibodies are currently in the clinic: urelumab (Bristol-Myers Squibb), a fully humanized IgG4 mAb, and utomilumab (PF-05082566, Pfizer), a fully human IgG2 mAb (Chester C., et al., Cancer Immunol Immunother October; 65(10):1243-8 (2016)). Although utilization of therapeutic antibodies agonizing CD137 is a very promising treatment strategy, it is coupled to such difficulties as low efficacy of anti-CD137 agonist antibodies, high toxicities and adverse events. CD137 agonist antibodies were shown to lead to alterations in immune system and organ function increasing risks of toxicities. High doses of CD137 agonist antibodies in naïve and tumor-bearing mice have been reported to induce T-cell infiltration to the liver and elevations of aspartate aminotransferase and alanine aminotransferase consistent with liver inflammation (Niu L, et al. J Immunol 178(7):4194-4213 (2007); Dubrot J, et al., Int J Cancer 128(1):105-118 (2011)). Initial clinical studies into the human therapeutic use of CD137 agonist antibody have also demonstrated elevations of liver enzymes and increased incidence of hepatitis (Sznol M., et al., J Clin Oncol26(115S):3007 (2008); Ascierto P A, et al., Semin Oncol 37(5):508-516 (2010); Chester C., et al., Cancer Immunol Immunother October; 65(10):1243-8 (2016)). Potentially fatal hepatitis was observed in a Bristol-Myers Squibb (BMS) phase II anti-CD137 study for previously treated stage III/IV melanoma, National Clinical Trial (NCT) 00612664. That study and several others (NCT00803374, NCT00309023, NCT00461110, NCT00351325) were terminated due to adverse events (Chester C., et al., Cancer Immunol Immunother October; 65(10):1243-8 (2016)). Such adverse events are most probably due to systemic overstimulation of T-cells.

Thus, there is a need in the field to generate improved therapeutic anti-human CD137 antibodies having higher efficacy without the inherent side effects of general anti-proliferative drugs, in particular having lower toxicities comparable to the currently available CD137 antibodies.

SUMMARY OF THE INVENTION

It is an object of the present invention to provide antibodies that specifically bind to human CD137 protein, and which have beneficial properties for use in therapies, such as higher affinity, improved efficacy, lower toxicities, and improved biophysical properties, such as solubility, developability, and stability. In particular, CD137 antibodies are yet to be found that do not directly and independent of other cell-surface molecules result in CD137 signaling upon binding.

In one aspect, the present invention relates to a novel CD137 antibody.

In one aspect, the present invention relates to a pharmaceutical composition comprising the isolated antibody of the invention, and a pharmaceutically acceptable carrier.

In another aspect, the present invention relates to the antibody of the invention, or the composition of the invention for use as a medicament In one aspect, the present invention relates to the antibody of the invention, or the composition of the invention for use in the treatment of a cancer in a subject in need thereof.

In one aspect, the present invention relates to use of the antibody of the invention, or the composition of the invention in the manufacture of a medicament for the treatment of a cancer in a subject in need thereof.

In another aspect, the present invention relates to a method of treating a cancer in a subject in need thereof comprising administering to the subject a therapeutically effective amount of the antibody of the invention, or the composition of the invention.

In yet another aspect, the present invention relates to a nucleic acid encoding the antibody of the invention. In a further aspect, the present invention relates to a vector comprising said nucleic acid. In a further aspect, the present invention relates to a host cell comprising said nucleic acid or said vector.

In another aspect, the present invention relates to a method of producing the antibody of the invention, the method comprising the step of culturing a host cell comprising the nucleic acid or the vector of the invention.

The aspects, advantageous features and preferred embodiments of the present invention summarized in the following items, respectively alone or in combination, further contribute to solving the object of the invention:

1. An isolated antibody having a binding specificity for human CD137, which comprises: (a) a heavy chain variable region CDR1 comprising, preferably consisting of, an amino acid sequence selected from any one of SEQ ID NOs: 1, 4, 5, 8 and 11, preferably SEQ ID NO: 1; (b) a heavy chain variable region CDR2 comprising, preferably consisting of, an amino acid sequence selected from any of SEQ ID NOs: 2, 6, 9 and 12, preferably SEQ ID NO: 2; (c) a heavy chain variable region CDR3 comprising, preferably consisting of, an amino acid sequence selected from any of SEQ ID NOs: 3, 7, 10 and 13, preferably SEQ ID NO: 3; (d) a light chain variable region CDR1 comprising, preferably consisting of, an amino acid sequence selected from any of SEQ ID NOs: 18, 21 and 24, preferably SEQ ID NO: 18; (e) a light chain variable region CDR2 comprising, preferably consisting of, an amino acid sequence selected from any of SEQ ID NOs: 19, 22 and 25, preferably SEQ ID NO: 19; and (f) a light chain variable region CDR3 comprising, preferably consisting of, an amino acid sequence selected from any of SEQ ID NOs: 20, 23 and 26, preferably SEQ ID NO: 20.

2. The antibody of item 1, wherein the antibody comprises: (a) HCDR1, HCDR2, and HCDR3 sequences of SEQ ID NOs: 1, 2 and 3, respectively, and LCDR1, LCDR2, and LCDR3 sequences of SEQ ID NOs: 18, 19 and 20, respectively; (b) HCDR1, HCDR2, and HCDR3 sequences of SEQ ID NOs: 4, 6, and 7, respectively, and LCDR1, LCDR2, and LCDR3 sequences of SEQ ID NOs: 21, 22, and 23, respectively; (c) HCDR1, HCDR2, and HCDR3 sequences of SEQ ID NOs: 5, 6, and 7, respectively, and LCDR1, LCDR2, and LCDR3 sequences of SEQ ID NOs: 21, 22, and 23, respectively; (d) HCDR1, HCDR2, and HCDR3 sequences of SEQ ID NOs: 8, 9, and 10, respectively, and LCDR1, LCDR2, and LCDR3 sequences of SEQ ID NOs: 18, 19, and 20, respectively; or (e) HCDR1, HCDR2, and HCDR3 sequences of SEQ ID NOs: 11, 12, and 13, respectively, and LCDR1, LCDR2, and LCDR3 sequences of SEQ ID NOs: 24, 25, and 26, respectively.

3. The isolated antibody of item 1, comprising: (a) a HCDR1 comprising, preferably consisting of, the amino acid sequence of SEQ ID NO: 1; (b) a HCDR2 comprising, preferably consisting of, the amino acid sequence of SEQ ID NO: 2; (c) a HCDR3 comprising, preferably consisting of, the amino acid sequence of SEQ ID NO: 3; (d) a LCDR1 comprising, preferably consisting of, the amino acid sequence of SEQ ID NOs: 18; (e) a LCDR2 comprising, preferably consisting of, the amino acid sequence of SEQ ID NOs: 19; and (f) a LCDR3 comprising, preferably consisting of, the amino acid sequence of SEQ ID NO: 20.

4. The isolated antibody of item 1, comprising: (a) a HCDR1 comprising, preferably consisting of, the amino acid sequence of SEQ ID NO: 4 or SEQ ID NO: 5; (b) a HCDR2 comprising, preferably consisting of, the amino acid sequence of SEQ ID NO: 6; (c) a HCDR3 comprising, preferably consisting of, the amino acid sequence of SEQ ID NO: 7; (d) a LCDR1 comprising, preferably consisting of, the amino acid sequence of SEQ ID NOs: 21; (e) a LCDR2 comprising, preferably consisting of, the amino acid sequence of SEQ ID NOs: 22; and (f) a LCDR3 comprising, preferably consisting of, the amino acid sequence of SEQ ID NO: 23.
5. The antibody of any one of the preceding items, wherein the antibody comprises a heavy chain variable region (VH), wherein said VH is VH3 or VH4, preferably VH3.
6. The antibody of any one of the preceding items, wherein the antibody comprises a light chain variable region (VL), wherein said VL comprises Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and Vλ FR4, particularly Vλ FR4 comprising the amino acid sequence having at least 60, 70, 80, 90 percent identity to an amino acid sequence selected from any of SEQ ID NO: 62 to SEQ ID NO: 68, preferably Vλ FR4 as set forth in any of SEQ ID NO: 62 to SEQ ID NO: 68, preferably Vλ FR4 as set forth in SEQ ID NO: 62 or 63, more preferably Vλ FR4 as set forth in SEQ ID NO: 62.
7. The antibody of any one of the preceding items, wherein the antibody comprises a heavy chain variable region comprising an amino acid sequence that is at least 90 percent identical to the amino acid sequence selected from the group consisting of SEQ ID NOs: 14, 15, 16 and 17, preferably SEQ ID NO: 14 and 17, more preferably SEQ ID NO: 17; and a light chain variable region comprising an amino acid sequence that is at least 90 percent identical to the amino acid sequence selected from the group consisting of SEQ ID NOs: 27, 28, 29 and 30, preferably SEQ ID NO: 27 and 30, more preferably SEQ ID NO: 30.
8. The antibody of any one of the preceding items, wherein the antibody comprises: a heavy chain variable region comprising an amino acid sequence selected from any of SEQ ID NOs: 14, 15, 16 and 17, preferably SEQ ID NO: 14 and 17, more preferably SEQ ID NO: 17; and a light chain variable region comprising an amino acid sequence selected from any of SEQ ID NOs: 27, 28, 29 and 30, preferably SEQ ID NO: 27 and 30, more preferably SEQ ID NO: 30.
9. The antibody of any one of the preceding items, comprising: (a) a VH comprising an amino acid sequence that is at least 90 percent identical to the amino acid sequence of SEQ ID NO: 14 and a VL comprising an amino acid sequence that is at least 90 percent identical to the amino acid sequence of SEQ ID NO: 27; (b) a VH comprising an amino acid sequence that is at least 90 percent identical to the amino acid sequence of SEQ ID NO: 15 and a VL comprising an amino acid sequence that is at least 90 percent identical to the amino acid sequence of SEQ ID NO: 28; (c) a VH comprising an amino acid sequence that is at least 90 percent identical to the amino acid sequence of SEQ ID NO: 16 and a VL comprising an amino acid sequence that is at least 90 percent identical to the amino acid sequence of SEQ ID NO: 29; or (d) a VH comprising an amino acid sequence that is at least 90 percent identical to the amino acid sequence of SEQ ID NO: 17 and a VL comprising an amino acid sequence that is at least 90 percent identical to the amino acid sequence of SEQ ID NO: 30.
10. The antibody of any one of the preceding items, comprising: (a) a VH sequence of SEQ ID NO: 14 and a VL sequence of SEQ ID NO: 27; (b) a VH sequence of SEQ ID NO: 15 and a VL sequence of SEQ ID NO: 28; (c) a VH sequence of SEQ ID NO: 16 and a VL sequence of SEQ ID NO: 29; or (d) a VH sequence of SEQ ID NO: 17 and a VL sequence of SEQ ID NO: 30.
11. The antibody of any of the preceding items, wherein said antibody:
    a) binds to human CD137 with a dissociation constant (KD) of less than 10 nM, particularly less than 5 nM, particularly less than 1 nM, in particular as measured by surface plasmon resonance (SPR), particularly wherein said antibody is an scFv (monovalent affinity);
    b) binds to human CD137 with a $K_{off}$ rate of $10^{-3}$ $s^{-1}$ or less, or $10^{-4}$ $s^{-1}$ or less, or $10^{-5}$ $s^{-1}$ or less as measured by SPR, particularly wherein said antibody is an scFv;
    c) binds to human CD137 with a $K_{on}$ rate of at least 104 $M^{-1}s^{-1}$ or greater, at least $10^5$ $M^{-1}s^{-1}$ or greater, at least $10^6$ $M^{-1}s^{-1}$ or greater, as measured by SPR, particularly wherein said antibody is an scFv; and/or
    d) is cross-reactive with *Macaca fascicularis* (Cynomolgus) CD137, in particular binds to Cynomolgus PDL1 with a KD of less than 15 nM, particularly less than 10 nM, particularly less than 5 nM as measured by SPR, particularly wherein said antibody is an scFv; and/or
    e) does not bind to human CD40 and/or human OX40, in particular as measured by SPR.
12. The antibody of any one of the preceding items, which binds to human CD137 with a KD of less than 5 nM.
13. The antibody of any of the preceding items, wherein said antibody:
    a) when in scFv format, has a melting temperature (Tm), determined by differential scanning fluorimetry, of at least 50° C., preferably of at least 55° C., more preferably at least 60° C., in particular wherein said antibody is formulated in 50 mM phosphate-citrate buffer at pH 6.4, 150 mM NaCl;
    b) when in scFv format, has a loss in monomer content, after storage for at least two weeks, particularly for at least four weeks, at 4° C., of less than 5%, e.g. less than 4%, less than 3%, less than 2%, preferably less than 1%, when the antibody of the invention is at a starting concentration of 10 mg/ml, and in particular wherein the antibody is formulated in 50 mM phosphate citrate buffer with 150 mM NaCl at pH 6.4; and/or
    c) when in scFv format, has a loss in monomer content, after storage for at least two weeks, particularly for at least four weeks, at 40° C., of less than 5%, e.g. less than 4%, less than 3%, less than 2%, preferably less than 1%, when the antibody of the invention is at a starting concentration of 10 mg/ml, and in particular wherein the antibody is formulated in 50 mM phosphate citrate buffer with 150 mM NaCl at pH 6.4.
14. The isolated antibody of any of the previous items, wherein the isolated antibody is selected from the group consisting of: a monoclonal antibody, a chimeric antibody, a Fab, an Fv, an scFv, dsFv, a scAb, STAB, and binding domains based on alternative scaffolds including but limited to ankyrin-based domains, fynomers, avimers, anticalins, fibronectins, and binding sites being built into constant regions of antibodies (e.g. F-star's Modular Antibody Technology™), preferably Fv or scFv.
15. The antibody of any one of the preceding items, which is a single-chain variable fragment (scFv).

16. The antibody of item 15, wherein said scFv has the amino acid sequence selected from the group consisting of SEQ ID NO: 32, SEQ ID NO: 33, SEQ ID NO: 34 and SEQ ID NO: 35, preferably SEQ ID NO: 32 and SEQ ID NO: 35, more preferably SEQ ID NO: 35.
17. The isolated antibody of item 14, wherein the antibody is an IgG selected from the group consisting of an IgG1, an IgG2, an IgG3 and an IgG4, preferably IgG4.
18. The isolated antibody of any of the previous items, wherein the antibody is chimeric or humanized.
19. An isolated antibody binding to essentially the same epitope as the antibody of any one of items 1 to 18.
20. The antibody of anyone of the preceding items which is a multispecific molecule, in particular a multispecific molecule having at least a second functional molecule.
21. The antibody of item 20, wherein said antibody is in a format selected from the group consisting of a single-chain diabody (scDb), a tandem scDb (Tandab), a linear dimeric scDb (LD-scDb), a circular dimeric scDb (CD-scDb), a bispecific T-cell engager (BiTE; tandem di-scFv), a tandem tri-scFv, a tribody (Fab-(scFv)2) or bibody (Fab-(scFv)1), Fab, Fab-Fv2, Morrison (IgG CH₃-scFv fusion (Morrison L) or IgG CL-scFv fusion (Morrison H)), triabody, scDb-scFv, bispecific Fab2, di-miniantibody, tetrabody, scFv-Fc-scFv fusion, scFv-HSA-scFv fusion, di-diabody, DVD-Ig, COVD, IgG-scFab, scFab-dsscFv, Fv2-Fc, IgG-scFv fusions, such as bsAb (scFv linked to C-terminus of light chain), Bs1Ab (scFv linked to N-terminus of light chain), Bs2Ab (scFv linked to N-terminus of heavy chain), Bs3Ab (scFv linked to C-terminus of heavy chain), Ts1Ab (scFv linked to N-terminus of both heavy chain and light chain), Ts2Ab (dsscFv linked to C-terminus of heavy chain), Bispecific antibodies based on heterodimeric Fc domains, such as Knob-into-Hole antibodies (KiHs); an Fv, scFv, scDb, tandem-di-scFv, tandem tri-scFv, Fab-(scFv)2, Fab-(scFv)1, Fab, Fab-Fv2, COVD fused to the N- and/or the C-terminus of either chain of a heterodimeric Fc domain or any other heterodimerization domain, a MATCH and DuoBodies.
22. A pharmaceutical composition comprising the antibody of any one of items 1-21, and a pharmaceutically acceptable carrier.
23. The antibody of any one of items 1-21, or the composition of item 22 for use as a medicament.
24. The antibody of any one of items 1-21, or the composition of item 22 for use in the treatment of a cancer in a subject in need thereof.
25. Use of the antibody of any one of items 1-21, or the composition of item 22 to treat a cancer in a subject in need thereof.
26. Use of the antibody of any one of items 1-21, or the composition of item 22 in the manufacture of a medicament for the treatment of a cancer in a subject in need thereof.
27. A method of treating a cancer in a subject in need thereof comprising administering to the subject a therapeutically effective amount of the antibody of any one of items 1-21, or the composition of item 22.
28. A nucleic acid encoding the antibody of items 1-21.
29. A vector comprising the nucleic acid of item 28.
30. A host cell comprising the nucleic acid of item 28 or the vector of item 29.
31. A method of producing the antibody of items 1-21, the method comprising the step of culturing a host cell comprising the nucleic acid of item 28 or the vector of item 29.
32. A kit comprising the antibody of any one of items 1 to 21, or the composition of item 22.

BRIEF DESCRIPTION OF THE DRAWINGS

FIG. 2 Heatmap of epitope binning results of PRO885 and PRO951 and urelumab and utomilumab. Binding level normalized to theoretical Rmax in percent (%) of analyte molecules (column) to immobilized molecules (row). No binding (dark grey) means same epitope, bright grey means the secondary molecule (analyte) can bind and has another epitope than the immobilized molecule.

FIG. 19 contains Table 26 which shows NFkB reporter gene activation by PDL1 × CD137 multispecific constructs.

DETAILED DESCRIPTION OF THE INVENTION

Figure 1:
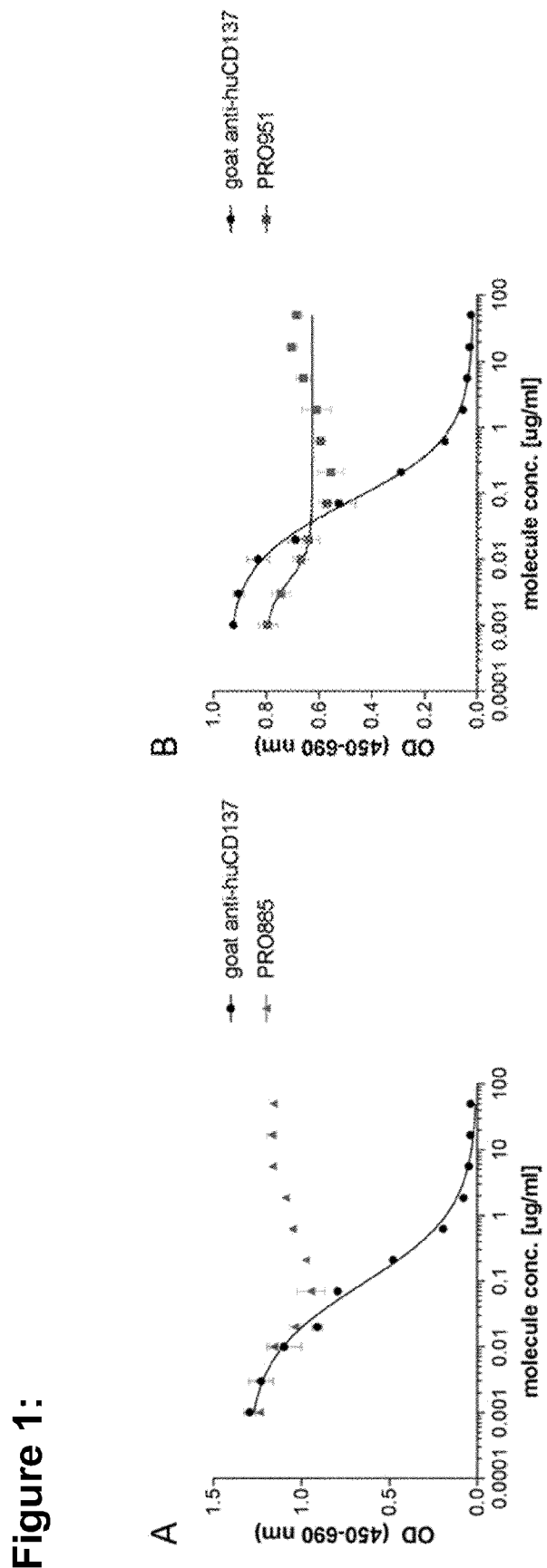
FIG. 1 No inhibition of CD137 binding to CD137L in competition ELISA. The absorbance measured in the competitive ELISA assessing the binding of CD137L to CD137 are represented in function of increasing concentrations of PRO885 (A) or PRO951 (B) respectively. The inhibitory antibody goat anti-human CD137 served as a reference.

The present invention provides antibodies that specifically bind to human CD137 protein, and pharmaceutical compositions, production methods, and methods of use of such antibodies and compositions.

Unless defined otherwise, all technical and scientific terms used herein have the same meaning as commonly understood by those of ordinary skill in the art to which this invention pertains.

The terms "comprising" and "including" are used herein in their open-ended and non-limiting sense unless otherwise noted. With respect to such latter embodiments, the term "comprising" thus includes the narrower term "consisting of".

The terms "a" and "an" and "the" and similar references in the context of describing the invention (especially in the context of the following claims) are to be construed to cover both the singular and the plural, unless otherwise indicated herein or clearly contradicted by context. For example, the term "a cell" includes a plurality of cells, including mixtures thereof. Where the plural form is used for compounds, salts, and the like, this is taken to mean also a single compound, salt, or the like.

In a first aspect, the present invention relates to antibodies that specifically bind to human CD137.

The term "antibody" and the like, as used herein, includes: whole antibodies or single chains thereof; and any antigen-binding fragment (i.e., "antigen-binding portion") or single chains thereof; and molecules comprising antibody CDRs, VH regions or VL regions (including without limitation multispecific antibodies). A naturally occurring "whole antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FRs). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The terms "antigen-binding fragment", "antigen-binding fragment thereof", "antigen binding portion", and the like, as used herein, refer to one or more fragments of an intact whole antibody that retain the ability to specifically bind to a given antigen (e.g., CD137). Antigen binding functions of an antibody can be performed by fragments of an intact antibody. Examples of binding fragments encompassed within the term "antigen binding portion" of an antibody include a Fab fragment, a monovalent fragment consisting of the VL, VH, CL and CH1 domains; a F(ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; and binding domains based on alternative scaffolds including but limited to ankyrin-based domains, fynomers, avimers, anticalins, fibronectins, and binding sites being built into constant regions of antibodies (e.g. F-star's Modular Antibody Technology™).

The term "Complementarity Determining Regions" ("CDRs") are amino acid sequences with boundaries determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme) and numbering scheme described in Honegger & Plückthun, J. Mol. Biol. 309 (2001) 657-670 ("AHo" numbering). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 24-34 (LCDR1), 50-56 (LCDR2), and 89-97 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (HCDR1), 51-57 (HCDR2) and 93-102 (HCDR3), and the CDR amino acid residues in the VL are numbered approximately 27-32 (LCDR1), 50-52 (LCDR2), and 89-97 (LCDR3) (numbering according to "Kabat"). Under IMGT, the CDRs of an antibody can be determined using the program IMGT/DomainGap Align. In the context of the present invention, the numbering system suggested by Honegger & Plückthun ("AHo") is used (Honegger & Plückthun, J. Mol. Biol. 309 (2001) 657-670), unless specifically mentioned otherwise. Furthermore, the following residues are defined as CDRs according to AHo numbering scheme: LCDR1 (also referred to as CDR-L1): L24-L42; LCDR2 (also referred to as CDR-L2): L58-L72; LCDR3 (also referred to as CDR-L3): L107-L138; HCDR1 (also referred to as CDR-H1): H27-H42; HCDR2 (also referred to as CDR-H2): H57-H76; HCDR3 (also referred to as CDR-H3): H108-H138. For the sake of clarity, the numbering system according to Honegger & Plückthun takes the length diversity into account that is found in naturally occurring antibodies, both in the different VH and VL subfamilies and, in particular, in the CDRs, and provides for gaps in the sequences. Thus, in a given antibody variable domain usually not all positions 1 to 149 will be occupied by an amino acid residue.

Antigen binding portions can also be incorporated into maxibodies, minibodies, intrabodies, diabodies, triabodies, tetrabodies, scDb-scFv, v-NAR and bis-scFv (see, e.g., Holliger and Hudson, 2005, Nature Biotechnology, 23, 1126-36). Antigen binding portions of antibodies can be grafted into scaffolds based on polypeptides such as Fibronectin type III (Fn3) (see U.S. Pat. No. 6,703,199, which describes fibronectin polypeptide monobodies). Antigen binding portions can be incorporated into single chain molecules comprising a pair of tandem Fv segments (VH-CH1-VH-CH1) which, together with complementary light chain polypeptides, form a pair of antigen binding regions (Zapata et al., 1995 Protein Eng. 8 (10): 1057-1062; and U.S. Pat. No. 5,641,870).

The term "binding specificity" as used herein refers to the ability of an individual antibody combining site to react with one antigenic determinant and not with a different antigenic determinant. As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In its most general form (and when no defined reference is mentioned), "specific binding" is referring to the ability of the antibody to discriminate between the target of interest and an unrelated molecule, as determined, for example, in accordance with a specificity assay methods known in the art. Such methods comprise, but are not limited to Western blots, ELISA, RIA, ECL, IRMA, SPR (Surface plasmon resonance) tests and peptide scans. For example, a standard ELISA assay can be carried out. The scoring may be carried out by standard colour development (e.g. secondary antibody with horseradish peroxide and tetramethyl benzidine with hydrogen peroxide). The reaction in certain wells is scored by the optical density, for example, at 450 nm. Typical background (=negative reaction) may be about 0.1 OD; typical positive reaction may be about 1 OD. This means the ratio between a positive and a negative score can be 10-fold or higher. In a further example, an SPR assay can be carried out, wherein at least 10-fold, preferably at least 100-fold difference between a background and signal indicates on specific binding. Typically, determination of binding specificity is performed by using not a single reference molecule, but a set of about three to five unrelated molecules, such as milk powder, transferrin or the like. The antibody of the invention has a binding specificity for human CD137. In a specific embodiment, the antibody of the invention or has a binding specificity for human CD137 and does not bind to human CD40 and/or does not bind to human OX40, in particular as determined by SPR.

Suitably, the antibody of the invention is an isolated antibody. The term "isolated antibody", as used herein, refers to an antibody that is substantially free of other antibodies having different antigenic specificities (e.g., an isolated antibody that specifically binds CD137 is substantially free of antibodies that specifically bind antigens other than CD137). An isolated antibody that specifically binds CD137 may, however, have cross-reactivity to other antigens, such CD137 molecules from other species. Thus, in one embodiment, the antibody of the invention has a binding specificity for human CD137 and *Macaca fascicularis* (also known as Cynomolgus monkey or "Cynomolgus") CD137. Moreover, an isolated antibody may be substantially free of other cellular material and/or chemicals.

Suitably, the antibody of the invention is a monoclonal antibody. The term "monoclonal antibody" or "monoclonal antibody composition" as used herein refers to antibodies that are substantially identical to amino acid sequence or are derived from the same genetic source. A monoclonal antibody composition displays a binding specificity and affinity for a particular epitope, or binding specificities and affinities for specific epitopes.

Antibodies of the invention include, but are not limited to, the chimeric and humanized.

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

A "humanized" antibody, as used herein, is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). Additional framework region modifications may be made within the human framework sequences as well as within the CDR sequences derived from the germline of another mammalian species. The humanized antibodies of the invention may include amino acid residues not encoded by human sequences (e.g., mutations introduced by random or site-specific mutagenesis in vitro or by somatic mutation in vivo, or a conservative substitution to promote stability or manufacturing). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239: 1534-1536, 1988; Padlan, Molec. Immun., 28:489-498, 1991; and Padlan, Molec. Immun., 31: 169-217, 1994. Other examples of human engineering technology include, but are not limited to Xoma technology disclosed in U.S. Pat. No. 5,766,886.

The term "recombinant humanized antibody" as used herein, includes all human antibodies that are prepared, expressed, created or isolated by recombinant means, such as antibodies isolated from a host cell transformed to express the humanized antibody, e.g., from a transfectoma, and antibodies prepared, expressed, created or isolated by any other means that involve splicing of all or a portion of a human immunoglobulin gene, sequences to other DNA sequences.

Suitably, the antibody of the invention is humanized. Suitably, the antibody of the invention is humanized and comprises rabbit-derived CDRs.

The term "CD137" refers in particular to human CD137 with UniProt ID number Q07011 reproduced herein as SEQ ID NO: 61. Suitably, the antibodies of the invention target CD137, in particular human CD137 as shown in UniProt ID number Q07011, reproduced herein as SEQ ID NO: 61. Suitably, the antibodies of the invention target human and cynomolgus (*Macaca fascicularis*) CD137. The antibodies of the invention specifically bind CD137. In particular, the antibodies of the invention do not bind to human OX40 and/or human CD40, in particular as measured by SPR. Preferably, the antibodies of the invention do not block CD137/CD137L interaction.

Suitably, the antibody of the present invention is CD137 agonist. An "activator" or "activating antibody" or "agonist" or "agonist antibody" is one that enhances or initiates signaling by the antigen to which it binds. In the context of the present invention, the term "CD137 agonist" encompasses the antibody of the present invention that is capable to activate CD137 signaling upon clustering of CD137-antigen-binding fragments thereof, e.g., wherein binding of at least two of said CD137-antigen-binding fragments allow for multimerization of the bound CD137 molecules and their activation. In some embodiments, agonist antibodies activate signaling without the presence of the natural ligand.

Antibodies of the invention include, but are not limited to, the humanized monoclonal antibodies isolated as described herein, including in the Examples. Examples of such anti-human CD137 antibodies are antibodies whose sequences are listed in Table 1. Additional details regarding the generation and characterization of the antibodies described herein are provided in the Examples.

The isolated antibody of the invention having a binding specificity for human CD137 comprises a heavy chain variable region (VH) and a light chain variable region (VL), wherein: (a) said VH comprises, in sequence, the three complementary determining regions HCDR1, HCDR2 and HCDR3, and (b) said VL comprises, in sequence, the three complementary determining regions LCDR1, LCDR2 and LCDR3.

The present invention provides antibodies that specifically bind to CD137 protein, said antibodies comprising a VH CDR having an amino acid sequence of any one of the VH CDRs listed in Table 1. In particular, the invention provides antibodies that specifically bind to CD137 protein, said antibodies comprising one, two, three, or more VH CDRs having an amino acid sequence of any of the VH CDRs listed in Table 1.

The present invention also provides antibodies that specifically bind to CD137 protein, said antibodies comprising a VL CDR having an amino acid sequence of any one of the VL CDRs listed in Table 1. In particular, the invention provides antibodies that specifically bind to CD137 protein, said antibodies comprising one, two, three or more VL CDRs having an amino acid sequence of any of the VL CDRs listed in Table 1.

Other antibodies of the invention include amino acids that have been mutated, yet specifically bind to CD137 and have at least 60, 70, 80, 90, 91, 92, 93, 94, 95, 96, 97, 98 or 99 percent identity in the CDR regions with the CDR regions depicted in the sequences described in Table 1. In one aspect, other antibodies of the invention includes mutant amino acid sequences that specifically bind to CD137 wherein no more than 1, 2, 3, 4 or 5 amino acids have been mutated in the CDR regions when compared with the CDR regions depicted in the sequence described in Table 1.

The terms "identical" or "identity", in the context of two or more nucleic acids or polypeptide sequences, refer to two or more sequences or subsequences that are the same. "Percent (%) sequence identity" and "homology" with respect to a nucleic acid, a peptide, a polypeptide or an antibody sequence are defined as the percentage of nucleotides or amino acid residues in a candidate sequence that are identical with the nucleotides or amino acid residues in the specific nucleic acid, peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2 or ALIGN software. Those skilled in the art can determine appropriate parameters for measuring alignment, including any algorithms needed to achieve maximal alignment over the full length of the sequences being compared.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Two examples of algorithms that are suitable for determining percent sequence identity and sequence similarity are the BLAST and BLAST 2.0 algorithms, which are described in Altschul et al., Nucl. Acids Res. 25:3389-3402, 1977; and Altschul et al., J. Mol. Biol. 215:403-410, 1990, respectively. Software for performing BLAST analyses is publicly available through the National Center for Biotechnology Information.

The percent identity between two amino acid sequences can also be determined using the algorithm of E. Meyers and W. Miller (Comput. Appl. Biosci., 4: 11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The present invention provides an isolated antibody having a binding specificity for human CD137, which comprises: (a) a heavy chain variable region CDR1 (HCDR1) comprising, preferably consisting of, an amino acid sequence selected from any one of SEQ ID NOs: 1, 4, 5, 8, 11, 39, 42 and 45, preferably SEQ ID NO: 1; (b) a heavy chain variable region CDR2 (HCDR2) comprising, preferably consisting of, an amino acid sequence selected from any of SEQ ID NOs: 2, 6, 9, 12, 40, 43 and 46, preferably SEQ ID NO: 2; (c) a heavy chain variable region CDR3 (HCDR3) comprising, preferably consisting of, an amino acid sequence selected from any of SEQ ID NOs: 3, 7, 10, 13, 41, 44 and 47, preferably SEQ ID NO: 3; (d) a light chain variable region CDR1 (LCDR1) comprising, preferably consisting of, an amino acid sequence selected from any of SEQ ID NOs: 18, 21, 24, 49, 52, and 55, preferably SEQ ID NO: 18; (e) a light chain variable region CDR2 (LCDR2) comprising, preferably consisting of, an amino acid sequence selected from any of SEQ ID NOs: 19, 22, 25, 50, 53, and 56, preferably SEQ ID NO: 19; and (f) a light chain variable region CDR3 (LCDR3) comprising, preferably consisting of, an amino acid sequence selected from any of SEQ ID NOs: 20, 23, 26, 51, 54, and 57, preferably SEQ ID NO: 20; wherein the antibody specifically binds human CD137. Suitably, the isolated antibody of the invention having a binding specificity for human CD137 comprises: (a) a heavy chain variable region CDR1 having at least 60, 70, 80, 90, 91, 92, 93, 94, 95, 96, 97, 98 or 99 percent identity to any one of SEQ ID NOs: 1, 4, 5, 8, 11, 39, 42 and 45, preferably SEQ ID NO: 1; (b) a heavy chain variable region CDR2 having at least 60, 70, 80, 90, 91, 92, 93, 94, 95, 96, 97, 98 or 99 percent identity to any of SEQ ID NOs: 2, 6, 9, 12, 40, 43 and 46, preferably SEQ ID NO: 2; (c) a heavy chain variable region CDR3 having at least 60, 70, 80, 90, 91, 92, 93, 94, 95, 96, 97, 98 or 99 percent identity to any of SEQ ID NOs: 3, 7, 10, 13, 41, 44 and 47, preferably SEQ ID NO: 3; (d) a light chain variable region CDR1 having at least 60, 70, 80, 90, 91, 92, 93, 94, 95, 96, 97, 98 or 99 percent identity to any of SEQ ID NOs: 18, 21, 24, 49, 52, and 55, preferably SEQ ID NO: 18; (e) a light chain variable region CDR2 having at least 60, 70, 80, 90, 91, 92, 93, 94, 95, 96, 97, 98 or 99 percent identity to any of SEQ ID NOs: 19, 22, 25, 50, 53, and 56, preferably SEQ ID NO: 19; and (f) a light chain variable region CDR3 having at least 60, 70, 80, 90, 91, 92, 93, 94, 95, 96, 97, 98 or 99 percent identity to any of SEQ ID NOs: 20, 23, 26, 51, 54, and 57, preferably SEQ ID NO: 20.

In one embodiment, the antibody of the invention having a binding specificity for human CD137 comprises: (a) HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively; (b) HCDR1, HCDR2, and HCDR3 sequences of SEQ ID NOs: 4, 6, and 7, respectively, and LCDR1, LCDR2, and LCDR3 sequences of SEQ ID NOs: 21, 22, and 23, respectively; (c) HCDR1, HCDR2, and HCDR3 sequences of SEQ ID NOs: 5, 6, and 7, respectively, and LCDR1, LCDR2, and LCDR3 sequences of SEQ ID NOs: 21, 22, and 23, respectively; (d) HCDR1, HCDR2, and HCDR3 sequences of SEQ ID NOs: 8, 9, and 10, respectively, and LCDR1, LCDR2, and LCDR3 sequences of SEQ ID NOs: 18, 19, and 20, respectively; (e) HCDR1, HCDR2, and HCDR3 sequences of SEQ ID NOs: 11, 12, and 13, respectively, and LCDR1, LCDR2, and LCDR3 sequences of SEQ ID NOs: 24, 25, and 26, respectively; (f) HCDR1, HCDR2, and HCDR3 sequences of SEQ ID NOs: 36, 37, and 38, respectively, and LCDR1, LCDR2, and LCDR3 sequences of SEQ ID NOs: 49, 50, and 51, respectively; (g) HCDR1, HCDR2, and HCDR3 sequences of SEQ ID NOs: 39, 40, and 41, respectively, and LCDR1, LCDR2, and LCDR3 sequences of SEQ ID NOs: 52, 53, and 54, respectively; (h) HCDR1, HCDR2, and HCDR3 sequences of SEQ ID NOs: 42, 43, and 44, respectively, and LCDR1, LCDR2, and LCDR3 sequences of SEQ ID NOs: 49, 50, and 51, respectively; (i) HCDR1, HCDR2, and HCDR3 sequences of SEQ ID NOs: 45, 46, and 47, respectively, and LCDR1, LCDR2, and LCDR3 sequences of SEQ ID NOs: 55, 56, and 57, respectively. In a preferred embodiment, the antibody of the invention having a binding specificity for human CD137 comprises HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively.

Suitably, the antibody of the invention having a binding specificity for human CD137 comprises: (a) HCDR1, HCDR2, and HCDR3 sequences having at least 60, 70, 80, 90, 91, 92, 93, 94, 95, 96, 97, 98 or 99 percent identity to SEQ ID NOs: 1, 2, and 3, respectively, and LCDR1, LCDR2, and LCDR3 sequences having at least 60, 70, 80, 90, 91, 92, 93, 94, 95, 96, 97, 98 or 99 percent identity to SEQ ID NOs: 18, 19, and 20, respectively; (b) HCDR1, HCDR2, and HCDR3 sequences having at least 60, 70, 80, 90, 91, 92, 93, 94, 95, 96, 97, 98 or 99 percent identity to SEQ ID NOs: 4, 6, and 7, respectively, and LCDR1, LCDR2, and LCDR3 sequences having at least 60, 70, 80, 90, 91, 92, 93, 94, 95, 96, 97, 98 or 99 percent identity to SEQ ID NOs: 21, 22, and 23, respectively; (c) HCDR1, HCDR2, and HCDR3 sequences having at least 60, 70, 80, 90, 91, 92, 93, 94, 95, 96, 97, 98 or 99 percent identity to SEQ ID NOs: 5, 6, and 7, respectively, and LCDR1, LCDR2, and LCDR3 sequences having at least 60, 70, 80, 90, 91, 92, 93, 94, 95, 96, 97, 98 or 99 percent identity to SEQ ID NOs: 21, 22, and 23, respectively; (d) HCDR1, HCDR2, and HCDR3 sequences having at least 60, 70, 80, 90, 91, 92, 93, 94, 95, 96, 97, 98 or 99 percent identity to SEQ ID NOs: 8, 9, and 10, respectively, and LCDR1, LCDR2, and LCDR3 sequences having at least 60, 70, 80, 90, 91, 92, 93, 94, 95, 96, 97, 98 or 99 percent identity to SEQ ID NOs: 18, 19, and 20, respectively; (e) HCDR1, HCDR2, and HCDR3 sequences having at least 60, 70, 80, 90, 91, 92, 93, 94, 95, 96, 97, 98 or 99 percent identity to SEQ ID NOs: 11, 12, and 13, respectively, and LCDR1, LCDR2, and LCDR3 sequences having at least 60, 70, 80, 90, 91, 92, 93, 94, 95, 96, 97, 98 or 99 percent identity to SEQ ID NOs: 24, 25, and 26, respectively; (f) HCDR1, HCDR2, and HCDR3 sequences having at least 60, 70, 80, 90, 91, 92, 93, 94, 95, 96, 97, 98 or 99 percent identity to SEQ ID NOs: 36, 37, and 38, respectively, and LCDR1, LCDR2, and LCDR3 sequences having at least 60, 70, 80, 90, 91, 92, 93, 94, 95, 96, 97, 98 or 99 percent identity to SEQ ID NOs: 49, 50, and 51, respectively; (g) HCDR1, HCDR2, and HCDR3 sequences having at least 60, 70, 80, 90, 91, 92, 93, 94, 95, 96, 97, 98 or 99 percent identity to SEQ ID NOs: 39, 40, and 41, respectively, and LCDR1, LCDR2, and LCDR3 sequences having at least 60, 70, 80, 90, 91, 92, 93, 94, 95, 96, 97, 98 or 99 percent identity to SEQ ID NOs: 52, 53, and 54, respectively; (h) HCDR1, HCDR2, and HCDR3 sequences having at least 60, 70, 80, 90, 91, 92, 93, 94, 95, 96, 97, 98 or 99 percent identity to SEQ ID NOs: 42, 43, and 44, respectively, and LCDR1, LCDR2, and LCDR3 sequences having at least 60, 70, 80, 90, 91, 92, 93, 94, 95, 96, 97, 98 or 99 percent identity to SEQ ID NOs: 49, 50, and 51, respectively; (i) HCDR1, HCDR2, and HCDR3 sequences having at least 60, 70, 80, 90, 91, 92, 93, 94, 95, 96, 97, 98 or 99 percent identity to SEQ ID NOs: 45, 46, and 47, respectively, and LCDR1, LCDR2, and LCDR3 sequences having at least 60, 70, 80, 90, 91, 92, 93, 94, 95, 96, 97, 98 or 99 percent identity to SEQ ID NOs: 55, 56, and 57, respectively. In a preferred embodiment, the antibody of the invention having a binding specificity for human CD137 comprises HCDR1, HCDR2, and HCDR3 sequences having at least 60, 70, 80, 90, 91, 92, 93, 94, 95, 96, 97, 98 or 99 percent identity to SEQ ID NOs: 1, 2, and 3, respectively, and LCDR1, LCDR2, and LCDR3 sequences having at least 60, 70, 80, 90, 91, 92, 93, 94, 95, 96, 97, 98 or 99 percent identity to SEQ ID NOs: 18, 19, and 20, respectively. Suitably, the antibody of the invention having a binding specificity for human CD137 comprises: (a) a HCDR1 comprising, preferably consisting of, the amino acid sequence having at least 60, 70, 80, 90, 91, 92, 93, 94, 95, 96, 97, 98 or 99 percent identity to SEQ ID NO: 1; (b) a HCDR2 comprising, preferably consisting of, the amino acid sequence having at least 60, 70, 80, 90, 91, 92, 93, 94, 95, 96, 97, 98 or 99 percent identity to SEQ ID NO: 2; (c) a HCDR3 comprising, preferably consisting of, the amino acid sequence having at least 60, 70, 80, 90, 91, 92, 93, 94, 95, 96, 97, 98 or 99 percent identity to SEQ ID NO: 3; (d) a LCDR1 comprising, preferably consisting of, the amino acid sequence having at least 60, 70, 80, 90, 91, 92, 93, 94, 95, 96, 97, 98 or 99 percent identity to SEQ ID NOs: 18; (e) a LCDR2 comprising, preferably consisting of, the amino acid sequence having at least 60, 70, 80, 90, 91, 92, 93, 94, 95, 96, 97, 98 or 99 percent identity to SEQ ID NOs: 19; and (f) a LCDR3 comprising, preferably consisting of, the amino acid sequence having at least 60, 70, 80, 90, 91, 92, 93, 94, 95, 96, 97, 98 or 99 percent identity to SEQ ID NO: 20.

In a further embodiment, the antibody of the invention having a binding specificity for human CD137 comprises: (a) a HCDR1 comprising, preferably consisting of, the amino acid sequence of SEQ ID NO: 4 or SEQ ID NO: 5; (b) a HCDR2 comprising, preferably consisting of, the amino acid sequence of SEQ ID NO: 6; (c) a HCDR3 comprising the amino acid sequence of SEQ ID NO: 7; (d) a LCDR1 comprising, preferably consisting of, the amino acid sequence of SEQ ID NOs: 21; (e) a LCDR2 comprising, preferably consisting of, the amino acid sequence of SEQ ID NOs: 22; and (f) a LCDR3 comprising, preferably consisting of, the amino acid sequence of SEQ ID NO: 23. Suitably, the antibody of the invention having a binding specificity for human CD137 comprises: (a) a HCDR1 comprising, preferably consisting of, the amino acid sequence having at least 60, 70, 80, 90, 91, 92, 93, 94, 95, 96, 97, 98 or 99 percent identity to SEQ ID NO: 4 or SEQ ID NO: 5; (b) a HCDR2 comprising, preferably consisting of, the amino acid sequence having at least 60, 70, 80, 90, 91, 92, 93, 94, 95, 96, 97, 98 or 99 percent identity to SEQ ID NO: 6; (c) a HCDR3 comprising, preferably consisting of, the amino acid sequence having at least 60, 70, 80, 90, 91, 92, 93, 94, 95, 96, 97, 98 or 99 percent identity to SEQ ID NO: 7; (d) a LCDR1 comprising, preferably consisting of, the amino acid sequence having at least 60, 70, 80, 90, 91, 92, 93, 94, 95, 96, 97, 98 or 99 percent identity to SEQ ID NOs: 21; (e) a LCDR2 comprising, preferably consisting of, the amino acid sequence having at least 60, 70, 80, 90, 91, 92, 93, 94, 95, 96, 97, 98 or 99 percent identity to SEQ ID NOs: 22; and (f) a LCDR3 comprising, preferably consisting of, the amino acid sequence having at least 60, 70, 80, 90, 91, 92, 93, 94, 95, 96, 97, 98 or 99 percent identity to SEQ ID NO: 23.

In yet a further embodiment, the antibody of the invention having a binding specificity for human CD137 comprises: (a) a HCDR1 comprising, preferably consisting of, the amino acid sequence of SEQ ID NO: 36; (b) a HCDR2 comprising, preferably consisting of, the amino acid sequence of SEQ ID NO: 37; (c) a HCDR3 comprising, preferably consisting of, the amino acid sequence of SEQ ID NO: 38; (d) a LCDR1 comprising, preferably consisting of, the amino acid sequence of SEQ ID NOs: 49; (e) a LCDR2 comprising, preferably consisting of, the amino acid sequence of SEQ ID NOs: 50; and (f) a LCDR3 comprising, preferably consisting of, the amino acid sequence of SEQ ID NO: 51. Suitably, the antibody of the invention having a binding specificity for human CD137 comprises (a) a HCDR1 comprising, preferably consisting of, the amino acid sequence having at least 60, 70, 80, 90, 91, 92, 93, 94, 95, 96, 97, 98 or 99 percent identity to SEQ ID NO: 36; (b) a HCDR2 comprising, preferably consisting of, the amino acid sequence having at least 60, 70, 80, 90, 91, 92, 93, 94, 95, 96, 97, 98 or 99 percent identity to SEQ ID NO: 37; (c) a HCDR3 comprising, preferably consisting of, the amino acid sequence having at least 60, 70, 80, 90, 91, 92, 93, 94, 95, 96, 97, 98 or 99 percent identity to SEQ ID NO: 38; (d) a LCDR1 comprising, preferably consisting of, the amino acid sequence having at least 60, 70, 80, 90, 91, 92, 93, 94, 95, 96, 97, 98 or 99 percent identity to SEQ ID NOs: 49; (e) a LCDR2 comprising, preferably consisting of, the amino acid sequence having at least 60, 70, 80, 90, 91, 92, 93, 94, 95, 96, 97, 98 or 99 percent identity to SEQ ID NOs: 50; and (f) a LCDR3 comprising, preferably consisting of, the amino acid sequence having at least 60, 70, 80, 90, 91, 92, 93, 94, 95, 96, 97, 98 or 99 percent identity to SEQ ID NO: 51.

In a further embodiment, the antibody of the invention having a binding specificity for human CD137 comprises: (a) a HCDR1 comprising, preferably consisting of, the amino acid sequence of SEQ ID NO: 39; (b) a HCDR2 comprising, preferably consisting of, the amino acid sequence of SEQ ID NO: 40; (c) a HCDR3 comprising, preferably consisting of, the amino acid sequence of SEQ ID NO: 41; (d) a LCDR1 comprising, preferably consisting of, the amino acid sequence of SEQ ID NOs: 52; (e) a LCDR2 comprising, preferably consisting of, the amino acid sequence of SEQ ID NOs: 53; and (f) a LCDR3 comprising, preferably consisting of, the amino acid sequence of SEQ ID NO: 54. Suitably, the antibody of the invention having a binding specificity for human CD137 comprises: (a) a HCDR1 comprising, preferably consisting of, the amino acid sequence having at least 60, 70, 80, 90, 91, 92, 93, 94, 95, 96, 97, 98 or 99 percent identity to SEQ ID NO: 39; (b) a HCDR2 comprising, preferably consisting of, the amino acid sequence having at least 60, 70, 80, 90, 91, 92, 93, 94, 95, 96, 97, 98 or 99 percent identity to SEQ ID NO: 40; (c) a HCDR3 comprising, preferably consisting of, the amino acid sequence having at least 60, 70, 80, 90, 91, 92, 93, 94, 95, 96, 97, 98 or 99 percent identity to SEQ ID NO: 41; (d) a LCDR1 comprising, preferably consisting of, the amino acid sequence having at least 60, 70, 80, 90, 91, 92, 93, 94, 95, 96, 97, 98 or 99 percent identity to SEQ ID NOs: 52; (e) a LCDR2 comprising, preferably consisting of, the amino acid sequence having at least 60, 70, 80, 90, 91, 92, 93, 94, 95, 96, 97, 98 or 99 percent identity to SEQ ID NOs: 53; and (f) a LCDR3 comprising, preferably consisting of, the amino acid sequence having at least 60, 70, 80, 90, 91, 92, 93, 94, 95, 96, 97, 98 or 99 percent identity to SEQ ID NO: 54.

In a further embodiment, the present invention provides an isolated antibody that specifically binds CD137 (e.g., human CD137 protein), wherein said antibody comprises a VH domain and a VL domain. In the context of the present invention the terms "VH" (variable heavy chain), "VL" (variable light chain), "Vx" and "Vκ" refer to families of antibody heavy and light chain sequences that are grouped according to sequence identity and homology. Methods for the determination of sequence homologies, for example by using a homology search matrix such as BLOSUM (Henikoff, S. & Henikoff, J. G., Proc. Natl. Acad. Sci. USA 89 (1992) 10915-10919), and methods for the grouping of sequences according to homologies are well known to one of ordinary skill in the art. For VH, Vκ and Vλ different subfamilies can be identified, as shown, for example, in Knappik et al., J. Mol. Biol. 296 (2000) 57-86, which groups VH in VH1A, VH1B and VH2 to VH6, Vκ in Vκ1 to Vκ4 and Vλ in Vλ1 to Vλ3. In vivo, antibody Vκ chains, Vλ chains, and VH chains are the result of the random rearrangement of germline κ chain V and J segments, germline λ chain V and J segments, and heavy chain V, D and J segments, respectively. To which subfamily a given antibody variable chain belongs is determined by the corresponding V segment, and in particular by the framework regions FR1 to FR3. Thus, any VH sequence that is characterized in the present application by a particular set of framework regions HFR1 to HFR3 only, may be combined with any HFR4 sequence, for example a HFR4 sequence taken from one of the heavy chain germline J segments, or a HFR4 sequence taken from a rearranged VH sequence.

Suitably, the present invention provides an isolated antibody that specifically binds CD137 (e.g., human CD137 protein), wherein said antibody comprises a VH4 or VH3 domain, preferably a VH4 domain, more preferably a VH3 domain.

A specific example of a VH belonging to VH3 family is represented under SEQ ID NO: 17. In particular, framework regions FR1 to FR4 taken from SEQ ID NO: 17 belong to VH3 family (Table 1, regions marked in non-bold). Suitably, a VH belonging to VH3 family, as used herein, is a VH comprising FR1 to FR4 having at least 85%, preferably at least 90%, more preferably at least 95% sequence identity to FR1 to FR4 of SEQ ID NO: 17.

A specific example of a VH belonging to VH4 family is represented under SEQ ID NO: 14. In particular, framework regions FR1 to FR4 taken from SEQ ID NO: 14 belong to VH4 family (Table 1, regions marked in non-bold). Suitably, a VH belonging to VH4 family, as used herein, is a VH comprising FR1 to FR4 having at least 85%, preferably at least 90%, more preferably at least 95% sequence identity to FR1 to FR4 of SEQ ID NO: 14.

Alternative examples of VH sequences may be found in Knappik et al., J. Mol. Biol. 296 (2000) 57-86.

Suitably, the present invention provides an isolated antibody that specifically binds CD137 (e.g., human CD137 protein), wherein said antibody comprises Vκ frameworks FR1, FR2 and FR3, particularly Vκ1 or Vκ3 frameworks, preferably Vκ1 frameworks FR1 to 3, and a framework FR4, which is selected from a Vκ FR4, particularly Vκ1 FR4, Vκ3 FR4, and a Vλ FR4. Suitable Vκ1 frameworks FR1 to 3 are set forth in SEQ ID NO: 27 (Table 1, FR regions are marked in non-bold). Suitable Vκ1 frameworks FR1 to 3 comprise the amino acid sequences having at least 60, 70, 80, 90 percent identity to amino acid sequences corresponding to FR1 to 3 and taken from SEQ ID NO: 27 (Table 1, FR regions are marked in non-bold).

Alternative examples of Vκ1 sequences, and examples of Vκ2, Vκ3 or Vκ4 sequences, may be found in Knappik et al., J. Mol. Biol. 296 (2000) 57-86.

Suitable Vλ FR4s are as set forth in SEQ ID NO: 62 to SEQ ID NO: 68. In a preferred embodiment, Vλ FR4 is as set forth in SEQ ID NO: 62 or 63, more preferably Vλ FR4 is as set forth in SEQ ID NO: 62. In one embodiment the present invention provides an isolated antibody that specifically binds CD137 (e.g., human CD137 protein), wherein said antibody comprises Vλ FR4 comprising the amino acid sequence having at least 60, 70, 80, 90 percent identity to comprising an amino acid sequence selected from any of SEQ ID NO: 62 to SEQ ID NO: 68, preferably to SEQ ID NO: 62 or 63, more preferably to SEQ ID NO: 62.

In one embodiment, the antibody of the invention having a binding specificity for human CD137 comprises:
(i) the HCDR1, HCDR2, and HCDR3 sequences of:
a. SEQ ID NOs: 1, 2, and 3, respectively, and the LCDR1, LCDR2, and LCDR3 sequences of SEQ ID NOs: 18, 19, and 20, respectively; or
b. SEQ ID NOs: 36, 37, and 38, respectively, and the LCDR1, LCDR2, and LCDR3 sequences of SEQ ID NOs: 49, 50, and 51, respectively;
(ii) VH3 or VH4 domain framework sequences FR1 to FR4; preferably VH3 domain framework sequences FR1 to FR4; and
(iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and a Vλ FR4, particularly Vλ FR4 comprising the amino acid sequence having at least 60, 70, 80, 90 percent identity to comprising an amino acid sequence selected from any of SEQ ID NO: 62 to SEQ ID NO: 68, more particularly Vλ FR4 comprising an amino acid sequence selected from any of SEQ ID NO: 62 to SEQ ID NO: 68, preferably Vλ FR4 comprising an amino acid sequence SEQ ID NO: 62.

In one embodiment, the present invention thus provides an antibody having a binding specificity for human CD137 comprising:
(i) the HCDR1, HCDR2, and HCDR3 sequences of:
a. SEQ ID NOs: 4, 6, and 7, respectively, and the LCDR1, LCDR2, and LCDR3 sequences of SEQ ID NOs: 21, 22, and 23, respectively;
b. SEQ ID NOs: 5, 6, and 7, respectively, and the LCDR1, LCDR2, and LCDR3 sequences of SEQ ID NOs: 21, 22, and 23, respectively; or
c. SEQ ID NOs: 39, 40, and 41, respectively, and the LCDR1, LCDR2, and LCDR3 sequences of SEQ ID NOs: 52, 53, and 54, respectively
(ii) VH3 or VH4 domain framework sequences FR1 to FR4; preferably VH4 domain framework sequences FR1 to FR4, more preferably VH3 domain framework sequences FR1 to FR4; and
(iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and a Vλ FR4, particularly Vλ FR4 comprising the amino acid sequence having at least 60, 70, 80, 90 percent identity to an amino acid sequence selected from any of SEQ ID NO: 62 to SEQ ID NO: 68, preferably Vλ FR4 is as set forth in SEQ ID NO: 62 to SEQ ID NO: 68, more preferably Vλ FR4 is as set forth in SEQ ID NO: 62.

In one embodiment, the present invention thus provides an antibody having a binding specificity for human CD137 and comprising a VL comprising:
(i) CDR domains CDR1, CDR2 and CDR3;
(ii) human Vκ framework regions FR1 to FR3, particularly human Vκ1 framework regions FR1 to FR3;
(iii) FR4, which is selected from (a) a human Vλ germ line sequence for FR4, particularly a Vλ germ line sequence selected from the list of: SEQ ID NO: 62 to 68, preferably SEQ ID NO: 62; and (b) a Vk-based sequence, which has one or two mutations, particularly one mutation, compared to the closest human Vλ germ line sequence for FR4 comprising an amino acid sequence selected from any of SEQ ID NO: 62 to SEQ ID NO: 68, preferably SEQ ID NO: 62.

In a preferred embodiment, the present invention provides an antibody having a binding specificity for human CD137 and comprising:
(i) the HCDR1, HCDR2, and HCDR3 sequences of:
   a. SEQ ID NOs: 4, 6, and 7, respectively, and the LCDR1, LCDR2, and LCDR3 sequences of SEQ ID NOs: 21, 22, and 23, respectively;
   b. SEQ ID NOs: 5, 6, and 7, respectively, and the LCDR1, LCDR2, and LCDR3 sequences of SEQ ID NOs: 21, 22, and 23, respectively; or
   c. SEQ ID NOs: 39, 40, and 41, respectively, and the LCDR1, LCDR2, and LCDR3 sequences of SEQ ID NOs: 52, 53, and 54, respectively
(ii) VH4 domain framework sequences; and
(iii) a VL domain comprising a VL framework comprising Vκ1 frameworks FR1, FR2 and FR3, and a Vλ FR4 comprising the amino acid sequence having at least 60, 70, 80, 90 percent identity to comprising an amino acid sequence selected from any of SEQ ID NO: 62 to SEQ ID NO: 68, particularly Vλ FR4 as set forth in SEQ ID NO: 62 to SEQ ID NO: 68, preferably SEQ ID NO: 62.

In a more preferred embodiment, the antibody of the invention having a binding specificity for human CD137 comprises:
(i) the HCDR1, HCDR2, and HCDR3 sequences of SEQ ID NOs: 1, 2, and 3, respectively, and the LCDR1, LCDR2, and LCDR3 sequences of SEQ ID NOs: 18, 19, and 20, respectively;
(ii) VH3 domain framework sequences; and
(iii) a VL domain comprising a VL framework comprising Vκ1 frameworks FR1, FR2 and FR3, and a Vλ FR4 comprising the amino acid sequence having at least 60, 70, 80, 90 percent identity to comprising an amino acid sequence selected from any of SEQ ID NO: 62 to SEQ ID NO: 68, particularly Vλ FR4 as set forth in SEQ ID NO: 62 to SEQ ID NO: 68, preferably SEQ ID NO: 62.

The present invention provides an isolated antibody that specifically binds CD137 (e.g., human CD137 protein), wherein said antibody comprises a VH domain listed in Table 1.

The invention also provides an isolated antibody that specifically binds to CD137, wherein said antibody comprises a VH amino acid sequence listed in Table 1, wherein no more than about 10 amino acids in a framework sequence (for example, a sequence which is not a CDR) have been mutated (wherein a mutation is, as various non-limiting examples, an addition, substitution or deletion).

The invention also provides an isolated antibody that specifically binds to CD137, wherein said antibody comprises a VH amino acid sequence listed in Table 1, wherein no more than about 20 amino acids in a framework sequence (for example, a sequence which is not a CDR) have been mutated (wherein a mutation is, as various non-limiting examples, an addition, substitution or deletion).

Other antibodies of the invention include amino acids that have been mutated, yet specifically bind to CD137 and have at least 60, 70, 80, 90, 91, 92, 93, 94, 95, 96, 97, 98 or 99 percent identity in the VH regions with the VH regions depicted in the sequences described in Table 1.

The present invention provides an isolated antibody that specifically binds to CD137 protein, said antibody comprises a VL domain listed in Table 1.

The invention also provides an isolated antibody that specifically binds to CD137, wherein said antibody comprises a VL amino acid sequence listed in Table 1, wherein no more than about 10 amino acids in a framework sequence (for example, a sequence which is not a CDR) have been mutated (wherein a mutation is, as various non-limiting examples, an addition, substitution or deletion).

The invention also provides an isolated antibody that specifically binds to CD137, wherein said antibody comprises a VL amino acid sequence listed in Table 1, wherein no more than about 20 amino acids in a framework sequence (for example, a sequence which is not a CDR) have been mutated (wherein a mutation is, as various non-limiting examples, an addition, substitution or deletion).

Other antibodies of the invention include amino acids that have been mutated, yet specifically bind to CD137 and have at least 60, 70, 80, 90, 91, 92, 93, 94, 95, 96, 97, 98 or 99 percent identity in the VL regions with the VL regions depicted in the sequences described in Table 1.

The invention also provides an isolated antibody that specifically binds to CD137, wherein said antibody comprises a heavy chain variable region comprising an amino acid sequence that is at least 60, 70, 80, 90, 91, 92, 93, 94, 95, 96, 97, 98 or 99 percent, preferably at least 90 percent, identical to the amino acid sequence selected from the group consisting of SEQ ID NOs: 14, 15, 16, 17 and 48, preferably SEQ ID NO: 17; and a light chain variable region comprising an amino acid sequence that is at least 60, 70, 80, 90, 91, 92, 93, 94, 95, 96, 97, 98 or 99 percent, preferably at least 90 percent, identical to the amino acid sequence selected from the group consisting of SEQ ID NOs: 27, 28, 29, 30 and 58, preferably SEQ ID NO: 30.

In one embodiment, the antibody of the invention having a binding specificity for human CD137 comprises: a heavy chain variable region comprising an amino acid sequence selected from any of SEQ ID NOs: 14, 15, 16, 17 and 48, preferably SEQ ID NO: 17; and a light chain variable region comprising an amino acid sequence selected from any of SEQ ID NOs: 27, 28, 29, 30 and 58, preferably SEQ ID NO: 30.

In one embodiment, the antibody of the invention having a binding specificity for human CD137 comprises:
(a) HCDR1, HCDR2, and HCDR3 sequences of SEQ ID NOs: 4, 6, and 7, respectively, and LCDR1, LCDR2, and LCDR3 sequences of SEQ ID NOs: 21, 22, and 23, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 14, and a VL sequence comprising an amino acid sequence that is at least 60, 70, 80, 90, 91, 92, 93, 94, 95, 96, 97, 98 or 99 percent, preferably at least 90 percent, identical to SEQ ID NO: 27;
(b) HCDR1, HCDR2, and HCDR3 sequences of SEQ ID NOs: 4, 6, and 7, respectively, and LCDR1, LCDR2, and LCDR3 sequences of SEQ ID NOs: 21, 22, and 23, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 15, and a VL sequence comprising an amino acid sequence that is at least 60, 70, 80, 90, 91, 92, 93, 94, 95, 96, 97, 98 or 99 percent, preferably at least 90 percent, identical to SEQ ID NO: 28;
(c) HCDR1, HCDR2, and HCDR3 sequences of SEQ ID NOs: 5, 6, and 7, respectively, and LCDR1, LCDR2, and LCDR3 sequences of SEQ ID NOs: 21, 22, and 23, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 16, and a VL sequence comprising an amino acid sequence that is at least 60, 70, 80, 90, 91, 92, 93, 94, 95, 96, 97, 98 or 99 percent, preferably at least 90 percent, identical to SEQ ID NO: 29; or (d) HCDR1, HCDR2, and HCDR3 sequences of SEQ ID NOs: 39, 40, and 41, respectively, and LCDR1, LCDR2, and LCDR3 sequences of SEQ ID NOs: 52, 53, and 54, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 48, and a VL sequence comprising an amino acid sequence that is at least 60, 70, 80, 90, 91, 92, 93, 94, 95, 96, 97, 98 or 99 percent, preferably at least 90 percent, identical to SEQ ID NO: 58.

In one embodiment, the antibody of the invention having a binding specificity for human CD137 comprises:

(a) HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively, a VH sequence at least 60, 70, 80, 90, 91, 92, 93, 94, 95, 96, 97, 98 or 99 percent identical to the amino acid sequence SEQ ID NO: 14, and a VL sequence at least 60, 70, 80, 90, 91, 92, 93, 94, 95, 96, 97, 98 or 99 percent identical to the amino acid sequence SEQ ID NO: 27;

(b) HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively, a VH sequence at least 60, 70, 80, 90, 91, 92, 93, 94, 95, 96, 97, 98 or 99 percent identical to the amino acid sequence SEQ ID NO: 15, and a VL sequence at least 60, 70, 80, 90, 91, 92, 93, 94, 95, 96, 97, 98 or 99 percent identical to the amino acid sequence SEQ ID NO: 28;

(c) HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively, a VH sequence at least 60, 70, 80, 90, 91, 92, 93, 94, 95, 96, 97, 98 or 99 percent identical to the amino acid sequence SEQ ID NO: 16, and a VL sequence at least 60, 70, 80, 90, 91, 92, 93, 94, 95, 96, 97, 98 or 99 percent identical to the amino acid sequence SEQ ID NO: 29;

(d) HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively, a VH sequence at least 60, 70, 80, 90, 91, 92, 93, 94, 95, 96, 97, 98 or 99 percent identical to the amino acid sequence SEQ ID NO: 17, and a VL sequence at least 60, 70, 80, 90, 91, 92, 93, 94, 95, 96, 97, 98 or 99 percent identical to the amino acid sequence SEQ ID NO: 30, preferably wherein said VH comprises a G51C mutation (AHo numbering) and said VL comprises T141C mutation (AHo numbering); or (e) HCDR1, HCDR2, and HCDR3 sequences of SEQ ID NOs: 36, 37, and 38, respectively, and LCDR1, LCDR2, and LCDR3 sequences of SEQ ID NOs: 49, 50, and 51, respectively, a VH sequence at least 60, 70, 80, 90, 91, 92, 93, 94, 95, 96, 97, 98 or 99 percent identical to the amino acid sequence SEQ ID NO: 48, and a VL sequence at least 60, 70, 80, 90, 91, 92, 93, 94, 95, 96, 97, 98 or 99 percent identical to the amino acid sequence SEQ ID NO: 58.

In a preferred embodiment, the antibody of the invention having a binding specificity for human CD137 comprises HCDR1, HCDR2, and HCDR3 sequences of SEQ ID NOs: 1, 2, and 3, respectively, and LCDR1, LCDR2, and LCDR3 sequences of SEQ ID NOs: 18, 19, and 20, respectively, a VH sequence at least 60, 70, 80, 90, 91, 92, 93, 94, 95, 96, 97, 98 or 99 percent identical to the amino acid sequence SEQ ID NO: 17, and a VL sequence at least 60, 70, 80, 90, 91, 92, 93, 94, 95, 96, 97, 98 or 99 percent identical to the amino acid sequence SEQ ID NO: 30, preferably wherein said VH comprises a G51C mutation (AHo numbering) and said VL comprises T141C mutation (AHo numbering).

Suitably, said antibody of the present invention is mutated to form an artificial interdomain disulfide bridge within the framework region, in particular wherein the pair of cysteins replaces Gly 51 (AHo numbering) on said VH and Thr 141 (AHo numbering) on said VL. It was surprisingly found that such antibody of the present invention comprising an interdomain disulfide bridge has a significantly increased thermostability.

The term "artificial" with reference to a disulfide bridge ("S—S bridge" or "diS") means that the S—S bridge is not naturally formed by the wild-type antibody, but is formed by an engineered mutant of a parent molecule, wherein at least one foreign amino acid contributes to the disulfide bonding. The site-directed engineering of artificial disulfide bridges clearly differentiates from those naturally available in native immunoglobulins or in modular antibodies, such as those described in WO 2009/000006A1, because at least one of the sites of bridge piers of an artificial disulfide bridge is typically located aside from the positions of Cys residues in the wild-type antibody, thus, providing for an alternative or additional disulfide bridge within the framework region. The artificial disulfide bridge of the present invention may be engineered within an antibody domain ("intradomain bridge"), which would stabilize the beta-sheet structure or bridging the domains ("interdomain bridge") or chains of domains ("interchain bridge"), to constrain the structure of the multispecific antibody according to the invention and support its interaction with potential binding partners.

In a further embodiment, the isolated antibody of the invention having a binding specificity for human CD137 comprises: (a) a VH sequence of SEQ ID NO: 14 and a VL sequence of SEQ ID NO: 27; (b) a VH sequence of SEQ ID NO: 15 and a VL sequence of SEQ ID NO: 28; (c) a VH sequence of SEQ ID NO: 16 and a VL sequence of SEQ ID NO: 29; (d) a VH sequence of SEQ ID NO: 17 and a VL sequence of SEQ ID NO: 30; or (e) a VH sequence of SEQ ID NO: 48 and a VL sequence of SEQ ID NO: 58. In a preferred embodiment, the isolated antibody of the invention having a binding specificity for human CD137 comprises a VH sequence of SEQ ID NO: 17 and a VL sequence of SEQ ID NO: 30.

In one embodiment, an antibody that specifically binds to CD137 is an antibody that is described in Table 1. In one embodiment, an antibody that specifically binds to CD137 is as set forth in SEQ ID NO: 32, SEQ ID NO: 33, SEQ ID NO: 34, SEQ ID NO: 35 or SEQ ID NO: 60. In one embodiment, an antibody that specifically binds to CD137 is as set forth in SEQ ID NO: 34. In one embodiment, an antibody that specifically binds to CD137 is as set forth in SEQ ID NO: 32 or SEQ ID NO: 35. In a preferred embodiment, an antibody that specifically binds to CD137 is as set forth in SEQ ID NO: 35.

Other antibodies of the invention include those wherein the amino acids or nucleic acids encoding the amino acids have been mutated, yet have at least 60, 70, 80, 90 or 95 percent identity to the sequences described in Table 1. In one embodiment, it includes mutant amino acid sequences wherein no more than 1, 2, 3, 4 or 5 amino acids have been mutated in the variable regions when compared with the variable regions depicted in the sequence described in Table 1, while retaining substantially the same therapeutic activity. The term "substantially the same activity" as used herein refers to the activity as indicated by substantially the same activity being at least 50%, at least 60%, at least 70%, at least 80%, at least 90%, at least 95%, at least 98% or even at least 100% or at least 110%, or at least 120%, or at least 130%, or at least 140%, or at least 150%, or at least 160%, or at least 170%, or at least 180%, or at least 190%, e.g. up to 200% of the activity as determined for the parent antibody, e.g., the antibody of the invention, in particular the antibody of the invention described in Table 1.

Given that each of these antibodies can bind to CD137 and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and match, although each antibody must contain a VH CDR1, 2 and 3 and a VL CDR1, 2 and 3 to create other CD137-binding binding molecules of the invention. Such "mixed and matched" CD137-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by mutating one or more VH and/or VL CDR region sequences with structurally similar sequences from the CDR sequences shown herein for monoclonal antibodies of the present invention.

In yet another embodiment, the present invention provides an antibody comprising amino acid sequences that are homologous to the sequences described in Table 1, and said antibody binds to CD137, and retains the desired functional properties of those antibodies described in Table 1.

For example, the invention provides an isolated monoclonal antibody comprising a heavy chain variable region and a light chain variable region, wherein the heavy chain variable region comprises an amino acid sequence that is at least 80 percent, at least 90 percent, or at least 95 percent identical to an amino acid sequence selected from the group consisting of SEQ ID NOs: 14, 15, 16, 17 and 48, preferably SEQ ID NO: 17; the light chain variable region comprises an amino acid sequence that is at least 80 percent, at least 90 percent, or at least 95 percent identical to an amino acid sequence selected from the group consisting of SEQ ID NOs: 27, 28, 29, 30 and 58, preferably SEQ ID NO: 30; wherein the antibody specifically binds to human CD137 protein.

In one embodiment, the VH and/or VL amino acid sequences may be 50 percent, 60 percent, 70 percent, 80 percent, 90 percent, 95 percent, 96 percent, 97 percent, 98 percent or 99 percent identical to the sequences set forth in Table 1. In one embodiment, the VH and/or VL amino acid sequences may be identical except an amino acid substitution in no more than 1, 2, 3, 4 or 5 amino acid positions.

In one embodiment, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the CD137-binding antibodies of the invention.

The term "conservatively modified variant" or "conservative variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations", which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" or "conservative variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In one embodiment, the term "conservative sequence modifications" are used to refer to amino acid modifications that do not significantly affect or alter the binding characteristics of the antibody containing the amino acid sequence.

Accordingly, the invention provides an isolated monoclonal antibody comprising or consisting of a heavy chain variable region comprising CDR1, CDR2, and CDR3 sequences and a light chain variable region comprising CDR1, CDR2, and CDR3 sequences, wherein: the heavy chain variable region CDR1 comprises, preferably consists of, an amino acid sequence selected from any of SEQ ID NOs: 1, 4, 5, 8, 11, 36, 39, 42 and 45, preferably SEQ ID NO: 1, or conservative variants thereof; the heavy chain variable region CDR2 comprises, preferably consists of, an amino acid sequence selected from any of SEQ ID NOs: 2, 6, 9, 12, 37, 40, 43 and 46, preferably SEQ ID NO: 2, or conservative variants thereof; the heavy chain variable region CDR3 comprises, preferably consists of, an amino acid sequence selected from any of SEQ ID NOs: 3, 7, 10, 13, 38, 41, 44 and 47, preferably SEQ ID NO: 3, or conservative variants thereof;

the light chain variable region CDR1 comprises, preferably consists of, an amino acid sequence selected from any of SEQ ID NOs: 18, 21, 24, 49, 52, and 55, preferably SEQ ID NO: 18, or conservative variants thereof; the light chain variable region CDR2 comprises, preferably consists of, an amino acid sequence selected from any of SEQ ID NOs: 19, 22, 25, 50, 53, and 56, preferably SEQ ID NO: 19, or conservative variants thereof; and the light chain variable region CDR3 comprises, preferably consists of, an amino acid sequence selected from any of SEQ ID NOs: 20, 23, 26, 51, 54, and 57, preferably SEQ ID NO: 20, or conservative variants thereof;

wherein the antibody specifically binds to CD137 and is capable of activating CD137 signaling with or without additional cross-linking.

In one embodiment, an antibody of the invention is optimized for expression in a mammalian cell has a heavy chain variable region and a light chain variable region, wherein one or more of these sequences have specified amino acid sequences based on the antibodies described herein or conservative modifications thereof, and wherein the antibodies retain the desired functional properties of the CD137-binding antibodies of the invention. Accordingly, the invention provides an isolated monoclonal antibody optimized for expression in a mammalian cell comprising a heavy chain variable region and a light chain variable region wherein: the heavy chain variable region comprises an amino acid sequence selected from any of SEQ ID NOs: 14, 15, 16, 17 and 48, preferably SEQ ID NO: 17, and conservative modifications thereof; and the light chain variable region comprises an amino acid sequence selected from any of SEQ ID NOs: 27, 28, 29, 30 and 58, preferably SEQ ID NO: 30, and conservative modifications thereof; wherein the antibody specifically binds to CD137 and is capable of activating CD137 signaling with or without additional cross-linking.

In one embodiment, an antibody of the invention is optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the CD137-binding antibodies of the invention.

As used herein, the term, "optimized" means that a nucleotide sequence has been altered to encode an amino acid sequence using codons that are preferred in the production cell or organism, generally a eukaryotic cell, for example, a cell of *Pichia*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation (s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

An "affinity-matured" antibody is one with one or more alterations in one or more variable domains thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al, Bio/Technology 10:779-783 (1992) describes affinity maturation by VH- and VL-domain shuffling. Random mutagenesis of hypervariable region (HVR) and/or framework residues is described by, for example: Barbas et al. Proc Nat. Acad. Sci. USA 91:3809-3813 (1994); Schier et al. Gene 169:147-155 (1995); Jackson et al, J. Immunol. 154(7): 3310-9 (1995); and Hawkins et al, J. Mol. Biol. 226:889-896 (1992).

In one embodiment, an "affinity-matured" antibody of the invention comprises: a VH4 comprising I44V; F89V; Y105F mutations, in particular comprising an amino acid sequence according to SEQ ID NO: 15; and a VL comprising A51P mutation, in particular comprising an amino acid sequence according to SEQ ID NO: 28.

In another embodiment, an "affinity-matured" antibody of the invention comprises: a VH4 comprising V25A; I44V; V82K; F89V; Y105F mutations, in particular comprising an amino acid sequence according to SEQ ID NO: 16; and a VL comprising I2L; A51P mutations, in particular comprising an amino acid sequence according to SEQ ID NO: 29.

An antibody of the invention further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad., U.S.A. 86: 10029-10033; U.S. Pat. No. 5,225,539 to Winter, and U.S. Pat. Nos. 5,530,101; 5,585,089; 5,693,762 and 6,180,370 to Queen et al.).

Such framework sequences can be obtained from public DNA databases or published references that include germline antibody gene sequences or rearranged antibody sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol.

227:776-798; and Cox, J. P. L. et al., 1994 Eur. J Immunol. 24:827-836; the contents of each of which are expressly incorporated herein by reference. For example, germline DNA sequences for human heavy and light chain variable region genes and rearranged antibody sequences can be found in "IMGT" database (available on the Internet at www.imgt.org; see Lefranc, M. P. et al., 1999 Nucleic Acids Res. 27:209-212; the contents of each of which are expressly incorporated herein by reference).

An example of framework sequences for use in the antibodies of the invention are those that are structurally similar to the framework sequences used by selected antibodies of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

A wide variety of antibody/immunoglobulin frameworks or scaffolds can be employed so long as the resulting polypeptide includes at least one binding region which specifically binds to CD137. Such frameworks or scaffolds include the five main idiotypes of human immunoglobulins, antigen-binding fragments thereof, and include immunoglobulins of other animal species, preferably having humanized aspects.

In one aspect, the invention pertains to a method of generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target CD137 protein. Known non-immunoglobulin frameworks or scaffolds include, but are not limited to, fibronectin (Compound Therapeutics, Inc., Waltham, Mass.), ankyrin (Molecular Partners AG, Zurich, Switzerland), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

Suitably, the antibodies of the invention specifically bind to CD137 and is characterized by one or more of the following parameters:
 (i) binds to human CD137 with a dissociation constant (KD) of less than 50 nM, particularly less than 10 nM, particularly less than 5 nM, particularly less than 1 nM, particularly less than 500 pM, more particularly less than 100 pM, more particularly less than 50 pM, in particular as measured by surface plasmon resonance (SPR), particularly wherein said antibody is an scFv;
 (ii) binds to human CD137 with a $K_{off}$ rate of $10^{-3}$ $s^{-1}$ or less, or $10^{-4}$ $s^{-1}$ or less, or $10^{-5}$ $s^{-1}$ or less as measured by SPR;
 (iii) binds to human CD137 with a $K_a$, rate of at least 104 $M^{-1}s^{-1}$ or greater, at least $10^5$ $M^{-1}s^{-1}$ or greater, at least $10^6$ $M^{-1}s^{-1}$ or greater, as measured by SPR;
 (iv) optionally, does not cross-compete with urelumab and/or utolimumab;
 (v) is cross-reactive with *Macaca fascicularis* (Cynomolgus) CD137, in particular binds to Cynomolgus PDL1 with a KD of less than 15 nM, particularly less than 10 nM, particularly less than 5 nM as measured by SPR, particularly wherein said antibody is an scFv; and/or
 (vi) does not bind to human CD40 and/or human OX40, in particular as measured by SPR;
 (vii) optionally, does not inhibit the interaction between CD137 and its ligand CD137L, in particular as measured by the competition ELISA.

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

"Binding affinity" generally refers to the strength of the sum total of non-covalent interactions between a single binding site of a molecule (e.g., of an antibody) and its binding partner (e.g., an antigen). Unless indicated otherwise, as used herein, "binding affinity", "bind to", "binds to" or "binding to" refers to intrinsic binding affinity that reflects a 1:1 interaction between members of a binding pair (e.g., an antibody fragment and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity, i.e. binding strength are described in the following.

The term "$K_{assoc}$", "Ka" or "$K_{on}$", as used herein, is intended to refer to the association rate of a particular antibody-antigen interaction, whereas the term "$K_{dis}$", "Kd" or "$K_{off}$", as used herein, is intended to refer to the dissociation rate of a particular antibody-antigen interaction. In one embodiment, the term "KD", as used herein, is intended to refer to the dissociation constant, which is obtained from the ratio of Kd to Ka (i.e. Kd/Ka) and is expressed as a molar concentration (M). The "KD" or "KD value" or "$K_D$" or "$K_D$ value" according to this invention is in one embodiment measured by using surface-plasmon resonance assays using a MASS-1 SPR instrument (Sierra Sensors). To measure affinity, an antibody specific for the Fc region of rabbit IgGs (Bethyl Laboratories, Cat. No. A120-111A) is immobilized on a sensor chip (SPR-2 Affinity Sensor, High Capacity Amine, Sierra Sensors) using a standard amine-coupling procedure. Rabbit monoclonal antibodies in B-cell supernatants are captured by the immobilized anti-rabbit IgG antibody. A minimal IgG concentration in the B-cell supernatants is required to allow sufficient capture. After capturing of the monoclonal antibodies, human CD137 ECD (Peprotech, cat. 310-15-1MG) is injected into the flow cells for 3 min at a concentration of 90 nM, and dissociation of the protein from the IgG captured on the sensor chip is allowed to proceed for 5 min. After each injection cycle, surfaces are regenerated with two injections of 10 mM Glycine-HCl. The apparent dissociation (kd) and association (ka) rate constants and the apparent dissociation equilibrium constant (KD) are calculated with the MASS-1 analysis software (Analyzer, Sierra Sensors) using one-to-one Langmuir binding model and quality of the fits is monitored based on relative Chi$^2$ (Chi$^2$ normalized to the extrapolated maximal binding level of the analyte), which is a measure for the quality of the curve fitting. The smaller the value for the Chi$^2$ the more accurate is the fitting to the one-to-one Langmuir binding model. Results are deemed valid if the response units (RU) for ligand binding are at least 2% of the RUs for antibody capturing. Samples with RUs for ligand binding with less than 2% of the RUs for antibody capturing are considered to show no specific binding of CD137 to the captured antibody. The equilibrium dissociation constant ($K_D$) is calculated as the ratio $k_{off}/k_{on}$. See, e.g., Chen et al, J. Mol. Biol. 293: 865-881 (1999).

Suitably, the affinity of the antibody of the invention to CD137 may be comparable to or higher than the affinity of CD137L to CD137. Suitably, the affinity of the antibody of the invention to CD137 may be comparable to or higher than the affinity of urelumab to CD137. It will be appreciated that the higher affinity of the CD137 antibody may be particularly suitable for use, wherein said antibody is monovalent for CD137. The binding affinity of an antibody, may be determined, for example, by the dissociation constant (KD). A stronger affinity is represented by a lower KD, while a weaker affinity is represented by a higher KD.

Thus, in a suitable embodiment, the antibody of the invention may have a KD of between 5 to 50,000 pM, 5 to 40,000 pM, 5 to 30,000 pM, 5 to 20,000 pM, 5 to 10,000 pM, 5 to 5,000 pM, 5 to 2,500 pM, 5 to 1,000 pM, 5 to 750 pM, 5 to 500 pM, 5 to 250 pM, 5 to 100 pM, 5 to 75 pM, 5 to 50 pM, 5 to 30 pM, in particular as measured by SPR. In a further embodiment, the antibody of the invention binds to human CD137 with a KD of between 10 nM and 10 pM, preferably between 10 nM and 0.1 nM, more preferably between 5 nM and 1 nM, in particular as measured by SPR.

In a suitable embodiment, the antibody of the invention may have a KD of less than approximately 50 nM, less than approximately 45 nM, less than approximately 40 nM, less than approximately 35 nM, less than approximately 30 nM, less than approximately 25 nM, less than 20 nM, less than approximately 15 nM, less than approximately 10 nM, less than approximately 9 nM, less than approximately 8 nM, less than approximately 7 nM, less than approximately 6 nM, less than approximately 5 nM, less than approximately 4 nM, less than approximately 3 nM, less than 2 nM, less than 1 nM, less than 0.5 nM, less than 0.25 nM, or less than 0.1 nM, less than 50 pM, less than 40 pM, less than 30 pM, less than 20 pM, in particular as measured by SPR. Suitably, the antibody of the invention has a KD of less than 10 nM, in particular as measured by SPR. Preferably, the c antibody of the invention binds to human CD137 with a KD of less than 5 nM, in particular as measured by SPR. Suitably, the antibody of the invention has a KD of less than 1 nM, in particular as measured by SPR. Suitably, the antibody of the invention has a KD of less than 50 pM, in particular as measured by SPR.

Suitably, the antibody of the invention binds to human CD137 with a $K_{o1}$ rate of at least $10^3$ M$^{-1}$s$^{-1}$ or greater, at least $10^4$ M$^{-1}$s$^{-1}$ or greater, at least $5\times10^4$ M$^{-1}$s$^{-1}$ or greater, at least $10^5$ M$^{-1}$s$^{-1}$ or greater, at least $5\times10^5$ M$^{-1}$s$^{-1}$ or greater, at least $10^6$ M$^{-1}$s$^{-1}$ or greater, at least $5\times10^6$ M$^{-1}$s$^{-1}$ or greater, at least $10^7$ M$^{-1}$s$^{-1}$ or greater, at least $5\times10^7$ M$^{-1}$s$^{-1}$ or greater as measured by surface plasmon resonance (SPR). Suitably, the antibody of the invention has a $K_{on}$ rate of at least $10^4$ M$^{-1}$s$^{-1}$ or greater, in particular at least $10^5$ M$^{-1}$s$^{-1}$ or greater, as measured by SPR.

Suitably, the antibody of the invention binds to human CD137 with a $K_{off}$ rate of $10^{-3}$ s$^{-1}$ or less, $3\times10^{-3}$ s$^{-1}$ or less, $5\times10^{-3}$ s$^{-1}$ or less, $10^{-4}$ s$^{-1}$ or less, $5\times10^{-4}$ s$^{-1}$ or less, $10^{-5}$ s$^{-1}$ or less, $5\times10^{-5}$ s$^{-1}$ or less, $10^{-6}$ s$^{-1}$ or less, or $10^{-7}$ s$^{-1}$ or less as measured by surface plasmon resonance (SPR). Suitably, the antibody of the invention has a $K_{off}$ rate of $10^{-4}$ s$^{-1}$ or less, in particular $10^{-5}$ s$^{-1}$ or less as measured by SPR.

Suitably, the antibody of the invention has beneficial biophysical properties.

Suitably, the antibodies of the invention, when in scFv format, has a melting temperature (Tm), determined by differential scanning fluorimetry, of at least 50° C., preferably of at least 55° C., more preferably at least 60° C., in particular wherein said antibody is formulated in 50 mM phosphate-citrate buffer at pH 6.4, 150 mM NaCl. DSF is described earlier (Egan, et al., MAbs, 9(1) (2017), 68-84; Niesen, et al., Nature Protocols, 2(9) (2007) 2212-2221). The midpoint of transition for the thermal unfolding of the scFv constructs is determined by Differential Scanning Fluorimetry using the fluorescence dye SYPRO® Orange (see Wong & Raleigh, Protein Science 25 (2016) 1834-1840). Samples in phosphate-citrate buffer at pH 6.4 are prepared at a final protein concentration of 50 μg/mL and containing a final concentration of 5× SYPRO® Orange in a total volume of 100 μl. Twenty-five microliters of prepared samples are added in triplicate to white-walled AB gene PCR plates. The assay is performed in a qPCR machine used as a thermal cycler, and the fluorescence emission is detected using the software's custom dye calibration routine. The PCR plate containing the test samples is subjected to a temperature ramp from 25° C. to 96° C. in increments of 1° C. with 30 s pauses after each temperature increment. The total assay time is about two hours. The Tm is calculated by the software GraphPad Prism using a mathematical second derivative method to calculate the inflection point of the curve. The reported Tm is an average of three measurements.

Suitably, the antibodies of the invention, when in scFv format, has a loss in monomer content, after storage for at least two weeks, particularly for at least four weeks, at 4° C., of less than 5%, e.g. less than 4%, less than 3%, less than 2%, preferably less than 1%, when the antibody of the invention is at a starting concentration of 10 mg/ml, and in particular wherein the antibody of the invention is formulated in 50 mM phosphate citrate buffer with 150 mM NaCl at pH 6.4. Suitably, the antibodies of the invention, when in scFv format, has a loss in monomer content, after storage for at least two weeks, particularly for at least four weeks, at 40° C., of less than 5%, e.g. less than 4%, less than 3%, less than 2%, preferably less than 1%, when the antibody of the invention is at a starting concentration of 10 mg/ml, and in particular wherein the antibody of the invention is formulated in 50 mM phosphate citrate buffer with 150 mM NaCl at pH 6.4. The loss in monomer content is as determined by area under the curve calculation of SE-HPLC chromatograms. SE-HPLC is a separation technique based on a solid stationary phase and a liquid mobile phase as outlined by the USP chapter 621. This method separates molecules based on their size and shape utilizing a hydrophobic stationary phase and aqueous mobile phase. The separation of molecules is occurring between the void volume (V0) and the total permeation volume (VT) of a specific column. Measurements by SE-HPLC are performed on a Chromaster HPLC system (Hitachi High-Technologies Corporation) equipped with automated sample injection and a UV detector set to the detection wavelength of 280 nm. The equipment is controlled by the software EZChrom Elite (Agilent Technologies, Version 3.3.2 SP2) which also supports analysis of resulting chromatograms. Protein samples are cleared by centrifugation and kept at a temperature of 4-6° C. in the autosampler prior to injection. For the analysis of scFv samples the column Shodex KW403-4F (Showa Denko Inc., # F6989202) is employed with a standardized buffered saline mobile phase (50 mM sodium-phosphate pH 6.5, 300 mM sodium chloride) at the recommended flow rate of 0.35 mL/min. The target sample load per injection was 5 μg. Samples are detected by an UV detector at a wavelength of 280 nm and the data recorded by a suitable software suite. The resulting chromatograms are analyzed in the range of V0 to VT thereby excluding matrix associated peaks with >10 min elution time.

In one embodiment, an antibody of the invention does not cross-compete for binding with urelumab. The present invention provides an antibody that binds to a different epitope than urelumab. Urelumab, also referred to as BMS-663513, is a fully humanized IgG4 mAb from Bristol-Myers Squibb, and is described in WO 2004/010947, U.S. Pat. Nos. 6,887,673 and 7,214,493, which are hereby incorporated into the present application by reference in their entirety.

In one embodiment, an antibody of the invention does not cross-compete for binding with utomilumab. The present invention provides an antibody that binds to a different epitope than utomilumab. Utomilumab, also referred to as PF-05082566, is a fully human IgG2 mAb from Pfizer, and is described in WO 2012/032433 and U.S. Pat. No. 8,821,867, which is hereby incorporated into the present application by reference in its entirety.

In a further embodiment, an antibody of the invention does not cross-compete for binding with urelumab and utomilumab. The present invention provides an antibody that binds to a different epitope than urelumab and utomilumab.

The term "recognize" as used herein refers to an antibody that finds and interacts (e.g., binds) with its conformational epitope.

The terms "compete" or "cross-compete" and related terms are used interchangeably herein to mean the ability of an antibody to interfere with the binding of other antibodies or binding agents to CD137 in a standard competitive binding assay.

The ability or extent to which an antibody or other binding agent is able to interfere with the binding of another antibody or binding molecule to CD137, and therefore whether it can be said to cross-compete according to the invention, can be determined using standard competition binding assays. One particularly suitable quantitative cross-competition assay uses a FACS- or an AlphaScreen-based approach to measure competition between the labelled (e.g. His tagged, biotinylated or radioactive labelled) an antibody or fragment thereof and the other an antibody or fragment thereof in terms of their binding to the target. In general, a cross-competing antibody or fragment thereof is for example one which will bind to the target in the cross-competition assay such that, during the assay and in the presence of a second antibody or fragment thereof, the recorded displacement of the immunoglobulin single variable domain or polypeptide according to the invention is up to 100% (e.g. in FACS based competition assay) of the maximum theoretical displacement (e.g. displacement by cold (e.g. unlabeled) antibody or fragment thereof that needs to be cross-blocked) by the to be tested potentially cross-blocking antibody or fragment thereof that is present in a given amount. Preferably, cross-competing antibodies or fragments thereof have a recorded displacement that is between 10% and 100%, more preferred between 50% and 100%.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. "Conformational" and "linear" epitopes are distinguished in that the binding to the former but not the latter is lost in the presence of denaturing solvents.

The term "conformational epitope" as used herein refers to amino acid residues of an antigen that come together on the surface when the polypeptide chain folds to form the native protein, and show a significantly reduced rate of HD exchange due to Fab binding. The conformation epitope contains, but is not limited to, the functional epitope.

The term "linear epitope" refers to an epitope with all of the points of interaction between the protein and the interacting molecule (such as an antibody) occurring linearly along the primary amino acid sequence of the protein (continuous).

The antibodies of the present invention does not inhibit the binding of urelumab or utomilumab to CD137 protein, which demonstrates that the antibody of the invention cannot compete with urelumab or utomilumab for binding to CD137; such an antibody may, according to non-limiting theory, bind to a different (e.g., a structurally different or spatially remote) epitope on CD137 as urelumab or utomilumab.

The present invention also provides antibodies that bind to the same epitope as do the CD137-binding antibodies listed in Table 1. Additional antibodies can therefore be identified based on their ability to cross-compete (e.g., to competitively inhibit the binding of, in a statistically significant manner) with other antibodies of the invention in CD137 binding assays.

Suitably, the isolated antibody of the present invention is selected from the group consisting of: a monoclonal antibody, a chimeric antibody, an IgG antibody, a Fab, an Fv, an scFv, dsFv, a scAb, STAB, and binding domains based on alternative scaffolds including but limited to ankyrin-based domains, fynomers, avimers, anticalins, fibronectins, and binding sites being built into constant regions of antibodies (e.g. F-star's Modular Antibody Technology™).

Suitably, the isolated antibody of the invention is an Fv. Suitably, the isolated antibody of the invention is scFv antibody fragment. "Single-chain Fv" or "scFv" or "sFv" antibody fragments comprise the VH and VL domains of an antibody, wherein these domains are present in a single polypeptide chain. Generally, the Fv polypeptide further comprises a polypeptide linker between the VH and VL domains which enables the sFv to form the desired structure for target binding. "Single-chain Fv" or "scFv" antibody fragments comprise the VH and VL domains of antibody, wherein these domains are present in a single polypeptide chain. Generally, the scFv polypeptides further comprises a polypeptide linker between the VH and VL domains which enables the scFv to form the desired structure for antigen binding (see, for example, Plickthun, The pharmacology of Monoclonal Antibodies, vol. 113, Rosenburg and Moore eds., (Springer-Verlag, New York, 1994), pp. 269-315). In particular embodiments, said functional fragment is an scFv format comprising the linker according to SEQ ID NO: 31. In a further embodiment, the isolated antibody of the invention is a single-chain variable fragment (scFv) as shown in SEQ ID NO: 27, SEQ ID NO: 33, SEQ ID NO: 34, SEQ ID NO: 35 or SEQ ID NO: 60, preferably SEQ ID NO: 35. In one embodiment, the isolated antibody of the invention is a single-chain variable fragment (scFv) as shown in SEQ ID NO: 33. In one embodiment, the isolated antibody of the invention is a single-chain variable fragment (scFv) as shown in SEQ ID NO: 34. In a preferred embodiment, the isolated antibody of the invention is a single-chain variable fragment (scFv) as shown in SEQ ID NO: 35.

Suitably, the isolated antibody of the invention is IgG antibody fragment. The term "isotype" refers to the antibody class (e.g., IgM, IgE, IgG such as IgG1 or IgG4) that is provided by the heavy chain constant region genes. Isotype also includes modified versions of one of these classes, where modifications have been made to after the Fc function, for example, to enhance or reduce effector functions or binding to Fc receptors. In one embodiment, the isolated antibody of the invention is IgG selected from the group consisting of an IgG1, an IgG2, an IgG3 and an IgG4, preferably IgG4. Suitably, the isolated antibody of the invention is IgG4 comprising HCDR1, HCDR2, and HCDR3 sequences of SEQ ID NOs: 4, 6, and 7, respectively, LCDR1, LCDR2, and LCDR3 sequences of SEQ ID NOs: 21, 22, and 23, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 14, and a VL sequence comprising an amino acid sequence that is at least 60, 70, 80, 90, 91, 92, 93, 94, 95, 96, 97, 98 or 99 percent, preferably at least 90 percent, identical to SEQ ID NO: 27. In a more specific embodiment, the antibody of the invention is IgG4 comprising HCDR1, HCDR2, and HCDR3 sequences of SEQ ID NOs: 4, 6, and 7, respectively, LCDR1, LCDR2, and LCDR3 sequences of SEQ ID NOs: 21, 22, and 23, respectively, a heavy chain sequence comprising an amino acid sequence that is at least 60, 70, 80, 90, 91, 92, 93, 94, 95, 96, 97, 98 or 99 percent, preferably at least 90 percent, identical to SEQ ID NO: 89, and a light chain sequence comprising an amino acid sequence that is at least 60, 70, 80, 90, 91, 92, 93, 94, 95, 96, 97, 98 or 99 percent, preferably at least 90 percent, identical to SEQ ID NO: 88. Suitably, the isolated antibody of the invention is IgG4 comprising HCDR1, HCDR2, and HCDR3 sequences of SEQ ID NOs: 1, 2, and 3, respectively, LCDR1, LCDR2, and LCDR3 sequences of SEQ ID NOs: 18, 19, and 20, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 14, and a VL sequence comprising an amino acid sequence that is at least 60, 70, 80, 90, 91, 92, 93, 94, 95, 96, 97, 98 or 99 percent, preferably at least 90 percent, identical to SEQ ID NO: 27. In a more specific embodiment, the antibody of the invention is IgG4 comprising HCDR1, HCDR2, and HCDR3 sequences of SEQ ID NOs: 1, 2, and 3, respectively, LCDR1, LCDR2, and LCDR3 sequences of SEQ ID NOs: 18, 19, and 20, respectively, a heavy chain sequence comprising an amino acid sequence that is at least 60, 70, 80, 90, 91, 92, 93, 94, 95, 96, 97, 98 or 99 percent, preferably at least 90 percent, identical to SEQ ID NO: 89, and a light chain sequence comprising an amino acid sequence that is at least 60, 70, 80, 90, 91, 92, 93, 94, 95, 96, 97, 98 or 99 percent, preferably at least 90 percent, identical to SEQ ID NO: 88. In another particular embodiment, the isolated antibody of the invention is IgG4 comprising HCDR1, HCDR2, and HCDR3 sequences of SEQ ID NOs: 1, 2, and 3, respectively, LCDR1, LCDR2, and LCDR3 sequences of SEQ ID NOs: 18, 19, and 20, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 17, and a VL sequence comprising an amino acid sequence that is at least 60, 70, 80, 90, 91, 92, 93, 94, 95, 96, 97, 98 or 99 percent, preferably at least 90 percent, identical to SEQ ID NO: 30.

In another particular embodiment, the isolated antibody of the invention is a multispecific molecule, in particular a multispecific molecule having at least a second functional molecule, e.g., bispecific molecule, trispecific molecule, tetraspecific, pentaspecific, hexaspecific molecule.

The term "multispecific molecule" or "multispecific antibody" as used herein, refers to an antibody that binds to two or more different epitopes on at least two or more different targets (e.g., CD137 and another target different from CD137), or binds to two or more different epitopes of the same target. The term "multispecific molecule" includes bispecific, trispecific, tetraspecific, pentaspecific and hexaspecific antibodies. The term "bispecific antibody" as used herein, refers to an antibody that binds to two different epitopes on two different targets or on the same target. The term "trispecific antibody" as used herein, refers to an antibody that binds to three different epitopes on three different targets or on the same target.

An antibody of the invention can be derivatized or linked to another functional molecule, e.g., another peptide or protein (e.g., another antibody or ligand for a receptor) to generate a multispecific molecule that binds to at least two binding sites and/or different target molecules. The antibody of the invention may in fact be derivatized or linked to more than one other functional molecule to generate multispecific molecules that bind to more than two different binding sites and/or target molecules. To create a multispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a multispecific molecule results.

Accordingly, the present invention includes multispecific molecules comprising at least one first binding specificity for CD137 and a second binding specificity for a second target epitope. For example, the second target epitope is present on another target molecule different from CD137.

Bivalent CD137 antibodies were shown to be generally weak in their ability to induce the signaling in the absence of an exogenous clustering. To illustrate, anti-CD137 antibody utomilumab is only capable to activate CD137 signaling when either cross-linked to anti-human F(ab')2 secondary antibody or immobilized to tissue culture plastic (Fisher at al., Cancer Immunol Immunother 61:1721-1733 (2012)). Studies in rodent agonistic antibodies to CD40 (TNFRSF5), another member of TNFRSF, have suggested that the exogenous clustering can be partially achieved through the interaction with Fcγ-receptor (Li F, Ravetch JV, Science 333(6045):1030-10 (2011); White A L, et al., J Immunol 187(4):1754-1763 (2011)). The interaction with Fcy-receptor can however deplete the CD137-expressing cells through effector mechanisms. The current bivalent antibodies targeting CD137 are thus either ineffective agonists or lead to depleting of CD137-positive cells. Suitably, second binding specificity of the multispecific molecule is capable of providing additional cross-linking of the CD137-binding antibody of the present invention. Accordingly, the present invention includes multispecific molecules comprising at least one first binding specificity for CD137 and a second binding specificity for a second target epitope. For example, the second target epitope is another epitope of CD137 different from the first target epitope. The multispecific molecule can further include a third binding specificity, in addition to the first and second target epitope.

In a further embodiment, the present invention includes multispecific molecules monovalent, bivalent or multivalent for CD137 specificity, preferably monovalent.

In another particular embodiment of the present invention, the isolated antibody of the present invention is a monovalent or multivalent for CD137 specificity molecule, e.g., bivalent, trivalent, tetravalent, pentavalent, hexavalent.

The term "monovalent molecule" or "monovalent antibody", as used herein, refers to an antibody that binds to a single epitope on a target molecule, such as CD137.

The term "multivalent antibody" refers to a single binding molecule with more than one valency, where "valency" is described as the number of antigen-binding moieties that binds to epitopes on identical target molecules. As such, the single binding molecule can bind to more than one target molecule, or more than one binding site on a target molecule that contains multiple copies of the epitope. Examples of multivalent antibodies include, but are not limited to bivalent antibodies, trivalent antibodies, tetravalent antibodies, pentavalent antibodies, and the like. The term "bivalent antibody" as used herein, refers to an antibody that has two antigen binding moieties, each of which binds to an identical epitope.

Suitably, the isolated antibody of the present invention is a multispecific molecule, e.g., bispecific molecule, and/or a multivalent molecule, e.g., monovalent for CD137 specificity molecule, bivalent for CD137 specificity molecule, which is an antibody format selected from any suitable multispecific, e.g. bispecific, format known in the art, including, by way of non-limiting example, formats based on a single-chain diabody (scDb), a tandem scDb (Tandab), a linear dimeric scDb (LD-scDb), a circular dimeric scDb (CD-scDb), a bispecific T-cell engager (BiTE; tandem di-scFv), a tandem tri-scFv, a tribody (Fab-(scFv)2) or bibody (Fab-(scFv)1), Fab, Fab-Fv2, Morrison (IgG CH$_3$-scFv fusion (Morrison L) or IgG CL-scFv fusion (Morrison H)), triabody, scDb-scFv, bispecific Fab2, di-miniantibody, tetrabody, scFv-Fc-scFv fusion, scFv-HSA-scFv fusion, di-diabody, DVD-Ig, COVD, IgG-scFab, scFab-dsscFv, Fv2-Fc, IgG-scFv fusions, such as bsAb (scFv linked to C-terminus of light chain), Bs1Ab (scFv linked to N-terminus of light chain), Bs2Ab (scFv linked to N-terminus of heavy chain), Bs3Ab (scFv linked to C-terminus of heavy chain), Ts1Ab (scFv linked to N-terminus of both heavy chain and light chain), Ts2Ab (dsscFv linked to C-terminus of heavy chain), Bispecific antibodies based on heterodimeric Fc domains, such as Knob-into-Hole antibodies (KiHs) (bispecific IgGs prepared by the KiH technology); an Fv, scFv, scDb, tandem-di-scFv, tandem tri-scFv, Fab-(scFv) 2, Fab-(scFv)1, Fab, Fab-Fv2, COVD fused to the N- and/or the C-terminus of either chain of a heterodimeric Fc domain or any other heterodimerization domain, a MATCH (described in WO 2016/0202457; Egan T., et al., mAbs 9 (2017) 68-84) and DuoBodies (bispecific IgGs prepared by the Duobody technology) (MAbs. 2017 February/March; 9(2): 182-212. doi: 10.1080/19420862.2016.1268307).

The term "diabodies" refers to antibody fragments with two antigen-binding sites, which fragments comprise a VH connected to VL in the same polypeptide chain (VH-VL). By using a linker that is too short to allow pairing between the two domains on the same chain, the domains are forced to pair with the complementary domains of another chain to create two antigen-binding sites. In particular embodiments, said polypeptide linker comprises one or two units of four (4) glycine amino acid residues and one (1) serine amino acid residue (GGGGS)n, wherein n=1 or 2, preferably 1 (SEQ ID NO: 156). Diabodies may be bivalent or bispecific. Diabodies are described more fully in, for example, EP404097, WO 93/01161, Hudson et al., Nat. Med. 9:129-134 (2003), and Holliger et al., Proc. Natl. Acad. Sci. USA 90: 6444-6448 (1993). Triabodies and tetrabodies are also described in Hudson et al., Nat. Med. 9:129-134 (2003).

The bispecific scDb, in particular the bispecific monomeric scDb, particularly comprises two variable heavy chain domains (VH) or fragments thereof and two variable light chain domains (VL) or fragments thereof connected by linkers L1, L2 and L3 in the order VHA-L1-VLB-L2-VHB-L3-VLA, VHA-L1-VHB-L2-VLB-L3-VLA, VLA-L1-VLB-L2-VHB-L3-VHA, VLA-L1-VHB-L2-VLB-L3-VHA, VHB-L1-VLA-L2-VHA-L3-VLB, VHB-L1-VHA-L2-VLA-L3-VLB, VLB-L1-VLA-L2-VHA-L3-VHB or VLB-L1-VHA-L2-VLA-L3-VHB, wherein the VLA and VHA domains jointly form the antigen binding site for the first antigen, and VLB and VHB jointly form the antigen binding site for the second antigen.

The linker L1 particularly is a peptide of 2-10 amino acids, more particularly 3-7 amino acids, and most particularly 5 amino acids, and linker L3 particularly is a peptide of 1-10 amino acids, more particularly 2-7 amino acids, and most particularly 5 amino acids. In particular embodiments, the linker L1 and/or L3 comprises one or more units of four (4) glycine amino acid residues and one (1) serine amino acid residue (GGGGS)n, wherein n=1 or 2, preferably n=1 (SEQ ID NO: 156).

The middle linker L2 particularly is a peptide of 10-40 amino acids, more particularly 15-30 amino acids, and most particularly 20-25 amino acids. In particular embodiments, said linker L2 comprises one or more units of four (4) glycine amino acid residues and one (1) serine amino acid residue (GGGGS)n, wherein n=1, 2, 3, 4, 5, 6, 7 or 8, preferably n=4 (SEQ ID NO: 157).

In one embodiment of the present invention, the isolated antibody is a multispecific and/or multivalent antibody in a scDb-scFv format. The term "scDb-scFv" refers to an antibody format, wherein a single-chain Fv (scFv) fragment is fused by a flexible Gly-Ser linker to a single-chain diabody (scDb). In one embodiment, said flexible Gly-Ser linker is a peptide of 2-40 amino acids, e.g., 2-35, 2-30, 2-25, 2-20, 2-15, 2-10 amino acids, particularly 10 amino acids. In particular embodiments, said linker comprises one or more units of four (4) glycine amino acid residues and one (1) serine amino acid residue (GGGGS)n, wherein n=1, 2, 3, 4, 5, 6, 7 or 8, preferably n=2 (SEQ ID NO: 158).

In one embodiment of the present invention, the isolated antibody is a multispecific and/or multivalent antibody in a MATCH format described in WO 2016/0202457; Egan T., et al., mAbs 9 (2017) 68-84.

Multispecific and/or multivalent molecules of the present invention can be produced using any convenient antibody manufacturing method known in the art (see, e.g., Fischer, N. & Leger, O., Pathobiology 74 (2007) 3-14 with regard to the production of bispecific constructs; Hornig, N. & Färber-Schwarz, A., Methods Mol. Biol. 907 (2012)713-727, and WO 99/57150 with regard to bispecific diabodies and tandem scFvs). Specific examples of suitable methods for the preparation of the bispecific construct of the present invention further include, inter alia, the Genmab (see Labrijn et al., Proc. Natl. Acad. Sci. USA 110 (2013) 5145-5150) and Merus (see de Kruif et al., Biotechnol. Bioeng. 106 (2010) 741-750) technologies. Methods for production of bispecific antibodies comprising a functional antibody Fc part are also known in the art (see, e.g., Zhu et al., Cancer Lett. 86 (1994) 127-134); and Suresh et al., Methods Enzymol. 121 (1986) 210-228).

Other antibodies which can be employed in the multispecific and in the multivalent molecules of the invention are murine, chimeric and humanized monoclonal antibodies.

The multispecific molecules of the present invention can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis (2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, two or more binding specificities can be encoded in the same vector and expressed and assembled in the same host cell. This method is particularly useful where the bispecific molecule is a mAb×mAb, mAb×Fab, Fab×F(ab')2 or ligand×Fab fusion protein. A multispecific molecule of the invention can be a single chain molecule comprising one single chain antibody and a binding determinant, or a single chain multispecific molecule comprising two binding determinants. Multispecific molecules may comprise at least two single chain molecules. Methods for preparing multispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In a further aspect, the invention provides a nucleic acid encoding the antibody of the invention. The present invention also provides nucleic acid sequences that encode CDRs, VH, VL, the full length heavy chain, and the full length light chain of the antibodies that specifically bind to CD137 protein. Such nucleic acid sequences can be optimized for expression in mammalian cells.

The term "nucleic acid" is used herein interchangeably with the term "polynucleotide(s)" and refers to one or more deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphorates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260: 2605-2608, 1985; and Rossolini et al., Mol. Cell. Probes 8:91-98, 1994).

The invention provides substantially purified nucleic acid molecules which encode polypeptides comprising segments or domains of the CD137-binding antibody chains described above. When expressed from appropriate expression vectors, polypeptides encoded by these nucleic acid molecules are capable of exhibiting CD137 antigen binding capacity.

Also provided in the invention are polynucleotides which encode at least one CDR region and usually all three CDR regions from the heavy or light chain of the CD137-binding antibody set forth in Table 1. Some other polynucleotides encode all or substantially all of the variable region sequence of the heavy chain and/or the light chain of the CD137-binding antibody set forth in Table 1. Because of the degeneracy of the code, a variety of nucleic acid sequences will encode each of the immunoglobulin amino acid sequences.

The polynucleotide sequences can be produced by de novo solid-phase DNA synthesis or by PCR mutagenesis of an existing sequence (e.g., sequences as described in the Examples below) encoding a CD137-binding antibody or its binding fragment. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68: 109, 1979; the diethylphosphoramidite method of Beaucage et al., Tetra. Lett., 22: 1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the CD137-binding antibodies described above.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

Various expression vectors can be employed to express the polynucleotides encoding the CD137-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet. 15:345, 1997). For example, nonviral vectors useful for expression of the CD137-binding polynucleotides and polypeptides in mammalian (e.g., human) cells include pThioHis A, B and C, pcDNA3.1/His, pEBVHis A, B and C, (Invitrogen, San Diego, Calif.), MPS V vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68: 143, 1992.

The choice of expression vector depends on the intended host cells in which the vector is to be expressed. Typically, the expression vectors contain a promoter and other regulatory sequences (e.g., enhancers) that are operably linked to the polynucleotides encoding a CD137-binding antibody. In one embodiment, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a CD137-binding antibody. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20: 125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted CD137-binding antibody sequences. More often, the inserted CD137-binding antibody sequences are linked to signal sequences before inclusion in the vector. Vectors to be used to receive sequences encoding CD137-binding antibody light and heavy chain variable domains sometimes also encode constant regions or parts thereof. Such vectors allow expression of the variable regions as fusion proteins with the constant regions thereby leading to production of intact antibodies and antigen-binding fragments thereof. Typically, such constant regions are human.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The host cells for harboring and expressing the CD137-binding antibody chains can be either prokaryotic or eukaryotic. E. coli is one prokaryotic host useful for cloning and expressing the polynucleotides of the present invention. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express CD137-binding polypeptides of the invention. Insect cells in combination with baculovirus vectors can also be used.

In one embodiment, mammalian host cells are used to express and produce the CD137-binding polypeptides of the present invention. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPS V promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express CD137-binding antibody chains or binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type. The present invention thus provides a method of producing the antibody of the invention, wherein said method comprises the step of culturing a host cell comprising, in particular expressing, a nucleic acid or a vector encoding the antibody of the invention, whereby said antibody of the invention or a fragment thereof is expressed.

In a further aspect, the present invention relates to a pharmaceutical composition comprising the antibody of the present invention, and a pharmaceutically acceptable carrier. Pharmaceutically acceptable carriers enhance or stabilize the composition, or facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. Administration can be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., antibody, and multispecific molecule, may be coated in a material to protect the compound from the action of acids and other natural conditions that may inactivate the compound.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the CD137-binding antibody is employed in the pharmaceutical compositions of the invention. The CD137-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

Antibody is usually administered on multiple occasions. Intervals between single dosages can be weekly, monthly or yearly. Intervals can also be irregular as indicated by measuring blood levels of CD137-binding antibody in the patient. Alternatively, antibody can be administered as a sustained release formulation, in which case less frequent administration is required. Dosage and frequency vary depending on the half-life of the antibody in the patient. In general, humanized antibodies show longer half-life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

In one aspect, the invention provides a pharmaceutical combination comprising the anti-CD137 antibody of the invention, as defined herein, with one or more additional therapeutic agents, e.g., one or more anti-cancer agents, cytotoxic or cytostatic agents, hormone treatment, vaccines, and/or other immunotherapies. Suitably, the anti-CD137 antibody of the invention can be used in combination with an inhibitor of an inhibitory (or immune checkpoint) molecule chosen from PD-1, PDL1, PDL2, CTLA-4, TIM-3, LAG-3, CEACAM (e.g., CEACAM-1, CEACAM-3, and/or CEACAM-5), VISTA, BTLA, TIGIT, LAIR1, CD160, 2B4, TGFR beta, and IDO (indoleamine-2,3 dioxygenase). Inhibition of an inhibitory molecule can be performed by inhibition at the DNA, RNA or protein level.

It has been surprisingly found that the anti-CD137 antibody of the invention have a strong beneficial synergistic interaction and improved anti-proliferative activity when used in combination with PDL1 inhibitors. Thus, the invention provides a pharmaceutical combination comprising the anti-CD137 antibody of the invention, as defined herein, and a PDL1 inhibitor, particularly for use in the treatment or prevention of a proliferative disease. The present invention further relates to a pharmaceutical combination comprising the anti-CD137 antibody of the invention, as defined herein, and a PDL1 inhibitor, particularly for simultaneous, separate or sequential use in the treatment or prevention of a proliferative disease.

The term "combination" or "pharmaceutical combination" is defined herein to refer to either a fixed combination in one dosage unit form, a non-fixed combination or a kit of parts for the combined administration where the therapeutic agents, e.g., the anti-CD137 antibody of the invention and the PDL1 inhibitor, may be administered together, independently at the same time or separately within time intervals that allow that the combination partners show a cooperative, e.g., synergistic, effect.

The term "fixed combination" means that the therapeutic agents, e.g. the anti-CD137 antibody of the invention and the PDL1 inhibitor, are administered to a patient simultaneously in the form of a single entity or dosage form.

The term "non-fixed combination" means that the therapeutic agents, e.g. the anti-CD137 antibody of the invention and the PDL1 inhibitor, are both administered to a patient as separate entities or dosage forms either simultaneously, concurrently or sequentially with no specific time limits, wherein such administration provides therapeutically effective levels of the two therapeutic agents in the body of the subject, e.g., a mammal or human, in need thereof.

The term "PDL1" refers in particular to human PDL1 with UniProt ID number Q9NZQ7.

The term "blocker" or "inhibitor" or "antagonist" refers to an agent that inhibits or reduces a biological activity of the target molecule it binds to. In some embodiments, an inhibitor substantially or completely inhibits the biological activity of the target molecule. A suitable PDL1 inhibitor targets, decreases, inhibits the binding ability of PDL1 to its binding partners, thereby interfering with the PDL1 function. In particular, suitable PDL1 inhibitor blocks the interaction of PDL1 with PD-1. In some embodiments, suitable PDL1 inhibitor blocks the interaction of PDL1 with PD-1 and B7-1. Suitably, the PDL1 inhibitor utilized in a pharmaceutical combination of the present invention is an anti-PDL1 antibody.

The term "synergistic effect" as used herein refers to action of two therapeutic agents such as, for example, (a) the anti-CD137 antibody of the invention, and (b) PDL1 inhibitor, producing an effect, for example, slowing the symptomatic progression of a proliferative disease, particularly a cancer, or symptoms thereof, which is greater than the simple addition of the effects of each therapeutic agent administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively. Synergy may be further shown by calculating the synergy score of the combination according to methods known by one of ordinary skill.

The term "combined administration" as used herein is defined to encompass the administration of the selected therapeutic agents to a single patient, and is intended to include treatment regimens in which the therapeutic agents are not necessarily administered by the same route of administration or at the same time.

The term "a combined preparation" is defined herein to refer to especially a "kit of parts" in the sense that the therapeutic agents (a) and (b) as defined above can be dosed independently or by use of different fixed combinations with distinguished amounts of the therapeutic agents (a) and (b) simultaneously or at different time points. The parts of the kit of parts can then, e.g., be administered simultaneously or chronologically staggered, that is at different time points and with equal or different time intervals for any part of the kit of parts. The ratio of the total amounts of the therapeutic agent (a) to the therapeutic agent (b) to be administered in the combined preparation can be varied, e.g., in order to cope with the needs of a patient sub-population to be treated or the needs of the single patient.

The term "jointly therapeutically active" or "joint therapeutic effect" as used herein means that the therapeutic agents may be given separately (in a chronologically staggered manner, especially a sequence-specific manner) in such time intervals that they prefer, in the warm-blooded animal, especially human, to be treated, still show a beneficial (preferably synergistic) interaction (joint therapeutic effect). Whether this is the case can, inter alia, be determined by following the blood levels, showing that both therapeutic agents are present in the blood of the human to be treated at least during certain time intervals.

Pharmaceutical combinations of the present invention comprise the anti-CD137 antibody of the invention, as defined herein, particularly for use in the treatment or prevention of a proliferative disease. In a preferred embodiment, the pharmaceutical combinations of the present invention comprise the antibody of the invention, wherein said antibody is an IgG4 comprising HCDR1, HCDR2, and HCDR3 sequences of SEQ ID NOs: 4, 6, and 7, respectively, LCDR1, LCDR2, and LCDR3 sequences of SEQ ID NOs: 21, 22, and 23, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 14, and a VL sequence comprising an amino acid sequence that is at least 60, 70, 80, 90, 91, 92, 93, 94, 95, 96, 97, 98 or 99 percent, preferably at least 90 percent, identical to SEQ ID NO: 27. In a more specific embodiment, the pharmaceutical combinations of the present invention comprise the antibody of the invention, wherein said antibody is an IgG4 comprising HCDR1, HCDR2, and HCDR3 sequences of SEQ ID NOs: 4, 6, and 7, respectively, LCDR1, LCDR2, and LCDR3 sequences of SEQ ID NOs: 21, 22, and 23, respectively, a heavy chain sequence comprising an amino acid sequence that is at least 60, 70, 80, 90, 91, 92, 93, 94, 95, 96, 97, 98 or 99 percent, preferably at least 90 percent, identical to SEQ ID NO: 89, and a light chain sequence comprising an amino acid sequence that is at least 60, 70, 80, 90, 91, 92, 93, 94, 95, 96, 97, 98 or 99 percent, preferably at least 90 percent, identical to SEQ ID NO: 88. In another preferred embodiment, the pharmaceutical combinations of the present invention comprise the antibody of the invention, wherein said antibody is an IgG4 comprising HCDR1, HCDR2, and HCDR3 sequences of SEQ ID NOs: 1, 2 and 3, respectively, LCDR1, LCDR2, and LCDR3 sequences of SEQ ID NOs: 18, 19, and 20 respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 17, and a VL sequence comprising an amino acid sequence that is at least 60, 70, 80, 90, 91, 92, 93, 94, 95, 96, 97, 98 or 99 percent, preferably at least 90 percent, identical to SEQ ID NO: 30. In one embodiment, the pharmaceutical combinations of the present invention comprise the antibody of the invention, wherein said antibody is an IgG4 comprising HCDR1, HCDR2, and HCDR3 sequences of SEQ ID NOs: 1, 2 and 3, respectively, LCDR1, LCDR2, and LCDR3 sequences of SEQ ID NOs: 18, 19 and 20, respectively, a heavy chain sequence comprising an amino acid sequence that is at least 60, 70, 80, 90, 91, 92, 93, 94, 95, 96, 97, 98 or 99 percent, preferably at least 90 percent, identical to SEQ ID NO: 89, and a light chain sequence comprising an amino acid sequence that is at least 60, 70, 80, 90, 91, 92, 93, 94, 95, 96, 97, 98 or 99 percent, preferably at least 90 percent, identical to SEQ ID NO: 88.

Pharmaceutical combinations of the present invention further comprise a PDL1 inhibitor. In one embodiment, said PDL1 inhibitor is an anti-PDL1 antibody. Suitable PDL1 inhibitors for use in the combination of the present invention include, but are not limited to, (i) avelumab (MSB0010718C; human IgG1 anti-PDL1 monoclonal antibody; Merck-Serono; described in WO 2013/079174, which is hereby incorporated into the present application by reference in its entirety);

(ii) atezolizumab (MPDL3280A, RG7446; human IgG anti-PDL1 monoclonal antibody; Hoffmann-La Roche);

(iii) MDX-1105 (BMS-936559; human IgG4 anti-PDL1 monoclonal antibody; Bristol-Myers Squibb; described in WO 2007/005874, which is hereby incorporated into the present application by reference in its entirety);

(iv) durvalumab (MEDI4736; humanized IgG1 anti-PDL1 monoclonal antibody; AstraZeneca; described in WO 2011/066389 and US 2013/034559, which are hereby incorporated into the present application by reference in their entirety);

(v) KN035 (anti-PDL1 monoclonal antibody; 3D Medicines); and (vi) LY3300054 (anti-PDL1 monoclonal antibody; Eli Lilly); and (vii) YW243.55.S70 (described in WO 2010/077634 and U.S. Pat. No. 8,217,149, which are hereby incorporated into the present application by reference in their entirety).

Preferred PDL1 inhibitors for use in the combination of the present invention include an anti-PDL1 antibody comprising: (a) HCDR1, HCDR2, and HCDR3 sequences of SEQ ID NOs: 90, 91, and 92, respectively, and LCDR1, LCDR2, and LCDR3 sequences of SEQ ID NOs: 106, 107, and 108, respectively; (b) HCDR1, HCDR2, and HCDR3 sequences of SEQ ID NOs: 93, 95, and 96, respectively, and LCDR1, LCDR2, and LCDR3 sequences of SEQ ID NOs: 109, 110, and 111, respectively; (c) HCDR1, HCDR2, and HCDR3 sequences of SEQ ID NOs: 94, 95, and 96, respectively, and LCDR1, LCDR2, and LCDR3 sequences of SEQ ID NOs: 109, 110, and 111, respectively; (d) HCDR1, HCDR2, and HCDR3 sequences of SEQ ID NOs: 121, 122, and 123, respectively, and LCDR1, LCDR2, and LCDR3 sequences of SEQ ID NOs: 137, 138, and 139, respectively; (e) HCDR1, HCDR2, and HCDR3 sequences of SEQ ID NOs: 124, 126, and 127, respectively, and LCDR1, LCDR2, and LCDR3 sequences of SEQ ID NOs: 140, 141, and 142, respectively; or (f) HCDR1, HCDR2, and HCDR3 sequences of SEQ ID NOs: 125, 126, and 127, respectively, and LCDR1, LCDR2, and LCDR3 sequences of SEQ ID NOs: 140, 141, and 142, respectively. In one embodiment, the PDL1 inhibitor for use in the combination of the present invention is an anti-PDL1 antibody comprising: (a) HCDR1, HCDR2, and HCDR3 sequences having at least 60, 70, 80, 90, 91, 92, 93, 94, 95, 96, 97, 98 or 99 percent identity to SEQ ID NOs: 90, 91, and 92, respectively, and LCDR1, LCDR2, and LCDR3 sequences having at least 60, 70, 80, 90, 91, 92, 93, 94, 95, 96, 97, 98 or 99 percent identity to SEQ ID NOs: 106, 107, and 108, respectively; (b) HCDR1, HCDR2, and HCDR3 sequences having at least 60, 70, 80, 90, 91, 92, 93, 94, 95, 96, 97, 98 or 99 percent identity to SEQ ID NOs: 93, 95, and 96, respectively, and LCDR1, LCDR2, and LCDR3 sequences having at least 60, 70, 80, 90, 91, 92, 93, 94, 95, 96, 97, 98 or 99 percent identity to SEQ ID NOs: 109, 110, and 111, respectively; (c) HCDR1, HCDR2, and HCDR3 sequences having at least 60, 70, 80, 90, 91, 92, 93, 94, 95, 96, 97, 98 or 99 percent identity to SEQ ID NOs: 94, 95, and 96, respectively, and LCDR1, LCDR2, and LCDR3 sequences having at least 60, 70, 80, 90, 91, 92, 93, 94, 95, 96, 97, 98 or 99 percent identity to SEQ ID NOs: 109, 110, and 111, respectively; (d) HCDR1, HCDR2, and HCDR3 sequences having at least 60, 70, 80, 90, 91, 92, 93, 94, 95, 96, 97, 98 or 99 percent identity to SEQ ID NOs: 121, 122, and 123, respectively, and LCDR1, LCDR2, and LCDR3 sequences having at least 60, 70, 80, 90, 91, 92, 93, 94, 95, 96, 97, 98 or 99 percent identity to SEQ ID NOs: 137, 138, and 139, respectively; (e) HCDR1, HCDR2, and HCDR3 sequences having at least 60, 70, 80, 90, 91, 92, 93, 94, 95, 96, 97, 98 or 99 percent identity to SEQ ID NOs: 124, 126, and 127, respectively, and LCDR1, LCDR2, and LCDR3 sequences having at least 60, 70, 80, 90, 91, 92, 93, 94, 95, 96, 97, 98 or 99 percent identity to SEQ ID NOs: 140, 141, and 142, respectively; or (f) HCDR1, HCDR2, and HCDR3 sequences having at least 60, 70, 80, 90, 91, 92, 93, 94, 95, 96, 97, 98 or 99 percent identity to SEQ ID NOs: 125, 126, and 127, respectively, and LCDR1, LCDR2, and LCDR3 sequences having at least 60, 70, 80, 90, 91, 92, 93, 94, 95, 96, 97, 98 or 99 percent identity to SEQ ID NOs: 140, 141, and 142, respectively.

In one embodiment, the pharmaceutical combination of the present invention comprises a PDL1 inhibitor, wherein said PDL1 inhibitor is an anti-PDL1 antibody comprising:

(i) the HCDR1, HCDR2, HCDR3, LCDR1, LCDR2, and LCDR3 sequences of:
  a. the HCDR1, HCDR2, and HCDR3 sequences of SEQ ID NOs: 93, 95, and 96, respectively, and the LCDR1, LCDR2, and LCDR3 sequences of SEQ ID NOs: 109, 110, and 111, respectively;
  b. the HCDR1, HCDR2, and HCDR3 sequences of SEQ ID NOs: 124, 126, and 127, respectively, and the LCDR1, LCDR2, and LCDR3 sequences of SEQ ID NOs: 140, 141, and 142, respectively; or
  c. the HCDR1, HCDR2, and HCDR3 sequences of SEQ ID NOs: 125, 126, and 127, respectively, and the LCDR1, LCDR2, and LCDR3 sequences of SEQ ID NOs: 140, 141, and 142, respectively;
(ii) VH3 or VH4 domain framework sequences FR1 to FR4; preferably VH4 domain framework sequences FR1 to FR4; and
(iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and a Vλ FR4, particularly Vλ FR4 comprising the amino acid sequence having at least 60, 70, 80, 90 percent identity to an amino acid sequence selected from any of SEQ ID NO: 62 to SEQ ID NO: 68, preferably Vλ FR4 is as set forth in SEQ ID NO: 62 to SEQ ID NO: 68, more preferably Vλ FR4 is as set forth in SEQ ID NO: 62.

In another embodiment, the pharmaceutical combination of the present invention comprises a PDL1 inhibitor, wherein said PDL1 inhibitor is an anti-PDL1 antibody comprising:
(i) the HCDR1, HCDR2, and HCDR3 sequences of: SEQ ID NOs: 94, 95, and 96, respectively, and the LCDR1, LCDR2, and LCDR3 sequences of SEQ ID NOs: 109, 110, and 111, respectively;
(ii) VH1A, VH1B, VH3 or VH4 domain framework sequences, preferably VH1A or VH1B domain framework sequences; and
(iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and a Vλ FR4, particularly Vλ FR4 comprising the amino acid sequence having at least 60, 70, 80, 90 percent identity to an amino acid sequence selected from any of SEQ ID NO: 62 to SEQ ID NO: 68, preferably Vλ FR4 comprising an amino acid sequence selected from any of SEQ ID NO: 62 to SEQ ID NO: 68, more preferably Vλ FR4 is as set forth in SEQ ID NO: 62.

In one embodiment, the pharmaceutical combination of the present invention comprises a PDL1 inhibitor, wherein said PDL1 inhibitor is an anti-PDL1 antibody comprising:
(i) the HCDR1, HCDR2, and HCDR3 sequences of SEQ ID NOs: 90, 91, and 92, respectively, and the LCDR1, LCDR2, and LCDR3 sequences of SEQ ID NOs: 106, 107, and 108, respectively;
(ii) VH3 or VH4 domain framework sequences FR1 to FR4; preferably VH3 domain framework sequences FR1 to FR4; and
(iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and a Vλ FR4, particularly Vλ FR4 comprising the amino acid sequence having at least 60, 70, 80, 90 percent identity to an amino acid sequence selected from any of SEQ ID NO: 62 to SEQ ID NO: 68, preferably Vλ FR4 is as set forth in SEQ ID NO: 62 to SEQ ID NO: 68, more preferably Vλ FR4 is as set forth in SEQ ID NO: 62.

In another embodiment, the pharmaceutical combination of the present invention comprises a PDL1 inhibitor, wherein said PDL1 inhibitor is an anti-PDL1 antibody comprising:
(i) the HCDR1, HCDR2, and HCDR3 sequences of: SEQ ID NOs: 121, 122, and 123, respectively, and the LCDR1, LCDR2, and LCDR3 sequences of SEQ ID NOs: 137, 138, and 139, respectively;
(ii) VH3 or VH4 domain framework sequences FR1 to FR4; preferably VH4 domain framework sequences FR1 to FR4; and
(iii) a VL domain comprising a VL framework comprising Vκ frameworks FR1, FR2 and FR3, particularly Vκ1 or Vκ3 FR1 to FR3, preferably Vκ1 FR1 to FR3, and a framework FR4, which is selected from a Vκ FR4, particularly Vκ1 FR4, Vκ3 FR4, and a Vλ FR4, particularly Vλ FR4 comprising the amino acid sequence having at least 60, 70, 80, 90 percent identity to an amino acid sequence selected from any of SEQ ID NO: 62 to SEQ ID NO: 68, preferably Vλ FR4 comprising an amino acid sequence selected from any of SEQ ID NO: 62 to SEQ ID NO: 68, more preferably Vλ FR4 is as set forth in SEQ ID NO: 62.

In one embodiment, the pharmaceutical combination of the present invention comprises a PDL1 inhibitor, wherein said PDL1 inhibitor is an anti-PDL1 antibody comprising:
(i) CDR domains CDR1, CDR2 and CDR3;
(ii) human Vκ framework regions FR1 to FR3, particularly human Vκ1 framework regions FR1 to FR3;
(iii) FR4, which is selected from (a) a human Vλ germ line sequence for FR4, particularly a Vλ germ line sequence selected from the list of: SEQ ID NO: 62 to 68, preferably SEQ ID NO: 62; and (b) a Vk-based sequence, which has one or two mutations, particularly one mutation, compared to the closest human Vλ germ line sequence for FR4 comprising an amino acid sequence selected from any of SEQ ID NO: 62 to SEQ ID NO: 68, preferably SEQ ID NO: 62.

In one embodiment, the pharmaceutical combination of the present invention comprises a PDL1 inhibitor, wherein said PDL1 inhibitor is an anti-PDL1 antibody comprising:
(a) HCDR1, HCDR2, and HCDR3 sequences of SEQ ID NOs: 90, 91, and 92, respectively, and the LCDR1, LCDR2, and LCDR3 sequences of SEQ ID NOs: 106, 107, and 108, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 103 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 115;
(b) HCDR1, HCDR2, and HCDR3 sequences of SEQ ID NOs: 90, 91, and 92, respectively, and the LCDR1, LCDR2, and LCDR3 sequences of SEQ ID NOs: 106, 107, and 108, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 105 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 116;

(c) HCDR1, HCDR2, and HCDR3 sequences of SEQ ID NOs: 93, 95, and 96, respectively, and the LCDR1, LCDR2, and LCDR3 sequences of SEQ ID NOs: 109, 110, and 111, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 103 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 115;

(d) the HCDR1, HCDR2, and HCDR3 sequences of: SEQ ID NOs: 94, 95, and 96, respectively, and the LCDR1, LCDR2, and LCDR3 sequences of SEQ ID NOs: 16, 21, and 22, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 104 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 115;

(e) HCDR1, HCDR2, and HCDR3 sequences of SEQ ID NOs: 121, 122 and 123, respectively, and the LCDR1, LCDR2, and LCDR3 sequences of SEQ ID NOs: 137, 138, and 139, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 135 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 147;

(f) HCDR1, HCDR2, and HCDR3 sequences of SEQ ID NOs: 121, 122 and 123, respectively, and the LCDR1, LCDR2, and LCDR3 sequences of SEQ ID NOs: 137, 138, and 139, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 136 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 146;

(g) HCDR1, HCDR2, and HCDR3 sequences of SEQ ID NOs: 124, 126, and 127, respectively, and the LCDR1, LCDR2, and LCDR3 sequences of SEQ ID NOs: 140, 141, and 142, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 134 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 146; or (h) HCDR1, HCDR2, and HCDR3 sequences of SEQ ID NOs: 125, 126, and 127, respectively, and the LCDR1, LCDR2, and LCDR3 sequences of SEQ ID NOs: 140, 141, and 142, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 135 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 147.

In one embodiment, the pharmaceutical combination of the present invention comprises a PDL1 inhibitor, wherein said PDL1 inhibitor is an anti-PDL1 antibody comprising:

(a) a VH sequence of SEQ ID NO: 103 and a VL sequence of SEQ ID NO: 115;

(b) a VH sequence of SEQ ID NO: 105 and a VL sequence of SEQ ID NO: 116;

(c) a VH sequence of SEQ ID NO: 103 and a VL sequence of SEQ ID NO: 115;

(d) a VH sequence of SEQ ID NO: 104 and a VL sequence of SEQ ID NO: 115;

(e) a VH sequence of SEQ ID NO: 135 and a VL sequence of SEQ ID NO: 147;

(f) a VH sequence of SEQ ID NO: 136 and a VL sequence of SEQ ID NO: 146;

(g) a VH sequence of SEQ ID NO: 134 and a VL sequence of SEQ ID NO: 146; or (h) a VH sequence of SEQ ID NO: 146 and a VL sequence of SEQ ID NO: 147.

In a preferred embodiment, the pharmaceutical combination of the present invention comprises a PDL1 inhibitor, wherein said PDL1 inhibitor is an anti-PDL1 IgG1 antibody comprising HCDR1, HCDR2, and HCDR3 sequences of SEQ ID NOs: 121, 122 and 123, respectively, and the LCDR1, LCDR2, and LCDR3 sequences of SEQ ID NOs: 137, 138, and 139, respectively, and: (i) a VH sequence comprising an amino acid sequence that is at least 60, 70, 80, 90, 91, 92, 93, 94, 95, 96, 97, 98 or 99 percent, preferably at least 90 percent, identical to SEQ ID NO: 135 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 147; or (ii) a VH sequence comprising an amino acid sequence that is at least 60, 70, 80, 90, 91, 92, 93, 94, 95, 96, 97, 98 or 99 percent, preferably at least 90 percent, identical to SEQ ID NO: 136 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 146.

In a preferred embodiment, the pharmaceutical combination of the present invention comprises a PDL1 inhibitor, wherein said PDL1 inhibitor is an anti-PDL1 IgG1 antibody comprising HCDR1, HCDR2, and HCDR3 sequences of SEQ ID NOs: 93, 95, and 96, respectively, and the LCDR1, LCDR2, and LCDR3 sequences of SEQ ID NOs: 109, 110, and 111, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 103 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 115. In a more specific embodiment, the pharmaceutical combination of the present invention comprises a PDL1 inhibitor, wherein said PDL1 inhibitor is an anti-PDL1 IgG1 antibody comprising HCDR1, HCDR2, and HCDR3 sequences of SEQ ID NOs: 93, 95, and 96, respectively, and the LCDR1, LCDR2, and LCDR3 sequences of SEQ ID NOs: 109, 110, and 111, respectively, a heavy chain sequence comprising an amino acid sequence that is at least 60, 70, 80, 90, 91, 92, 93, 94, 95, 96, 97, 98 or 99 percent, preferably at least 90 percent, identical to SEQ ID NO: 155 and a light chain sequence comprising an amino acid sequence that is at least 60, 70, 80, 90, 91, 92, 93, 94, 95, 96, 97, 98 or 99 percent, preferably at least 90 percent, identical to SEQ ID NO: 154.

In another specific embodiment, the pharmaceutical combination of the present invention comprises a PDL1 inhibitor, wherein said PDL1 inhibitor is an anti-PDL1 IgG1 antibody comprising HCDR1, HCDR2, and HCDR3 sequences of SEQ ID NOs: 121, 122 and 123, respectively, and the LCDR1, LCDR2, and LCDR3 sequences of SEQ ID NOs: 137, 138, and 139, respectively, and: (i) a VH sequence comprising an amino acid sequence that is at least 60, 70, 80, 90, 91, 92, 93, 94, 95, 96, 97, 98 or 99 percent, preferably at least 90 percent, identical to SEQ ID NO: 135 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 147; or (ii) a VH sequence comprising an amino acid sequence that is at least 60, 70, 80, 90, 91, 92, 93, 94, 95, 96, 97, 98 or 99 percent, preferably at least 90 percent, identical to SEQ ID NO: 136 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 146.

In another specific embodiment, the pharmaceutical combination of the present invention comprises a PDL1 inhibitor, wherein said PDL1 inhibitor is an anti-PDL1 IgG1 antibody comprising HCDR1, HCDR2, and HCDR3 sequences of SEQ ID NOs: 124, 126, and 127, respectively, and the LCDR1, LCDR2, and LCDR3 sequences of SEQ ID NOs: 140, 141, and 142, respectively, a VH sequence comprising an amino acid sequence that is at least 60, 70, 80, 90, 91, 92, 93, 94, 95, 96, 97, 98 or 99 percent, preferably at least 90 percent, identical to SEQ ID NO: 134 and a VL sequence comprising an amino acid sequence that is at least 60, 70, 80, 90, 91, 92, 93, 94, 95, 96, 97, 98 or 99 percent, preferably at least 90 percent, identical to SEQ ID NO: 146. In a more specific embodiment, the pharmaceutical combination of the present invention comprises a PDL1 inhibitor, wherein said PDL1 inhibitor is an anti-PDL1 IgG1 antibody comprising HCDR1, HCDR2, and HCDR3 sequences of SEQ ID NOs: 124, 126, and 127, respectively, and the LCDR1, LCDR2, and LCDR3 sequences of SEQ ID NOs: 126, 127, and 142, respectively, a heavy chain sequence comprising an amino acid sequence that is at least 60, 70, 80, 90, 91, 92, 93, 94, 95, 96, 97, 98 or 99 percent, preferably at least 90 percent, identical to SEQ ID NO: 153 and a light chain sequence comprising an amino acid sequence that is at least 60, 70, 80, 90, 91, 92, 93, 94, 95, 96, 97, 98 or 99 percent, preferably at least 90 percent, identical to SEQ ID NO: 152.

Hereinafter, the pharmaceutical combination comprising (a) the anti-CD137 antibody of the invention, as defined herein, and (b) a PDL1 inhibitor, as defined herein, will be referred to as a "combination of the invention".

The nature of proliferative diseases is multifactorial. Under certain circumstances, therapeutic agents with different mechanisms of action may be combined. However, just considering any combination of therapeutic agents having different mode of action does not necessarily lead to combinations with advantageous effects. It has been found that the administration of the combination of the invention has improved antitumor activity as compared to each monotherapy and may be effective for the treatment of proliferative disease, particularly a cancer. In the present invention, the administration of the combination of the invention is expected to result in a more beneficial effect, e.g. synergistic or improved anti-proliferative effect, e.g., with regard to the delay of progression or inhibiting the proliferative disease or its symptoms, but also further beneficial effects, e.g. fewer side-effects, e.g. an improved quality of life or e.g. a decreased morbidity, as compared to either monotherapy.

The combination of the invention is particularly useful for the treatment or prevention of a proliferative disease in a subject in need thereof. The therapeutic agents of the combination of the invention may be separately, simultaneously or sequentially administered to a subject in need thereof. Preferably, these therapeutic agents are administered at therapeutically effective dosages which, when combined, provide a beneficial effect. Thus, in one embodiment of the present invention, the combination of the invention is used for the treatment or prevention of a proliferative disease, particularly a cancer.

In one aspect, the present invention relates to the antibody of the present invention, or the composition of the present invention, or the combination of the present invention for use as a medicament.

In one aspect, the present invention relates to the antibody of the present invention, or the composition of the present invention, or the combination of the present invention for use in the treatment of a proliferative disease, in particular a cancer in a subject in need thereof.

In another aspect, the present invention relates to use of the antibody of the present invention, or the composition of the present invention, or the combination of the present invention to treat a proliferative disease, in particular a cancer, in a subject in need thereof.

In a further aspect, the present invention relates to use of the antibody of the present invention, or the composition of the present invention, or the combination of the present invention in the manufacture of a medicament for the treatment of a proliferative disease, in particular a cancer, in a subject in need thereof.

In one aspect, the present invention provides a method of treating a proliferative disease, in particular a cancer in a subject in need thereof comprising administering to the subject a therapeutically effective amount of the antibody of the invention, or the composition of the invention, or the combination of the present invention.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The terms "treatment", "treating", "treat", "treated", and the like, as used herein, refer to obtaining a desired pharmacologic and/or physiologic effect. The effect may be therapeutic in terms of a partial or complete cure for a disease and/or adverse effect attributable to the disease or delaying the disease progression. "Treatment", as used herein, covers any treatment of a disease in a mammal, e.g., in a human, and includes: (a) inhibiting the disease, i.e., arresting its development; and (b) relieving the disease, i.e., causing regression of the disease.

The term "therapeutically effective amount" or "efficacious amount" refers to the amount of an agent that, when administered to a mammal or other subject for treating a disease, is sufficient to effect such treatment for the disease. The "therapeutically effective amount" will vary depending on the agent, the disease and its severity and the age, weight, etc., of the subject to be treated.

In one embodiment, the proliferative disease is a cancer. The term "cancer" refers to a disease characterized by the rapid and uncontrolled growth of aberrant cells. Cancer cells can spread locally or through the bloodstream and lymphatic system to other parts of the body.

The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors. The term "cancer" is used herein to mean a broad spectrum of tumors, including all solid and haematological malignancies. Examples of such tumors include, but are not limited to: a benign or especially malignant tumor, solid tumors, brain cancer, kidney cancer, liver cancer, adrenal gland cancer, bladder cancer, breast cancer, stomach cancer (e.g., gastric tumors), oesophageal cancer, ovarian cancer, cervical cancer, colon cancer, rectum cancer, prostate cancer, pancreatic cancer, lung cancer (e.g. non-small cell lung cancer and small cell lung cancer), vaginal cancer, thyroid cancer, melanoma (e.g., unresectable or metastatic melanoma), renal cell carcinoma, sarcoma, glioblastoma, multiple myeloma or gastrointestinal cancer, especially colon carcinoma or colorectal adenoma, a tumor of the neck and head, endometrial cancer, Cowden syndrome, Lhermitte-Duclos disease, Bannayan-Zonana syndrome, prostate hyperplasia, a neoplasia, especially of epithelial character, preferably mammary carcinoma or squamous cell carcinoma, chronic lymphocytic leukemia, chronic myelogenous leukemia (e.g., Philadelphia chromosome-positive chronic myelogenous leukemia), acute lymphoblastic leukemia (e.g., Philadelphia chromosome-positive acute lymphoblastic leukemia), non-Hodgkin's lymphoma, plasma cell myeloma, Hodgkin's lymphoma, a leukemia, and any combination thereof. In a preferred embodiment, the cancer is a lung cancer, preferably non-small cell lung cancer (NSCLC). In another embodiment, said cancer is a colorectal cancer.

The antibody of the present invention, or the composition of the present invention, or the combination of the present invention inhibits the growth of solid tumors, but also liquid tumors. In a further embodiment, the proliferative disease is a solid tumor. The term "solid tumor" especially means a breast cancer, ovarian cancer, colon cancer, rectum cancer, prostate cancer, stomach cancer (especially gastric cancer), cervical cancer, lung cancer (e.g., non-small cell lung cancer and small cell lung cancer), and a tumor of the head and neck. Further, depending on the tumor type and the particular combination used, a decrease of the tumor volume can be obtained. The antibody of the present invention, or the composition of the present invention, or the combination of the present invention is also suited to prevent the metastatic spread of tumors and the growth or development of micrometastases in a subject having a cancer.

The term "prevent" or "prevention" refers to a complete inhibition of development of a disease, or any secondary effects of disease. The term "prevent" or "prevention" as used herein covers prevention of a disease or condition from occurring in an individual who may be predisposed to the disease but has not yet been diagnosed as having it.

In one aspect, the present invention relates to a kit comprising the antibody of the invention or the pharmaceutical composition of the invention or the combination of the present invention. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody molecule for administration; pharmaceutically acceptable carriers; and devices or other materials for administration to a subject. In a specific embodiment, the kit comprises the antibody of the invention in a pharmaceutically effective amount. In a further embodiment, the kit comprises a pharmaceutically effective amount of the antibody of the invention in lyophilized form and a diluent and, optionally, instructions for use. Said kit may further comprise a filter needle for reconstitution and a needle for injecting.

TABLE 1

Examples of CD137 antibodies of the present invention
(CDR residues shown in bold and italic letters).

| SEQ ID NUMBER | Ab region | Sequence |
|---|---|---|
| 38-02-A04 | | |
| SEQ ID NO: 1 | HCDR1 (H27-H42; AHo numbering) | GFSFSNSYWIC |
| SEQ ID NO: 2 | HCDR2 (H57-H76; AHo numbering) | CTFVGSSDSTYYANWAKG |
| SEQ ID NO: 3 | HCDR3 (H108-H138; AHo numbering | RHPSDAVYGYANNL |
| SEQ ID NO: 4 | HCDR1 (AHo definition) (38-02-A04-sc01) (38-02-A04 sc05 IF) | VSGFSFSNSYW |
| SEQ ID NO: 5 | HCDR1 (AHo definition) (38-02-A04 sc06 Full) | ASGFSFSNSYW |
| SEQ ID NO: 6 | HCDR2 (AHo definition) | TFVGSSDSTYYANWAKGR |
| SEQ ID NO: 7 | HCDR3 (AHo definition) | HPSDAVYGYANN |
| SEQ ID NO: 8 | HCDR1 (Kabat definition) | NSYWIC |
| SEQ ID NO: 9 | HCDR2 (Kabat definition) | CTFVGSSDSTYYANWAKG |
| SEQ ID NO: 10 | HCDR3 (Kabat definition) | HPSDAVYGYANNL |
| SEQ ID NO: 11 | HCDR1 (Chothia definition) | GFSFSNSY |
| SEQ ID NO: 12 | HCDR2 (Chothia definition) | VGSSD |
| SE1 ID NO: 13 | HCDR3 (Chothia definition) | PSDAVYGYANN |

TABLE 1-continued

Examples of CD137 antibodies of the present invention
(CDR residues shown in bold and italic letters).

| SEQ ID NUMBER | Ab region | Sequence |
| --- | --- | --- |
| SEQ ID NO: 14 | VH (VH4) (38-02-A04 sc01) | QVQLQESGPGLVKPSETLSLTCKVS*GFSFSNSYWIC*WIRQPPGKGLEWIG *CTFVGSSDSTYYANWAKG*RVTISVDSSKNQFSLKLSSVTAADTAVYYCA *RHPSDAVYGYANNL*WGQGTLVTVSS |
| SEQ ID NO: 15 | VH (VH4) (38-02-A04 sc05 IF) Mutations VH: I44V; F89V; Y105F. | QVQLQESGPGLVKPSETLSLTCKVS*GFSFSNSYWIC*WVRQPPGKGLEWIG *CTFVGSSDSTYYANWAKG*RVTISVDSSKNQVSLKLSSVTAADTAVYFCAR *RHPSDAVYGYANNL*WGQGTLVTVSS |
| SEQ ID NO: 16 | VH (VH4) (38-02-A04 sc06 Full) Mutations VH: V25A; I44V; V82K; F89V; Y105F | QVQLQESGPGLVKPSETLSLTCKAS*GFSFSNSYWIC*WVRQPPGKGLEWIG *CTFVGSSDSTYYANWAKG*RVTISKDSSKNQVSLKLSSVTAADTAVYFCA *RHPSDAVYGYANNL*WGQGTLVTVSS |
| SEQ ID NO: 17 | VH (VH3) (38-02-A04 sc13) Mutations VH: G51C (AHo numbering) | EVQLVESGGGLVQPGGSLRLSCAAS*GFSFSNSYWIC*WVRQAPGKGLEWIG *CTFVGSSDSTYYANWAKG*RFTISRDNSKNTVYLQMNSLRAEDTAVYYCA *RHPSDAVYGYANNL*WGQGTLVTVSS |
| SEQ ID NO: 18 | LCDR1 (L24-L42; AHo numbering) (Kabat definition) | QASQSINNVLA |
| SEQ ID NO: 19 | LCDR2 (L58-L72; AHo numbering) (Kabat definition) | RASTLAS |
| SEQ ID NO: 20 | LCDR3 (L107-L138; AHo numbering) (Kabat definition) | QSSYGNYGD |
| SEQ ID NO: 21 | LCDR1 (AHo definition) | ASQSINNV |
| SEQ ID NO: 22 | LCDR2 (AHo definition) | RASTLASGVPSR |
| SEQ ID NO: 23 | LCDR3 (AHo definition) | SYGNYG |
| SEQ ID NO: 24 | LCDR1 (Chothia definition) | SQSINNV |
| SEQ ID NO: 25 | LCDR2 (Chothia definition) | RAS |
| SEQ ID NO: 26 | LCDR3 (Chothia definition) | SYGNYG |
| SEQ ID NO: 27 | VL (Vk1-sk17) (38-02-A04 sc01) | DIQMTQSPSSLSASVGDRVTITC*QASQSINNVLA*WYQQKPGKAPKLLIY *RASTLAS*GVPSRFSGSGSGTDFTLTISSLQPEDFATYYC*QSSYGNYGD* FGTGTKVTVLG |
| SEQ ID NO: 28 | VL (Vk1-sk17) (38-02-A04 sc05 IF) Mutations VL: A51P | DIQMTQSPSSLSASVGDRVTITC*QASQSINNVLA*WYQQKPGKPPKLLIY *RASTLAS*GVPSRFSGSGSGTDFTLTISSLQPEDFATYYC*QSSYGNYGD* FGTGTKVTVLG |
| SEQ ID NO: 29 | VL (Vk1-sk17) (38-02-A04 sc06 Full) Mutations VL: I2L; A51P | DLQMTQSPSSLSASVGDRVTITC*QASQSINNVLA*WYQQKPGKPPKLLIY *RASTLAS*GVPSRFSGSGSGTDFTLTISSLQPEDFATYYC*QSSYGNYGD* FGTGTKVTVLG |
| SEQ ID NO: 30 | VL (Vk1-sk17) (28-02-A04 sc13) Mutations VL: T141C (AHo numbering) | DIQMTQSPSSLSASSVGDRVTITC*QASQSINNVLA*WYQQKPGKAPKLLIY *RASTLAS*GVPSRFSGSGSGTDFTLTISSLQPEDFATYYC*QSSYGNYGD* FGCGTKVTVLG |
| SEQ ID NO: 31 | Linker | GGGGSGGGGSGGGGSGGGGS |
| SEQ ID NO: 32 | scFv (VL-linker-VH) (38-02-A04 sc01) | DIQMTQSPSSLSASVGDRVTITC*QASQSINNVLA*WYQQKPGKAPKLLIY *RASTLAS*GVPSRFSGSGSGTDFTLTISSLQPEDFATYYC*QSSYGNYGD* FGTGTKVTVLGGGGGSGGGGSGGGGSGGGGSQVQLQESGPGLVKPSETLSL TCKVS*GFSFSNSYWIC*WIRQPPGKGLEWIG*CTFVGSSDSTYYANWAKG*RVT ISVDSSKNQFSLKLSSVTAADTAVYYCA*RHPSDAVYGYANNL*WGQGTLVTV SS |
| SEQ ID NO: 33 | scFv (VL-linker-VH) (38-02-A04 sc05 IF) | DIQMTQSPSSLSASVGDRVTITC*QASQSINNVLA*WYQQKPGKPPKLLIY *RASTIAS*GVPSRFSGSGSGTDFTLTISSLQPEDFATYYC*QSSYGNYGD* FGTGTKVTVLGGGGGSGGGGSGGGGSGGGGSQVQLQESGPGLVKPSETLSL TCKVS*GFSFSNSYWIC*WVRQPPGKGLEWIG*CTFVGSSDSTYYANWAKG*RVT ISVDSSKNQVSLKLSSVTAADTAVYFCA*RHPSDAVYGYANNL*WGQGTLVTV SS |

TABLE 1-continued

Examples of CD137 antibodies of the present invention
(CDR residues shown in bold and italic letters).

| SEQ ID NUMBER | Ab region | Sequence |
|---|---|---|
| SEQ ID NO: 34 | scFv (VL-linker-VH) (38-02-A04 sc06 Full) | DLQMTQSPSSLSASVGDRVTITC*QASQSINNVLA*WYQQKPGKPPKLLIY*RASTLAS*GVPSRFSGSGSGTDFTLTISSLQPEDFATYYC*QSSYGNYGD*FGTGTKVTVLGGGGSGGGGSGGGGSGGGGSQVQLQESGPGLVKPSETLSLTCKAS*GFSFSNSYWIC*WVRQPPGKGLEWIG*CTFVGSSDSTYYANWAKG*RVTISKDSSKNQVSLKLSSVTAADTAVYFCA*RHPSDAVYGYANNI*WGQGTLVTVSS |
| SEQ ID NO: 35 | scFv (VL-linker-VH) (38-02-A04 sc13) | DIQMTQSPSSLSASVGDRVTITC*QASQSINNVLA*WYQQKPGKAPKLLIY*RASTLAS*GVPSRFSGSGSGTDFTLTISSLQPEDFATYYC*QSSYGNYGD*FGCGTKVTVLGGGGSGGGGSGGGGSGGGGSEVQLVESGGGLVQPGGSLRLSCAAS*GFSFSNSYWIC*WVRQAPGKCLEWIG*CTFVGSSDSTYYANWAKG*RFTISRDNSKNTVYLQMNSLRAEDTAVYYCA*RHPSDAVYGYANNI*WGQGTLVTVSS |

38-27-C05 sc01

| SEQ ID NUMBER | Ab region | Sequence |
|---|---|---|
| SEQ ID NO: 36 | HCDR1 (H27-H42; AHo numbering) | GFSFNNDYDMC |
| SEQ ID NO: 37 | HCDR2 (H57-H76; AHo numbering) | CIDTGDGSTYYASWAKG |
| SEQ ID NO: 38 | HCDR3 (H108-H138; AHo numbering) | REAASSSGYGMGYFDL |
| SEQ ID NO: 39 | HCDR1 (AHo definition) | VSGFSFNNDYD |
| SEQ ID NO: 40 | HCDR2 (AHo definition) | IDTGDGSTYYASWAKGR |
| SEQ ID NO: 41 | HCDR3 (AHo definition) | EAASSSGYGMGYFD |
| SEQ ID NO: 42 | HCDR1 (Kabat definition) | NDYDMC |
| SEQ ID NO: 43 | HCDR2 (Kabat definition) | CIDTGDGSTYYASWAKG |
| SEQ ID NO: 44 | HCDR3 (Kabat definition) | EAASSSGYGMGYFDL |
| SEQ ID NO: 45 | HCDR1 (Chothia definition) | GFSFNNDY |
| SEQ ID NO: 46 | HCDR2 (Chothia definition) | TGDG |
| SEQ ID NO: 47 | HCDR3 (Chothia definition) | AASSSGYGMGYFD |
| SEQ ID NO: 48 | VH (VH4) | QVQLQESGPGLVKPSETLSLTCKVS*GFSFNNDYDMC*WIRQPPGKGLEWIG*CIDTGDGSTYYASWAKG*RVTISVDSSKNQFSLKLSSVTAADTAVYYCA*REAASSSGYGMGYFDL*WGQGTLVTVSS |
| SEQ ID NO: 49 | LCDR1 (L24-L42; AHo numbering) (Kabat definition) | QSSQSVYDNNWLA |
| SEQ ID NO: 50 | LCDR2 (L58-L72; AHo numbering) (Kabat definition) | RASNLAS |
| SEQ ID NO: 51 | LCDR3 (L107-L138; AHo numbering) (Kabat definition) | QGTYLSSNWYWA |
| SEQ ID NO: 52 | LCDR1 (AHo definition) | SSQSVYDNNW |
| SEQ ID NO: 53 | LCDR2 (AHo definition) | RASNLASGVPSR |
| SEQ ID NO: 54 | LCDR3 (AHo definition) | TYLSSNWYW |
| SEQ ID NO: 55 | LCDR1 (Chothia definition) | SQSVYDNNW |
| SEQ ID NO: 56 | LCDR2 (Chothia definition) | RAS |
| SEQ ID NO: 57 | LCDR3 (Chothia definition) | TYLSSNWYW |
| SEQ ID NO: 58 | VL (Vk1-sk17) | DIQMTQSPSSLSASVGDRVTITC*QSSQSVYDNNWLA*WYQQKPGKAPKLLIY*RASNLAS*GVPSRFSGSGSGTDFTLTISSLQPEDFATYYC*QGTYLSSNWYWA*FGTGTKVTVLG |

TABLE 1-continued

Examples of CD137 antibodies of the present invention
(CDR residues shown in bold and italic letters).

| SEQ ID NUMBER | Ab region | Sequence |
|---|---|---|
| SEQ ID NO: 59 | Linker | GGGGSGGGGSGGGGSGGGGS |
| SEQ ID NO: 60 | scFv (VL-linker-VH) | DIQMTQSPSSLSASVGDRVTITC*QSSQSVYDNNWLA*WYQQKPGKAPKLLIY*RASNLAS*GVPSRFSGSGSGTDFTLTISSLQPEDFATYYC*QGTYLSSNWYWA*FGTGTKVTVLGGGGSGGGGSGGGGSGGGGSGGGGSQVQLQESGPGLVKPSETLSLTCKVS*GFSFNNDYDMC*WIRQPPGKGLEWIG*CIDTGDGSTYYASWAKG*RVTISVDSSKNQFSLKLSSVTAADTAVYYCA*REAASSSGYGMGYFDL*WGQGTLVTVSS |

TABLE 2

Other sequences related to the present invention.

| SEQ ID NUMBER | Ab region | Sequence |
|---|---|---|
| SEQ ID NO: 61 | Human CD137 | MGNSCYNIVATLLLVLNFERTRSLQDPCSNCPAGTFCDNNRNQICSPCPPNSFSSAGGQRTCDICRQCKGVFRTRKECSSTSNAECDCTPGFHCLGAGCSMCEQDCKQGQELTKKGCKDCCFGTFNDQKRGICRPWTNCSLDGKSVLVNGTKERDVVCGPSPADLSPGASSVTPPAPAREPGHSPQIISFFLALTSTALLFLLFFLTLRFSVVKRGRKKLLYIFKQPFMRPVQTTQEEDGCSCRFPEEEEGGCEL |
| SEQ ID NO: 62 | Vλ germline-based FR4 (Sk17) | FGTGTKVTVLG |
| SEQ ID NO: 63 | Vλ germline-based FR4 (Sk12) | FGGGTKLTVLG |
| SEQ ID NO: 64 | Vλ germline-based FR4 | FGGGTQLIILG |
| SEQ ID NO: 65 | Vλ germline-based FR4 | FGEGTELTVLG |
| SEQ ID NO: 66 | Vλ germline-based FR4 | FGSGTKVTVLG |
| SEQ ID NO: 67 | Vλ germline-based FR4 | FGGGTQLTVLG |
| SEQ ID NO: 68 | Vλ germline-based FR4 | FGGGTQLTALG |

TABLE 3A

Examples of molecules comprising the antibody of the invention.

| SEQ ID NUMBER | Ab Format | Sequence |
|---|---|---|
| PRO885 (38-02-A04 sc01 scDb-i/33-03-G02 sc01scDb-o) | | |
| SEQ ID NO: 69 | scDb | DIQMTQSPSSLSASVGDRVTITCQASQSINDYLAWYQQKPGKAPKWYKASTLASGVPSRFSGSGSGTDFTLTISSLQPEDFATYYCQQGYIITDIDNVFGTGTKVTVLGGGGGSQVQLQESGPGLVKPSETLSLTCKVSGFSFSNSYWICWIRQPPGKGLEWIGCTFVGSSDSTYYANWAKGRVTISVDSSKNQFSLKLSSVTAADTAVYYCARHPSDAVYGYANNLWGQGTLVTVSSGGGGSGGGGSGGGGSGGGGSIQMTQSPSSLSASVGDRVTITCQASQSINNVLAWYQQKPGKAPKLLIYRASTLASGVPSRFSGSGSGTDFTLTISSLQPEDFATYYCQSSYGNYGDFGTGTKVTVLGGGGGSQVQLQESGPGLVKPSETLSLTCKVSGFSFSSGYDMCWIRQPPGKGLEWIGCVVAGSVDITYYASWAKGRVTISVDSSKNQFSLKLSSVTAADTAVYYCARKDAYSDAFNLWGQGTLVTVSS |
| PRO951 (38-27-C05 sc02 scDb-i/33-03-G02 sc01 scDb-o) | | |
| SEQ ID NO: 70 | scDb | DIQMTQSPSSLSASVGDRVTITCQASQSINDYLAWYQQKPGKAPKWYKASTLASGVPSRFSGSGSGTDFTLTISSLQPEDFATYYCQQGYIITDIDNVFGTGTKVTVLGGGGGSEVQLVESGGGLVQPGGSLRLSCAASGFSFNNDYDMCWVRQAPGKGLEWIGCIDTGDGSTYYASWAKGRFTISRDNSKNTVYLQMNSLRAEDTAVYYCAREAASSSGYGMGYFDLWGQGTLVTVSSGGGGSGGGGSGGGGSGGGGSIQMTQSPSSLSASVGDRVTITCQSSQSVYDNNWLAWYQQKPGKAPKLLIYRASNLASGVPSRFSGSGSGTDFTLTISSLQPEDFATYYCQGTYLSSNWYWAFGTGTKVTVLGGGGGSQVQLQESGPGLVKPSETLSLTCKVSGFSFSSGYDMCWIRQPPGKGLEWIGCVVAGSVDITYYASWAKGRVTISVDSSKNQFSLKLSSVTAADTAVYYCARKDAYSDAFNLWGQGTLVTVSS |

TABLE 3A-continued

Examples of molecules comprising the antibody of the invention.

| SEQ ID NUMBER | Ab Format | Sequence |
|---|---|---|
| | PRO1123 (38-02-A04 sc05 IF scDb-i/33_03_G02 sc01 scDb-o) | |
| SEQ ID NO: 71 | scDb | DIQMTQSPSSLSASVGDRVTITCQASQSINDYLAWYQQKPGKAPKWYKASTLASGVP<br>SRFSGSGSGTDFTLTISSLQPEDFATYYCQQGYIITDIDNVFGTGTKVTVLGGGGS<br>QVQLQESGPGLVKPSETLSLTCKVSGFSFSNSYWICWVRQPPGKGLEWIGCTFVGSS<br>DSTYYANWAKGRVTISVDSSKNQVSLKLSSVTAADTAVYFCARHPSDAVYGYANNLW<br>GQGTLVTVSSGGGGSGGGGSGGGGSGGGGSIQMTQSPSSLSASVGDRVTITCQASQS<br>INNVLAWYQQKPGKPPKWYRASTLASGVPSRFSGSGSGTDFTLTISSLQPEDFATYY<br>CQSSYGNYGDFGTGTKVTVLGGGGSQVQLQESGPGLVKPSETLSLTCKVSGFSFSS<br>GYDMCWIRQPPGKGLEWIGCVVAGSVDITYYASWAKGRVTISVDSSKNQFSLKLSSV<br>TAADTAVYYCARKDAYSDAFNLWGQGTLVTVSS |
| | PRO1124 (38-02-A04 sc06 Full scDb-i/33_03_G02 scDb-o) | |
| SEQ ID NO: 72 | scDb | DIQMTQSPSSLSASVGDRVTITCQASQSINDYLAWYQQKPGKAPKWYKASTLASGVP<br>SRFSGSGSGTDFTLTISSLQPEDFATYYCQQGYIITDIDNVFGTGTKVTVLGGGGS<br>QVQLQESGPGLVKPSETLSLTCKASGFSFSNSYWICWVRQPPGKGLEWIGCTFVGSS<br>DSTYYANWAKGRVTISKDSSKNQVSLKLSSVTAADTAVYFCARHPSDAVYGYANNLW<br>GQGTLVTVSSGGGGSGGGGSGGGGSGGGGSLQMTQSPSSLSASVGDRVTITCQASQS<br>INNVLAWYQQKPGKPPKWYRASTLASGVPSRFSGSGSGTDFTLTISSLQPEDFATYY<br>CQSSYGNYGDFGTGTKVTVLGGGGSQVQLQESGPGLVKPSETLSLTCKVSGFSFSS<br>GYDMCWIRQPPGKGLEWIGCVVAGSVDITYYASWAKGRVTISVDSSKNQFSLKLSSV<br>TAADTAVYYCARKDAYSDAFNLWGQGTLVTVSS |
| | PRO1125 (38-02-A04 scDb-i/33_03_G02 sc02 IF scDb-o) | |
| SEQ ID NO: 73 | scDb | DIQMTQSPSSLSASVGDRVTITCQASQSINDYLAWYQQKPGKSPKWYKASTLASGVP<br>SRFSGSGSGTDFTLTISSLQPEDFATYYCQQGYIITDIDNVFGTGTKVTVLGGGGS<br>QVQLQESGPGLVKPSETLSLTCKVSGFSFSNSYWICWIRQPPGKGLEWIGCTFVGSS<br>DSTYYANWAKGRVTISVDSSKNQFSLKLSSVTAADTAVYYCARHPSDAVYGYANNLW<br>GQGTLVTVSSGGGGSGGGGSGGGGSGGGGSIQMTQSPSSLSASVGDRVTITCQASQS<br>INNVLAWYQQKPGKAPKWYRASTLASGVPSRFSGSGSGTDFTLTISSLQPEDFATYY<br>CQSSYGNYGDFGTGTKVTVLGGGGSQVQLQESGPGLVKPSETLSLTCKVSGFSFSS<br>GYDMCWVRQPPGKGLEWIACVVAGSVDITYYASWAKGRVTISVDSSKNQFSLKLSSV<br>TAADTAVYFCARKDAYSDAFNLWGQGTLVTVSS |
| | PRO1126 (38-02-A04 sc01 scDb-i/33_03_G02 sc03 Full scDb-o) | |
| SEQ ID NO: 74 | scDb | DFQLTQSPSSLSASVGDRVTITCQASQSINDYLAWYQQKPGKSPKLLIYKASTLASG<br>VPSRFSGSGSGTDFTLTISSLQPEDFATYYCQQGYIITDIDNVFGTGTKVTVLGGG<br>GSQVQLQESGPGLVKPSETLSLTCKVSGFSFSNSYWICWIRQPPGKGLEWIGCTFVG<br>SSDSTYYANWAKGRVTISVDSSKNQFSLKLSSVTAADTAVYYCARHPSDAVYGYANN<br>LWGQGTLVTVSSGGGGSGGGGSGGGGSGGGGSIQMTQSPSSLSASVGDRVTITCQAS<br>QSINNVLAWYQQKPGKAPKWYRASTLASGVPSRFSGSGSGTDFTLTISSLQPEDFAT<br>YYCQSSYGNYGDFGTGTKVTVLGGGGSQSQLQESGPGLVKPSETLSLTCKASGFSF<br>SSGYDMCWVRQPPGKGLEWIACVVAGSVDITYYASWAKGRVTISKDSSKNQVSLKLS<br>SVTAADTAVYFCARKDAYSDAFNLWGQGTLVTVSS |
| | PRO1134 (38-02-A04 sc01 scDb-i/33_03_G02 sc07 GL VH3 scDb-o) | |
| SEQ ID NO: 75 | scDb | DIQMTQSPSSLSASVGDAVTITCQASQSINDYLAWYQQKPGKSPKWYKASTLASGVP<br>SRFSGSGSGTDFTLTISSLQPEDFATYYCQQGYIITDIDNVFGTGTKVTVLGGGGS<br>QVQLQESGPGLVKPSETLSLTCKVSGFSFSNSYWICWIRQPPGKGLEWIGCTFVGSS<br>DSTYYANWAKGRVTISVDSSKNQFSLKLSSVTAADTAVYYCARHPSDAVYGYANNLW<br>GQGTLVTVSSGGGGSGGGGSGGGGSGGGGSIQMTQSPSSLSASVGDRVTITCQASQS<br>INNVLAWYQQKPGKAPKLLIYRASTLASGVPSRFSGSGSGTDFTLTISSLQPEDFAT<br>YYCQSSYGNYGDFGTGTKVTVLGGGGSEVQLVESGGGLVQPGGSLRLSCAASGFSF<br>SSGYDMCWVRQAPGKGLEWVGCVVAGSVDITYYASWAKGRFTISRDNSKNTVYLQMN<br>SLRAEDTATYYCARKDAYSDAFNLWGPGTLVTVSS |
| | PRO096 (= PRO1051) (38_02_A04 sc01 scDb-i/33-03-G02 sc01 scDb-o/19-01-H04-sc03 scFv) | |
| SEQ ID NO: 76 | scDb-scFv | DIQMTQSPSSLSASVGDRVTITCQASQSINDYLAWYQQKPGKAPKWYKASTLASGVP<br>SRFSGSGSGTDFTLTISSLQPEDFATYYCQQGYIITDIDNVFGTGTKVTVLGGGGS<br>QVQLQESGPGLVKPSETLSLTCKVSGFSFSNSYWICWIRQPPGKGLEWIGCTFVGSS<br>DSTYYANWAKGRVTISVDSSKNQFSLKLSSVTAADTAVYYCARHPSDAVYGYANNLW<br>GQGTLVTVSSGGGGSGGGGSGGGGSGGGGSIQMTQSPSSLSASVGDRVTITCQASQS<br>INNVLAWYQQKPGKAPKLLIYRASTLASGVPSRFSGSGSGTDFTLTISSLQPEDFAT<br>YYCQSSYGNYGDFGTGTKVTVLGGGGSQVQLQESGPGLVKPSETLSLTCKVSGFSF<br>SSGYDMCWIRQPPGKGLEWIGCVVAGSVDITYYASWAKGRVTISVDSSKNQFSLKLS<br>SVTAADTAVYYCARKDAYSDAFNLWGQGTLVTVSSGGGGSGGGGSIQMTQSPSSLSA<br>SVGDRVTITCQSSESVYSNNQLSWYQQKPGQPPKLLIYDASDLASGVPSRFSGSGSG<br>TDFTLTISSLQPEDFATYYCAGGFSSSSDTAFGGGTKLTVLGGGGGSGGGGSGGGGS |

TABLE 3A-continued

Examples of molecules comprising the antibody of the invention.

| SEQ ID NUMBER | Ab Format | Sequence |
|---|---|---|
| | | GGGGSEVQLVESGGGLVQPGGSLRLSCAASGFSLSSNAMGWVRQAPGKGLEYIGIIS VGGFTYYASWAKGRFTISRDNSKNTVYLQMNSLRAEDTATYFCARDRHGGDSSGAFY LWGQGTLVTVSS |

PRO966 (= PRO1052) (38_27_C05 sc01 scDb-i/33-03-G02 sc01 scDb-o/19-01-H04-sc03 scFv)

| SEQ ID NO: 77 | scDb-scFv | DIQMTQSPSSLSASVGDRVTITCQASQSINDYLAWYQQKPGKAPKWYKASTLASGVP SRFSGSGSGTDFTLTISSLQPEDFATYYCQQGYIITDIDNVFGTGTKVTVLGGGGGS QVQLQESGPGLVKPSETLSLTCKVSGFSFNNDYDMCWIRQPPGKGLEWIGCIDTGDG STYYASWAKGRVTISVDSSKNQFSLKLSSVTAADTAVYYCAREAASSSGYGMGYFDL WGQGTLVTVSSGGGGSGGGGSGGGGSGGGGSIQMTQSPSSLSASVGDRVTITCQSSQ SVYDNNWLAWYQQKPGKAPKLLIYRASNLASGVPSRFSGSGSGTDFTLTISSLQPED FATYYCQGTYLSSNWYWAFGTGTKVTVLGGGGGSQVQLQESGPGLVKPSETLSLTCK VSGFSFSSGYDMCWIRQPPGKGLEWIGCVVAGSVDITYYASWAKGRVTISVDSSKNQ FSLKLSSVTAADTAVYYCARKDAYSDAFNLWGQGTLVTVSSGGGGSGGGGSIQMTQS PSSLSASVGDRVTITCQSSESVYSNNQLSWYQQKPGQPPKLLIYDASDLASGVPSRF SGSGSGTDFTLTISSLQPEDFATYYCAGGFSSSSDTAFGGGTKLTVLGGGGSGGGG SGGGGSGGGGSEVQLVESGGGLVQPGGSLRLSCAASGFSLSSNAMGWVRQAPGKGLE YIGIISVGGFTYYASWAKGRFTISRDNSKNTVYLQMNSLRAEDTATYFCARDRHGGD SSGAFYLWGQGTLVTVSS |

PRO1057 (38_02_A04 sc01 scDb-i/33-03-G02 sc01scDb-o/mxr HSA (23-13-A01-sc03, sk17sh4))

| SEQ ID NO: 78 | scDb-scFv | DIQMTQSPSSLSASVGDRVTITCQASQSINDYLAWYQQKPGKAPKWYKASTLASGVP SRFSGSGSGTDFTLTISSLQPEDFATYYCQQGYIITDIDNVFGTGTKVTVLGGGGS QVQLQESGPGLVKPSETLSLTCKVSGFSFSNSYWICWIRQPPGKGLEWIGCTFVGSS DSTYYANWAKGRVTISVDSSKNQFSLKLSSVTAADTAVYYCARHPSDAVYGYANNLW GQGTLVTVSSGGGGSGGGGSGGGGSGGGGSIQMTQSPSSLSASVGDRVTITCQASQS INNVLAWYQQKPGKAPKLLIYRASTLASGVPSRFSGSGSGTDFTLTISSLQPEDFAT YYCQSSYGNYGDFGTGTKVTVLGGGGSQVQLQESGPGLVKPSETLSLTCKVSGFSF SSGYDMCWIRQPPGKGLEWIGCVVAGSVDITYYASWAKGRVTISVDSSKNQFSLKLS SVTAADTAVYYCARKDAYSDAFNLWGQGTLVTVSSGGGGSGGGGSVVMTQSPSSLSA SVGDRVTITCQASQIISSRSAWYQQKPGQPPKLLIYQASKLASGVPSRFSGSGSGTD FTLTISSLQPEDFATYYCQCTYIDSNFGAFGGGTKLTVLGGGGSGGGGSGGGGSGG GGSEVQLVESGGGLVQPGGSLRLSCAASGFSSSSYWICWVRQAPGKGLEWVGCVFT GDGTTYYASWAKGRFTISRDNSKNTVYLQMNSLRAEDTATYFCARPVSVYYYGMDLW GQGTLVTVSS |

PRO1058 (38_27_C05 sc01 scDb-i/33-03-G02 sc01 scDb-o/mxr HSA (23-13-A01-sc03, sk17sh4))

| SEQ ID NO: 79 | scDb-scFv | DIQMTQSPSSLSASVGDRVTITCQASQSINDYLAWYQQKPGKAPKWYKASTLASGVP SRFSGSGSGTDFTLTISSLQPEDFATYYCQQGYIITDIDNVFGTGTKVTVLGGGGS QVQLQESGPGLVKPSETLSLTCKVSGFSFNNDYDMCWIRQPPGKGLEWIGCIDTGDG STYYASWAKGRVTISVDSSKNQFSLKLSSVTAADTAVYYCAREAASSSGYGMGYFDL WGQGTLVTVSSGGGGSGGGGSGGGGSGGGGSIQMTQSPSSLSASVGDRVTITCQSSQ SVYDNNWLAWYQQKPGKAPKLLIYRASNLASGVPSRFSGSGSGTDFTLTISSLQPED FATYYCQGTYLSSNWYWAFGTGTKVTVLGGGGGSQVQLQESGPGLVKPSETLSLTCK VSGFSFSSGYDMCWIRQPPGKGLEWIGCVVAGSVDITYYASWAKGRVTISVDSSKNQ FSLKLSSVTAADTAVYYCARKDAYSDAFNLWGQGTLVTVSSGGGGSGGGGSVVMTQS PSSLSASVGDRVTITCQASQIISSRSAWYQQKPGQPPKLLIYQASKLASGVPSRFSG SGSGTDFTLTISSLQPEDFATYYCQCTYIDSNFGAFGGGTKLTVLGGGGSGGGGSG GGGSGGGGSEVQLVESGGGLVQPGGSLRLSCAASGFSSSSYWICWVRQAPGKGLEW VGCVFTGDGTTYYASWAKGRFTISRDNSKNTVYLQMNSLRAEDTATYFCARPVSVYY YGMDLWGQGTLVTVSS |

PRO1059 (33-03-G02 IgG1 LC with 38_02_A04 sc01 scFv, PDL1/CD137(ScFv) silent Morrison)

| SEQ ID NO: 80 | Morrison-L Light chain | DIQMTQSPSSLSASVGDRVTITCQASQSINDYLAWYQQKPGKAPKLLIYKASTLASG VPSRFSGSGSGTDFTLTISSLQPEDFATYYCQQGYIITDIDNVFGTGTKVTVLGTVA APSVFIFPPSDEQLKSGTASVVCLLNNFYPREAKVQWKVDNALQSGNSQESVTEQDS KDSTYSLSSTLTLSKADYEKHKVYACEVTHQGLSSPVTKSFNRGECGGGGSGGGGSI QMTQSPSSLSASVGDRVTITCQASQSINNVLAWYQQKPGKAPKLLIYRASTLASGVP SRFSGSGSGTDFTLTISSLQPEDFATYYCQSSYGNYGDFGTGTKVTVLGGGGSGGGG GSGGGGSGGGGSQVQLQESGPGLVKPSETLSLTCKVSGFSFSNSYWICWIRQPPGKG LEWIGCTFVGSSDSTYYANWAKGRVTISVDSSKNQFSLKLSSVTAADTAVYYCARHP SDAVYGYANNLWGQGTLVTVSS |
| SEQ ID NO: 81 | Morrison-L Heavy chain | QVQLQESGPGLVKPSETLSLTCKVSGFSFSSGYDMCWIRQPPGKGLEWIGCVVAGSV DITYYASWAKGRVTISVDSSKNQFSLKLSSVTAADTAVYYCARKDAYSDAFNLWGQG TLVTVSSASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKRVEPKSCDKTH TCPPCPAPEAAGGPSVFLFPPKPKDTLMISRTPEVTCVVVDVSHEDPEVKFNWYVDG |

TABLE 3A-continued

Examples of molecules comprising the antibody of the invention.

| SEQ ID NUMBER | Ab Format | Sequence |
|---|---|---|
| | | VEVHNAKTKPREEQYNSTYRVVSVLTVLHQDWLNGKEYKCKVSNKALGAPIEKTISK<br>AKGQPREPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSPGK |

PRO1060 (33-03-G02 IgG1 HC with 38_02_A04 sc01 scFv, PDL1/CD137(scFv) silent Morrison)

| SEQ ID NO: 82 | Morrison-H Light chain | DIQMTQSPSSLSASVGDRVTITCQASQSINDYLAWYQQKPGKAPKLLIYKASTLASG<br>VPSRFSGSGSGTDFTLTISSLQPEDFATYYCQQGYIITDIDNVFGTGTKVTVLGTVA<br>APSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC |
| SEQ ID NO: 83 | Morrison-H Heavy chain | QVQLQESGPGLVKPSETLSLTCKVSGFSFSSGYDMCWIRQPPGKGLEWIGCVVAGSV<br>DITYYASWAKGRVTISVDSSKNQFSLKLSSVTAADTAVYYCARKDAYSDAFNLWGQG<br>TLVTVSSASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKRVEPKSCDKTH<br>TCPPCPAPEAAGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALGAPIEKTISK<br>AKGQPREPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSPGKGGGGS<br>GGGGSIQMTQSPSSLSASVGDRVTITCQASQSINNVLAWYQQKPGKAPKLLIYRAST<br>LASGVPSRFSGSGSGTDFTLTISSLQPEDFATYYCQSSYGNYGDFGTGTKVTVLGGG<br>GGSGGGGSGGGGSGGGGSQVQLQESGPGLVKPSETLSLTCKVSGFSFSNSYWICWIR<br>QPPGKGLEWIGCTFVGSSDSTYYANWAKGRVTISVDSSKNQFSLKLSSVTAADTAVY<br>YCARHPSDAVYGYANNLWGQGTLVTVSS |

PRO1061 (33-03-G02 sc01 IgG1 LC with 38_27_C05 sc01 scFv, PDL1/CD137(scFv) silent Morrison)

| SEQ ID NO: 84 | Morrison-L Light chain | DIQMTQSPSSLSASVGDRVTITCQASQSINDYLAWYQQKPGKAPKLLIYKASTLASG<br>VPSRFSGSGSGTDFTLTISSLQPEDFATYYCQQGYIITDIDNVFGTGTKVTVLGTVA<br>APSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGECGGGGSGGGGSI<br>QMTQSPSSLSASVGDRVTITCQASQSINNVLAWYQQKPGKAPKLLIYRASTLASGVP<br>SRFSGSGSGTDFTLTISSLQPEDFATYYCQSSYGNYGDFGTGTKVTVLGGGGGSGGG<br>GSGGGGSGGGGSQVQLQESGPGLVKPSETLSLTCKVSGFSFSNSYWICWIRQPPGKG<br>LEWIGCTFVGSSDSTYYANWAKGRVTISVDSSKNQFSLKLSSVTAADTAVYYCARHP<br>SDAVYGYANNLWGQGTLVTVSS |
| SEQ ID NO: 85 | Morrison-L Heavy chain | QVQLQESGPGLVKPSETLSLTCKVSGFSFSSGYDMCWIRQPPGKGLEWIGCVVAGSV<br>DITYYASWAKGRVTISVDSSKNQFSLKLSSVTAADTAVYYCARKDAYSDAFNLWGQG<br>TLVTVSSASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKRVEPKSCDKTH<br>TCPPCPAPEAAGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALGAPIEKTISK<br>AKGQPREPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSPGK |

PRO1062 (33-03-G02 sc01 IgG1 HC with 38_27_C05 sc01 scFv, PDL1/CD137(scFv) silent Morrison)

| SEQ ID NO: 86 | Morrison-H Light chain | DIQMTQSPSSLSASVGDRVTITCQASQSINDYLAWYQQKPGKAPKLLIYKASTLASG<br>VPSRFSGSGSGTDFTLTISSLQPEDFATYYCQQGYIITDIDNVFGTGTKVTVLGTVA<br>APSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGEC |
| SEQ ID NO: 87 | Morrison-H Heavy chain | QVQLQESGPGLVKPSETLSLTCKVSGFSFSSGYDMCWIRQPPGKGLEWIGCVVAGSV<br>DITYYASWAKGRVTISVDSSKNQFSLKLSSVTAADTAVYYCARKDAYSDAFNLWGQG<br>TLVTVSSASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKRVEPKSCDKTH<br>TCPPCPAPEAAGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALGAPIEKTISK<br>AKGQPREPQVYTLPPSREEMTKNQVSLTCLVKGFYPSDIAVEWESNGQPENNYKTTP<br>PVLDSDGSFFLYSKLTVDKSRWQQGNVFSCSVMHEALHNHYTQKSLSLSPGKGGGGS<br>GGGGSIQMTQSPSSLSASVGDRVTITCQASQSINNVLAWYQQKPGKAPKLLIYRAST<br>LASGVPSRFSGSGSGTDFTLTISSLQPEDFATYYCQSSYGNYGDFGTGTKVTVLGGG<br>GGSGGGGSGGGGSGGGGSQVQLQESGPGLVKPSETLSLTCKVSGFSFSNSYWICWIR<br>QPPGKGLEWIGCTFVGSSDSTYYANWAKGRVTISVDSSKNQFSLKLSSVTAADTAVY<br>YCARHPSDAVYGYANNLWGQGTLVTVSS |

PRO1138 (38-02-A04 sc01 IgG4)

| SEQ ID NO: 88 | Light chain IgG | DIQMTQSPSSLSASVGDRVTITCQASQSINNVLAWYQQKPGKAPKLLIYRASTLASG<br>VPSRFSGSGSGTDFTLTISSLQPEDFATYYCQSSYGNYGDFGTGTKVTVLGTVAAPS<br>VFIFPPSDEQLKSGTASVVCLLNNFYPREAKVQWKVDNALQSGNSQESVTEQDSKDS<br>TYSLSSTLTLSKADYEKHKVYACEVTHQGLSSPVTKSFNRGEC |
| SEQ ID NO: 89 | Heavy chain IgG | QVQLQESGPGLVKPSETLSLTCKVSGFSFSNSYWICWIRQPPGKGLEWIGCTFVGSS<br>DSTYYANWAKGRVTISVDSSKNQFSLKLSSVTAADTAVYYCARHPSDAVYGYANNLW<br>GQGTLVTVSSASTKGPSVFPLAPCSRSTSESTAALGCLVKDYFPEPVTVSWNSGALT<br>SGVHTFPAVLQSSGLYSLSSVVTVPSSSLGTKTYTCNVDHKPSNTKVDKRVESKYGP<br>PCPPCPAPEFLGGPSVFLFPPKPKDTLMISRTPEVTCVVVDVSQEDPEVQFNWYVDG |

TABLE 3A-continued

Examples of molecules comprising the antibody of the invention.

| SEQ ID NUMBER | Ab Format | Sequence |
|---|---|---|
| | | VEVHNAKTKPREEQFNSTYRVVSVLTVLHQDWLNGKEYKCKVSNKGLPSSIEKTISK AKGQPREPQVYTLPPSQEEMTKNQVSLTCLVKGFYPSDIAVEWESNGQPENNYKTTP PVLDSDGSFFLYSRLTVDKSRWQEGNVFSCSVMHEALHNHYTQKSLSLSLGK |

TABLE 3B

Examples of PDL1 antibodies suitable for the pharmaceutical combination of the present invention (CDR residues shown in bold and italic letters).

| SEQ ID NUMBER | Ab region | Sequence |
|---|---|---|
| | | 37-20-B03 |
| SEQ ID NO: 90 | HCDR1 (H27-H42; AHo numbering) | GFSFNSDYWIY |
| SEQ ID NO: 91 | HCDR2 (H57-H76; AHo numbering) | SIYGGSSGNTQYASWAQG |
| SEQ ID NO: 92 | HCDR3 (H108-H138; AHo numbering) | RGYVDYGGATDL |
| SEQ ID NO: 93 | HCDR1 (AHo definition) (37-20-B03 sc01) | VSGFSFNSDYW |
| SEQ ID NO: 94 | HCDR1 (AHo definition) (37-20-B03 sc02) (37-20-B03 sc09.1) | ASGFSFNSDYW |
| SEQ ID NO: 95 | HCDR2 (AHo definition) | IYGGSSGNTQYASWAQGR |
| SEQ ID NO: 96 | HCDR3 (AHo definition) | GYVDYGGATD |
| SEQ ID NO: 97 | HCDR1 (Kabat definition) | SDYWIY |
| SEQ ID NO: 98 | HCDR2 (Kabat definition) | SIYGGSSGNTQYASWAQG |
| SEQ ID NO: 99 | HCDR3 (Kabat definition) | GYVDYGGATDL |
| SEQ ID NO: 100 | HCDR1 (Chothia definition) | GFSFNSDY |
| SEQ ID NO: 101 | HCDR2 (Chothia definition) | GGSSG |
| SEQ ID NO: 102 | HCDR3 (Chothia definition) | YVDYGGATD |
| SEQ ID NO: 103 | VH (VH4) (37-20-B03sc01) | QVQLQESGPGLVKPSETLSLTCKVS*GFSFNSDYWIY*WIRQPPGKGLEWIG *SIYGGSSGNTQYASWAQG*RVTISVDSSKNQFSLKLSSVTAADTAVYYCA *RGYVDYGGATDL*WGQGTLVTVSS |
| SEQ ID NO: 104 | VH (VH1) (37-20-B03sc02) | QVQLVQSGAEVKKPGASVKVSCKAS*GFSFNSDYWIY*WVRQAPGQGLEWMG *SIYGGSSGNTQYASWAQG*RVTMTRDTSISTAYMELSSLRSEDTAVYYCA *RGYVDYGGATDL*WGQGTLVTVSS |
| SEQ ID NO: 105 | VH (VH3) (37-20-B03 sc09.1) Mutations: G56A; Y105F | EVQLVESGGGLVQPGGSLRLSCAAS*GFSFNSDYWIY*WVRQAPGKGLEWIA *SIYGGSSGNTQYASWAQG*RFTISRDNSKNTVYLQMNSLRAEDTAVYFCA *RGYVDYGGATDL*WGQGTLVTVSS |
| SEQ ID NO: 106 | LCDR1 (L24-L42; AHo numbering) (Kabat definition) | QASQSIGTYLA |
| SEQ ID NO: 107 | LCDR2 (L58-L72; AHo numbering) (Kabat definition) | RAFILAS |
| SEQ ID NO: 108 | LCDR3 (L107-L138; AHo numbering) (Kabat definition) | QSNFYSDSTTIGPNA |
| SEQ ID NO: 109 | LCDR1 (AHo definition) | ASQSIGTY |
| SEQ ID NO: 110 | LCDR2 (AHo definition) | RAFILASGVPSR |
| SEQ ID NO: 111 | LCDR3 (AHo definition) | NFYSDSTTIGPN |

TABLE 3B-continued

Examples of PDL1 antibodies suitable for the pharmaceutical combination of the present invention (CDR residues shown in bold and italic letters).

| SEQ ID NUMBER | Ab region | Sequence |
|---|---|---|
| SEQ ID NO: 112 | LCDR1 (Chothia definition) | SQSIGTY |
| SEQ ID NO: 113 | LCDR2 (Chothia definition) | RAF |
| SEQ ID NO: 114 | LCDR3 (Chothia definition) | NFYSDSTTIGPN |
| SEQ ID NO: 115 | VL (Vk1-sk17) (37-20-B03sc01) (37-20-B03sc02) | DIQMTQSPSSLSASVGDRVTITC*QASQSIGTYLA*WYQQKPGKAPKLLIY*RAFILAS*GVPSRFSGSGSGTDFTLTISSLQPEDFATYYC*QSNFYSDSTTIGPNA*FGTGTKVTVLG |
| SEQ ID NO: 116 | VL (Vk1-sk17) (37-20-B03 sc09.1) Mutations: 59A; A51P | DIQMTQSPASLSASVGDRVTITC*QASQSIGTYLA*WYQQKPGKPPKLLIY*RAFILAS*GVPSRFSGSGSGTDFTLTISSLQPEDFATYYC*QSNFYSDSTTIGPNA*FGTGTKVTVLG |
| SEQ ID NO: 117 | Linker | GGGGSGGGGSGGGGSGGGGS |
| SEQ ID NO: 118 | scFv (VL-linker-VH) (37-20-B03sc01) | DIQMTQSPSSLSASVGDRVTITC*QASQSIGTYLA*WYQQKPGKAPKLLIY*RAFILAS*GVPSRFSGSGSGTDFTLTISSLQPEDFATYYC*QSNFYSDSTTIGPNA*FGTGTKVTVLGGGGGSGGGGSGGGGSGGGGSQVQLQESGPGLVKPSETLSLTCKVS*GFSFNSDYWIY*WIRQPPGKGLEWIG*SIYGGSSGNTQYASWAQG*RVTISVDSSKNQFSLKLSSVTAADTAVYYCA*RGYVDYGGATDL*WGQGTLVTVSS |
| SEQ ID NO: 119 | scFv (VL-linker-VH) | DIQMTQSPSSLSASVGDRVTITC*QASQSIGTYLA*WYQQKPGKAPKLLIY*RAFILAS*GVPSRFSGSGSGTDFTLTISSLQPEDFATYYC*QSNFYSDSTTIGPNA*FGTGTKVTVLGGGGGSGGGGSGGGGSGGGGSQVQLVQSGAEVKKPGASVKVSCKAS*GFSFNSDYWIY*WVRQAPGKGLEWMG*SIYGGSSGNTQYASWAQG*RVTMTRDTSISTAYMELSSLRSEDTAVYYCA*RGYVDYGGATDL*WGQGTLVTVSS |
| SEQ ID NO: 120 | scFv (VL-linker-VH) (37-20-B03 sc09.1) | DIQMTQSPASLSASVGDRVTITC*QASQSIGTYLA*WYQQKPGKPPKLLIY*RAFILAS*GVPSRFSGSGSGTDFTLTISSLQPEDFATYYC*QSNFYSDSTTIGPNA*FGTGTKVTVLGGGGGSGGGGSGGGGSGGGGSEVQLVESGGGLVQPGGSLRLSCAAS*GFSFNSDYWIY*WVRQAPGKGLEWIAS*IYGGSSGNTQYASWAQG*RFTISRDNSKNTVYLQMNSLRAECTAVYFCAR*GYVDYGGATDL*WGQGTLVTVSS |

33-03-G02

| SEQ ID NO: 121 | HCDR1 (H27-H42; AHo numbering) | GFSFSSGYDMC |
| SEQ ID NO: 122 | HCDR2 (H57-H76; AHo numbering) | CVVAGSVDITYYASWAKG |
| SEQ ID NO: 123 | HCDR3 (H108-H138; AHo numbering) | RKDAYSDAFNL |
| SEQ ID NO: 124 | HCDR1 (AHo definition) (33-03-G02 sc01) | VSGFSFSSGYD |
| SEQ ID NO: 125 | HCDR1 (AHo definition) (33-03-G02 sc03 Full) (33-03-G02 sc18) | ASGFSFSSGYD |
| SEQ ID NO: 126 | HCDR2 (AHo definition) | VVAGSVDITYYASWAKGR |
| SEQ ID NO: 127 | HCDR3 (AHo definition) | KDAYSDAFN |
| SEQ ID NO: 128 | HCDR1 (Kabat definition) | SGYDMC |
| SEQ ID NO: 129 | HCDR2 (Kabat definition) | CVVAGSVDITYYASWAKG |
| SEQ ID NO: 130 | HCDR3 (Kabat definition) | KDAYSDAFNL |
| SEQ ID NO: 131 | HCDR1 (Chothia definition) | GFSFSSGY |
| SEQ ID NO: 132 | HCDR2 (Chothia definition) | AGSVD |
| SEQ ID NO: 133 | HCDR3 (Chothia definition) | DAYSDAFN |
| SEQ ID NO: 134 | VH (VH4) (33-03-G02 sc01) | QVQLQESGPGLVKPSETLSLTCKVS*GFSFSSGYDMC*WIRQPPGKGLEWIG*CVVAGSVDITYYASWAKG*RVTISVDSSKNQFSLKLSSVTAADTAVYYCA*RKDAYSDAFNL*WGQGTLVTVSS |

TABLE 3B-continued

Examples of PDL1 antibodies suitable for the pharmaceutical combination of the present invention (CDR residues shown in bold and italic letters).

| SEQ ID NUMBER | Ab region | Sequence |
|---|---|---|
| SEQ ID NO: 135 | VH (VH4) (33-03-G02 sc03 Full) (Mutations: V25; V25A; I44V; G56A; V82K; F89V; Y105F) | |
| SEQ ID NO: 136 | VH (VH4) (33-03-G02 sc18) Mutations VH: V25A; I44; G56A; V82K; F89V (AHo numbering) | QVQLQESGPGLVKPSETLSLTCKASGFSFSSGYDMCNVRQPPGKGLEWIACVVAGSVDITYYASWAKGRVTISKDSSKNQVSLKLSSVTAADTAVYYCRKDAYSDAFNLWGQGTLVTVSS |
| SEQ ID NO: 137 | LCDR1 (L24-L42; AHo numbering) (Kabat definition) | QASQSINDYLA |
| SEQ ID NO: 138 | LCDR2 (L58-L72; AHo numbering) (Kabat definition) | KASTLAS |
| SEQ ID NO: 139 | LCDR3 (L107-L138; AHo numbering) (Kabat definition) | QQGYIITDIDNV |
| SEQ ID NO: 140 | LCDR1 (AHo definition) | ASQSINDY |
| SEQ ID NO: 141 | LCDR2 (AHo definition) | KASTLASGVPSR |
| SEQ ID NO: 142 | LCDR3 (AHo definition) | GYIITDIDN |
| SEQ ID NO: 143 | LCDR1 (Chothia definition) | SQSINDY |
| SEQ ID NO: 144 | LCDR2 (Chothia definition) | KAS |
| SEQ ID NO: 145 | LCDR3 (Chothia definition) | GYIITDIDN |
| SEQ ID NO: 146 | VL (Vk1-sk17) (33_03_G02 sc01) (33-03-G02 sc18) | DIQMTQSPSSLSASVGDRVTITCQASQSINDYLAWYQQKPGKAPKLLIYKASTIASGVPSRFSGSGSGTDFTLTISSLQPEDFATYYCQQGYIITDIDNVFGTGTKVTVLG |
| SEQ ID NO: 147 | VL (Vk1-sk17) (33_03_G02 sc03 Full) (Mutations VL: I2F; M4L; A51P) | DFQLTQSPSSLSASVGDRVTITCQASQSINDYLAWYQQKPGKSPKLLIYKASTLASGVPSRFSGSGSGTDFTLTISSLQPEDFATYYCQQGYIITDIDNVFGTGTKVTVLG |
| SEQ ID NO: 148 | Linker | GGGGSGGGGSGGGGSGGGGS |
| SEQ ID NO: 149 | scFv (VL-linker-VH) (33-03-G02 sc01) | DIQMTQSPSSLSASVGDRVTITCQASQSINDYLAWYQQKPGKAPKLLIYKASTIASGVPSRFSGSGSGTDFTLTISSLQPEDFATYYCQQGYIITDIDNVFGTGTKVTVLGGGGGSGGGGSGGGGSGGGGSQVQLQESGPGLVKPSETLSLTCKVSGFSFSSGYDMCIRQPPGKGLEWIGCVVAGSVDITYYASWAKGRVTISVDSSKNQFSLKLSSVTAADTAVYYCARKDAYSDAFNLWGQGTLVTVSS |
| SEQ ID NO: 150 | scFv (VL-linker-VH) (33-03-G02 sc03 Full) | DFQLTQSPSSLSASVGDRVTITCQASQSINDYLAWYQQKPGKSPKLLIYKASTLASGVPSRFSGSGSGTDFTLTISSLQPEDFATYYCQQGYIITDIDNVFGTGTKVTVLGGGGGSGGGGSGGGGSGGGGSQSQLQESGPGLVKPSETLSLTCKASGFSFSSGYDMCNVRQPPGKGLEWIACVVAGSVDITYYASWAKGRVTISKDSSKNQVSLKLSSVTAADTAVYFCARKDAYSDAFNLWGQGTLVTVSS |
| SEQ ID NO: 151 | scFv (VL-linker-VH) (33-03-G02 sc18) | DIQMTQSPSSLSASVGDRVTITCQASQSINDYLAWYQQKPGKAPKLLIYKASTIASGVPSRFSGSGSGTDFTLTISSLQPEDFATYYCQQGYIITDIDNVFGTGTKVTVLGGGGGSGGGGSGGGGSGGGGSQVQLQESGPGLVKPSETLSLTCKASGFSFSSGYDMCNVRQPPGKGLEWIACVVAGSVDITYYASWAKGRVTISKDSSKNQVSLKLSSVTAADTAVYYCARKDAYSDAFNLWGQGTLVTVSS |

PRO1137 (33-03-G02-sc01 IgG1)

| SEQ ID NO: 152 | Light chain IgG | DIQMTQSPSSLSASVGDRVTITCQASQSINDYLAWYQQKPGKAPKLLIYKASTLASGVPSRFSGSGSGTDFTLTISSLQPEDFATYYCQQGYIITDIDNVFGTGTKVTVLGTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| SEQ ID NO: 153 | Heavy chain IgG | QVQLQESGPGLVKPSETLSLTCKVSGFSFSSGYDMCWIRQPPGKGLEWIGVVAGSVDITYYASWAKGRVTISVDSSKNQFSLKLSSVTAADTAVYYCARKDAYSDAFNLWGQGTLVTVSSASTKGPSVFPLAPSSKSTSGGTAALGCLVKDYFPEPVTVSWNSGALTSGVHTFPAVLQSSGLYSLSSVVTVPSSSLGTQTYIC |

TABLE 3B-continued

Examples of PDL1 antibodies suitable for the pharmaceutical combination of the present invention (CDR residues shown in bold and italic letters).

| SEQ ID NUMBER | Ab region | Sequence |
|---|---|---|
| | | NVNHKPSNTSVDKKVEPKSCDKTHTCPPCPAPELLGGPSVFLFPPKPKDTL<br>MISRTPEVTCVVVDVSHEDPEVKFNWYVDGVEVHNAKTKPREEQYNSTYRV<br>VSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSF<br>FLYSKLTVDKSRWQQGNVFSCSVMHEALHNHYTQKSLSLSPGK |
| | PRO1196 (37-20-B03 sc01 IgG1) | |
| SEQ ID NO: 154 | Light chain IgG | DIQMTQSPSSLSASVGDRVTITCQASQSIGTYLAWYQQKPGKAPKLLIYRA<br>FILASGVPSRFSGSGSGTDFTLTISSLQPEDFATYYCQSNFYSDSTTIGPN<br>AFGTGTKVTVLGTVAAPSVFIFPPSDEQLKSGTASVVCLLNNFYPREAKVQ<br>WKVDNALQSGNSQESVTEQDSKDSTYSLSSTLTLSKADYEKHKVYACEVTH<br>QGLSSPVTKSFNRGEC |
| SEQ ID NO: 155 | Heavy chain IgG | QVQLQESGPGLVKPSETLSLTCKVSGFSFNSDYWIYQIRQPPGKGLEWIGS<br>IYGGSSGNTQYASWAQGRVTISVDSSKNQFSLKLSSVTAADTAVYYCARGY<br>VDYGGATDLWGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTYI<br>CNVNHKPSNTSVDKKVEPKSCDKTHTCPPCPAPELLGGPSVFLFPPKPKDT<br>LMISRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVYTLP<br>PSRDELTKNQVSLTCLVKGFYPSDIAVEWESNGQPENNYKTTPPVLDSDGS<br>FFLYSKLTVDKSRWQQGNVFSCSVMHEALHNHYTQKSLSLSPGK |

Throughout the text of this application, should there be a discrepancy between the text of the specification (e.g., Tables 1 to 3) and the sequence listing, the text of the specification shall prevail.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

To the extent possible under the respective patent law, all patents, applications, publications, test methods, literature, and other materials cited herein are hereby incorporated by reference.

The following Examples illustrates the invention described above, but is not, however, intended to limit the scope of the invention in any way. Other test models known as such to the person skilled in the pertinent art can also determine the beneficial effects of the claimed invention.

EXAMPLES

Novel Antibodies Directed Against Human CD137

Example 1: Generation of Rabbit Antibodies Directed Against Human CD137

Rabbits have been immunized with recombinantly produced and purified human CD137 extracellular domain (Peprotech, cat. 310-15-1MG). During the immunization, the strength of the humoral immune response against the antigen was qualitatively assessed by determining the maximal dilution (titer) for the serum of each rabbit that still produced detectable binding of the polyclonal serum antibodies to the antigen. Serum antibody titers against the immobilized antigen (recombinant human CD137 ECD) were assessed using an enzyme-linked immunosorbent assay (ELISA). All rabbits immunized showed very high titers of at least 1:702'175 dilution of the serum. Serum from the same rabbits before the first antigen injection was used as background control.

Example 2: Hit Identification and Selection

Within the Hit identification procedure, a flow-cytometry-based sorting procedure was developed that specifically detects and allows for the isolation of high-affinity human CD137 ECD binding B-cells. To identify CD137 binding B-cells, CD137 ECD was labeled with the fluorescent dye R-Phycoerythrin (RPE). Since the CD137L binding site as well as the binding site of an anti-CD137 antibody on the labeled CD137 could potentially be blocked by the bulky RPE label, accessibility of the epitopes was confirmed by flow-cytometry. CD137L ECD fused to the Fc part of a human IgG1, urelumab, rabbit polyclonal anti-human CD137 or goat polyclonal anti-human CD137 were captured on protein G beads, and binding of R-PE labeled CD137 was confirmed by flow-cytometry. The fluorescence intensity is proportional to the amount of labeled CD137 bound to CD137L immobilized on the beads. Binding of CD137 to CD137L and anti-CD137 antibodies was found while no binding of RPE-labeled CD137 to Infliximab was detected.

Screening:

The results obtained during the screening phase are based on assays performed with non-purified antibodies from culture supernatants of antibody secreting cells (ASC), as the scale of the high-throughput culture does not allow for purification of the individual rabbit antibodies. Such supernatants allow to rank large numbers of antibodies relative to each other, however do not provide absolute values except for binding affinity. During the course of at least four weeks, supernatants from every individually cultured clone were collected. At the end of the cultivation period, the rabbit monoclonal antibodies in each cell culture supernatant were characterized in a high-throughput ELISA for binding to recombinant human CD137 ECD. CD137-binding supernatants were further characterized for binding kinetics to human and cynomolgus CD137. In addition, neutralization potential of the CD137 interaction to CD137L as well as to urelumab was determined by competition ELISA. Binding to membranous CD137 expressed on stable transduced Jurkat cells was also assessed. Mouse CD137 binding potential of the supernatants was analyzed by direct ELISA and binding kinetics were determined only for the positive supernatants.

Direct ELISA

ELISA plates were coated by adding 50 µl of PBS containing 250 ng/ml human CD137 (Peprotech, cat. 310-15-1MG) overnight at 4° C. Next day, plates were washed three times in overflow mode with 300 µl wash buffer (PBS, 0.005% Tween 20) per wells and 270 µl of blocking buffer (PBS, 1% BSA, 0.2% Tween 20) were added to each well for 1 h at RT without shaking. Then, plates were washed three times in overflow mode with 300 µl wash buffer and 50 µl of each supernatant was added, plates were incubated 1.5 h at RT under gentle agitation. After 3 washes in overflow mode with 300 µl wash buffer, 50 µl of a HRP-coupled goat-anti-rabbit IgG antibody 1:5,000 diluted in blocking buffer was added to each well. After 1 h incubation at RT on a nutating mixer, plates were washed three times in overflow mode with 300 µl wash buffer per well prior to the addition of 50 µl TMB (3,3',5,5'-tetramethylbenzidine). After 5 to 10 minutes development the enzymatic reaction was stopped by addition of 50 µl of 1 M HCl per well and plate was read at 450 nm using 690 nm as a reference wavelength.

Affinity to hCD137 by SPR

Binding affinities of antibodies towards human CD137 were measured by SPR using a MASS-1 SPR instrument (Sierra Sensors). For affinity screening, an antibody specific for the Fc region of rabbit IgGs (Bethyl Laboratories, Cat. No. A120-111A) was immobilized on a sensor chip (MASS-1 Affinity Sensor, High Capacity Amine, Sierra Sensors) using a standard amine-coupling procedure. Rabbit monoclonal antibodies in B-cell supernatants were captured by the immobilized anti-rabbit IgG antibody. A minimal IgG concentration in the B-cell supernatants is required to allow sufficient capture. After capturing of the monoclonal antibodies, human CD137 ECD (Peprotech, cat. 310-15-1MG) was injected into the flow cells for 3 min at a concentration of 90 nM and dissociation of the protein from the IgG captured on the sensor chip was allowed to proceed for 5 min. After each injection cycle, surfaces were regenerated with two injections of 10 mM Glycine-HCl. The apparent dissociation ($k_d$) and association ($k_a$) rate constants and the apparent dissociation equilibrium constant ($K_D$) were calculated with the MASS-1 analysis software (Analyzer, Sierra Sensors) using one-to-one Langmuir binding model and quality of the fits was monitored based on relative $Chi^2$ ($Chi^2$ normalized to the extrapolated maximal binding level of the analyte), which is a measure for the quality of the curve fitting. The smaller the value for the $Chi^2$ the more accurate is the fitting to the one-to-one Langmuir binding model. For most of the hits the relative $Chi^2$ value was below 15%. Results were deemed valid if the response units (RU) for ligand binding were at least 2% of the RUs for antibody capturing. Samples with RUs for ligand binding with less than 2% of the RUs for antibody capturing were considered to show no specific binding of CD137 to the captured antibody.

CD137/CD137L Competition ELISA

ELISA plates were coated by adding 50 µl of PBS containing 50 ng/ml CD137 Fc chimera (R&D Systems, cat. 838-4B-100) overnight at 4° C. Next day, plates were washed three times in overflow mode with 450 µl wash buffer (PBS, 0.005% Tween 20) per wells and 300 µl of blocking buffer (PBS with 1% BSA and 0.2 Tween 20) were added to each well for 1 h at RT on a nutating mixer. Then, the positive control (neutralizing goat anti-CD137 antibody) was diluted in 100% negative supernatant of sort 38 and 50 µl of the neutralizing antibody was added to the corresponding wells of the binding plate. In addition, 50 µl of the supernatant of the positive hits were transferred to the binding plate and incubated for 1 h at RT with shaking. Next, ELISA plates were washed 3 times in overflow mode with 450 µl wash buffer per well and 50 µl of 20 ng/ml biotinylated recombinant human CD137 ligand (Acro Biosystem, cat. 41L-H5257) diluted in blocking buffer was added to the wells. After 1 h of incubation at RT with shaking, the ELISA plates were washed 3 times in overflow mode with 450 µl wash buffer per well. Then, 50 µl of 10 ng/ml streptavidin-poly-HRP diluted in blocking buffer was added to each wells of the ELISA plates. After 1 h incubation at RT, plates were washed three times with 450 µl wash buffer and developed for 5 to 10 minutes after addition of 50 µl TMB. Finally, the enzymatic reaction was stopped by addition of 50 µl of 1 M HCl and plate was read at 450 nm using 690 nm as a reference wavelength.

Species Specificity by SPR: Cyno

Binding kinetics to cynomolgus CD137 were also determined using the same SPR setup as described for the binding to human CD137, but replacing human CD137 ECD by cynomolgus monkey CD137 ECD (Acro Biosystem, cat. 41B-C52H4).

Urelumab Competition ELISA

ELISA plates were coated by adding 50 µl of PBS containing 2 µg/ml urelumab (produced by Evitria, Schlieren, Switzerland) overnight at 4° C. Next day, plates were washed three times in overflow mode with 450 µl wash buffer (PBS, 0.005% Tween 20) per wells and 300 µl of blocking buffer (PBS with 1% BSA and 0.2 Tween 20) were added to each well for 1 h at RT on a nutating mixer. Then, urelumab was diluted in 95% negative supernatant of sort 38 spiked and pre-incubated for 1 h with 5% biotinylated CD137 ECD (Peprotech, cat. 310-15-1MG) at 7.5 ng/ml and was added to the corresponding wells of the binding plate. In addition, 55 µl of the supernatant of the positive hits were also spiked and pre-incubated for 1 h with 5% biotinylated CD137 ECD at 7.5 ng/ml and transferred to the binding plate and incubated for 1 h at RT with shaking. Next, the ELISA plates were washed 3 times in overflow mode with 450 µl wash buffer per well. Then, 50 µl of 10 ng/ml streptavidin-poly-HRP diluted in blocking buffer was added to each well of the ELISA plate. After 1 h incubation at RT, plates were washed three times with 450 µl wash buffer and developed for 5 to 10 minutes after addition of 50 µl TMB. Finally, the enzymatic reaction was stopped by addition of 50 µl of 1 M HCl and plate was read at 450 nm using 690 nm as a reference wavelength.

Cell-Based Binding Assay by FC: Human CD137

Method:

Jurkat wild type (control cells that do not express CD137) and Jurkat CD137 cells (clone C6, 1) were harvested and cell number was determined. Cell suspensions were centrifuged for 5 min at 400×g and 40 µl of cell suspensions (40,000 cells) diluted in PBS-EB (lx DPBS, 2% BCS H.I., 2 mM EDTA) were added to designated wells in a non-binding plate. Supernatants from positive hits of sort 38 were directly transferred into 96 well plate according to plate layout. Positive control samples (urelumab) were diluted in PBS-EB and transferred to the plate, final samples were of 95% negative supernatant of sort 38. After incubation at 4° C. for 1 h, plates washed 3 times using 100 µl of PBS-EB. Then, cell pellets were re-suspended with 50 µl secondary antibody solution at a concentration of 2 µg/ml (for B-cell clones: goat-anti-rabbit IgG labeled with AF647; for urelumab: goat-anti-human IgG labeled with PE) and incubated for 1 h at 4° C. Next, cells were washed again three times using 100 µl of PBS-EB. The cell pellets were then re-suspended with 50 µl PBS-EB and analyzed with NovoCyte 2060 flow cytometer device. Fluorescence intensity of PE and AF647 for 20,000 events was recorded for each sample and the geometric mean of fluorescence intensity MFI was calculated. The data were first corrected for unspecific antibody binding (blank and Jurkat wild type cell binding) and then normalized to binding levels obtained for urelumab.

Direct ELISA Mouse CD137

ELISA plates were coated by adding 50 µl of PBS containing 250 ng/ml mouse CD137 (Acro Biosystem, cat. 41B-M52H7) overnight at 4° C. Next day, plates were washed three times in overflow mode with 300 µl wash buffer (PBS, 0.005% Tween 20) per wells and 270 µl of blocking buffer (PBS, 1% BSA, 0.2% Tween 20) were added to each well for 1 h at RT without shaking. Then, plates were washed three times in overflow mode with 300 µl wash buffer and 50 µl of each supernatant was added, plates were incubated 1.5 h at RT under gentle agitation. After 3 washes in overflow mode with 300 µl wash buffer, 50 µl of a HRP-coupled goat-anti-rabbit IgG antibody 1:5,000 diluted in blocking buffer was added to each well. After 1 h incubation at RT on a nutating mixer, plates were washed three times in overflow mode with 300 µl wash buffer per well prior to the addition of 50 µl TMB. After 5 to 10 minutes development the enzymatic reaction was stopped by addition of 50 µl of 1 M HCl per well and plate was read at 450 nm using 690 nm as a reference wavelength. In this assay, supernatants from 85 B-cell clones produced a signal that was clearly above background (>0.1 OD).

Species Specificity by SPR: Mouse

Binding kinetics to mouse CD137 were also determined using the same setup as described for the binding to the human CD137, but in this case human CD137 ECD was replaced by mouse CD137 ECD (Acro Biosystem, cat. 41B-M52H7).

Selection of Screening Hits

Pharmacologic properties of monoclonal antibodies of final clones in B-cell supernatant are presented in Table 4. In a next step, selected clones were used for RNA isolation and RT-PCR to amplify the sequence of rabbit antibody light and heavy chain variable regions (38-02-A04 and 38-27-C05).

Example 3: Selection of Clones for Humanization

Based on data obtained during hit screening, 2 mouse cross-reactive CD137 binder 38-02-A04 and 38-27-C05 were humanized by grafting the CDRs on VH4 or VH3 based framework and implemented into a scDb format together with an anti-PDL1 domain. In addition, CDR regions of the selected clones were also grafted on VH3 based framework and produced in an scFv format. In order to achieve the best affinity and potency, further optimization with 2 different structural grafts (STR and IF grafting) was done for one clone which displayed the best affinity to human CD137 as scDb, namely 38-02-A04.

The following grafting variants were applied for clone 38-02-A04: CDR graft—grafting of rabbit CDRs on human framework; IF graft—CDR graft plus grafting of all rabbit VL/VH interface residues; full graft—CDR graft plus framework residues following AHo humanization protocol (AIF residues (rabbit residues potentially in contact with antigen (according to AHo)) were limited to residues with >20% change in solvent accessibility upon interface formation in order to reduce total number of mutations (rabbit framework residues)). Variants 38-02-A04 sc09 and 38-02-A04 sc13 are both CDR grafts on VH3 based framework, with 38-02-A04 sc13 comprising a G51C mutation (AHo numbering) on the VH and a T141C mutation (AHo numbering) on a VL chains, leading to a formation of an artificial interdomain disulfide bridge within the framework region. It was surprisingly found that 38-02-A04 sc13 comprising an interdomain disulfide bridge has a significantly increased thermostability.

Heterologous expression of the proteins was performed in E. coli as insoluble inclusion bodies by induced overnight expression in small scale (as indicated in Table 5 below). Inclusion bodies were isolated from the homogenized cell pellet by a centrifugation protocol that included several washing steps to remove cell debris and other host cell impurities. The purified inclusion bodies were solubilized in a denaturing buffer and the scFvs were refolded by a scalable refolding protocol that generated milligram amounts of natively folded, monomeric scFv. At this point a standardized protocol was employed to purify the scFvs. The product after refolding was captured by an affinity chromatography to yield the purified scFvs. Table 5 summarizes manufacture of scFv molecules. Expression of mammalian constructs was performed in CHO-S cells using CHOgro transient transfection kit (Mirus). Cultures were harvested after 5-7 days (cell viability <70%) of expression at 37° C. by centrifugation and proteins were purified from clarified culture supernatants by Protein L affinity chromatography followed, if needed, by a polishing step by size-exclusion chromatography. For the quality control of the manufactured material standard analytical methods, such as SE-HPLC, UV280 and SDS-PAGE were used.

Example 4: Pharmacodynamics Characterization of Humanized scFvs 4.1 Affinity to Human CD137

Affinity of the humanized scFvs to human CD137 was determined by SPR analysis on a T200 device (Biacore, GE Healthcare). In this experiment, Fc tagged human CD137 (R&D Systems, cat. 838-4B-100) was captured using the Human Antibody Capture kit from GE healthcare (cat. BR-1008-39). After each analyte injection cycle, the anti-human Fc-specific IgG was regenerated and new antigen was captured. The scFvs were injected as analyte using a dose response multi-cycle kinetic assay over the captured CD137 with concentrations of the analyte ranging from 0.19 to 45 nM (three-fold dilutions steps) diluted in running buffer. Association and dissociation time were set to 300 s and 720 s, respectively. Obtained sensorgrams were fitted using the 1:1 binding model. Data are shown in Table 6.

4.2 Species Cross-Reactivity (Binding to Cynomolgus Monkey and Mouse CD137 by SPR)

Cross-reactivity to cynomolgus CD137 was measured with cynomolgus monkey Fc-tagged CD137 (R&D Systems, cat. 9324-4B-100) in a similar assay as used to measure binding to human CD137. Table 7 summarizes the affinities obtained for all tested scFvs.

Because cross reactivity to mouse CD137 would be required for testing of antibodies in syngeneic mouse cancer models, scFvs produced based on the clone selection for direct humanization were tested for binding to mouse CD137. Cross-reactivity to mouse CD137 was measured with mouse Fc-tagged mouse CD137 (R&D Systems, cat. 937-4B-050) in a similar assay as used to measure binding to human CD137. Table 8 summarizes the affinities obtained for all tested scFvs.

4.3 Neutralization of CD137/CD137L Interaction by Competition ELISA

To show that anti-human CD137 scFvs did not interfere with the binding of CD137L to CD137, a competitive ELISA was employed. The commercial inhibitory polyclonal anti-CD137 goat antibody (Anti-bodies online, Cat # ABIN636609) served as a reference. Regarding the experimental setup, 50 ng/ml of human CD137 (tagged with Fc, R&D Systems, cat. 838-4B-100) was coated on ELISA plates overnight and serial dilutions of three fold steps of the scFvs starting at 50 µg/ml were added to the ELISA plates. Afterwards, biotinylated CD137L (in-house biotinylation of CD137L, Acro Biosystem, cat. 41L-H5257) was added and bound ligand was detected by addition of Streptavidin-HRP. Finally, the HRP substrate TMB was added. After development for 5 min, the reaction was stopped with 1 M HCl solution. The absorbance was measured at 450 nm and 690 nm as reference wave-length. The data are shown in Table 9. The scFv based on 38-02-A04 clone did not block CD137/CD137L interaction.

4.4 Binding to Human CD137 Expressing Cells by Flow Cytometry

Binding potency affinity to human CD137 expressing cells was also determined for selected scFvs. 50,000 CD137 expressing Jurkat cells (or as reference cell line Jurkat NFAT) were distributed to round bottom non-tissue culture treated 96 well plates. Cells were washed twice with 100 µl PBS by centrifugation at 400×g for 5 min. Cells were resuspended in 100 µl of serial dilutions of five-fold steps prepared in staining buffer (PBS, 2% BCS heat inactivated, 2 mM EDTA) of the tested scFvs as well as of the control IgG urelumab and ranging from 10,000 to 0.64 ng/ml (for scFvs: from 381.19 to 0.02 nM). After 1 h incubation at 4° C. on a nutating mixer, cells were washed 3 times with 100 µl staining buffer and centrifugation steps of 5 min at 400×g. Then, cells treated with scFvs were resuspended in 100 µl of staining buffer containing 0.5 µg/ml of APC labelled protein-L and cells treated with urelumab (human IgG4) were resuspended in 100 µl of staining buffer containing 2 µg/ml of goat anti-human IgG labelled with APC. Plates were incubated 1 h at 4° C. on a nutating mixer, then washed 3 times with 100 µl of staining buffer and resuspended in a final volume of 50 µl of staining buffer. Finally, APC signal of 20,000 events per well was analyzed by flow cytometry using a Novocyte flow cytometer system (ACEA Bioscience). Individual $EC_{50}$ values on each plate were calibrated against the $EC_{50}$ of the reference molecule urelumab that was taken along on each plate (relative $EC_{50}$: $EC_{50}$, urelumab/$EC_{50}$, test scFv).

As summarized in Table 10, binding to CD137 expressing cells could be confirmed for the scFv based on 38-02-A04 clone.

4.5 Selectivity for CD137 Versus CD40 and OX40 by SPR

In addition to cross-reactivity to cynomolgus monkey CD137, selectivity of binding of the anti-human CD137 scFvs to human CD137 and not to other members of the TNFR superfamily, such as CD40 and OX40, is desired. Therefore, binding of selected scFvs to human CD40 and OX40 was tested. Binding of scFvs to human Fc-tagged CD40 (AcroBiosystems, cat. CDO-H5253) and human Fc-tagged OX40 (Acro-Biosystems, cat. OXO-H5255) was determined by SPR analysis on a T200 device (Biacore, GE Healthcare). In this experiment, Fc-tagged CD40 and OX40 were captured using the Human Antibody Capture kit from GE healthcare (cat. BR-1008-39). After each analyte injection cycle, the anti-human Fc-specific IgG was regenerated and new antigen was captured. The scFvs were injected as analyte using a high concentration of 180 nM of the analyte diluted in running buffer. Association and dissociation time were set to 300 s and 720 s, respectively. Obtained sensorgrams were fitted using the 1:1 binding model. As summarized in Table 11, no binding to human Fc-tagged CD40 or human Fc-tagged OX40 was observed for the scFv based on 38-02-A04 clone.

TABLE 4

Pharmacodynamic properties of monoclonal antibodies in B-cell supernatants: 38-02-A04 and 38-27-C05.

| Clone ID | Affinity to human CD137 (SPR) | | | Affinity to cyno CD137 (SPR) | | | Affinity ratio cyno CD137/ human CD137 |
|---|---|---|---|---|---|---|---|
| | $k_a$ [M$^{-1}$s$^{-1}$] | $k_d$ [s$^{-1}$] | $K_D$ [M] | $k_a$ [M$^{-1}$s$^{-1}$] | $k_d$ [s$^{-1}$] | $K_D$ [M] | |
| 38-02-A04 | 4.38E+05 | 1.00E−06 | 2.29E−12 | 1.26E+05 | 1.00E−06 | 7.94E−12 | 3.46 |
| 38-27-C05 | 5.96E+05 | 2.86E−04 | 4.80E−10 | 2.38E+05 | 1.96E−04 | 8.26E−10 | 1.72 |

| Clone ID | Affinity to mouse CD137 (SPR) | | | Affinity ratio mouse CD137/ human CD137 | Urelumab competition ELISA | Binding to cellular human CD137 % relative binding to control |
|---|---|---|---|---|---|---|
| | $k_a$ [M$^{-1}$s$^{-1}$] | $k_d$ [s$^{-1}$] | $K_D$ [M] | | % inhibition | |
| 38-02-A04 | 8.89E+04 | 1.00E−06 | 1.13E−11 | 0.20 | 17.02 | 92.31 |
| 38-27-C05 | 1.08E+05 | 2.43E−04 | 2.25E−09 | 0.21 | 3.22 | 87.44 |

TABLE 5

ScFv production summary table.

| Clone ID | Protein ID | Grafting Strategy | Expression volume [mL] | Expression system | Protein amount post protein L [mg] | Yield post protein L [mg/L] | SEC Y/N? | Final yield [mg] | Yield per L expression [mg/L] | Purity SE-HPLC [% monomer] |
|---|---|---|---|---|---|---|---|---|---|---|
| 38-02-A04-sc01 | PRO1180 | CDR | 1200 | BL21 | 8.2 | 6.8 | Y | 0.1 | 0.0 | 90.0 |
| 38-02-A04-sc05 | PRO1181 | IF | 1200 | BL21 | 9.3 | 7.8 | Y | 4.7 | 3.9 | 88.0 |
| 38-02-A04-sc06 | PRO1182 | FULL | 1200 | BL21 | 19.8 | 16.5 | Y | 5.6 | 4.7 | 95.0 |
| 38-02-A04-sc09 | PRO1348 | CDR | 200 | CHO | 16.6 | 83.1 | N | 8.0 | 39.8 | 97.0 |
| 38-02-A04-sc13 | PRO1352 | CDR with ID diS | 200 | CHO | 12.2 | 61.0 | Y | 3.9 | 19.3 | 99.1 |
| 38-27-C05-sc03 | PRO1038 | CDR, FTO mut | 1200 | BL21 | 30.7 | 6.1 | Y | 12.1 | 10.1 | 98.8 |

TABLE 6

Affinities of scFv to human CD137.

| | | | | Affinity to human CD137 (SPR) | | | |
|---|---|---|---|---|---|---|---|
| Clone ID | Protein ID | Framework | Grafting Strategy | $k_a$ [M$^{-1}$ s$^{-1}$] | $k_d$ [s$^{-1}$] | $K_D$ [M] | Binding level normalized to theoretical Rmax |
| 38-02-A04-sc01 | PRO1180 | VH4 | CDR | not producible | | | |
| 38-02-A04-sc05 | PRO1181 | VH4 | IF | 3.50E+05 | 4.80E−04 | 1.37E−09 | 133.1% |
| 38-02-A04-sc06 | PRO1182 | VH4 | FULL | 1.44E+06 | 2.58E−05 | 1.79E−11 | 85% |
| 38-02-A04 sc09 | PRO1348 | VH3 | CDR | 7.40E+05 | 1.80E−04 | 2.44E−10 | 80.4% |
| 38-02-A04 sc13 | PRO1352 | VH3 | CDR with diS | 7.01E+05 | 1.03E−03 | 1.47E−09 | 83.5% |
| 38-27-C05-sc03 | PRO1038 | VH3 FTO | CDR | 1.63E+06 | 4.85E−03 | 2.97E−09 | 64.7% |

TABLE 7

Affinities of scFv to cynomolgus monkey CD137.

| | | | | Affinity to cynomolgus monkey CD137 (SPR) | | | |
|---|---|---|---|---|---|---|---|
| Clone ID | Protein ID | Framework | Grafting Strategy | $k_a$ [M$^{-1}$ s$^{-1}$] | $k_d$ [s$^{-1}$] | $K_D$ [M] | Binding level normalized to theoretical Rmax |
| 38-02-A04-sc01 | PRO1180 | VH4 | CDR | not producible | | | |
| 38-02-A04-sc05 | PRO1181 | VH4 | IF | 3.88E+05 | 5.30E−04 | 1.36E−09 | 112.5% |
| 38-02-A04-sc06 | PRO1182 | VH4 | FULL | 1.29E+06 | 1.83E−05 | 1.42E−11 | 79.9% |
| 38-02-A04 sc09 | PRO1348 | VH3 | CDR | not measured | | | |
| 38-02-A04 sc13 | PRO1352 | VH3 | CDR with diS | 6.95E+05 | 1.02E−03 | 1.47E−09 | 85.2% |
| 38-27-C05-sc03 | PRO1038 | VH3 FTO | CDR | 1.20E+06 | 7.31E−03 | 6.07E−09 | 69.2% |

TABLE 8

Affinities of scFv to mouse CD137.

| | | | | Affinity to mouse CD137 (SPR) | | | |
|---|---|---|---|---|---|---|---|
| Clone ID | Protein ID | Framework | Grafting Strategy | $k_a$ [$M^{-1} s^{-1}$] | $k_d$ [$s^{-1}$] | $K_D$ [M] | Binding level normalized to theoretical Rmax |
| 38-02-A04-sc01 | PRO1180 | VH4 | CDR | not producible | | | |
| 38-02-A04-sc05 | PRO1181 | VH4 | IF | not measured | | | |
| 38-02-A04-sc06 | PRO1182 | VH4 | FULL | not measured | | | |
| 38-02-A04 sc09 | PRO1348 | VH3 | CDR | not measured | | | |
| 38-02-A04 sc13 | PRO1352 | VH3 | CDR with diS | no binding | | | 7.5% |
| 38-27-C05-sc03 | PRO1038 | VH3 FTO | CDR | 4.05E+04 | 1.12E−03 | 2.76E−08 | 12.9% |

TABLE 9

Potencies of selected scFvs to inhibit the interaction between CD137 and CD137L.

| | | | | Potency in CD137/CD137L competition ELISA | | |
|---|---|---|---|---|---|---|
| Clone ID | Protein ID | Framework | Grafting Strategy | IC$_{50}$ [ng/ml] | rel. IC$_{50}$ (IC$_{50, reference}$/IC$_{50, scFv}$) | Maximum activation (relative to reference in %) |
| 38-02-A04-sc13 | PRO1352 | VH3 | CDR with diS | no inhibition | | |

TABLE 10

Summary of binding affinity to cellular CD137 of the tested scFvs.

| | | | | Binding to cellular human CD137 | | |
|---|---|---|---|---|---|---|
| Clone ID | Protein ID | Framework | Grafting Strategy | EC$_{50}$ [ng/ml] | rel. EC$_{50}$ (EC$_{50, urelumab}$/EC$_{50, scFv}$) | Maximum binding (relative to urelumab) |
| 38-02-A04-sc13 | PRO1352 | VH3 | CDR with diS | 1096 | 0.057 | 10% |

TABLE 11

ScFvs tested for binding to human CD40 and OX40 by SPR.

| | | | | Affinity to human CD40 (SPR) | | | | Affinity to human OX40 (SPR) | | | |
|---|---|---|---|---|---|---|---|---|---|---|---|
| Clone ID | Protein ID | Framework | Grafting Strategy | $k_a$ [$M^{-1} s^{-1}$] | $k_d$ [$s^{-1}$] | $K_D$ [M] | Binding level normalized to theoretical Rmax | $k_a$ [$M^{-1} s^{-1}$] | $k_d$ [$s^{-1}$] | $K_D$ [M] | Binding level normalized to theoretical Rmax |
| 38-02-A04-sc13 | PRO1352 | VH3 | CDR with diS | no binding | | | | no binding | | | |

Example 5: Biophysical Characterization of the Humanized scFvs

Selected molecules were produced at larger scale (0.2 L-1.2 L expression volume), and were concentrated to >10 mg/mL using centrifugal concentration tubes after purification (Table 14).

ScFvs were subjected to stability studies such as a four-week stability study, in which the scFvs were formulated in an aqueous buffer (50 mM phosphate citrate buffer with 150 mM NaCl at pH 6.4) at 10 mg/ml and stored at <−80° C., 4° C. and 40° C. for four weeks. At the minimum, the fraction of monomers and oligomers in the formulation were evaluated by integration of SE-HPLC peak areas after one week, two weeks and at the end of each study. Additional time points were recorded for some of the molecules. Table 15 compares d7 and endpoint measurements obtained at d28 of the study.

In addition, the compatibility of the scFv molecules was assessed with respect to freeze-thawing (F/T) cycles (colloidal stability). For the F/T stability assessment the same analytical methods and parameters (% monomer content and % monomer loss) as for the storage stability study (SE-HPLC, SDS-PAGE) were applied to monitor the quality of the molecules over five F/T cycles. Table 16 shows the course of monomer content in % over five repeated F/T cycles. None of the molecules lost >4% monomeric content after repeated F/T cycles.

Thermal unfolding of the molecules was assessed by using the fluorescence dye SYPRO orange. Samples in relevant excipient conditions were prepared and the assay was performed in a qPCR machine. Fluorescence emission was detected using the software's custom dye calibration routine. The PCR plate containing the test samples was subjected to a temperature ramp from 25° C. to 96° C. in increments of 1° C. The midpoint of the unfolding transition (Tm) was calculated by the software GraphPad Prism using a mathematical second derivative method to calculate the inflection point of the curve. The reported Tm is an average of three measurements. Table 17 shows melting temperatures of the molecules formulated in generic buffer (phosphate-citrate buffer at pH 6.4, 150 mM NaCl).

Top selected molecules were subjected to a short-term pH stress stability study, in which the scFv molecules were formulated at 1 mg/ml in a set of aqueous (phosphate-citrate) buffer systems with pH values between 3.5 and 7.5. Monomeric content in % and % monomer loss was analyzed after storage for 2 weeks at 40° C. in the respective buffer systems (data not shown). A tabulated summary of monomeric content, monomeric loss, concentration and concentration loss over the course of the study is shown in Table 18.

TABLE 12

Manufacture of domains for stability study.

| Clone ID | Protein ID | Grafting Strategy | Expression volume [mL] | Expression system | Protein amount post protein L [mg] | Yield post protein L [mg/L] | SEC Y/N? | Final yield [mg] | Yield per L expression [mg/L] | Purity SE-HPLC [% monomer] | Monomeric content at 10 mg/mL [%] | Monomeric loss upon concentration to 10 mg/mL |
|---|---|---|---|---|---|---|---|---|---|---|---|---|
| 38-02-A04-sc05 | PRO1181 | IF | 1200 | BL21 | 9.3 | 7.8 | Y | 4.7 | 3.9 | 88 | 77.8 | 10.2 |
| 38-02-A04-sc06 | PRO1182 | FULL | 1200 | BL21 | 19.8 | 16.5 | Y | 5.6 | 4.7 | 95 | 72.9 | 22.1 |
| 38-02-A04-sc09 | PRO1348 | CDR | 200 | CHO | 16.6 | 83.1 | N | 8 | 39.8 | 97 | 94.3 | 2.7 |
| 38-02-A04-sc13 | PRO1352 | CDR with ID diS | 200 | CHO | 12.2 | 61 | Y | 3.9 | 19.3 | 99.1 | 99.0 | 0.1 |

TABLE 13

Four week stability study of the scFv domains.

| Clone ID | Protein ID | Temp. [° C.] | Initial monomeric content [%] | monomeric content [%] d0 | monomeric content [%] d7 | monomeric content [%] d28 | monomeric content loss [%] d7 | monomeric content loss [%] d28 | Protein concentration [mg/mL] d0 | Protein concentration [mg/mL] d7 | Protein concentration [mg/mL] d28 | protein content loss [%] d7 | protein content loss [%] d28 |
|---|---|---|---|---|---|---|---|---|---|---|---|---|---|
| 38-02-A04-sc05 | PRO1181 | −80 | 77.8 | NA | NA | NA | NA | NA | NA | NA | NA | NA | NA |
|  |  | 4 |  | NA | NA | NA | NA | NA | NA | NA | NA | NA | NA |
|  |  | 40 |  | 77.8 | 78.2 | 77.8 | −0.5 | 0.1 | 10.4 | 10.4 | 9.6 | 0.2 | 7.7 |
| 38-02-A04-sc06 | PRO1182 | −80 | 72.9 | 72.9 | 72.8 | 72.9 | 0.1 | 0.0 | 20.6 | 21.0 | 24.8 | −2.0 | −20.5 |
|  |  | 4 |  | 72.9 | 72.8 | 73.5 | 0.1 | −0.8 | 20.6 | 20.7 | 19.9 | −0.7 | 3.3 |
|  |  | 40 |  | 72.9 | 72.8 | 72.1 | 0.1 | 1.1 | 20.6 | 20.5 | 20.7 | 0.3 | −0.6 |
| 38-02-A04-sc09 | PRO1348 | −80 | 94.3 | 94.3 | 93.2 | 91.2 | 1.1 | 3.3 | 10.0 | 11.0 | 11.2 | −10.3 | −11.8 |
|  |  | 4 |  | 94.3 | 84.6 | 83.4 | 10.3 | 11.5 | 10.0 | 11.2 | 11.3 | −12.1 | −13.2 |
|  |  | 40 |  | 94.3 | 85.7 | 84.5 | 9.1 | 10.4 | 10.0 | 11.5 | 12.0 | −15.2 | −20.5 |
| 38-02-A04-sc13 | PRO1352 | −80 | 99.0 | 99.0 | 99.1 | 99.1 | 0.0 | −0.1 | 11.4 | 11.8 | 11.7 | −3.6 | −2.7 |
|  |  | 4 |  | 99.0 | 99.1 | 99.1 | −0.1 | −0.1 | 11.4 | 11.9 | 11.8 | −4.3 | −3.7 |
|  |  | 40 |  | 99.0 | 99.1 | 99.0 | −0.1 | 0.0 | 11.4 | 12.5 | 12.9 | −9.3 | −13.2 |

TABLE 14

Assessment of F/T stability over time course of 28 d.

| Clone ID | PRO ID | F/T-1* | F/T-2* |
|---|---|---|---|
| 38-02-A04-sc13 | PRO1352 | 0.0 | 0.1 |

*monomeric loss % upon F/T

TABLE 15

Differential Scanning Fluorimetry of the scFv domains.

| Clone ID | Protein ID | Grafting Strategy | Tm [° C.] |
|---|---|---|---|
| 38-02-A04-sc09 | PRO1348 | CDR | 61.1 |
| 38-02-A04-sc13 | PRO1352 | CDR with ID diS | 55.2 |

TABLE 16

Tabulated summary of pH stability assessment.

| Clone ID | Protein ID | Temperature | Final buffer | monomeric content [%] d0 | d7 | d14 | monomeric loss [%] d7 | d14 | protein concentration [mg/mL] d0 | d7 | d14 | content loss [%] d7 | d14 |
|---|---|---|---|---|---|---|---|---|---|---|---|---|---|
| 38-02-A04-sc13 | PRO1352 | 4° C. | pH 3.5 | 98.2 | 98.4 | 98.2 | 0.2 | −0.2 | 1.1 | 1.0 | 1.1 | −3.3 | 3.0 |
| | | | pH 4.5 | 98.2 | 98.4 | 98.3 | 0.2 | −0.2 | 0.9 | 1.0 | 1.0 | 10.1 | −0.5 |
| | | | pH 5.5 | 98.1 | 98.4 | 98.2 | 0.4 | −0.2 | 1.0 | 1.0 | 1.1 | −0.6 | 9.5 |
| | | | pH 6.5 | NA | 98.0 | 98.1 | NA | 0.1 | 1.0 | 0.8 | 1.0 | −14.1 | 26.5 |
| | | | pH 7.5 | NA | 98.0 | 98.2 | NA | 0.2 | 1.0 | 1.0 | 1.0 | 1.1 | 6.7 |
| | | 40° C. | pH 3.5 | 98.2 | 98.0 | 98.2 | −0.2 | 0.2 | 1.1 | 1.1 | 1.1 | 6.5 | −6.6 |
| | | | pH 4.5 | 98.2 | 98.0 | 98.1 | 1.1 | 0.1 | 0.9 | 1.1 | 1.0 | 18.4 | −4.1 |
| | | | pH 5.5 | 98.1 | 98.0 | 98.1 | 1.3 | 0.1 | 1.0 | 1.0 | 1.1 | 3.6 | 3.3 |
| | | | pH 6.5 | NA | 98.0 | 98.2 | 1.4 | 0.2 | 1.0 | 1.0 | 1.1 | 6.7 | 2.8 |
| | | | pH 7.5 | NA | 98.0 | 98.1 | 1.4 | 0.1 | 1.0 | 1.0 | 1.1 | 4.1 | 6.3 |

The Multispecific Molecules Comprising the Antibody of the Invention

The exemplary multispecific molecules comprising the antibody of the invention are included in Table 3.

Example 6: Affinities to PDL1, CD137, HSA and MSA

Methods:

Affinity to PDL1 of the different species was determined by SPR measurements using a Biacore T200 device (GE Healthcare). An antibody specific for the Fc region of human IgGs was immobilized on a sensor chip (CM5 sensor chip, GE Healthcare) by amine-coupling. For all formats, with the exception of the Fc containing Morrison formats, PDL1-Fc chimeric protein from different species were captured by the immobilized antibody. Three-fold serial dilutions of the molecules specific for PDL1 (0.12-90 nM) were injected into the flow cells for three minutes and dissociation was monitored for 10 minutes. After each injection cycle, surfaces were regenerated with one injection of a 3 M $MgCl_2$ solution. The apparent dissociation ($k_d$) and association ($k_a$) rate constants and the apparent dissociation equilibrium constant (KD) were calculated using one-to-one Langmuir binding model. Affinity to CD137 of the different species was determined using the identical setup as for PDL1 with the exception that CD137-Fc chimeric proteins from different species were captured by the immobilized antibody.

The Fc containing formats were directly captured by the antibody specific for the Fc region of human IgGs. Two-fold serial dilutions of PDL1 extracellular domain or CD137 extracellular domain ranging from 90 to 0.35 nM were tested for binding to the IgG captured on the biosensor chip. After each injection cycle, surfaces were regenerated with one injection of a 3 M MgCl2 solution.

Affinity of molecules to serum albumin (SA) of the different species was determined by SPR measurements using a Biacore T200 device (GE Healthcare). SA was directly coupled to a CM5 sensor chip (GE Healthcare) using amine coupling chemistry. After performing a regeneration scouting and surface performance test to find best assay conditions, a dose response was measured and obtained binding curves were double-referenced (empty reference channel and zero analyte injection) and fitted using the 1:1 Langmuir model to retrieve kinetic parameters. The assay was run in a 1×PBS-Tween buffer at pH 5.5.

Results:

The measurement of binding kinetics for the CDR grafts of the two CD137 specific humanized constructs derived from clone 38-02-A04 and 38-27-C05 show nearly identical affinities (compare PRO885 and PRO951 in Table 17). For clone 38-02-04 the described structural residues engrafted in the framework regions led to an improvement of affinity of more than 200-fold (compare PRO885 and PRO1124 in Table 17). In addition for constructs derived from clone 38-02-04 binding to mouse CD137 was observed, however with very much reduced affinity.

TABLE 17

Affinities of different formats to PDL1, CD137 and serum albumin from different species.

| PRO ID | Clone ID PD-L1 | Clone ID CD137 | Clone ID SA | Format |
|---|---|---|---|---|
| PRO885 | 33-03-G02 CDR | 38-02-A04 CDR | NA | scDb |
| PRO951 | 33-03-G02 CDR | 38-27-005 CDR | NA | scDb |
| PRO1123 | 33-03-G02 CDR | 38-02-A04 IF | NA | scDb |
| PRO1124 | 33-03-G02 CDR | 38-02-A04 STR | NA | scDb |
| PRO1125 | 33-03-G02 IF | 38-02-A04 CDR | NA | scDb |
| PRO1126 | 33-03-G02 STR | 38-02-A04 CDR | NA | scDb |
| PRO1134 | 33-03-G02 STR2, VH3 | 38-02-A04 CDR | NA | scDb |
| PRO963 | 33-03-G02 CDR | 38-02-A04 CDR | 19-01-H04 STR | scDb-scFv |
| PRO966 | 33-03-G02 CDR | 38-27-C05 CDR | 19-01-H04 STR | scDb-scFv |
| PRO1057 | 33-03-G02 CDR | 38-02-A04 CDR | 23-13-A01 STR | scDb-scFv |
| PRO1058 | 33-03-G02 CDR | 38-27-C05 CDR | 23-13-A01 STR | scDb-scFv |
| PRO1059 | 33-03-G02 CDR | 38-02-A04 CDR | NA | Morrison-L |
| PRO1060 | 33-03-G02 CDR | 38-02-A04 CDR | NA | Morrison-H |
| PRO1061 | 33-03-G02 CDR | 38-27-C05 CDR | NA | Morrison-L |
| PRO1062 | 33-03-G02 CDR | 38-27-C05 CDR | NA | Morrison-H |
| PRO997 | 37-20-B03 CDR | NA | NA | scFv |
| PRO1013 | 37-20-B03 CDR, VH1 | NA | NA | scFv |
| PRO830 | 33-03-G02 CDR | NA | NA | scFv |
| PRO1186 | 37-20-B03 sc01 | 38-02-A04 sc01 | 23-13-A01 sc03 | scDb-scFv |
| PRO1430 | 37-20-B03 sc01 | 38-02-A04 sc013 | 19-01-H04 sc03 | scDb-scFv |
| PRO1479 | 37-20-B03 sc09.1 | 38-02-A04 sc013 | 19-01-H04 sc03 | scDb-scFv |
| PRO1482 | 37-20-B03 sc09.1 | 38-02-A04 sc013 | 19-01-H04 sc03 | scDb-scFv |
| PR01431 | 33-03-G02 sc18 | 38-02-A04 sc013 | 19-01-H04 sc03 | scDb-scFv |
| PR01473 | 33-03-G02 sc03 | 38-02-A04 sc013 | 19-01-H04 sc03 | scDb-scFv |
| PR01476 | 33-03-G02 sc03 | 38-02-A04 sc013 | 19-01-H04 sc03 | scDb-scFv |
| PR01432 | 33-03-G02 sc18 | 38-02-A04 sc018 | 19-01-H04 sc03 | scDb-scFv |

| | Affinity to human PD-L1 | | | Affinity to cynomolgus PD-L1 | | |
|---|---|---|---|---|---|---|
| PRO ID | $k_a$ (M$^{-1}$ s$^{-1}$) | $k_d$ (s$^{-1}$) | KD (M) | $k_a$ (M$^{-1}$ s$^{-1}$) | $k_d$ (s$^{-1}$) | KD (M) |
| PRO885 | 2.1E+06 | 1.4E−04 | 6.5E−11 | ND | ND | ND |
| PRO951 | 2.2E+06 | 1.5E−04 | 7.0E−11 | ND | ND | ND |
| PRO1123 | 2.3E+06 | 1.7E−04 | 7.5E−11 | ND | ND | ND |
| PRO1124 | 3.1E+06 | 2.0E−04 | 6.7E−11 | ND | ND | ND |
| PRO1125 | 1.7E+06 | 1.1E−04 | 6.7E−11 | ND | ND | ND |
| PRO1126 | 2.8E+06 | <1.0E−05 | 3.5E−12 | ND | ND | ND |
| PRO1134 | 2.8E+06 | 7.6E−05 | 2.8E−11 | ND | ND | ND |
| PRO963 | 2.0E+06 | 1.3E−04 | 6.6E−11 | ND | ND | ND |
| PRO966 | 1.6E+06 | 1.4E−04 | 8.3E−11 | ND | ND | ND |
| PRO1057 | 1.6E+06 | 1.7E−04 | 1.1E−10 | ND | ND | ND |
| PRO1058 | 1.2E+06 | 1.9E−04 | 1.6E−10 | ND | ND | ND |
| PRO1059 | 1.2E+06 | 6.5E−05 | 5.6E−11 | ND | ND | ND |
| PRO1060 | 1.3E+06 | 4.6E−05 | 3.6E−41 | ND | ND | ND |
| PRO1061 | ND | ND | ND | ND | ND | ND |
| PRO1062 | 1.3E+06 | 5.0E−05 | 3.8E−11 | ND | ND | ND |
| PRO997 | 5.9E+06 | <1.0E−05 | 1.7E−12 | 6.0E+06 | <1.0E−05 | <1.67E−12 |
| PRO1013 | 6.0E+06 | 2.7E−04 | 4.5E−11 | 5.9E+06 | 3.2E−04 | 5.3E−11 |
| PRO830 | 2.1E+06 | 1.6E−04 | 7.6E−11 | 2.2E+06 | 2.0E−04 | 9.4E−11 |
| PRO1186 | 6.2E+06 | 2.3E−05 | 3.7E−12 | TBD | TBD | TBD |
| PRO1430 | 5.3E+06 | 2.4E−05 | 4.5E−12 | TBD | TBD | TBD |
| PRO1479 | 4.2E+06 | 3.9E−05 | 9.2E−12 | TBD | TBD | TBD |
| PRO1482 | 3.4E+06 | 3.3E−05 | 9.8E−12 | TBD | TBD | TBD |
| PRO1431 | 3.3E+06 | 4.5E−05 | 1.4E−11 | ND | ND | ND |
| PRO1473 | 3.6E+06 | 2.9E−05 | 8.2E−12 | ND | ND | ND |
| PRO1476 | 3.4E+06 | 3.1E−05 | 9.0E−12 | ND | ND | ND |
| PRO1432 | 4.2E+06 | 4.4E−05 | 1.1E−11 | ND | ND | ND |

| | Affinity to human CD137 | | | Affinity to cynomolgus CD137 | | |
|---|---|---|---|---|---|---|
| PRO ID | $k_a$ (M$^{-1}$ s$^{-1}$) | $k_d$ (s$^{-1}$) | KD (M) | $k_a$ (M$^{-1}$ s$^{-1}$) | $k_d$ (s$^{-1}$) | KD (M) |
| PRO885 | 2.4E+05 | 7.6E−04 | 3.2E−09 | 3.4E+05 | 7.0E−04 | 2.1E−09 |
| PRO951 | 1.5E−06 | 6.3E−03 | 4.2E−09 | 1.5E+06 | 1.0E−02 | 6.9E−09 |
| PRO1123 | 3.1E+05 | 2.7E−04 | 8.8E−10 | 2.6E+05 | 3.3E−04 | 1.3E−09 |
| PRO1124 | 6.8E+05 | <1.0E−05 | 1.5E−11 | 5.6E+05 | 3.3E−04 | 5.9E−10 |
| PRO1125 | 2.0E+05 | 7.5E−04 | 3.7E−09 | ND | ND | ND |
| PRO1126 | 2.1E+05 | 7.5E−04 | 3.5E−09 | ND | ND | ND |
| PRO1134 | 2.5E+05 | 8.4E−04 | 3.4E−09 | ND | ND | ND |
| PRO963 | 2.0E+05 | 6.2E−04 | 3.0E−09 | ND | ND | ND |
| PRO966 | 1.0E+06 | 2.2E−03 | 2.2E−09 | ND | ND | ND |
| PRO1057 | 1.4E+05 | 7.0E−04 | 5.1E−09 | 1.6E+05 | 7.9E−04 | 4.8E−09 |
| PRO1058 | 1.7E+06 | 2.1E−03 | 1.2E−09 | ND | ND | ND |
| PRO1059 | 1.8E+05 | 4.2E−04 | 2.3E−09 | ND | ND | ND |
| PRO1060 | 3.0E+05 | 3.9E−04 | 1.3E−09 | ND | ND | ND |
| PRO1061 | ND | ND | ND | ND | ND | ND |

TABLE 17-continued

Affinities of different formats to PDL1, CD137 and serum albumin from different species.

| PRO ID | $k_a$ (M⁻¹ s⁻¹) | $k_d$ (s⁻¹) | KD (M) | | | |
|---|---|---|---|---|---|---|
| PRO1062 | 2.8E+05 | 3.7E−04 | 1.3E−09 | ND | ND | ND |
| PRO997 | NA | NA | NA | NA | NA | NA |
| PRO1013 | NA | NA | NA | NA | NA | NA |
| PRO830 | NA | NA | NA | NA | NA | NA |
| PRO1186 | 1.9E+05 | 5.0E−04 | 2.6E−09 | TBD | TBD | TBD |
| PRO1430 | 4.6E+05 | 7.1E−04 | 1.5E−09 | TBD | TBD | TBD |
| PRO1479 | 3.3E+05 | 5.4E−04 | 1.7E−09 | TBD | TBD | TBD |
| PRO1482 | 3.2E+05 | 3.6E−04 | 1.1E−09 | TBD | TBD | TBD |
| PRO1431 | 4.5E+05 | 7.5E−04 | 1.7E−09 | TBD | TBD | TBD |
| PRO1473 | 3.1E+05 | 6.0E−04 | 2.0E−09 | TBD | TBD | TBD |
| PRO1476 | 3.5E+05 | 3.7E−04 | 1.1E−09 | TBD | TBD | TBD |
| PRO1432 | 6.0E+05 | 4.5E−04 | 7.5E−10 | TBD | TBD | TBD |

| | Affinity to mouse CD137 | | | Affinity to human SA | | |
|---|---|---|---|---|---|---|
| PRO ID | $k_a$ (M⁻¹ s⁻¹) | $k_d$ (s⁻¹) | KD (M) | $k_a$ (M⁻¹ s⁻¹) | $k_d$ (s⁻¹) | KD (M) |
| PRO885 | 2.9E+05 | 1.8E−01 | 6.0E−07 | NA | NA | NA |
| PRO951 | NB | NB | NB | NA | NA | NA |
| PRO1123 | 6.5E+04 | 2.7E−02 | 4.1E−07 | NA | NA | NA |
| PRO1124 | 2.0E+05 | 2.2E−03 | 1.1E−08 | NA | NA | NA |
| PRO1125 | 5.4E+05 | 2.7E−01 | 5.1E−07 | NA | NA | NA |
| PRO1126 | NB | NB | NB | NA | NA | NA |
| PRO1134 | 4.5E+05 | 1.9E−01 | 4.2E−07 | NA | NA | NA |
| PRO963 | NB | NB | NB | 1.1E+05 | 3.0E−04 | 2.8E−09 |
| PRO966 | 5.1E+03 | 1.0E−03 | 2.0E−07 | ND | ND | ND |
| PRO1057 | 6.9E+04 | 8.5E−02 | 1.2E−06 | 2.4E+05 | 6.7E−04 | 2.8E−09 |
| PRO1058 | 1.1E+06 | 7.5E−04 | 7.0E−10 | ND | ND | ND |
| | | | | NA | NA | NA |
| PRO1059 | ND | ND | ND | NA | NA | NA |
| PRO1060 | ND | ND | ND | NA | NA | NA |
| PRO1061 | ND | ND | ND | NA | NA | NA |
| PRO1062 | ND | ND | ND | NA | NA | NA |
| PRO997 | NA | NA | NA | NA | NA | NA |
| PRO1013 | NA | NA | NA | NA | NA | NA |
| PRO830 | NA | NA | NA | NA | NA | NA |
| PRO1186 | ND | ND | ND | 2.5E+05 | 7.2E−04 | 2.9E−09 |
| PRO1430 | ND | ND | ND | TBD | TBD | TBD |
| PRO1479 | ND | ND | ND | TBD | TBD | TBD |
| PRO1482 | ND | ND | ND | TBD | TBD | TBD |
| PRO1431 | ND | ND | ND | ND | ND | ND |
| PRO1473 | ND | ND | ND | ND | ND | ND |
| PRO1476 | ND | ND | ND | ND | ND | ND |
| PRO1432 | ND | ND | ND | ND | ND | ND |

| | Affinity to mouse SA | | |
|---|---|---|---|
| PRO ID | $k_a$ (M⁻¹ s⁻¹) | $k_d$ (s⁻¹) | KD (M) |
| PRO885 | NA | NA | NA |
| PRO951 | NA | NA | NA |
| PRO1123 | NA | NA | NA |
| PRO1124 | NA | NA | NA |
| PRO1125 | NA | NA | NA |
| PRO1126 | NA | NA | NA |
| PRO1134 | NA | NA | NA |
| PRO963 | NB | NB | NB |
| PRO966 | NA | NA | NA |
| PRO1057 | 1.3E+05 | 8.5E−03 | 6.6E−08 |
| PRO1058 | ND | ND | ND |
| | NA | NA | NA |
| PRO1059 | NA | NA | NA |
| PRO1060 | NA | NA | NA |
| PRO1061 | NA | NA | NA |
| PRO1062 | NA | NA | NA |
| PRO997 | NA | NA | NA |
| PRO1013 | NA | NA | NA |
| PRO830 | NA | NA | NA |
| PRO1186 | 2.2E+05 | 9.5E−03 | 43E−08 |
| PRO1430 | NA | NA | NA |
| PRO1479 | NA | NA | NA |
| PRO1482 | NA | NA | NA |
| PRO1431 | NA | NA | NA |
| PRO1473 | NA | NA | NA |
| PRO1476 | NA | NA | NA |
| PRO1432 | NA | NA | NA |

NA: not applicable TBD: to be determined NB: no significant binding ND: not determined Example 7: No Inhibition of CD137 and CD137 Neutralization by Humanized Anti-CD137 Domains To show that PRO885 does not interfere with the binding of CD137 ligand (CD137L) to CD137, a competitive ELISA was employed. The commercial inhibitory polyclonal anti-CD137 goat antibody (Antibodies online, Cat # ABIN636609) served as a reference. In brief, CD137 was coated on the ELISA plate overnight and serial dilutions of PRO885 were added to the ELISA plate. Afterwards, biotinylated CD137L was added and bound ligand was detected by addition of Streptavidin-HRP. Finally, the HRP substrate TMB was added. After development for 5 min, the reaction was stopped with 1 M HCl solution. The absorbance was measured at 450 nm and 690 nm as reference.

The titration curves obtained for PRO885 containing the CD137 domain derived from clone 38-02-A04 are represented in FIG. 1A and the binding curves obtained for PRO951 containing the CD137 domain derived from clone 38-27-C05 are represented in FIG. 1B. While the reference antibody completely prevented binding of CD137L to CD137, PRO885 and PRO951 did not significantly inhibit the CD137L binding to CD137 and therefore were defined as non-neutralizing.

Example 8: Epitope Binning of 38-02-A04 and 38-27-C05 Against Urelumab and Utolimumab The binding epitopes on CD137 of the proteins PRO885 (scDb containing 38-02-A04 CDR graft), PRO951 (scDb containing 38-27-C05 CDR graft) and urelumab (BMS) and utomilumab Pfizer) were compared in a SPR epitope binning assay using a MASS-1 device (Sierra Sensors). A sandwich setup was chosen to examine if the molecules block one another's binding to CD137. Therefore, PRO885 and PRO951 were immobilized on high capacity amine sensor chips (HCA, Sierra Sensors). Then, 90 nM of the antigen CD137 was captured on the scDbs, followed immediately by an injection of 22.5 nM of the second antibody (PRO885, PRO951, urelumab and utolimumab). The capture levels of CD137 on each protein and the second binder response levels were determined (response units, RU). By calculating the theoretical maximum response (Rmax), which depends on the molecular weights of the involved proteins and the capture levels, the relative binding level (%) of the proteins on the captured antigen were determined. If the molecules bind overlapping or similar epitopes on CD137, no binding of the antibody injected over the captured CD137 should be observed. Consequently, when binding of the antibody is observed the two antibody pairs bind non-overlapping epitopes.

Figure 3:
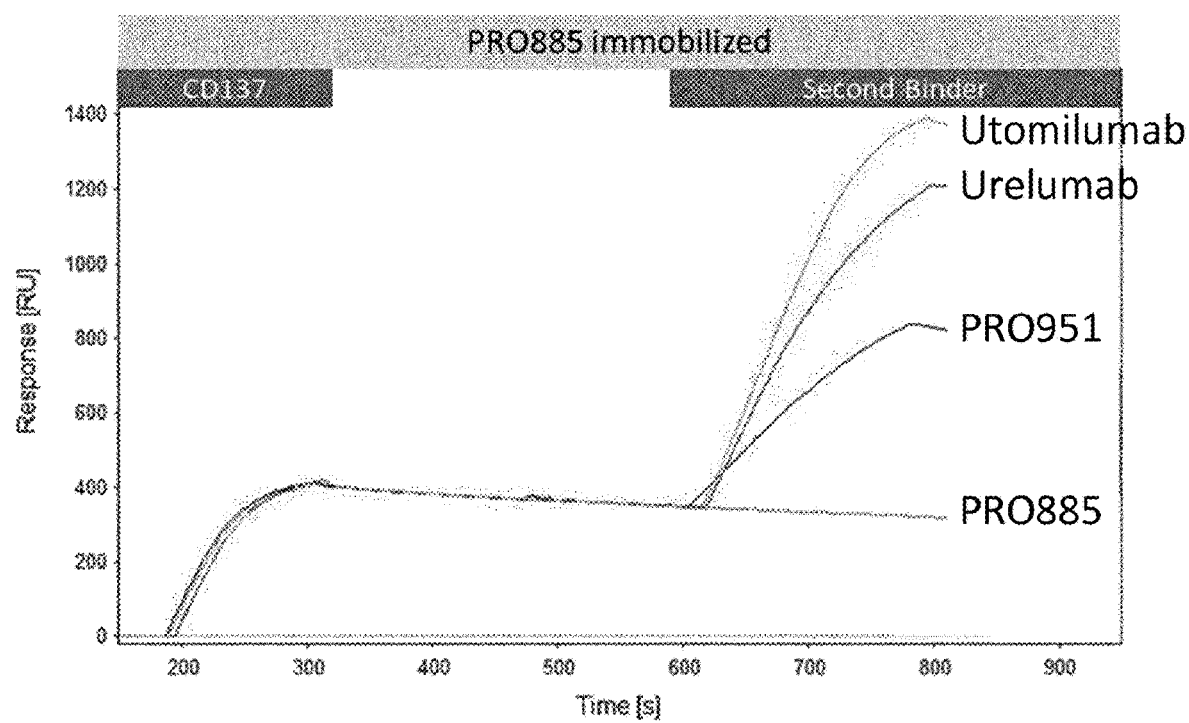
FIG. 3 Epitope binning sensorgram of PRO885. PRO885 was immobilized on sensor chip and CD137 was captured by PRO885 in a first step (left hand side) followed by injections of the 4 different antibodies (right hand side). PRO951 as well as competitors were able to bind to captured CD137 whereas an injection of PRO885 did not show any binding.
Figure 4:
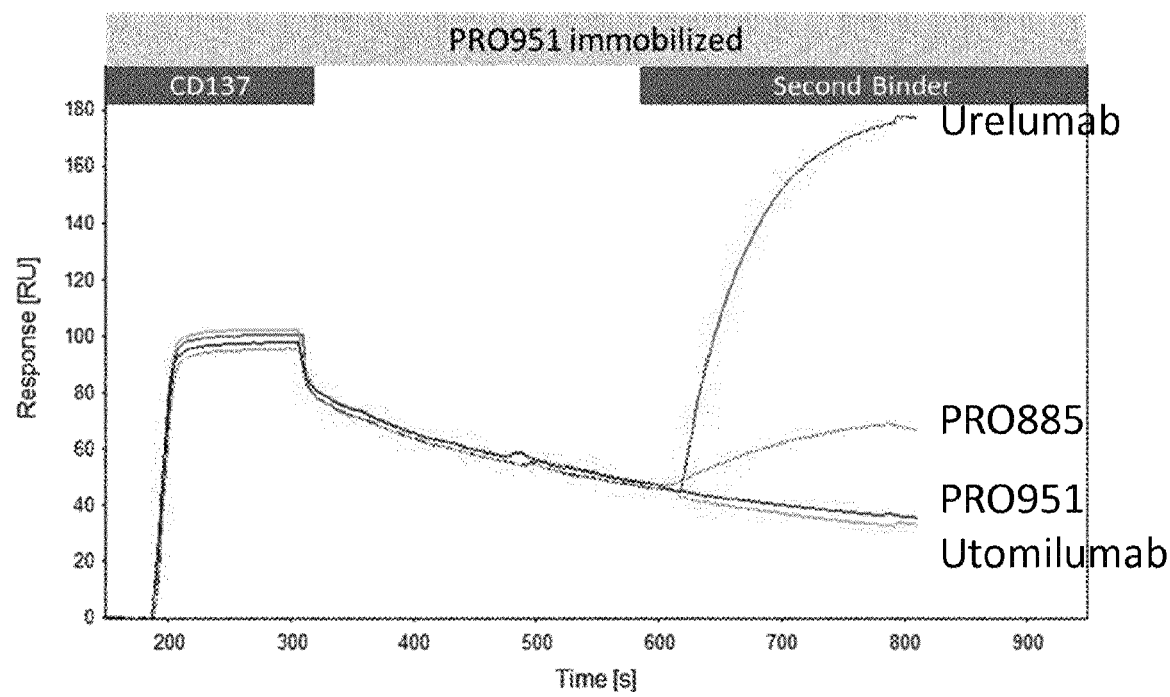
FIG. 4 Epitope binning sensorgram of PRO951. PRO951 was immobilized on sensor chip and CD137 was captured by PRO951 in a first step (left hand side) followed by injections of the 4 different antibodies (right hand side). PRO885 as well as urelumab was able to bind to captured CD137 whereas an injection of utomilumab and PRO951 did not show further binding.

When PRO885 was immobilized on a sensor chip, all 3 antibodies PRO951, urelumab and utomilumab showed binding to CD137 captured by PRO885. As expected, no binding was observed for PRO885 that was used a control (FIG. 2 and FIG. 3). When PRO951 was immobilized on the sensor chip, urelumab and PRO885 showed binding while utomilumab and PRO951 that was used as control did not show any significant binding (FIG. 2 and FIG. 3). These results show that PRO885 derived from clone 38-02-A04 binds to different epitopes on CD137 than urelumab, utolimumab and PRO951 derived from 38-27-C05. In contrast, PRO951 binds to an epitope that is overlapping with utolimumab but not with urelumab and PRO885.

Example 9: Assessment of the CD137 Agonistic Effect of Anti-PDL1×CD137 Molecules by Using a Cell-Based Assay of Transgenic NFkB Jurkat Reporter Cell Line Expressing CD137

In this assay the activation of CD137 signaling in Jurkat cells was assessed. The activity of CD137 signaling is reported by measurement of Luciferase expression which is driven by CD137 induced NFkB activation in a Jurkat reporter cell line. The expression of Luciferase directly correlates with the activity of CD137. Moreover, clustering of CD137 which is required for activation of the signal pathway is facilitated via then formation of an immunological synapse between the Jurkat cells and a PDL1 expressing cell line. Therefore, PDL1 expression is needed for clustering and activation of CD137 on the reporter cell line.

PDL1 expressing CHO (clone A2) and HCC827 cells unstimulated or stimulated for 24 h with 10 ng/ml IFNy to increase PDL1 expression were seeded at 25,000 cells per well on 96-well culture plates. As a negative control, CHO WT cells without PDL1 expression were seeded at the same cell density. Then, serial dilutions of the anti-PDL1×CD137 molecules as well as the competitor urelumab were prepared and added to the cells. Next, Jurkat reporter cells were prepared in assay medium containing HSA at 25 mg/ml or without and added at a cell density of 40,000 cells per well. Luciferase expression was detected by addition of Luciferase reagent and was read by a luminescence reader 6 or 24 h after addition of Jurkat cells. Data were analyzed by normalization the relative luminescence units (RLU) of the test samples to the RLU measured for urelumab (FIG. 11A) or PRO885 (FIG. 11B) yielding values of the relative activation of CD137 signaling.

Results

Figure 5:
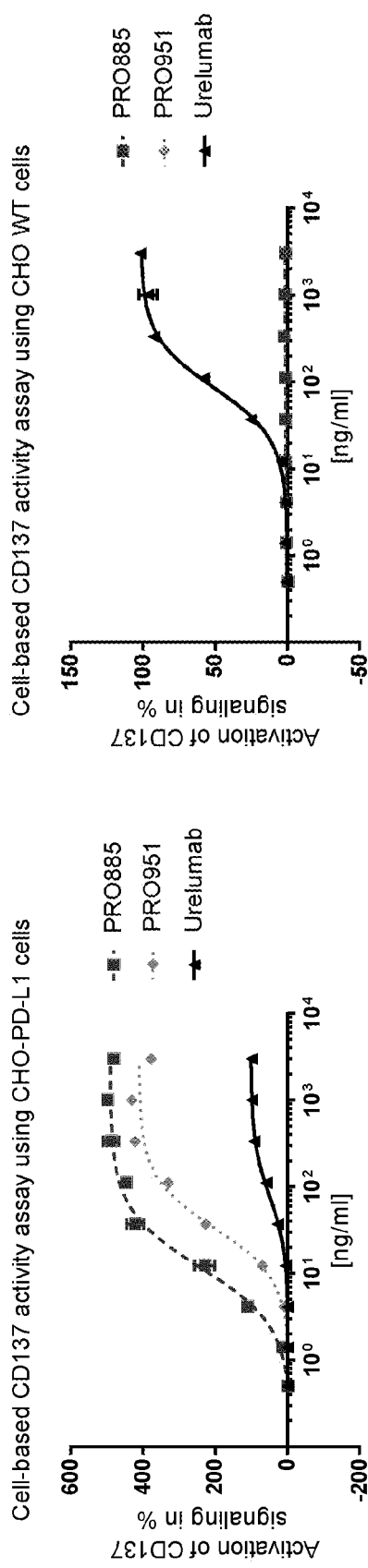
FIG. 5 CD137 activation by PRO885 and PRO951 as assessed in the NFkB-Luciferase reporter gene assay. In the presence of PDL1 expressing cells, PRO885 and PRO951 activated CD137 signaling in Jurkat cells whereas no activation was observed when CHO WT cells were tested. urelumab activated CD137 signaling independently of PDL1 expression. Luminescence was read 6 h after addition of Jurkat reporter cells and data were fitted using sigmoidal 4PL fit (GraphPad Prism).

I. Test of PRO885 and PRO951 using CHO-PDL1 Cells:

As shown in FIG. 5, PRO885 and PRO951 activated CD137 signaling more efficient in the presence of PDL1 expressing CHO cells than urelumab. PRO885 showed the best potency and highest signal of activation (PRO885, $EC_{50}$=11.72 ng/ml, PRO951: $EC_{50}$=33.68 ng/ml; urelumab: $EC_{50}$=79.11 ng/ml, Table 18). In the absence of PDL1, neither PRO885 nor PRO951 could activate CD137 in reporter cells while urelumab showed activation of CD137 signaling independently of PDL1.

TABLE 18

$EC_{50}$ values for anti-PDL1×CD137 molecules using CHO-PDL1 cells.

|  | urelumab | PRO885 | PRO951 |
| --- | --- | --- | --- |
| Bottom | −0.4628 | −8.1 | −4.066 |
| Top | 101.5 | 491.2 | 411.4 |
| $EC_{50}$ in ng/ml | 79.11 | 11.72 | 33.68 |
| R square | 0.995 | 0.9922 | 0.9899 |

Figure 6:
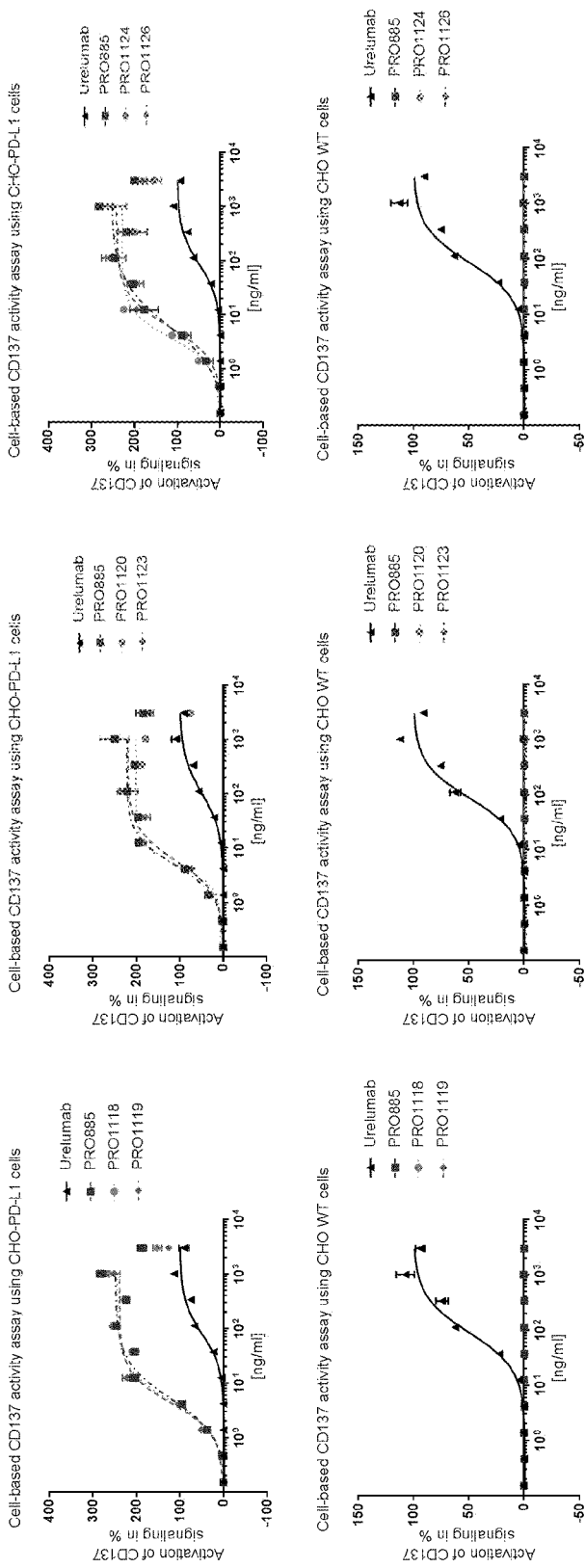
FIG. 6 CD137 activation in the NFkB-Luciferase reporter gene assay by scDb with different affinities to PDL1 and CD137. In the presence of PDL1 expressing CHO cells, all scDb activated CD137 signaling in Jurkat cells whereas no activation was observed when CHO WT cells were tested. urelumab activated CD137 signaling independently of PDL1 expression. Luminescence was read 6 h after addition of Jurkat reporter cells and data were fitted using sigmoidal 4PL fit (GraphPad Prism).

II. Test of STR-Grafted scDbs Using CHO-PDL1 Cells:

As shown in FIG. 6 and Table 21, the anti-PDL1×CD137 scDb molecules stimulated CD137 signaling more efficiently than urelumab. In contrast to urelumab, the stimulatory effect was only seen for the scDb when PDL1 expressing target cells were present. All scDbs showed identical potency to stimulate NFkB reporter gene activation in presence of CHO cells expressing PDL1 at high levels. Next, the same molecules were tested in the presence of cells expressing a lower amount of PDL1.

Figure 7:
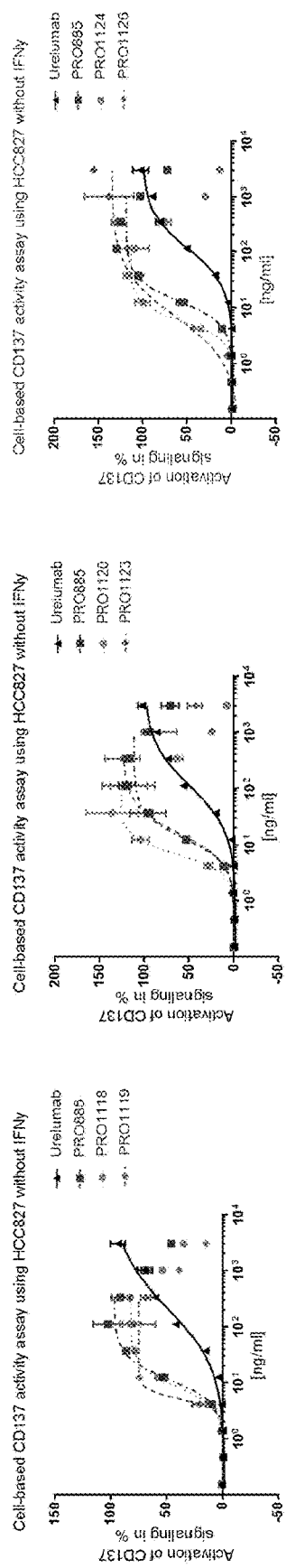
FIG. 7 CD137 activation in the NFkB-Luciferase reporter gene assay by scDb with different affinities to PDL1 and CD137. In the presence of PDL1 expressing HCC827 cells, all scDb activated CD137 signaling in Jurkat cells. urelumab served as reference molecule to assess the relative activation of CD137 signaling. Potency increased slightly with increasing affinity to CD137 and PDL1. A signal decrease at high concentrations (bell-shaped curve) was more pronounced with increasing affinity to CD137, while increased affinity to PDL1 did not contribute to this effect. Luminescence was read 6 h after addition of Jurkat reporter cells and data were fitted using sigmoidal 4PL fit (GraphPad Prism).

III. Test of STR-Grafted scDb Using HCC827 Cells without IFNy:

As shown in FIG. 7 and Table 20, the anti-PDL1×CD137 scDb molecules stimulated CD137 signaling more efficiently than urelumab. The scDbs with affinity improved CD137 domain (STR grafts of 38-02-A04, PRO1120 and PRO1124) showed an improved potency in CD137 activation when compared to the CDR grafted CD137 domain (for instance, PRO885, $EC_{50}$=13.02 ng/ml, PRO1124: $EC_{50}$=5.62 ng/ml, Table 22). Of note, increased affinity to PDL1 as it was found for the STR graft of the PDL1 domain lated CD137 signaling to the same extend as urelumab did. There was a difference when the Morrison formats (PRO1060, PRO1062) were compared to the scDb-scFv formats (PRO1057, PRO1058). While the Morrison formats showed a higher potency, the maximum signal of activation was substantially increased when the scDb-scFv were tested. Of note, after 24 h of incubation PRO1057 showed a remarkable high signal of activation. All tested long half-life molecules activated CD137 signaling only in the presence

| PRO Number | Protein description | Affinity to human CD137: SPR data | | | | Affinity to mouse CD137: SPR data | | | |
|---|---|---|---|---|---|---|---|---|---|
| | | $k_a$ [M$^{-1}$s$^{-1}$] | $k_d$ [s$^{-1}$] | $K_D$ [M] | Binding level normalized to theoretical Rmax (%) | $k_a$ [M$^{-1}$s$^{-1}$] | $k_d$ [s$^{-1}$] | $K_D$ [M] | Binding level normalized to theoretical Rmax (%) |
| PRO1118 | 38-02-404 sc01 scDb-i/33_02_G02 sc01 scDb-o | 2.75E+05 | 7.23E−04 | 2.63E−09 | 79.8 | 8.29E+04 | 2.27E−04 | 2.73E−09 | 11.5 |
| PRO1119 | 38-02-A04 sc05 If scDb-i/33_02_G02 sc01 scDb-o | 3.81E+05 | 2.76E−04 | 7.24E−10 | 79.1 | 1.40E+05 | 2.48E−02 | 1.77E−07 | 81.0 |
| PRO1120 | 38-02-A04 sc06 Full scDb-i/33_02_G02 sc01 scDb-o | 5.78E+05 | <1.00E−05 | <1.73E−11 | 74.7 | 2.12E+05 | 3.25E−03 | 1.54E−08 | 87.5 |

| PRO Number | Affinity to human PD-L1: SPR data | | | |
|---|---|---|---|---|
| | $k_a$ [M$^{-1}$s$^{-1}$] | $k_d$ [s$^{-1}$] | $K_D$ [M] | Binding level normalized to theoretical Rmax (%) |
| PRO1118 | 1.34E+06 | <1.00E−05 | <7.46E−12 | 79.2 |
| PRO1119 | 1.50E+06 | <1.00E−05 | <6.67E−12 | 77.5 |
| PRO1120 | 1.27E+06 | <1.00E−05 | <7.87E−12 | 76.8 |

(PRO1126) also resulted in increased potency when compared to the parental molecule PRO885 (PRO885, $EC_{50}$=13.02 ng/ml, PRO1126: $EC_{50}$=6.97 ng/ml, Table 20). At high concentrations, the STR grafted scDb showed a tendency of decreasing signal of activation. This was more pronounced for molecules having a STR grafted CD137 domain (PRO1120 and PRO1126). Interestingly, when the STR graft of the PDL1 domain was combined with the CDR graft of CD137 the signal decrease at high concentrations was not observed (compare PRO885 and PRO1124 in FIG. 7). Thus, potency increased slightly with increasing affinity to CD137 and PDL1. A signal decrease at high concentrations (bell-shaped curve) was more pronounced with increasing affinity to CD137, while increased affinity to PDL1 did not contribute to this effect. Thus, rather the ratio between affinity to CD137 and PDL1, than the absolute affinities of each domain seems critical to extend the concentration window of maximal activity.

[see page 123A]

Figure 8:
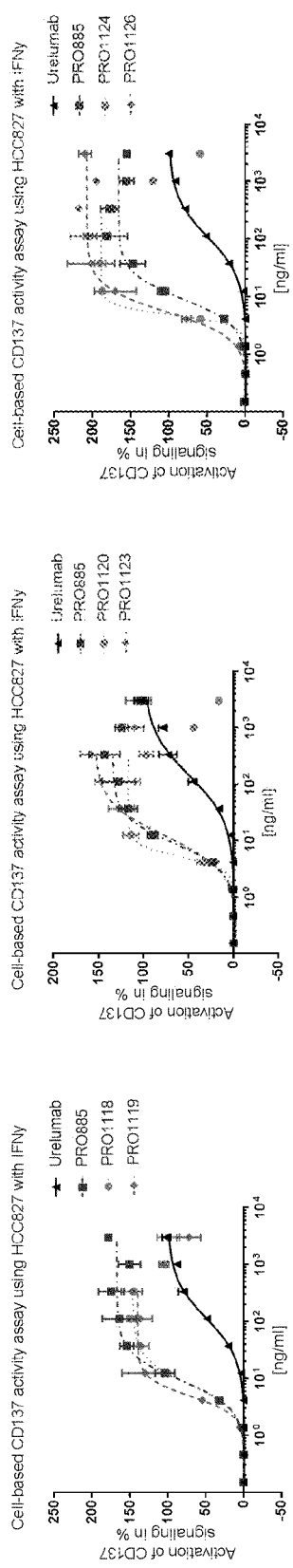
FIG. 8 CD137 activation in the NFkB-Luciferase reporter gene assay by scDb with different affinities to PDL1 and CD137. In the presence of PDL1 expressing HCC827 cells stimulated with IFNy for 24 h at 10 ng/ml, STR grafted scDb activated CD137 signaling in Jurkat cells. urelumab served as reference molecule to assess the relative activation of CD137 signaling. Potency increased slightly with increasing affinity to CD137 and PDL1. A signal decrease at high concentrations (bell-shaped curve) was more pronounced with increasing affinity to CD137, while increased affinity to PDL1 did not contribute to this effect. Luminescence was read 6 h after addition of Jurkat reporter cells and data were fitted using sigmoidal 4PL fit (GraphPad Prism).
Figure 9:
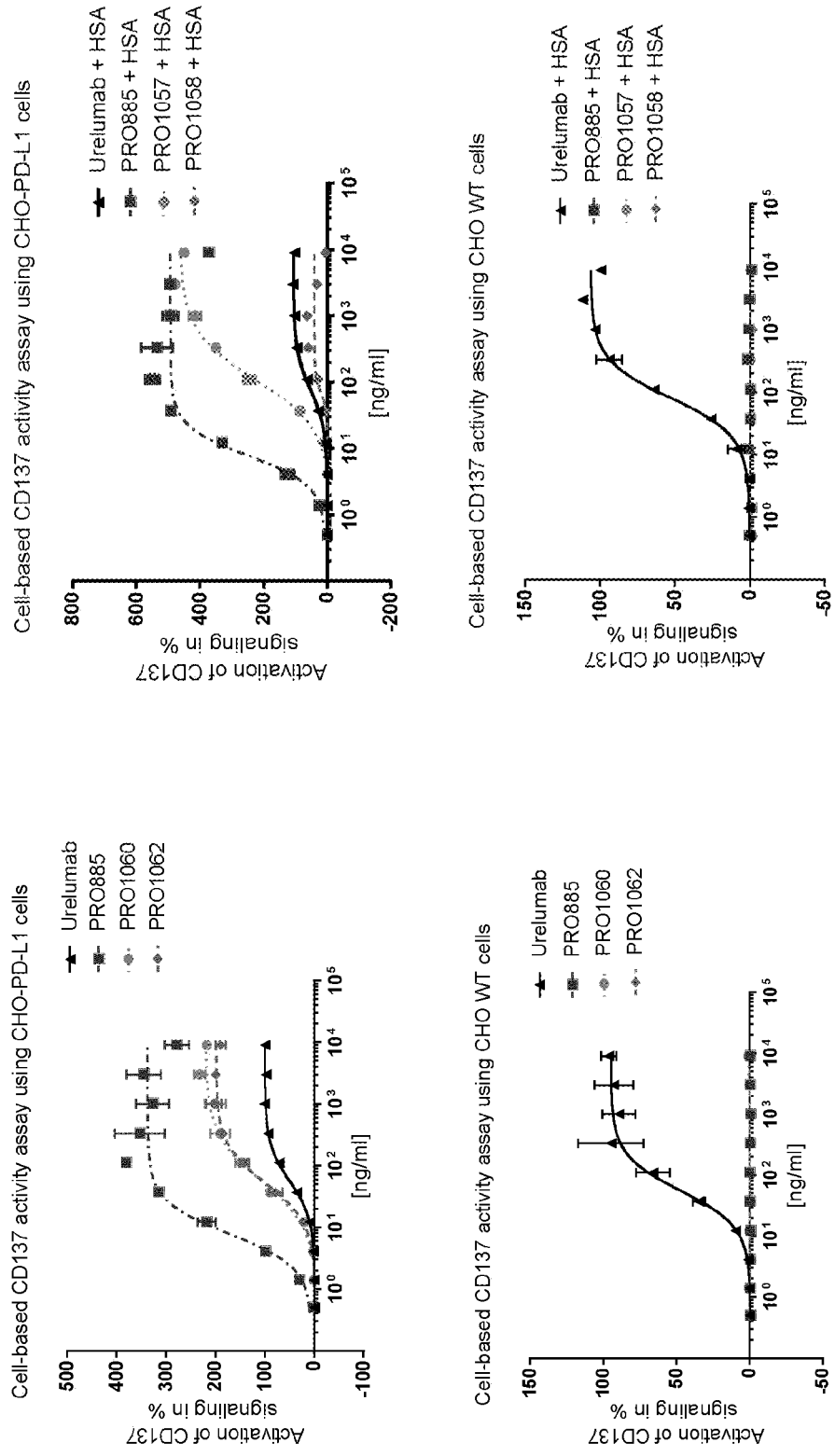
FIG. 9 CD137 activation by molecules with prolonged serum half-life in the NFkB-Luciferase reporter gene assay after 6 h. In the presence of PDL1 expressing CHO cells, long half-life molecules activated CD137 signaling in Jurkat cells whereas no activation was observed when CHO WT cells were tested. Urelumab activated CD137 signaling independently of PDL1 expression. Interestingly, despite similar affinities to both targets, PRO1057 showed a much higher maximal signal than PRO1058. And further, the monovalent scDb-scFv PRO1057 showed stronger activation than the respective bivalent Morrison format PRO1060. Luminescence was read 6 h after addition of Jurkat reporter cells and data were fitted using sigmoidal 4PL fit (GraphPad Prism).
Figure 10:
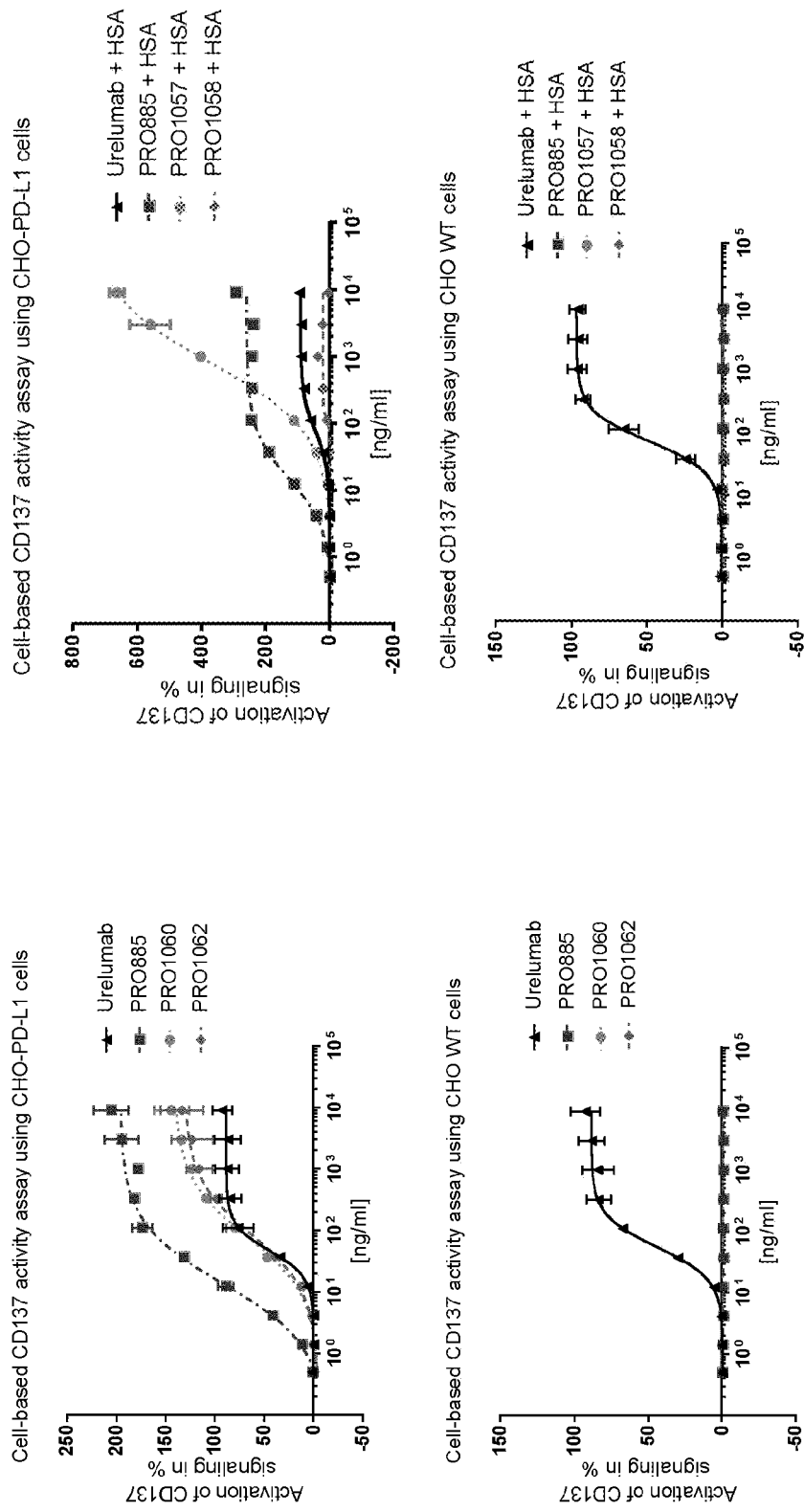
FIG. 10 CD137 activation by molecules with prolonged serum half-life in the NFkB-Luciferase reporter gene assay after 24 h. In the presence of PDL1 expressing CHO cells, long half-life molecules activated CD137 signaling in Jurkat cells whereas no activation was observed when CHO WT cells were tested. Urelumab activated CD137 signaling independently of PDL1 expression. Interestingly, despite similar affinities to both targets, PRO1057 showed a much higher maximal signal than PRO1058, which after 24 h exceeded even the activity of the scDb Pro885. And further, the monovalent scDb-scFv PRO1057 showed much stronger activation than the respective bivalent Morrison format PRO1060. Luminescence was read 24 h after addition of Jurkat reporter cells and data were fitted using sigmoidal 4PL fit (GraphPad Prism).

IV. Test of STR-Grafted scDb Using HCC827 Cells with IFNy:

Stimulation of HCC827 with IFNy led to increased signal of activation without changing the potency of the scDb molecules. Of note, the drop of signal at high concentration of the tested scDb was less obvious in this setting suggesting a correlation with PDL1 expression (FIG. 8 and Table 21).

Figure 11:
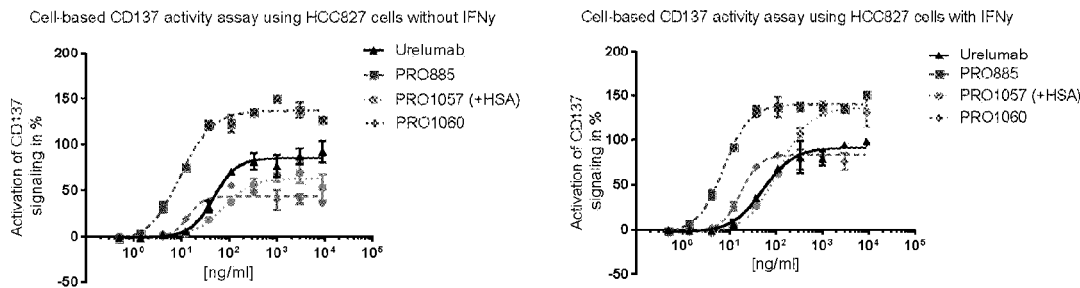
FIG. 11 (A) CD137 activation by molecules with prolonged half-life, after 24 h. In the presence of HCC827 cells either unstimulated or stimulated with IFNy at 10 ng/ml for 24 h, long half-life molecules activated CD137 signaling in Jurkat cells. Urelumab served as reference molecule to assess the relative activation of CD137 signaling. The monovalent scDb-scFv PRO1057 showed higher maximal activation than the respective bivalent Morrison format PRO1060. Luminescence was read 24 h after addition of Jurkat reporter cells and data were fitted using sigmoidal 4PL fit (GraphPad Prism). (B) Tri-specific scDb-scFv molecules PRO1430, PRO1431, PRO1432, PRO1473, PRO1476, PRO1479, and PRO1482 were tested in CD137 activity assay in the presence of IFNy (10 ng/ml) stimulated HCC827 for 6 h and 24 h. In this experiment, PRO885 served as reference molecule to assess the relative activation of CD137 signaling. Tri-specific scDb-scFv molecule PRO1186 was taken along on each plate to compare its activity with the other scDb-scFv molecules. Luminescence was read 6 h or 24 h after addition of Jurkat reporter cells and concentrations of tested molecules with increasing RLU values only were fitted using sigmoidal 4PL fit (GraphPad Prism).
Figure 11:
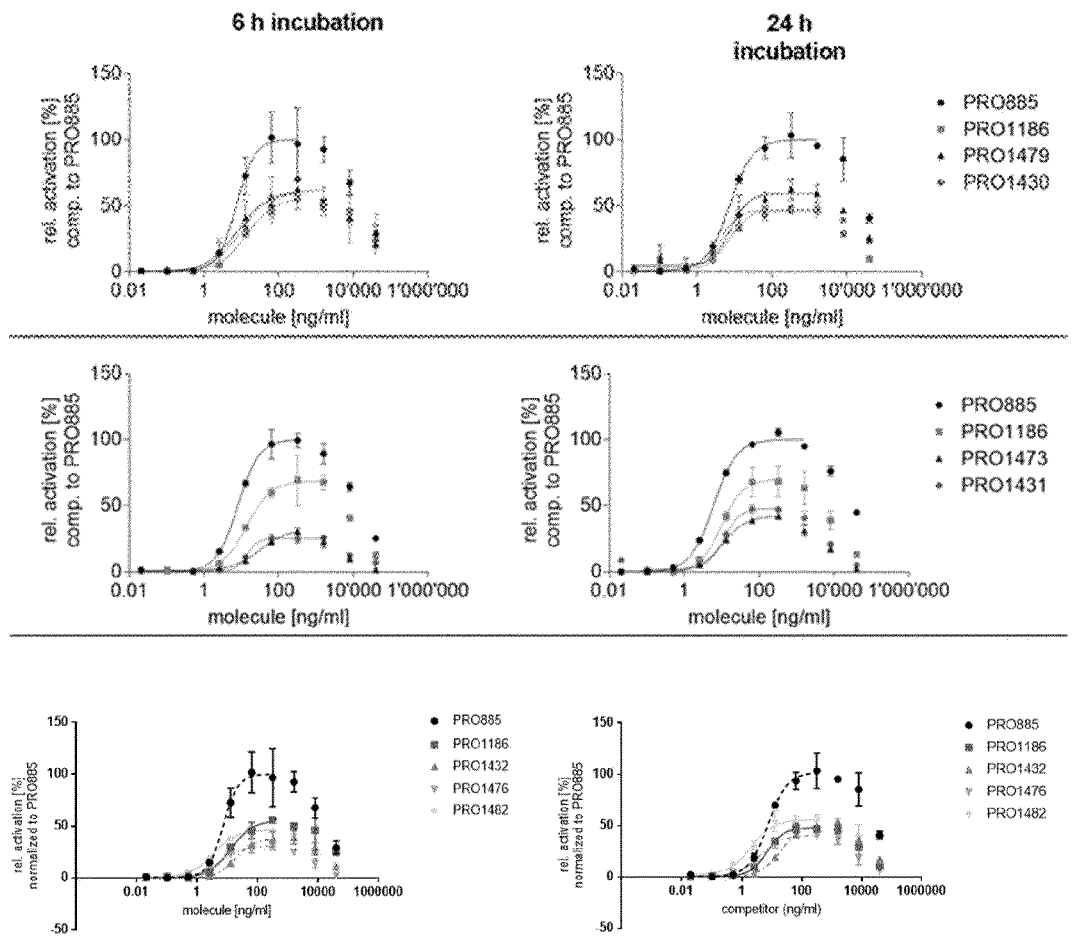
Figure 12:
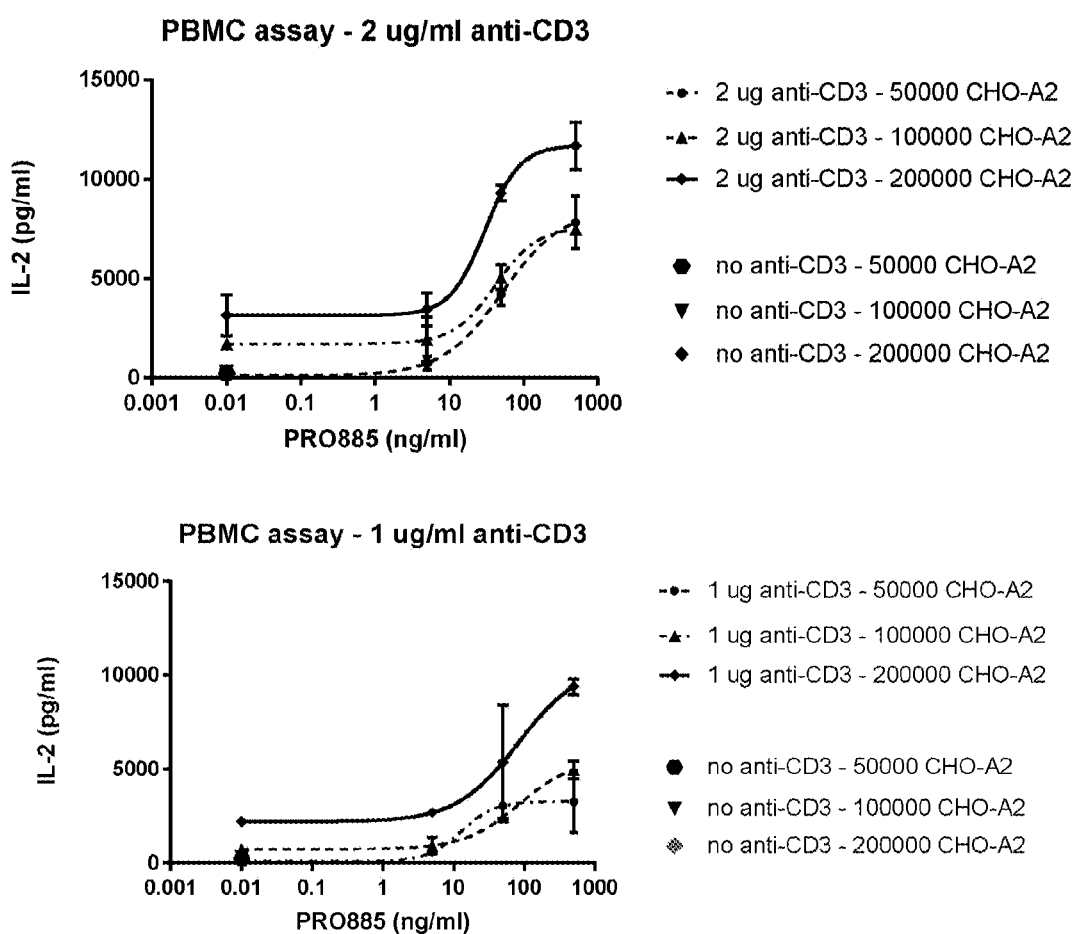
FIG. 12 Ex vivo T cell activation. The costimulatory engagement of PDL1 and CD137 by PRO885 is shown, leading to IL-2 production clearly above background IL-2 levels. CHO-A2 cells are transgenic CHO cells expressing PDL1.

V. Test of Long Half-Life Molecules Using CHO-PDL1 Cells:

As shown in FIG. 11 and FIG. 12 and Tables 22 and 23, tested long half-life anti-PDL1×CD137 molecules stimuof PDL1 expressing cells. Interestingly, despite similar affinities to both targets, PRO1057 showed a much higher maximal signal than PRO1058. And further, the monovalent scDb-scFv PRO1057 showed stronger activation than the respective bivalent Morrison format PRO1060.

VI. Test of Long Half-Life Molecules Using HCC827 Cells without and with IFNy

As shown in FIG. 11 and Table 24, tested long half-life anti-PDL1×CD137 molecules stimulated CD137 signaling to the same extend as urelumab in the presence of cells expressing lower amounts of PDL1. The maximum activation of tested molecules was further increased when the target cells were stimulated by IFNy suggesting a direct correlation of CD137 activation with the levels of PDL1 expression on the target cells. As already stated above, PRO1057 showed a higher level of reporter gene activation when compared to the Morrison formats.

Data for NFkB reporter gene activation by PDL1×CD137 multispecific constructs are summarized in Tables 26 and 27.

Example 10: Assessment of T Cell Stimulatory Effect of Concomitant PDL1 Blockade and CD137 Stimulation in a Cell-Based Assay Using Human PBMC and Transgenic CHO Cells Expressing PDL1

CHO-A2 cells expressing PDL1 were seeded at three different densities, ranging from 50,000 to 200,000 cells per well on 96-well culture plates pre-coated with an anti-human CD3 antibody. The plates were incubated overnight at 37°

C., 5% $CO_2$. On the next day, peripheral blood mononuclear cells (PBMC) were isolated from fresh human whole blood by means of density gradient centrifugation. 100,000 PBMCs per well were added to the 96-well plate, followed by the addition of the anti-PDL1×CD137 scDb PRO885 at concentrations of 500, 50 and 5 ng/ml. After 76 hours of incubation, cell supernatants were harvested. Human interleukin-2 (IL-2) levels in the culture supernatants were quantified using the IL-2 human ELISA MAX assay from BioLegend, according to kit instructions. IL-2 concentrations were interpolated from a IL-2 standard curve, back-calculated and plotted against PRO885 concentrations for calculation of $EC_{50}$ values.

As shown in FIG. 12, IL-2 was secreted by T cells following concomitant blockade of PD-1/PDL1 interaction and stimulation of CD137 by the addition of the bispecific molecule PRO885. Secreted IL-2 levels increased with augmenting anti-CD3 antibody and CHO-A2 cell-densities, and increasing PRO885 concentrations. In the absence of anti-CD3 antibodies, IL-2 levels were comparable to basal IL-2 secretion. PRO885 only activated T-cells co-stimulated by an anti-CD3 antibody. This finding demonstrates that PRO885 only stimulates activated T-cells and suggests that in vivo PRO885 would specifically stimulate tumor specific T-cells.

TABLE 19

$EC_{50}$ values for anti-PDL1×CD137 molecules using CHO-PDL1 cells.

|  | Urelumab | PRO885 | PRO1118 | PRO1119 |
|---|---|---|---|---|
| Bottom | −0.5169 | −6.408 | −2.387 | 2.039 |
| Top | 99.99 | 249.1 | 245.3 | 238.9 |
| EC50 in ng/ml | 79.47 | 5.135 | 4.596 | 4.22 |
| R square | 0.9637 | 0.9708 | 0.9761 | 0.9726 |
|  | Urelumab | PRO885 | PRO1120 | PRO1123 |
| Bottom | −0.6273 | 0.5392 | 6.497 | −1.816 |
| Top | 100 | 222.1 | 201.1 | 219.2 |
| EC50 in ng/ml | 104.2 | 4.856 | 4.689 | 5.753 |
| R square | 0.9677 | 0.9769 | 0.963 | 0.9568 |
|  | Urelumab | PRO885 | PR01124 | PR01126 |
| Bottom | −0.499 | −11.51 | 2.552 | −2.922 |
| Top | 100 | 253.8 | 228.6 | 242.1 |
| EC50 in ng/ml | 86.51 | 6.299 | 3.681 | 5.997 |
| R square | 0.979 | 0.9714 | 0.9561 | 0.9467 |

TABLE 20

$EC_{50}$ values for anti-PDL1×CD137 molecules using HCC827 cells without IFNγ.

|  | Urelumab | PRO885 | PRO1118 | PRO1119 |
|---|---|---|---|---|
| Bottom | −2.035 | −0.5477 | −0.3666 | 0.1789 |
| Top | 100 | 96.45 | 81.98 | 74.91 |
| $EC_{50}$ in ng/ml | 212.5 | 11.5 | 8.559 | 5.045 |
| R square | 0.9815 | 0.9852 | 0.995 | 0.9725 |
|  | Urelumab | PRO885 | PRO1120 | PR01123 |
| Bottom | −1.986 | −0.2298 | 0.0807 | −0.8367 |
| Top | 99.96 | 111.1 | 126.5 | 123.2 |
| EC50 in ng/ml | 109.9 | 13.06 | 6.685 | 16.12 |
| R square | 0.9895 | 0.9759 | 0.9609 | 0.96 |

TABLE 20-continued

|  | Urelumab | PRO885 | PR01124 | PR01126 |
|---|---|---|---|---|
| Bottom | −1.384 | −0.3237 | −1.084 | −8.28 |
| Top | 99.98 | 118.7 | 113.2 | 135.1 |
| EC50 in ng/ml | 111.7 | 13.02 | 5.616 | 6.966 |
| R square | 0.9941 | 0.9816 | 0.9875 | 0.9577 |

TABLE 21

$EC_{50}$ values for STR grafted scDb using HCC827 cells stimulated with IFNγ.

|  | Urelumab | PRO885 | PRO1118 | PRO1119 |
|---|---|---|---|---|
| Bottom | −1.208 | −1.446 | −1.564 | 0.1399 |
| Top | 100 | 167.4 | 146.5 | 139.9 |
| EC50 in ng/ml | 114.2 | 9.266 | 7.965 | 4.855 |
| R square | 0.9939 | 0.9803 | 0.996 | 0.9767 |
|  | Urelumab | PRO885 | PRO1120 | PR01123 |
| Bottom | −1.009 | −2.023 | 0.1813 | −3.584 |
| Top | 99.98 | 134.2 | 117.3 | 154.4 |
| EC50 in ng/ml | 144.8 | 8.883 | 5.15 | 11.87 |
| R square | 0.9811 | 0.9795 | 0.9554 | 0.9883 |
|  | Urelumab | PRO885 | PR01124 | PR01126 |
| Bottom | −1.28 | −0.7258 | 1.572 | −1.561 |
| Top | 100 | 165.8 | 188.5 | 207.7 |
| EC50 in ng/ml | 108.2 | 9.229 | 4.833 | 5.48 |
| R square | 0.9976 | 0.9764 | 0.9906 | 0.9825 |

TABLE 22

$EC_{50}$ values for long half-life molecules using PDL1 expressing CHO cells (6 h).

|  | Urelumab | PRO885 | PRO1060 | PR01062 |
|---|---|---|---|---|
| Bottom | −0.09762 | 6.019 | −5.304 | −1.947 |
| Top | 99.96 | 337.5 | 220.4 | 199.1 |
| E050 in ng/ml | 56.45 | 7.843 | 56.42 | 52.16 |
| R square | 0.9948 | 0.9474 | 0.9874 | 0.993 |
|  | Urelumab + HSA | PRO885 + HSA | PRO1057 + HSA | PRO1058 + HSA |
| Bottom | −0.8837 | 6.69 | −7.721 | −0.5282 |
| Top | 106.3 | 492.8 | 462.9 | 40.06 |
| EC50 in ng/ml | 77.72 | 7.916 | 111.5 | 70.93 |
| R square | 0.9957 | 0.9457 | 0.9943 | 0.6132 |

TABLE 23

$EC_{50}$ values for long half-life molecules using PDL1 expressing CHO cells (24 h).

|  | Urelumab | PRO885 | PRO1060 | PR01062 |
|---|---|---|---|---|
| Bottom | 0.2207 | −11.83 | −5.151 | −3.914 |
| Top | 88.59 | 196.1 | 141.1 | 130.5 |
| EC50 in ng/ml | 46.63 | 13.75 | 80.85 | 86.87 |
| R square | 0.9739 | 0.9869 | 0.991 | 0.9737 |
|  | Urelumab + HBA | PRO885 + HBA | PRO1057 + HBA | PRO1058 + HBA |
| Bottom | −0.3454 | −5.805 | −7.71 | −0.4289 |
| Top | 90.45 | 258.5 | 744.9 | 20.53 |
| EC50 in ng/ml | 78.17 | 14.85 | 792.4 | 121.4 |
| R square | 0.9893 | 0.9812 | 0.9955 | 0.6294 |

TABLE 24

EC$_{50}$ values for long half-life molecules using HCC827 cells stimulated with IFNγ.

HCC827 without IFNy stimulation

|  | Urelumab | PRO885 | PRO1057 (+HSA) | PRO1060 |
|---|---|---|---|---|
| Bottom | −0.7119 | −5.806 | 0.08644 | −0.6993 |
| Top | 85.16 | 136.6 | 63.18 | 43.56 |
| EC50 in ng/ml | 47.49 | 9.518 | 76.61 | 13.57 |
| R square | 0.975 | 0.9838 | 0.9478 | 0.9255 |

HCC827 with IFNy stimulation

|  | Urelumab | PRO885 | PRO1057 (+HSA) | PRO1060 |
|---|---|---|---|---|
| Bottom | −2.649 | −3.386 | −3.323 | −1.177 |
| Top | 91.62 | 140.2 | 136.6 | 83.61 |
| EC50 in ng/ml | 52.77 | 7.515 | 115 | 17.51 |
| R square | 0.9743 | 0.9901 | 0.9911 | 0.972 |

TABLE 25

Induction of IL-2 secretion by T cells upon treatment with PRO885.

| μg/ml of anti-CD3 antibody | 2 | | | 1 | | |
|---|---|---|---|---|---|---|
| CHO-A1 cells/well | 50,000 | 100,000 | 200,000 | 50,000 | 100,000 | 200,000 |
| EC$_{50}$ (ng/ml) | 52.01 | 41.85 | 30.05 | 12.85 | 86.22 | 80.62 |

TABLE 27

NFkB reporter gene activation by PDL1 × CD137 multispecific constructs.

| | | | | | | Activation of NF-kB reporter gene HCC827 +IFNg | | | | |
|---|---|---|---|---|---|---|---|---|---|---|
| PRO ID | Clone ID PD-L1 | Clone ID CD137 | Clone ID SA | Format | Timepoint (h) | IC$_{50}$ (ng/ml) | rel. IC$_{50}$[&] | max. activation (%) | HSA |
| PRO1430 | 37-20-B03 sc01 | 38-02-A04 sc013 | 19-01-H04 sc03 | scDb-scFv | 6 | 9.80 | 1.31 | 110.1 | yes |
|  |  |  |  |  | 24 | 4.42 | 1.51 | 98.6 | yes |
| PRO1479 | 37-20-B03 sc09.1 | 38-02-A04 sc013 | 19-01-H04 sc03 | scDb-scFv | 6 | 7.38 | 1.74 | 108.2 | yes |
|  |  |  |  |  | 24 | 7.61 | 0.87 | 118.6 | yes |
| PRO1482 | 37-20-B03 sc09.1 | 38-02-A04 sc013 | 19-01-H04 sc03 | scDb-scFv | 6 | 20.05 | 0.55 | 108.6 | yes |
|  |  |  |  |  | 24 | 7.24 | 1.23 | 92.7 | yes |
| PRO1431 | 33-03-G02 sc18 | 38-02-A04 sc013 | 19-01-H04 sc03 | scDb-scFv | 6 | 21.02 | 0.68 | 55.3 | yes |
|  |  |  |  |  | 24 | 18.39 | 1.02 | 68.6 | yes |
| PRO1473 | 33-03-G02 sc03 | 38-02-A04 sc013 | 19-01-H04 sc03 | scDb-scFv | 6 | 2.40 | 2.30 | 36.2 | yes |
|  |  |  |  |  | 24 | 0.91 | 3.55 | 67.4 | yes |
| PRO1476 | 33-03-G02 sc03 | 38-02-A04 sc013 | 19-01-H04 sc03 | scDb-scFv | 6 | 5.97 | 2.02 | 36.4 | yes |
|  |  |  |  |  | 24 | 3.90 | 1.83 | 76.1 | yes |
| PRO1432 | 33-03-G02 sc18 | 38-02-A04 sc013 | 19-01-H04 sc03 | scDb-scFv | 6 | 19.36 | 0.67 | 63.4 | yes |
|  |  |  |  |  | 24 | 21.89 | 0.75 | 83.8 | yes |

NA: not applicable
ND: not determined
[&]IC$_{50, PRO1186}$ (ng/ml)/IC$_{50, test molecule}$ (ng/ml)

Example 11: Assessment of the Stimulatory Effect of Concomitant PDL1 Blockade and CD137 Stimulation in a Cell-Based Assay Using Human PBMC Stimulated with Superantigen SEA In this experiment, the synergistic effect of PD-1/PDL1 inhibition and CD137 agonism was assessed. The assay used peripheral blood mononuclear cells (PBMC) that were stimulated with the superantigen Staphylococcal Enterotoxin A (SEA) in order to induce expression of PDL1 on antigen-presenting cells (APC) and T cells respectively and CD137 on T-cells. By applying anti-PDL1×CD137 molecules two T-cell regulatory signaling pathways were targeted concomitantly: inhibition of the inhibitory PD-1/PDL1 pathway as well as activation of the CD137 pathway via formation of an immunological synapse mediated by the bispecific anti-PDL1×CD137 molecule (PRO885). The activation of T-cells was assessed by the secretion of Interleukin-2 (IL-2) and compared to the effect mediated by PDL1 inhibition mediated by the benchmarking reference antibody avelumab. In addition, the anti-PDL1 scFv, PRO997, was tested and compared to avelumab in the same experimental setup.

Peripheral blood mononuclear cells (PBMC) were isolated from fresh human whole blood by means of density gradient centrifugation. Then, PBMC were depleted for NK cells using anti-CD56 antibody and the MACS cell separation kit (Miltenyi Biotec). Next, 100,000 PBMCs per well were added to the 96-well plate, followed by the addition of serial dilutions of PRO885, PRO997 and avelumab in assay buffer containing SEA at a concentration of 10 ng/ml. After 96 hours of incubation at 37° C. and 5% CO$_2$, cell supernatants were harvested and human Interleukin-2 (IL-2) levels in the culture supernatants were quantified using the IL-2 human ELISA MAX assay from BioLegend according to kit instructions. IL-2 concentrations were interpolated from a IL-2 standard curve, back-calculated and plotted against avelumab and PRO885 concentrations for calculation of EC$_{50}$ values.

Figure 13:
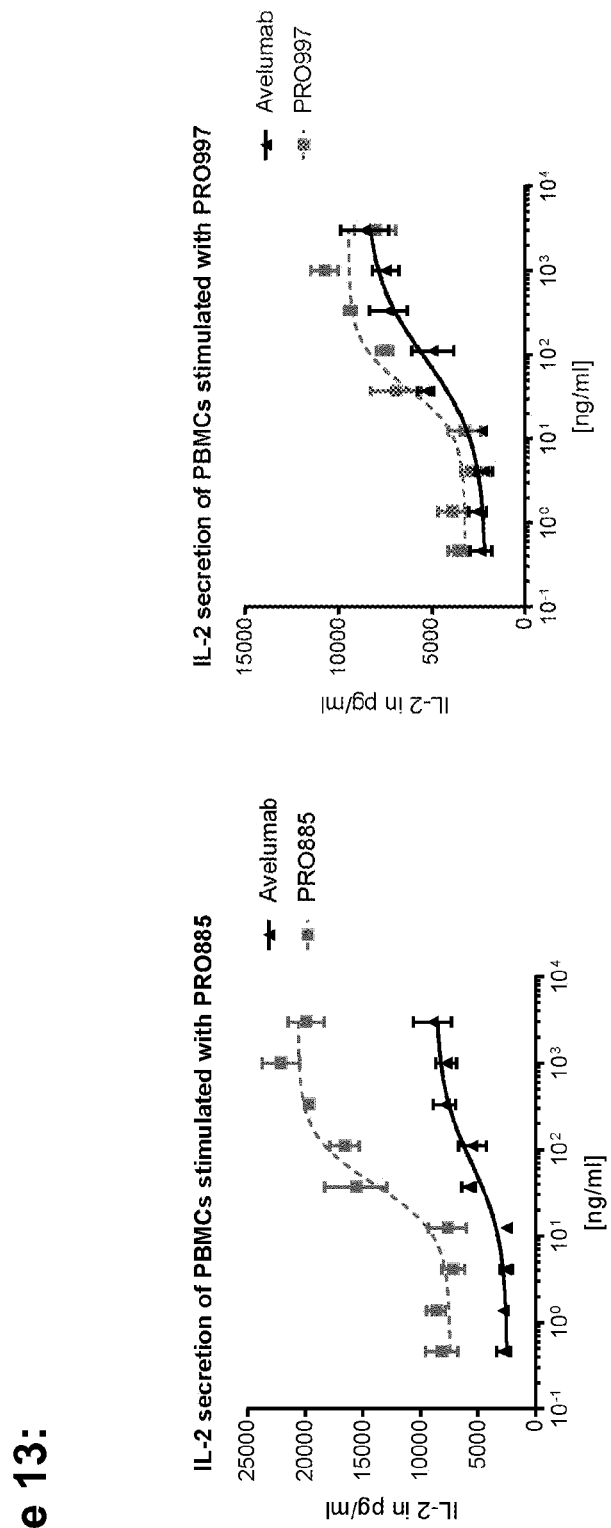
FIG. 13 Ex vivo T cell activation assay. PBMC were stimulated with 10 ng/ml SEA and treated with serial dilutions of the scFv PRO997 or the scDb PRO885 for 96 h. Activation of T-cells was assessed by quantification of IL-2 in harvested supernatants by ELISA. Treatment with PRO885 and PRO997 resulted in pronounced IL-2 secretion. PRO997 showed higher potency than avelumab. PRO885 showed much increased effect size when compared to avelumab. Data were fitted using sigmoidal 4PL fit (GraphPad Prism).

As shown in FIG. 13, IL-2 was secreted by T-cells following concomitant blockade of PD-1/PDL1 interaction and stimulation of CD137 by the addition of the bispecific molecule PRO885. When compared to avelumab, PRO885 showed higher T cell activation and better potency (PRO885, EC$_{50}$=39.92 ng/ml; avelumab, EC$_{50}$=69.89 ng/ml, Table 31). This finding demonstrates that the bispecific anti-PDL1×CD137 scDb PRO885 is able to induce stronger T cell stimulation than mere PDL1 blockade by avelumab. Moreover, the high-affinity anti-PDL1 scFv PRO997 was found to be more potent in stimulation of T-cells than avelumab (PRO997, EC$_{50}$=40.86 ng/ml; avelumab, EC$_{50}$=90.18 ng/ml, Table 28).

TABLE 28

EC$_{50}$ values for PRO885 and PRO997 in PBMC assay using SEA stimulation.

|  | Avelumab | PRO885 |  | Avelumab | PRO997 |
|---|---|---|---|---|---|
| Bottom | 2479 | 7463 | Bottom | 2117 | 3226 |
| Top | 8687 | 20663 | Top | 8588 | 9480 |
| EC$_{50}$ in ng/ml | 69.89 | 39.92 | EC$_{50}$ in ng/ml | 90.18 | 40.86 |
| R square | 0.8589 | 0.9052 | R square | 0.8783 | 0.867 |

Example 12: Assessment of the Anti-Tumor Efficacy of the Anti-CD137 Antibody in the Human Cell Line-Derived Lung Cancer Xenograft Model HCC827

Anti-tumor activity of the anti-CD137 antibody PRO1138 was assessed in human HCC827 NSCLC xenografts using the immunodeficient NOG mice strain from Taconic and allogeneic human peripheral blood mononuclear cells. Engrafted human T lymphocytes show xeno-reactivity against foreign major histocompatibility (MHC) class I and II and other antigens from mice cells. As a result, T lymphocytes cause an inflammatory infiltrate in different organs that leads to death of the animals after several weeks, a process known as xenograft-versus-host disease (xGVHD). Treatment with immunomodulatory antibodies such as anti-PDL1 and anti-CD137 was shown to exacerbate xGVHD (Sanmamed M F et al. Nivolumab and urelumab enhance antitumor activity of human T lymphocytes engrafted in Rag2−/−IL2Rgnull immunodeficient mice. Cancer Res 2015; 75(17):3466-3478).

Study Set-Up and Treatment Schedule

Female NOG mice received unilateral injections of 5×10$^6$ HCC827 cells. Cells were injected in a mixture of 50% cell suspension in PBS and 50% matrigel in a total injection volume of 100 µl. After injection of tumor cells into NOG mice and successful tumor engraftment (median group tumor volume of 80-100 mm$^3$), mice were substituted with 5×10$^6$ human PBMCs by intravenous injection. On the day of randomization, four mice of each group were reconstituted with PBMCs of donor A and another four mice with PBMCs of donor B. Treatment started 1-2 hours after the injection of PBMCs and was applied as follows.

| group ID | compound | total daily dose [mg] | dosing days | route | no of mice |
|---|---|---|---|---|---|
| 1 | Vehicle | na | 0, 3, 7, 10 | ip | 8 |
| 2 | urelumab | 0.2 | 0, 3, 7, 10 | ip | 8 |
| 3 | PRO1138 | 0.2 | 0, 3, 7, 10 | ip | 8 |

Body weight measurements and tumor volume by caliper measurements were performed twice weekly. Animals were terminated at defined time-points depending on the study results.

All but one animal were terminated at the 'same' time-point (on day 17 and day 18). One animal was euthanized already on day 14 due to the onset of xenograft-versus-host disease (xGVHD). Sample collection and processing of the first half of each group were performed on the first day, and sample collection and processing of the second half of each group were performed on the following day for capacity reasons. Animals reconstituted with PBMCs from the two different donors were equally represented in the two sampling cohorts.

Results

Figure 14:
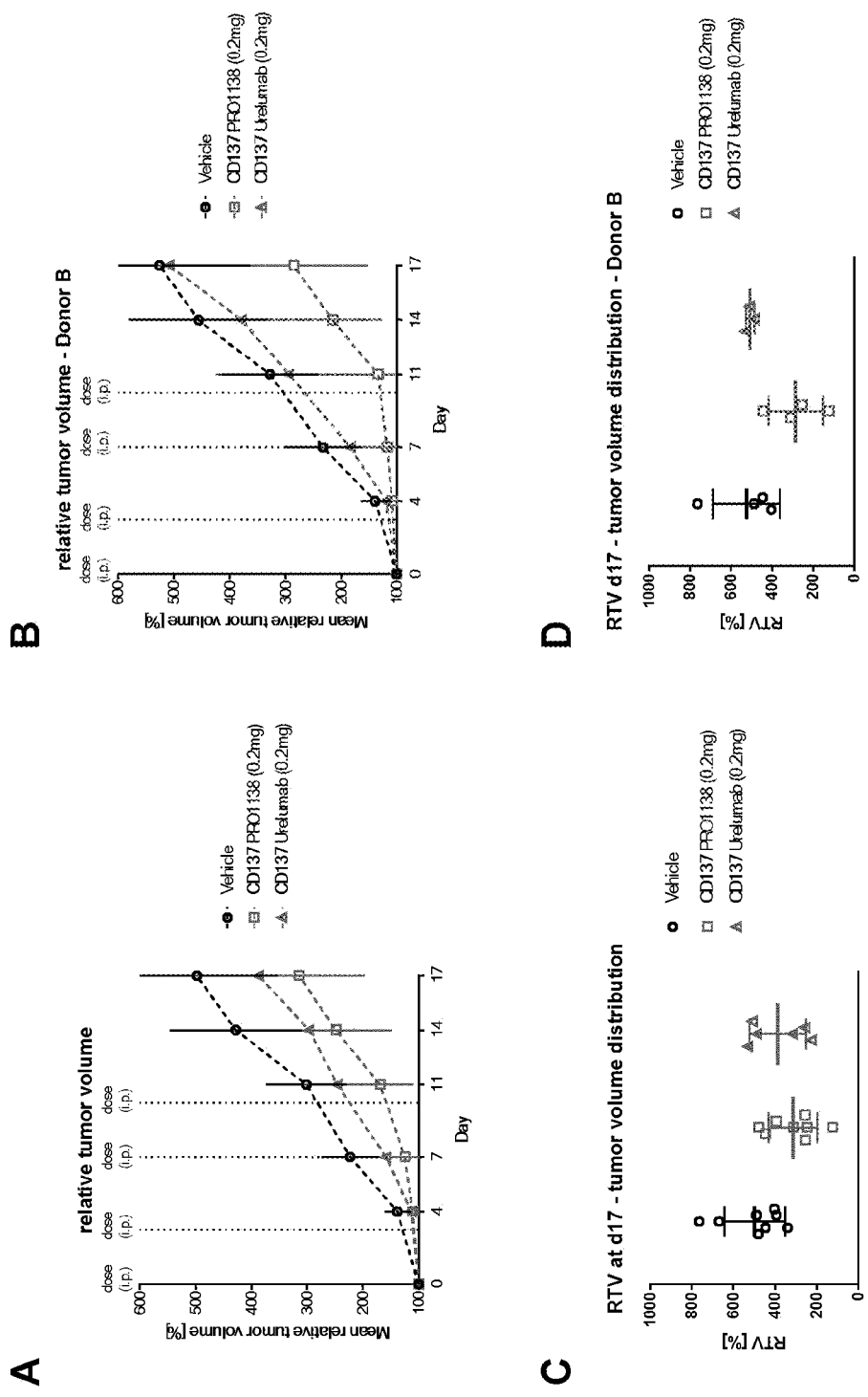
FIG. 14 Anti-tumor activity of the anti-CD137 (PRO1138 or urelumab) therapy in human HCC827 NSCLC xenografts using the immunodeficient NOG mice strain and allogeneic human peripheral blood mononuclear cells (hPBMC). Mice were treated with the anti-CD137 (PRO1138 or urelumab) or vehicle i.p. on days 0, 3, 7 and 10. Tumor volumes were measured twice per week until mice were sacrificed on day 17 or 18. Tumor volumes are normalized to the tumor volume at the start of the treatment (relative tumor volume). (A) Mean relative tumor volumes (n=8 mice per group) of mice reconstituted with PBMCs from two donors. The dotted line indicates the time of treatment. (B) Mean relative tumor volumes from mice reconstituted with PBMCs from donor B (n=4 mice per group). (C) Individual relative tumor volumes of mice reconstituted with PBMCs from two donors. Each symbol represents an individual animal within the same treatment group. (D) Individual relative tumor volumes of mice reconstituted with PBMCs from donor B. Each symbol represents an individual animal within the same treatment group.
Figure 15:
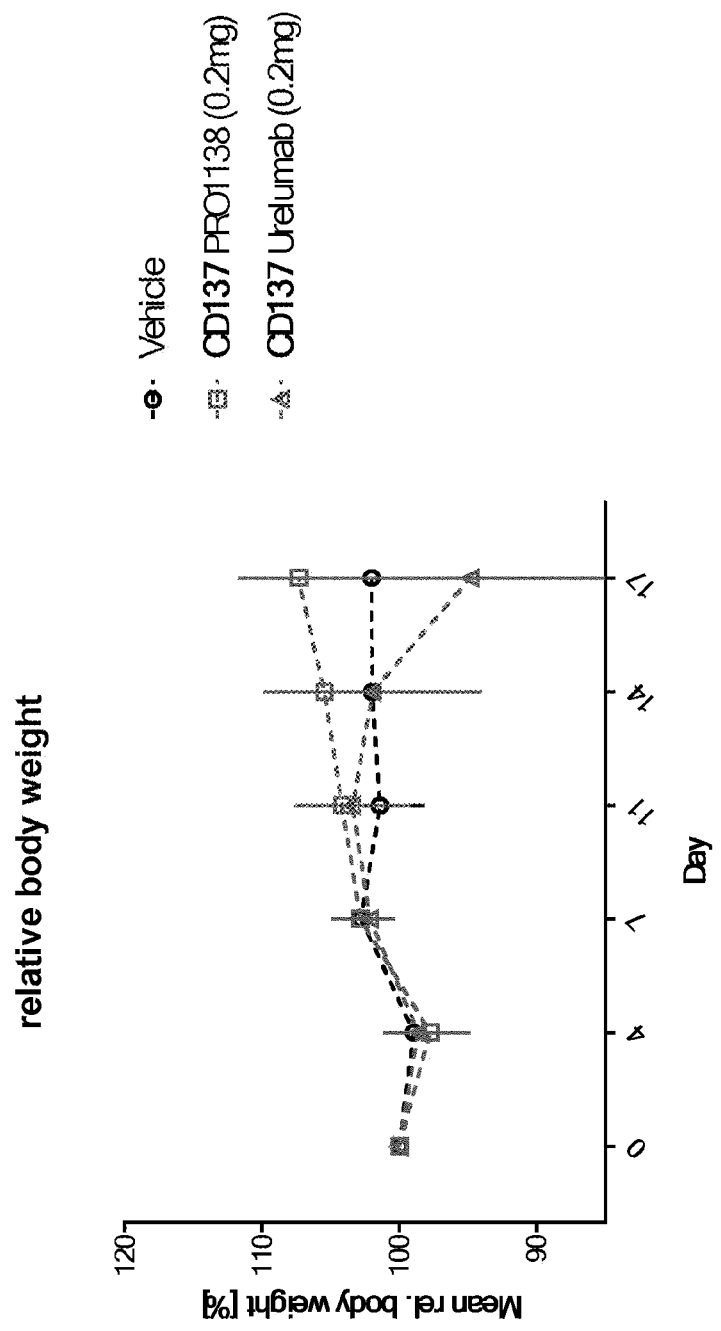
FIG. 15 Body weight of HCC827 xenograft in hPBMC substituted NOG mice upon treatment with the anti-CD137 (PRO1138 or urelumab) or a vehicle control. Body weight was measured twice per week until mice were sacrificed on day 17 or 18. Body weight was normalized to the body weight at the start of the treatment (relative body weight).

Anti-tumor activity of the anti-CD137 IgG4 (PRO1138 or urelumab) in human HCC827 NSCLC xenografts using the immunodeficient NOG mice strain and allogeneic human peripheral blood mononuclear cells (hPBMC) was assessed by measuring tumor volumes (FIG. 14). Tumor volumes were measured twice per week until mice were sacrificed on day 17 or day 18. Tumor volumes were normalized to the tumor volume at the start of the treatment (relative tumor volume). As shown in FIG. 14, treatment with PRO1138 (anti-CD137 IgG4) monoclonal antibodies showed reduced tumor growth in comparison to the vehicle control group or to urelumab. Notably, treatment with PRO1138 did not lead to loss in median body weight implicating that the molecule is well tolerated at the dose levels tested, while treatment with urelumab leads to a decrease in median body weight 17 days after the start of the treatment (FIG. 15).

Example 13: Assessment of the Anti-Tumor Efficacy of the Combination Therapy of Anti-CD137 Antibody with Anti-PDL1 Antibody in NOG Mice Engrafted with Human Umbilical Cord Blood-Derived CD34+ Hematopoietic Stem Cells (UCB HSCs)

Anti-tumor activity of the combination therapy of anti-CD137 IgG4 of the present invention (PRO1138, SEQ ID Nos: 88 and 89) with an anti-PDL1 IgG1 (PRO1196, SEQ ID NOs: 154 and 155) was assessed in human HCC827 NSCLC xenografts using NOG mice strain engrafted with human umbilical cord blood-derived CD34+ hematopoietic stem cells (UCB HSCs)

Study Set-Up and Treatment Schedule

Female NOG mice engrafted with human umbilical cord blood-derived CD34+ hematopoietic stem cells (UCB HSCs) were subcutaneously injected with HCC827 NSCLC cells. The mice received unilateral injections of 5×10$^6$ HCC827 cells. Cells were injected in a mixture of 50% cell suspension in PBS and 50% matrigel in a total injection volume of 100 µl. After injection of tumor cells into NOG mice and successful tumor engraftment (median group tumor volume of 80-100 mm$^3$), the mice (n=10) were randomized into treatment groups:

| group ID | compound | total daily dose [mg] | dosing days | route | no. of mice |
|---|---|---|---|---|---|
| 1 | Vehicle (palivizumab) | 0.1 mg | 0, 5, 10, 15, 20 | ip | 10 |
| 2 | anti-PDL1 IgG1 (PRO1196) | 0.1 mg | 0, 5, 10, 15, 20 | ip | 10 |
| 3 | avelumab | 0.1 mg | 0, 5, 10, 15, 20 | ip | 10 |
| 4 | urelumab | 0.1 mg | 0, 5, 10, 15, 20 | ip | 10 |
| 8 | Combination anti-PDL1 IgG1 (PRO1196) and anti-CD137 IgG4 (PRO1138) | 0.1 mg each | 0, 5, 10, 15, 20 | ip | 10 |

Body weight measurements and tumor volume measurements by caliper were performed twice weekly.

Results

Figure 16:
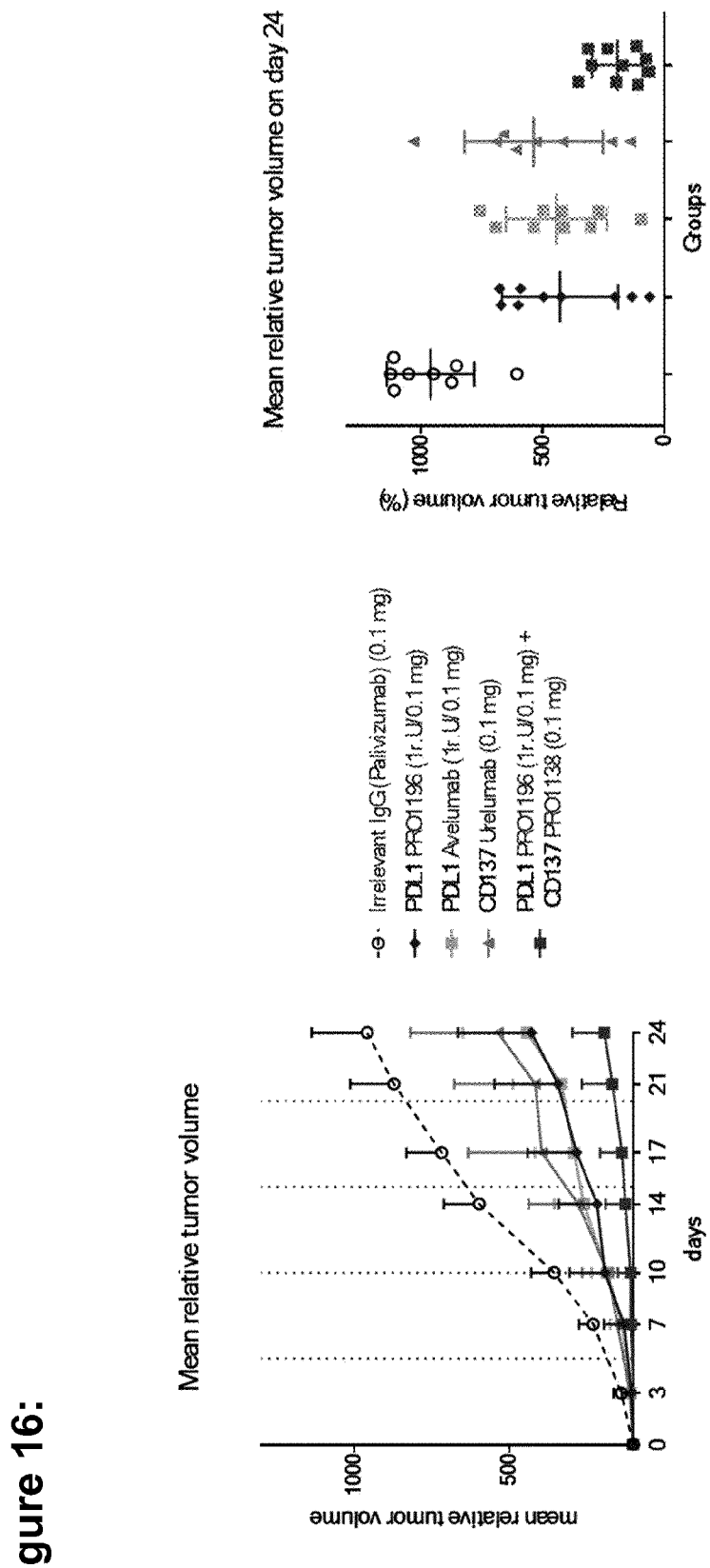
FIG. 16 Assessment of the anti-tumor efficacy of the combination of the anti-CD137 antibody PRO1138 (SEQ ID Nos: 88 and 89) with anti-PDL1 antibody PRO1196 (SEQ ID Nos: 154 and 155) in NOG mice engrafted with human umbilical cord blood-derived CD34+ hematopoietic stem cells (UCB HSCs). Anti-tumor activity of the combination of PRO1138 with PRO1196 (0.1 mg each) was compared to a vehicle treatment Palivizumab (0.1 mg), anti-PDL1 IgG1 (0.1 mg; PRO1196 or avelumab), anti-CD137 IgG4 (0.1 mg; urelumab). Mice were treated on day 0, 5, 10, 15 and 20 (dotted line). Tumor growth and body weight were recorded twice weekly. Tumor volumes were normalized to the tumor volume at the start of the treatment (relative tumor volume, RTV).
Figure 17:
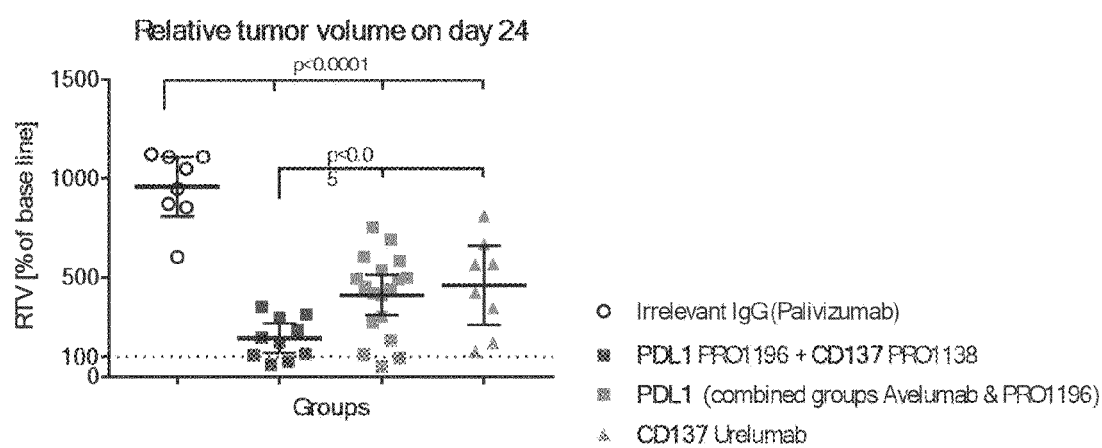
FIG. 17 Relative tumor volume on day 24 in NOG mice engrafted with human umbilical cord blood-derived CD34+ hematopoietic stem cells (UCB HSCs) after the combination therapy of the anti-CD137 antibody PRO1138 with anti-PDL1 antibody PRO1196. Tumor growth was recorded twice weekly. Tumor volumes were normalized to the tumor volume at the start of the treatment (relative tumor volume, RTV). All statistics were calculated using GraphPad Prism Version 6. Statistical significance was determined using One-way ANOVA test applying Bonferroni correction. Graphs show mean with 95% CI (confidence interval).
Figure 18:
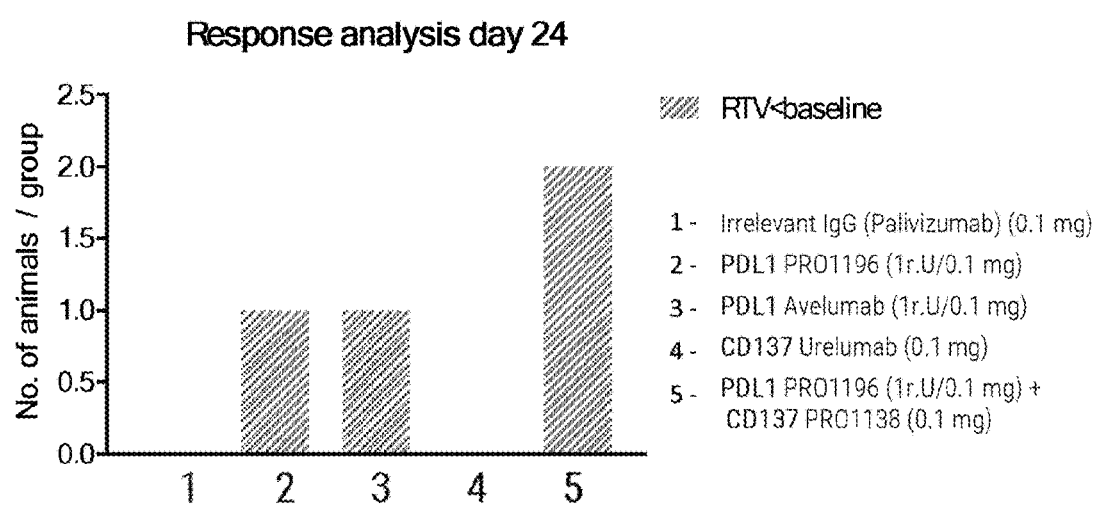
FIG. 18 Response analysis on day 24 to the combination therapy of the anti-CD137 antibody PRO1138 with anti-PDL1 antibody PRO1196 in NOG mice engrafted with human umbilical cord blood-derived CD34+ hematopoietic stem cells (UCB HSCs). Tumor volumes were normalized to the tumor volume at the start of the treatment (relative tumor volume, RTV).

Anti-tumor activity of the combination of the anti-CD137 antibody of the present invention with a PDL1 inhibitor (PRO1138 in combination with PRO1196) was assessed by measuring tumor volumes (FIG. 16 to 18). Tumor volumes were measured twice per week until mice were sacrificed on day 25, 29 or 30. Tumor volumes were normalized to the tumor volume at the start of the treatment (relative tumor volume, RTV). As shown in FIG. 16 to 18, the combination of PRO1138 with PRO1196 resulted in a synergistic effect and clear stabilization of the tumor growth. The combination therapy resulted in stronger reduction in tumor growth than therapy with single agents. All statistics were calculated using GraphPad Prism Version 6. Statistical significance was determined using One-way ANOVA test applying Bonferroni correction. Graphs show mean with 95% CI (confidence interval).

Example 14: Assessment of the Anti-Tumor Efficacy of PDL1 Blockade and Concomitant Localized Stimulation of CD137 in a Syngeneic MC38 Colon Cancer Model In addition, anti-tumor activity of the multispecific antibody of the present invention will be tested in a MC38 colon carcinoma model in syngeneic C57BL/6 mice with an intact immune system. This model has been used by others to show enhanced antitumor activity by combination treatment with CD137 agonists and PD-1/PDL1 antagonists (Chen S et al. Combination of 4-1BB agonist and PD-1 antagonist promotes antitumor effector/memory CD8 T cells in a poorly immunogenic tumor model. Cancer Immunol Res 2014; 3(2):149-160 and Rodriguez-Ruiz M E et al. Abscopal effects of radiotherapy are enhanced by combined immunostimulatory mAbs and are dependent on CD8 T cells and crosspriming. Cancer Res 2016; 76(20):5994-6005).

Since both, the anti-CD137 domain and the anti-PDL1 domain of the multispecific antibody of the present invention are not cross-reactive to mouse PDL1 an engineered human CD137 knock-in model established by CrownBio will be used. In this model, the extracellular and transmembrane domain of mouse CD137 was replaced by the respective sequence of human CD137 in the C57BL/6 mice background using the CRISPR/Cas9 system. In addition, a modified MC38 tumor cell line expressing human PDL1 under control of a CMV promoter instead of mouse PDL1 will be used. Effects of the multispecific antibody of the present invention on tumor volume will be compared to combination treatment with the humanized IgG1 containing the same PDL1 specific variable domain as ND021 and with the humanized IgG4 with the same CD137 specific variable domain. To provide further evidence of localized antitumor immune response, frequency of tumor infiltrating lymphocytes such as CD8+, CD4+ and regulatory T cells will be analyzed by flow cytometry. To explore modulation of the immune system systemically following anti-CD137/anti-PDL1 treatment, the frequency of CD4+ and CD8+ T cells in liver and spleen will be analyzed by flow cytometry and possibly immunohistochemistry. Moreover, systemic IFNy levels could be analyzed using a quantitative ELISA method. To further characterize the safety profile of the anti-CD137/anti-PDL1 combination therapy, clinical chemistry pathology parameters associated primarily with liver toxicity (observed for anti-CD137 therapy in the clinic), such as increased levels of alanine aminotransferase, glutamate dehydrogenase and aspartate aminotransferase could be assessed.

The invention claimed is:

1. An isolated antibody having a binding specificity for human CD137, which comprises an HCDR1, HCDR2, and HCDR3 sequences of SEQ ID NOs: 1, 2 and 3, respectively, and an LCDR1, LCDR2 and LCDR3 sequences of SEQ ID NOs: 18, 19 and 20, respectively.

2. The antibody of claim 1, wherein the antibody comprises a heavy chain variable region (VH), wherein said VH is VH3 or VH4.

3. The antibody of claim 1, wherein the antibody comprises a light chain variable region (VL), wherein said VL comprises Vκ frameworks FR1, FR2 and FR3, and a framework FR4, which is selected from a Vκ FR4 and Vλ FR4.

4. The antibody of claim 1, wherein the antibody comprises a heavy chain variable region comprising an amino acid sequence that is at least 90 percent identical to the amino acid sequence selected from the group consisting of SEQ ID NOs: 14, 15, 16 and 17; and a light chain variable region comprising an amino acid sequence that is at least 90 percent identical to the amino acid sequence selected from the group consisting of SEQ ID NOs: 27, 28, 29 and 30.

5. The antibody of claim 4, comprising: (a) a VH sequence of SEQ ID NO: 14 and a VL sequence of SEQ ID NO: 27; (b) a VH sequence of SEQ ID NO: 15 and a VL sequence of SEQ ID NO: 28; (c) a VH sequence of SEQ ID NO: 16 and a VL sequence of SEQ ID NO: 29; or (d) a VH sequence of SEQ ID NO: 17 and a VL sequence of SEQ ID NO: 30.

6. The antibody of claim 1, wherein said antibody:
(i) binds to human CD137 with a dissociation constant (KD) of less than 10 nM as measured by surface plasmon resonance (SPR), wherein said antibody is an scFv;
(ii) binds to human CD137 with a $K_{off}$ rate of $10^{-3}$ $s^{-1}$ or less as measured by SPR, wherein said antibody is an scFv;
(iii) binds to human CD137 with a $K_{on}$ rate of at least $10^4$ $M^{-1}s^{-1}$ or greater, as measured by SPR, wherein said antibody is an scFv;
(iv) is cross-reactive with *Macaca fascicularis* CD137 as measured by SPR, wherein said antibody is an scFv; and/or
(v) does not bind to human CD40 and/or human OX40, as measured by SPR.

7. The antibody of claim 1, wherein said antibody:
(i) when in scFv format, has a melting temperature (Tm), determined by differential scanning fluorimetry, of at least 50° C., wherein said antibody is formulated in 50 mM phosphate-citrate buffer at pH 6.4, 150 mM NaCl;
(ii) when in scFv format, has a loss in monomer content, after storage for at least two weeks of less than 5%, when the antibody of the invention is at a starting concentration of 10 mg/ml, wherein the antibody is formulated in 50 mM phosphate citrate buffer with 150 mM NaCl at pH 6.4; and/or
(iii) when in scFv format, has a loss in monomer content, after storage for at least two weeks at 40° C., of less than 5%, when the antibody of the invention is at a starting concentration of 10 mg/ml, wherein the antibody is formulated in 50 mM phosphate citrate buffer with 150 mM NaCl at pH 6.4.

8. The antibody of claim 1, wherein the isolated antibody is selected from the group consisting of: a monoclonal antibody, a chimeric antibody, a Fab, an Fv, an scFv, dsFv, a scAb, STAB, and binding domains based on alternative scaffolds including but not limited to ankyrin-based domains, fynomers, avimers, anticalins, fibronectins, and binding sites being built into constant regions of antibodies.

9. The antibody of claim 8, wherein said scFv has the amino acid sequence selected from the group consisting of SEQ ID NO: 32, SEQ ID NO: 33, SEQ ID NO: 34 and SEQ ID NO: 35.

10. The antibody of claim 1, wherein said antibody is a multispecific molecule, wherein said multispecific molecule comprises at least a second functional molecule.

11. A pharmaceutical composition comprising the antibody of claim 1 and a pharmaceutically acceptable carrier.

12. The antibody of claim 1 as a medicament.

13. The antibody of claim 1 for use in the treatment of a cancer.

14. A nucleic acid encoding the antibody of claim 1.

15. A method of producing the antibody of claim 1, the method comprising the step of culturing a host cell comprising a nucleic acid encoding the antibody of claim 1.

* * * * *

UNITED STATES PATENT AND TRADEMARK OFFICE
CERTIFICATE OF CORRECTION

PATENT NO. : 11,578,133 B2
APPLICATION NO. : 16/754097
DATED : February 14, 2023
INVENTOR(S) : Tea Gunde et al.

It is certified that error appears in the above-identified patent and that said Letters Patent is hereby corrected as shown below:

On the Title Page

In item (73), in Column 1, in "Assignee", Line 1, delete "Namab Therapeutics AG," and insert
-- Numab Therapeutics AG, --, therefor.

Signed and Sealed this
Twenty-third Day of April, 2024

Katherine Kelly Vidal
*Director of the United States Patent and Trademark Office*